United States Patent
Fyfe et al.

(10) Patent No.: US 10,442,828 B2
(45) Date of Patent: Oct. 15, 2019

(54) KINASE INHIBITORS

(71) Applicant: Topivert Pharma Limited, London (GB)

(72) Inventors: Matthew Colin Thor Fyfe, London (GB); Stephen Malcolm Thom, Nottingham (GB)

(73) Assignee: Topivert Pharma Limited, London (GB)

( * ) Notice: Subject to any disclaimer, the term of this patent is extended or adjusted under 35 U.S.C. 154(b) by 0 days.

(21) Appl. No.: 16/021,519

(22) Filed: Jun. 28, 2018

(65) Prior Publication Data

US 2018/0305383 A1  Oct. 25, 2018

Related U.S. Application Data

(62) Division of application No. 15/480,689, filed on Apr. 6, 2017, now Pat. No. 10,072,034.

(30) Foreign Application Priority Data

Apr. 6, 2016 (GB) .................................. 1605844.8

(51) Int. Cl.
| | | |
|---|---|---|
| A61K 31/44 | (2006.01) | |
| A61K 31/443 | (2006.01) | |
| A61K 31/4436 | (2006.01) | |
| A61K 31/4439 | (2006.01) | |
| A61K 31/501 | (2006.01) | |
| A61K 31/505 | (2006.01) | |
| A61K 31/675 | (2006.01) | |
| C07D 213/73 | (2006.01) | |
| C07D 239/47 | (2006.01) | |
| C07D 401/12 | (2006.01) | |
| C07D 405/12 | (2006.01) | |
| C07D 409/12 | (2006.01) | |
| C07D 413/12 | (2006.01) | |

(Continued)

(52) U.S. Cl.
CPC .............. *C07F 9/58* (2013.01); *A61K 31/44* (2013.01); *A61K 31/443* (2013.01); *A61K 31/4412* (2013.01); *A61K 31/4436* (2013.01); *A61K 31/4439* (2013.01); *A61K 31/501* (2013.01); *A61K 31/505* (2013.01); *A61K 31/506* (2013.01); *A61K 31/675* (2013.01); *A61K 45/06* (2013.01); *C07D 213/73* (2013.01); *C07D 213/74* (2013.01); *C07D 239/47* (2013.01); *C07D 401/12* (2013.01); *C07D 403/12* (2013.01); *C07D 405/12* (2013.01); *C07D 409/12* (2013.01); *C07D 413/12* (2013.01)

(58) Field of Classification Search
None
See application file for complete search history.

(56) References Cited

U.S. PATENT DOCUMENTS 6,319,921 B1  11/2001  Cirillo et al.
6,492,393 B1  12/2002  Breitfelder et al.
(Continued)

FOREIGN PATENT DOCUMENTS

WO  WO 99/23091  5/1999
WO  WO 00/041698  7/2000
(Continued)

OTHER PUBLICATIONS

Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
Biancheri, et al. 2016 "Effect of Narrow Spectrum Versus Selective Kinase Inhibitors on the Intestinal Proinflammatory Immune Response in Ulcerative Colitis" *Inflamm Bowel Dis* 22: 1306-1315.
Boehm, et al. 2000 "New inhibitors of p38 kinase" *Expert Opinion on Therapeutic Patents* 10(1): 25-37.
Brinkmann, et al. 2010 "Fingolimod (FTY720): discovery and development of an oral drug to treat multiple sclerosis" *Nature Reviews* 9: 883-897.
(Continued)

*Primary Examiner* — Zinna Northington Davis
(74) *Attorney, Agent, or Firm* — McCarter & English, LLP; Steven G. Davis; Yun Wang

(57) ABSTRACT

There are provided compounds of:

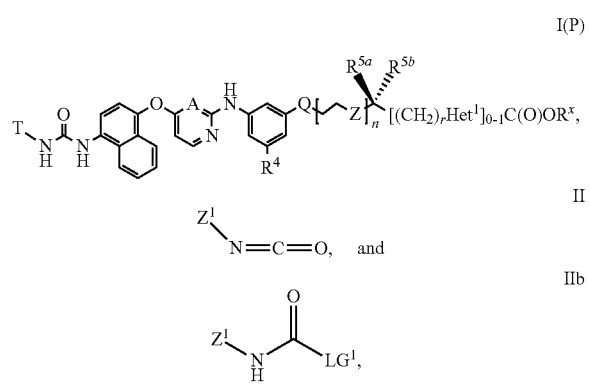

wherein T, A, Q, Z, $R^4$, $R^{5a}$, $R^{5b}$, n, r, $Het^1$ and $R^x$ have meanings given in the description, which compounds are useful in synthesizing compounds that have antiinflammatory activity (e.g., through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

9 Claims, 2 Drawing Sheets

(51) Int. Cl.

| | |
|---|---|
| *C07D 403/12* | (2006.01) |
| *A61K 31/506* | (2006.01) |
| *C07D 213/74* | (2006.01) |
| *A61K 45/06* | (2006.01) |
| *A61K 31/4412* | (2006.01) |
| *C07F 9/58* | (2006.01) |

(56) References Cited

U.S. PATENT DOCUMENTS

| | | |
|---|---|---|
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,872,726 B2 | 3/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Sun et al. |
| 7,279,475 B2 | 10/2007 | Cirillo et al. |
| 7,790,756 B2 | 9/2010 | Flynn et al. |
| 7,838,541 B2 | 11/2010 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,642,773 B2 | 2/2014 | Ito et al. |
| 8,927,563 B2 | 1/2015 | Fyfe |
| 8,933,228 B2 | 1/2015 | Murray et al. |
| 9,024,041 B2 | 5/2015 | King-Underwood |
| 9,079,893 B2 | 7/2015 | Cass |
| 9,108,950 B2 | 8/2015 | Ito et al. |
| 9,249,125 B2 | 2/2016 | Duffy et al. |
| 9,447,076 B2 | 9/2016 | Longshaw et al. |
| 9,475,796 B2 | 10/2016 | Ito et al. |
| 9,481,648 B2 | 11/2016 | Baker et al. |
| 9,499,486 B2 | 11/2016 | Fyfe |
| 9,624,196 B2 | 4/2017 | Longshaw et al. |
| 9,796,742 B2 | 10/2017 | Fyfe et al. |
| 9,890,185 B2 | 2/2018 | Fyfe et al. |
| 10,072,034 B2 * | 9/2018 | Fyfe ............ A61K 31/44 |
| 10,125,100 B2 | 11/2018 | Baker et al. |
| 2001/0011135 A1 | 8/2001 | Riedl et al. |
| 2004/0152725 A1 | 8/2004 | Moss et al. |
| 2012/0244120 A1 | 9/2012 | Charron et al. |
| 2013/0029990 A1 | 1/2013 | King-Underwood et al. |
| 2013/0040995 A1 | 2/2013 | King-Underwood et al. |
| 2013/0123260 A1 | 5/2013 | Charron et al. |
| 2013/0150343 A1 | 6/2013 | Van Niel et al. |
| 2015/0218137 A1 | 8/2015 | Cariou et al. |
| 2015/0225427 A1 | 8/2015 | Fyfe et al. |
| 2015/0329523 A1 | 11/2015 | Frickel et al. |
| 2016/0039797 A1 | 2/2016 | Fyfe |
| 2016/0102059 A1 | 4/2016 | Baker et al. |
| 2016/0318909 A1 | 11/2016 | Fyfe |
| 2016/0318958 A1 | 11/2016 | Fyfe et al. |
| 2016/0340343 A1 | 11/2016 | Fyfe et al. |
| 2016/0340375 A1 | 11/2016 | Fyfe et al. |
| 2017/0029378 A1 | 2/2017 | Fyfe |
| 2017/0057945 A1 | 3/2017 | Longshaw et al. |
| 2017/0182039 A1 | 6/2017 | Lonshaw et al. |
| 2017/0209445 A1 | 7/2017 | Fyfe |
| 2018/0118719 A1 | 5/2018 | Longshaw et al. |
| 2018/0319748 A1 | 11/2018 | Baker et al. |

FOREIGN PATENT DOCUMENTS

| | | |
|---|---|---|
| WO | WO 00/43384 | 7/2000 |
| WO | WO 00/055139 | 9/2000 |
| WO | WO 2001/04115 | 1/2001 |
| WO | WO 01/36403 A1 | 5/2001 |
| WO | WO 02/083628 | 10/2002 |
| WO | WO 02/083642 | 10/2002 |
| WO | WO 02/092576 | 11/2002 |
| WO | WO 02/096876 | 12/2002 |
| WO | WO 2003/005999 | 1/2003 |
| WO | WO 2003/068223 | 8/2003 |
| WO | WO 2003/068228 | 8/2003 |
| WO | WO 2003/072569 | 9/2003 |
| WO | WO 2004/014870 | 2/2004 |
| WO | WO 2005/023761 | 3/2004 |
| WO | WO 2004/113352 | 12/2004 |
| WO | WO 2005/005396 | 1/2005 |
| WO | WO 2005/018624 | 3/2005 |
| WO | WO 2005/044825 | 5/2005 |
| WO | WO 2006/015775 | 2/2006 |
| WO | WO 2006/043090 | 4/2006 |
| WO | WO 2007/004749 | 1/2007 |
| WO | WO 2007/053394 | 5/2007 |
| WO | WO 2010/038085 A2 | 4/2010 |
| WO | WO 2010/038086 A2 | 4/2010 |
| WO | WO 2010/067130 A1 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |
| WO | WO 2014/140582 A1 | 9/2014 |
| WO | WO 2014/162121 | 10/2014 |
| WO | WO 2014/162122 | 10/2014 |
| WO | WO 2014/162126 | 10/2014 |
| WO | WO 2015/092423 A1 | 6/2015 |
| WO | WO 2015/121444 A1 | 8/2015 |
| WO | WO 2015/121660 A1 | 8/2015 |
| WO | WO 2016/051186 A1 | 4/2016 |
| WO | WO 2016/051187 A1 | 4/2016 |
| WO | WO 2016/051188 A1 | 4/2016 |

OTHER PUBLICATIONS

CAS Registry No. 1379397-83-7, 2012 American Chemical Society.
CAS Registry No. 1379401-24-7, 2012 American Chemical Society.
CAS Registry No. 1379462-42-6, 2012 American Chemical Society.
CAS Registry No. 1379457-84-7, 2012 American Chemical Society.
CAS Registry No. 1379462-36-8, 2012 American Chemical Society.
CAS Registry No. 1384608-34-7, 2012 American Chemical Society.
CAS Registry No. 1384595-05-4, 2012 American Chemical Society.
CAS Registry No. 1384611-77-1, 2012 American Chemical Society.
CAS Registry No. 1384610-90-5, 2012 American Chemical Society.
Cirillo, et al. 2009 "Discovery and characterization of the N-phenyl-N'-naphthylurea class of p38 kinase inhibitors" *Bioorganic & Medicinal Chemistry* 19; 2386-2391.
Cogan, et al. 2008 "Structure-based design and subsequent optimization of 2-tolyl-(1,2,3-triazol-1-yl-4-carboxamide) inhibitors of p38 MAP kinase" *Bioorganic & Medicinal Chemistry* 18; 3251-3255.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Dietrich, et al. 2010 "The design, synthesis, and evaluation of 8 hybrid DFG-out allosteric kinase inhibitors: A structural analysis of

(56) References Cited

OTHER PUBLICATIONS the binding interactions of Gleevec ®, Nexavar®, and BIRB-796" *Bioorganic & Medicinal Chemistry* 18; 5738-5748.

Dodeller, et al. 2006 "The p38 mitogen-activated protein kinase signaling cascade in CD4 T cells" *Arthritis Research & Therapy* 8(2): 1-11.

Dumas; et al. 2004 "Recent developments in the discovery of protein kinase inhibitors from the urea class" *Current Opinion in Drug Discovery & Development* 7(5):600-616.

Goldberg, et al. 2007 "Discovery and optimization of p38 inhibitors via computer-assisted drug design" *J. Med. Chem.* 50: 4016-4026.

Hagan, S. et al. 2018 "Narrow Spectrum Kinase Inhibitors Demonstrate Promise for the Treatment of Dry Eye Disease and Other Ocular Inflammatory Disorders" *Invest Ophthalmol Vis Sci.* 59:1443-1453.

Jope, et al. 2007 "Glycogen synthase kinase-3 (GSK3): Inflammation, diseases, and therapeutics" *Neurochem Res* 32: 577-595.

Judge, et al. 2006 "Potassium channel blockers in multiple sclerosis: Neuronal Kv channels and effects of symptomatic treatment" *Pharmacology & Therapeutics* 111: 224-259.

Kim, et al. 2009 "Src family kinases as mediators of endothelial permeability: effects on inflammation and metastasis" *Cell Tissue Res* 335: 249-259.

Kuster 2012 "Kinase inhibitors, Methods and Protocols" *Methods in Molecular Biology* 795 Chapters 1 and 2 (in 46 pages).

Lima, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.

Liu, et al. 2011 "Src phosphorylation of endothelial cell surface intercellular adhesion molecule-1 mediates neutrophil adhesion and contributes to the mechanism of lung inflammation" *Arterioscler Thromb Vasc Biol* 31: 1342-1350.

Masuda, et al. 2008 "Syk inhibitors as treatment for allergic rhinitis" *Pulmonary Pharmacology & Therapeutics* 21: 461-467.

Menard, et al. 2009 "Novel potent BRAF inhibitors: Toward 1 nM compounds through optimization of the Central Phenyl Ring" *Journal of Medicinal Chemistry* 52; 3881-3891.

Montalban, et al. 2010 "KR-003048, a potent, orally active inhibitors of p38 mitogen-activated protein kinase" *European Journal of Pharmacology* 632; 93-102.

Montalban, et al. 2010 "Optimization of α-ketoamide based p38 inhibitors through modifications to the region that binds to the allosteric site" *Bioorganic & Medicinal Chemistry* 20; 4819-4824.

McDermott, et al. 2009 "Personalized cancer therapy with selective kinase inhibitors: An emerging paradigm in medical oncology" *Journal of Clinical Oncology* 27(33): 5650-5659.

Onions, et al. 2016 "The discovery of narrow spectrum kinase inhibitors: New therapeutic agents for the treatment of COPD and steroid-resistant asthma" *Journal of Medicinal Chemistry* 59: 1727-1746.

Pettus, et al. 2008 "Small molecule p38 MAP kinase inhibitors for the treatment of inflammatory diseases: Novel structures and developments during 2006-2008" *Current Topics in Medicinal Chemistry* 8(16):1452-1467.

Sawyers 2008 "The cancer biomarker problem" *Nature* 452: 548-552.

Singh, et al. 2007 "Spleen tyrosine kinase (Syk) biology, inhibitors and therapeutic applications" *Annual Reports in Medicinal Chemistry* 42: 379-391.

Singh, et al. 2010 "A randomized, placebo-controlled study of the effects of the p38 MAPK inhibitor SB-681323 on blood biomarkers of inflammation in COPD patients" *J Clin Pharmacol* 50: 94-100.

Sutherland, et al. 2004 "Management of chronic obstructive pulmonary disease" *The New England Journal of Medicine* 350: 2689-2697.

To, et al. 2015 "Potent anti-inflammatory effects of the narrow spectrum kinase inhibitor RV1088 on rheumatoid arthritis synovial membrane cells" *Britch Journal of Pharmacology* 172: 3805-3816.

Traore, T. et al. 2013 "New aminopyrimidine derivatives as inhibitors of the TAM family" *European Journal of Medicinal Chemistry* 70: 789-801.

Weinblatt, et al. 2010 "An oral spleen tyrosine kinase (Syk) inhibitor for rheumatoid arthritis" *The New England Journal of Medicine* 363(14): 1303-1312.

Yamamoto, et al. 2003 "The orally available spleen tyrosine kinase inhibitor 2-[7-(3,4-Dimethoxyphenyl)-imidazo[1,2-c]pyrimidin-5-ylamino]- nicotinamide dihydrochloride (BAY 61-3606) blocks antigen-induced airway inflammation in rodents" *The Journal of Pharmacology and Experimental Therapeutics* 306(3): 1174-1181.

Zambon, et al. 2010 "Novel hinge binder improves activity and pharmacokinetic properties of BRAF inhibitors" *Journal of Medicinal Chemistry* 53; 5639-5655.

U.S. Appl. No. 16/366,103, filed Mar. 27, 2019.

U.S. Appl. No. 15/480,689, filed Apr. 6, 2017, U.S. Pat. No. 10,072,034, Issued.

U.S. Appl. No. 16/508,253, filed Jul. 10, 2019, Pending.

* cited by examiner

KINASE INHIBITORS

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis or keratoconjunctivitis sicca (dry eye disease, also known as xerophthalmia)) and gastrointestinal tract (such as Crohn's disease and ulcerative colitis).

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body, are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance, Smith describes the inhibitory effect of p38 MAP kinase inhibitors on TNFα (but not IL-8) release from human PBMCs (Smith, S. J., Br. J. Pharmacol., 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. J., Br. J. Pharmacol., 2006, 149:393-404);
- biopsies from IBD patients (Docena, G. et al., J. Trans. Immunol., 2010, 162:108-115); and
- in vivo animal models (Underwood, D. C. et al., Am. J. Physiol., 2000, 279:L895-902; Nath, P. et al., Eur. J. Pharmacol., 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., J. Allergy Clin. Immunol., 2002, 109:649-657). Clinical investigations in inflammatory diseases with a range of p38 MAP kinase inhibitors, including AMG548, BIRB 796, VX702, SCIO0469 and SCIO0323, have been described (Lee, M. R. and Dominguez, C., Current Med. Chem., 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the antiinflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; American Thoracic Society Abstract A56) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. p38 has become an obvious target for investigation in IBD models as a consequence of its ubiquitous expression in inflammatory cells. Studies investigating the efficacy of p38 inhibitors in animal models of IBD and human biopsies from IBD patients indicated that p38 could be a target for the treatment of IBD (Hove, T. ten et al., Gut, 2002, 50:507-512, Docena, G. et al., J. Trans. Immunol. 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a p38 and Jnk inhibitor, in patients with severe Crohn's disease showed significant improvement in clinical score over 8 weeks (Hommes, D. et al. *Gastroenterology.* 2002 122:7-14).

T cells are known to play a key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNγ/IL-2) or Th2 (IL5/TGFβ) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Bechets patients (Chi W. et al. *Invest Ophthalmol Vis Sci.* 2008 49:3058-64). In support of these observations, Direskeneli and colleagues demonstrated that Bechets patients have increased Th17 cells and decreased Treg cells in their peripheral blood (Direskeneli H. et al. J Allergy Clin Immunol. 2011 128:665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989, 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994, 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation motifs (ITAM), it plays an important role in regulating T cell and B cell expansion as well as mediating immune-receptor signalling in inflammatory cells. Syk activation leads to IL-6 and MMP release-inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharski kinases") have been found to alter the frequency of micronucleus formation in vitro (Olaharski, A. J. et al., *PLoS Comput. Biol.,* 2009, 5(7), e1000446; doi: 10.1371/journal.pcbi.1000446). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharski kinases such as GSK3α by optimisation of the dose and/or by changing the route of administration of a molecule, it would be advantageous to identify further therapeutically useful molecules with low or negligible inhibition of Olaharski kinases, such as GSK 3α and/or have low or negligible disruption of mitotic processes (e.g. as measured in a mitosis assay).

Various compounds, including urea derivatives, are disclosed as inhibiting one or more kinases. Examples of such compounds may be found in WO 99/23091, WO 00/041698, WO 00/043384, WO 00/055139, WO 01/36403, WO 01/4115, WO 02/083628, WO 02/083642, WO 02/092576, WO 02/096876, WO 2003/005999, WO 2003/068223, WO 2003/068228, WO 2003/072569, WO 2004/014870, WO 2004/113352, WO 2005/005396, WO 2005/018624, WO 2005/023761, WO 2005/044825, WO 2006/015775, WO 2006/043090, WO 2007/004749, WO 2007/053394, WO 2013/050756, WO 2013/050757, WO 2014/027209, WO 2014/033446, WO 2014/033447, WO 2014/033448, WO 2014/033449, WO 2014/076484, WO 2014/140582 WO 2014/162121, WO 2014/162122, WO 2014/162126, WO 2015/092423, WO 2015/121444, WO 2015/121660 WO 2016/051187 and WO 2016/051188. Further examples may be found in articles published in:

*Curr. Opin. Drug Devel.* (2004, 7(5), 600-616);
*J. Med. Chem.* (2007, 50, 4016-4026; 2009, 52, 3881-3891; 2010, 53, 5639-5655; and 2016, 59, 1727-1746);
*Bioorg. Med. Chem. Lett.* (2007, 17, 354-357; 2008, 18, 3251-3255; 2009, 19, 2386-2391; and 2010, 20, 4819-4824);
*Curr. Top. Med. Chem.* (2008, 8, 1452-1467);
*Bioorg. Med. Chem.* (2010, 18, 5738-5748);
*Eur. J. Pharmacol.* (2010, 632, 93-102);
*J. Chem. Inf. Model.* (2011, 51, 115-129);
*Br. J. Pharmacol.* (2015, 172, 3805-3816); and
*Inflamm. Bowel Dis.* (2016, 22, 1306-1315).

Nevertheless, there remains a need to identify and develop new kinase inhibitors, specifically alternative p38 MAP kinase inhibitors that are suitable for the treatment of inflammation. There is particularly a need for such inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

We have now discovered, surprisingly, that certain aniline-substituted diarylureas inhibit one or more of p38 MAP kinase, Syk and Src family kinases and therefore possess good anti-inflammatory properties.

Thus, according to a first aspect of the invention, there is provided a compound of formula I, wherein:

T represents

W represents O, S or NCH$_3$;
V represents N or CR$^1$;
R$^1$ represents C$_{1-3}$ alkoxy, C$_{1-3}$ alkyl, C$_{2-3}$ alkenyl, C$_{2-3}$ alkynyl, which latter four groups are optionally substituted by one or more substituents selected from halo, hydroxy and C$_{1-2}$ alkoxy, or R$^1$ represents H;
R$^2$ represents —NR$^{A1}$S(O)$_2$R$^{B1}$, —S(O)$_{1-2}$R$^{B2}$, —P(O)R$^{B3}$R$^{B4}$, —C(O)NR$^{A2}$R$^{A3}$ or —CH$_2$NR$^{A4}$C(O)R$^{A5}$;
R$^{A1}$ to R$^{A5}$ independently represent H or C$_{1-3}$ alkyl optionally substituted by one or more substituents selected from halo, hydroxy, NR$^C$R$^D$ and C$_{1-2}$ alkoxy, or R$^{A2}$ and R$^{A3}$ together represent C$_{3-6}$ n-alkylene or C$_{4-5}$ n-alkylene interrupted between C2 and C3 by —O—, —S(O)$_q$— or —N(R$^E$)—;
R$^{B1}$ to R$^{B4}$ independently represent C$_{1-3}$ alkyl or C$_{3-6}$ cycloalkyl, which latter two groups are optionally substituted by one or more halo substituents;
R$^C$ and R$^D$ independently represent H or C$_{1-3}$ alkyl, which latter substituent is optionally substituted by hydroxyl or C$_{1-2}$ alkoxy, or R$^C$ and R$^D$ together combine to form C$_{4-6}$ alkylene optionally interrupted between C2 and C3 by —O—, —S(O)$_q$— or —N(R$^E$)—;
R$^E$ represents H or methyl;
q represents 0, 1 or 2;
R$^3$ represents C$_{2-7}$ alkyl, C$_{2-7}$ alkenyl, C$_{2-7}$ alkynyl or C$_{3-7}$ cycloalkyl, which latter four groups are optionally substituted by hydroxyl, C$_{1-2}$ alkoxy or halo, or R$^3$ represents morpholinyl or trimethylsilyl;
A represents CH or N;
R$^4$ represents C$_{1-3}$ alkoxy, C$_{3-5}$ cycloalkoxy, or C$_{1-3}$ alkyl, which latter three groups are optionally substituted by one or more halo substituents, or R$^4$ represents ethynyl, cyano, S(O)$_2$CH$_3$, halo or H;
Q represents O, S(O)$_p$, SO$_2$N(R$^6$) or C(O)N(R$^6$);
n represents 1, 2 or 3;
p represents 0, 1 or 2;
R$^{5a}$ and R$^{5b}$ independently represent H, methyl or halo, or R$^{5a}$ and R$^{5b}$ together represent C$_{2-6}$ n-alkylene;
  when n represents 1, Z represents O, S or NR$^7$ or,
  when n represents 2 or 3, Z represents either
    an O-atom on each occurrence, or
    either an S-atom or NR$^7$ on one occurrence and an O-atom on each other occurrence;
R$^6$ and R$^7$ independently represent H or methyl;

G represents —[(CH$_2$)$_r$-Het$^1$]$_{0-1}$—C(O)$_2$H or a carboxylic acid isostere;
r represents 0 or, when Het$^1$ is attached to (CH$_2$)$_r$ via a ring heteroatom, r may alternatively represent 1; and
Het$^1$ represents
  a 5- or 6-membered heterocyclic group that is fully aromatic, which group contains one or more heteroatoms selected from N, O and S or
  a 4- to 7-membered heterocyclic group that is fully saturated or partially unsaturated, and is monocyclic or is fused or bridged bicyclic, which group contains one or more heteroatoms selected from N, O and S,
  wherein Het$^1$ is optionally substituted by one or more substituents selected from C$_{1-3}$ alkyl, C$_{1-3}$ alkoxy, halo, hydroxyl and oxo,
or a pharmaceutically acceptable salt thereof,
which compounds may be referred to hereinafter as "the compounds of the invention".

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

For the avoidance of doubt, oxo substituents that may be present on heterocyclic groups represented by Het$^1$ may be attached to any appropriate atoms in the heterocyclic ring including, where valencies allow, to C-, N- and/or S-atoms within the ring (thereby forming keto, N-oxide, S(O) and/or S(O)$_2$ groups).

Het$^1$ groups that may be mentioned include the following, where the positions of attachment specified are to the C(R$^{5a}$)(R$^{5b}$) and —CO$_2$H groups of the compound of formula I: furanyl (e.g. furanyl attached at the 2 and 4 or, particularly, 2 and 5 positions), oxadiazolyl (e.g. oxadiazolyl, such as 1,2,4-oxadiazolyl, attached at the 3 and 5 positions), pyrazolyl (e.g. pyrazolyl, such as pyrazolyl or 3-methylpyrazolyl, attached at the 1 and 4 positions), pyridazinyl (e.g. pyridazinyl attached at the 3 and 6 positions), pyrrolyl (e.g. pyrrolyl, such as 1-methylpyrrolyl, attached at the 2 and 5 positions), tetrahydrofuranyl (e.g. tetrahydrofuranyl attached at the 2 and 4 or, particularly, 2 and 5 positions) and thienyl (e.g. thienyl attached at the 2 and 4 or 2 and 5 positions).

Unless otherwise specified, the term "halo" includes references to fluoro, chloro, bromo or iodo, in particular to fluoro, chloro or bromo, especially fluoro or chloro.

When used herein in connection with the group G, the term "carboxylic acid isostere" includes references to carboxylic acid isosteres known to those skilled in the art, such as those disclosed in Lassalas et al., *J. Med. Chem.* (2016), 59, 3183-3203, Ballatore et al., *Chem. Med. Chem.* (2013), 8(3), 385-395 and Boyd et al., *Bioorg. Med. Chem. Lett.* (2015), 25, 1990-1994, the disclosures of which documents are hereby incorporated by reference.

Thus, carboxylic acid isosteres that G may represent include:
(a) a phosphonic or phosphinic acid moiety, or a salt thereof, such as —P(O)(OH)$_2$ or —P(O)(H)(OH);
(b) a sulfonic or sulfinic acid moiety, or a salt thereof, such as —S(O)$_2$(OH) or —S(O)(OH);
(c) a hydroxamic acid, or a salt thereof, such as —C(O)N(H)OH or —N(C(O)CH$_3$)OH;
(d) a hydroxamic acid ester, such as —C(O)N(H)OCH$_3$ or —O—N(H)—C(O)CH$_3$;
(e) a sulfonamide, such as —S(O)$_2$NH$_2$ or —N(H)—S(O)$_2$CH$_3$;
(f) an acylsulfonamide, such as —C(O)N(H)—S(O)$_2$CH$_3$, or an acylsulfamide, such as —C(O)N(H)—S(O)$_2$N(CH$_3$)$_2$ or —C(O)N(H)—S(O)$_2$NH$_2$;
(g) an acylurea, such as —N(H)C(O)N(H)—C(O)CH$_3$;
(h) a sulfonylurea, such as —N(H)C(O)N(H)—S(O)$_2$CH$_3$;
(i) an electron-poor phenol moiety, such as a 2,6-difluorophenol (e.g. attached to the rest of the molecule via the 3- or 4-position on the phenyl ring);
(j) —S(O)$_{0-2}$-phenol (e.g. where the phenol moiety is attached to the S-atom via the 2-position of the phenyl ring);
(k) —C(H)(OH)CF$_3$ or —C(O)CF$_3$ (or a hydrated form thereof, —C(OH)$_2$CF$_3$);
(l) a 3- or 4-hydroxyquinoline-2-one;
(m) a tetrazole;
(n) a hydroxy-, thio- or oxo-substituted, 4- or 5-membered heterocycle that is fully aromatic, partially unsaturated or fully saturated, which group contains one or more heteroatoms selected from N, O and S, for example a hydroxy- or oxo-substituted heterocyclic group selected from a thiazolidinedione, an oxazolidinedione, a thiazolidinone, an oxazolidinone, a thiadiazolinone, an oxadiazole-5(4H)-thione, an oxathiadiazole-2-oxide, or a hydroxy-substituted isoxazole, isothiazole or oxadiazole; or (o) a carbocyclic acid, such as tetronic acid, tetramic acid, a cyclopentane-1,3-dione, a cyclopentane-1,2-dione, and squaric acid, which latter group is optionally attached to the rest of the molecule via a —N(H)— moiety.

For example, the carboxylic acid isostere may be any of the moieties mentioned at (a) to (l) above or a cyclic moiety selected from:

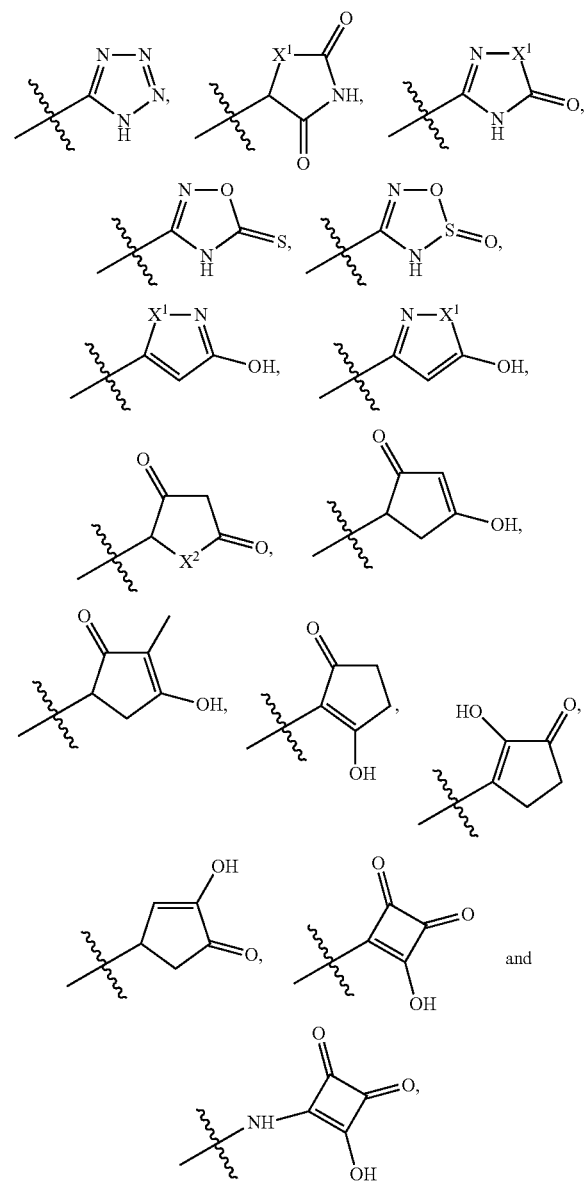

or a tautomer thereof, wherein X$^1$ represents O or S and X$^2$ represents O or NH.

Particular carboxylic acid isosteres that may be mentioned include tetrazolyl, acylsulfonamides, such as —C(O)N(H)—S(O)$_2$CH$_3$, acylsulfamides, such as —C(O)N(H)—S(O)$_2$N(CH$_3$)$_2$, a hydroxy-substituted isoxazole, such as:

or a tautomer thereof, such as or a 5-hydroxy-substituted 1,2,4-oxadiazole, such as:

or a tautomer thereof, such as

Embodiments of the invention that may be mentioned include those in which:
(a) T represents (b) $R^4$ represents $C_{1-3}$ alkoxy or $C_{1-3}$ alkyl, which latter two groups are optionally substituted by one or more halo substituents, or $R^4$ represents ethynyl, cyano, $S(O)_2CH_3$, halo or H;
(c) $R^{5a}$ and $R^{5b}$ independently represent H, methyl or halo;
(d) Z represents an O-atom on each occurrence; and
(e) G represents —$C(O)_2H$.

In such embodiments, the compound of formula I may be represented as a compound of formula Ix, Ix in which:
$R^1$ to $R^3$, A and Q are as defined above;
$R^4$ represents $C_{1-3}$ alkoxy or $C_{1-3}$ alkyl, which latter two groups are optionally substituted by one or more halo substituents, or $R^4$ represents ethynyl, cyano, $S(O)_2CH_3$, halo or H; and
$R^{5a}$ and $R^{5b}$ independently represent H, methyl or halo.

Other embodiments of the invention that may be mentioned include those in which one or more of the following definitions apply to the compounds of formula I:
(a1) T represents (b1) $R^4$ represents $C_{3-5}$ cycloalkoxy optionally substituted by one or more halo substituents;
(c1) $R^{5a}$ and $R^{5b}$ together represent $C_{2-6}$ n-alkylene;
(d1) when n represents 2 or 3, Z represents either an S-atom or $NR^7$ on one occurrence and an O-atom on each other occurrence;
(e1) G represents —$[(CH_2)_r$-Het$^1]$-$C(O)_2H$ or a carboxylic acid isostere.

In particular, embodiments of the invention that may be mentioned include those in which any one or, any two of, any three of, any four of or all of (a1) to (e1) above apply.

Embodiments of the invention that may be mentioned include those in which one or more of the following definitions apply to the compounds of formula I or Ix:
(a) W represents O;
(b) V represents N;
(c) $R^1$ represents deuterated $C_{1-2}$ alkoxy (e.g. $OCD_3$) or, particularly, $C_{1-2}$ alkoxy or H;
(d) $R^2$ represents —$P(O)R^{B3}R^{B4}$, —$S(O)_2R^{B2}$ or, particularly, —$NR^{A1}S(O)_2R^{B1}$ (e.g. —$NHS(O)_2R^{B1}$), —$S(O)R^{B2}$ or —$C(O)NHR^{A2}$;
(e) $R^{A1}$ to $R^{A5}$ independently represent H or methyl optionally substituted by one or more halo substituents;
(f) $R^{B1}$ to $R^{B4}$ independently represent $C_{1-2}$ alkyl optionally substituted by one or more halo substituents;
(g) $R^3$ represents $C_{3-5}$ alkyl, $C_{3-6}$ alkynyl or trimethylsilyl;
(h) A represents N or, particularly, CH;
(i) $R^4$ represents $C_{3-4}$ cycloalkoxy or, particularly, ethynyl, cyano, halo, $C_{1-2}$ alkoxy or $C_{1-2}$ alkyl, which latter two groups are optionally substituted by one or more halo substituents;
(j) Q represents represents S, $SO_2N(R^6)$ or, particularly, $C(O)NH$, $S(O)$, $S(O)_2$ or O;

(k) n represents 1 or, particularly, 2 or 3;
(l) p represents 0 or, particularly, 1 or 2;
(m) $R^{5a}$ and $R^{5b}$ together represent —$(CH_2)_{2-4}$— or, particularly, $R^{5a}$ and $R^{5b}$ independently represent H or methyl;
(n) Z represents an O atom (on each occurrence) or, when n represents 2 or 3, Z may alternatively represents either an S-atom on one occurrence and an O-atom on each other occurrence (e.g. on each occurrence, Z represents an O atom);
(o) G represents a carboxylic acid isostere (e.g. as defined above), —$(CH_2)$—$Het^1$-$C(O)_2H$, -$Het^1$-$C(O)_2H$ or, particularly, —$C(O)_2H$;
(p) $Het^1$ represents
  a 5- or 6-membered heterocyclic group that is fully aromatic, which group contains one to three heteroatoms selected from N, O and S (e.g. $Het^1$ represents furanyl, oxadiazolyl (such as 1,2,4-oxadiazolyl), pyrazolyl, pyridazinyl, pyrrolyl or thienyl) or
  a 5- or 6-membered heterocyclic group that is fully saturated or partially unsaturated, and is monocyclic or is fused or bridged bicyclic, which group contains one or two heteroatoms selected from N, O and S (e.g. $Het^1$ represents tetrahydrofuranyl),
wherein $Het^1$ is optionally substituted by one or more substituents selected from $C_{1-2}$ alkyl, hydroxyl and oxo (e.g. wherein $Het^1$ is optionally substituted by one or more methyl groups).

Embodiments of the invention that may be mentioned include those in which the compound of formula I or Ix is a compound of formula Ia, (h) $R^{5a}$ and $R^{5b}$ together represent —$(CH_2)_2$— or, particularly, $R^{5a}$ and $R^{5b}$ independently represent H or methyl (e.g. $R^{5a}$ represents H and $R^{5b}$ represents methyl, $R^{5a}$ and $R^{5b}$ both represent methyl or, particularly, $R^{5a}$ and $R^{5b}$ both represent H);
(i) G represents —$CO_2H$ or -$Het^1$-$CO_2H$, wherein the -$Het^1$-$CO_2H$ moiety is a structural fragment selected from

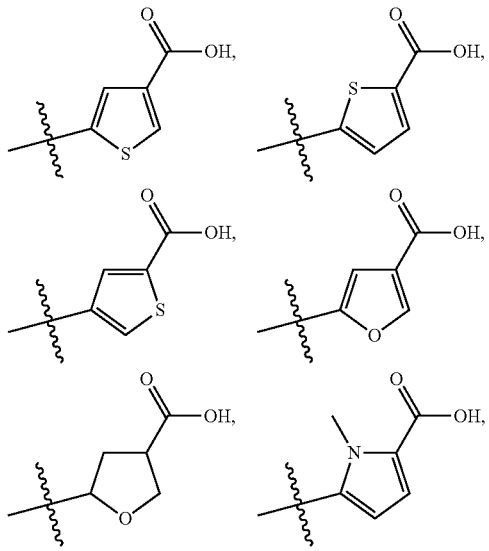

Ia

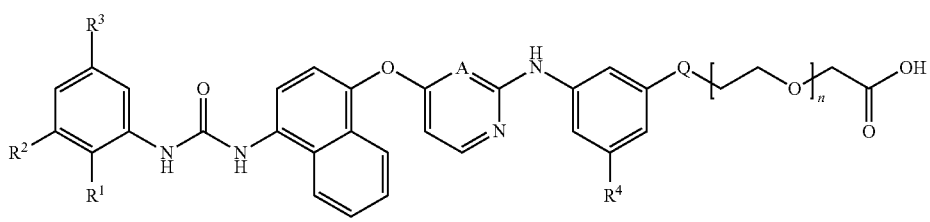

wherein $R^1$ to $R^4$, A, Q and n are as hereinbefore defined.
Embodiments of the invention that may be mentioned include those in which one or more of the following definitions apply to the compounds of formula I, Ix and Ia:
(a) $R^1$ represents deuterated methoxy (e.g. $OCD_3$) or, particularly, methoxy;
(b) $R^2$ represents —$C(O)NH_2$, —$C(O)NHCH_3$, —$S(O)_{1-2}CH_3$, —$S(O)_{1-2}CH_2CH_3$, —$P(O)(CH_3)_2$, —$N(CH_3)S(O)_2CH_3$, —$NHS(O)_2CH_2CH_3$ or —$NHS(O)_2CH_3$ (e.g. —$C(O)NH_2$, —$C(O)NHCH_3$, —$S(O)CH_3$ or, particularly, —$NHS(O)_2CH_3$);
(c) $R^3$ represents trimethylsilyl or, particularly, —$C(CH_3)_2$—R, wherein R represents ethynyl or, particularly, methyl (e.g. $R^3$ represents tert-butyl);
(d) A represents N or, particularly, CH;
(e) $R^4$ represents cyclopropoxy or methoxy, which latter group is optionally substituted by one or more halo substituents (e.g. methoxy optionally substituted by one or more (e.g. two or three) fluoro substituents), or, particularly, $R^4$ represents methoxy;
(f) Q represents S or, particularly, C(O)NH, S(O), S(O)$_2$ or O;
(g) n represents 3 or, particularly, 2;

-continued

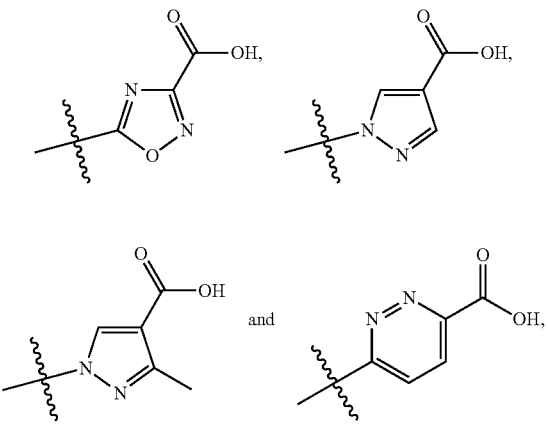

or G represents a carboxylic acid isostere selected from tetrazolyl, —$C(O)N(H)$—$S(O)_2CH_3$, —$C(O)N(H)$—$S(O)_2N(CH_3)_2$,

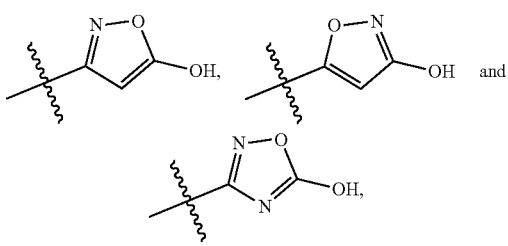

or a tautomer of any of the latter three groups.

Further embodiments of the invention that may be mentioned include those in which the compound of formula I, Ix or Ia is a compound of formula b,

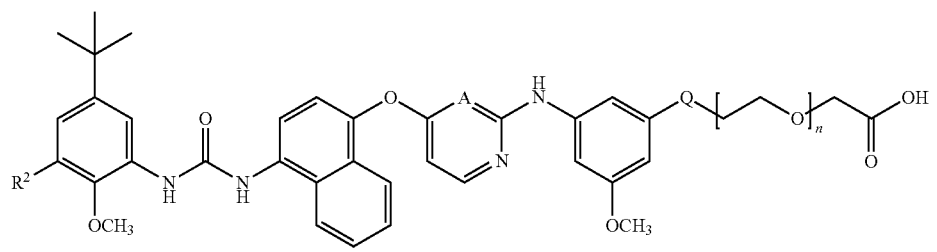

wherein R², A, Q and n are as hereinbefore defined.

Embodiments of the invention that may be mentioned include those in which one or more of the following definitions apply to the compounds of formula I, Ix, Ia and Ib:
(a) R² represents —NHS(O)₂CH₃;
(d) A represents CH;
(e) Q represents C(O)NH, S(O), S(O)₂ or, particularly, O;
(g) n represents 2.

In this respect, particular embodiments of the invention that may be mentioned include those in which the compound of formula I is a compound of formula Iy,

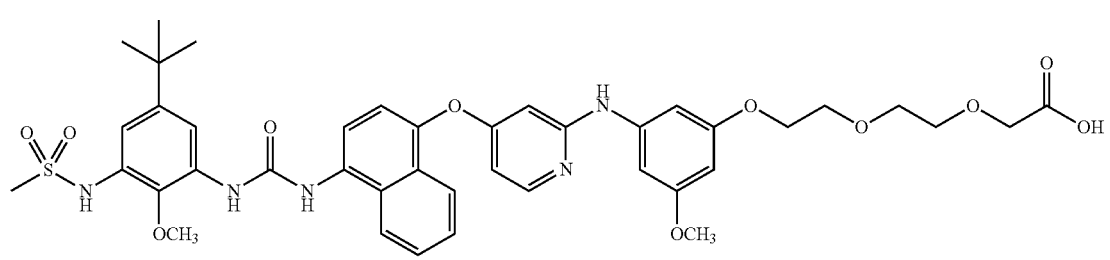

or a pharmaceutically acceptable salt thereof.

Other compounds of formula I, Ix, Iy, Ia or Ib that may be mentioned include the compounds of the examples described hereinafter. Thus, embodiments of the invention that may be mentioned include those in which the compound of formula I, Ia or Ib is a compound selected from the list:

2-(2-(2-(3-((4-((4-(3-(5-(tert-butyl)-2-methoxy-3-(methylsulfonamido)phenyl) ureido)-naphthalen-1-yl)oxy)pyridin-2-yl)amino)-5-methoxybenzamido)ethoxy)ethoxy)acetic acid;

2-(2-(2-(3-((4-((4-(3-(5-(tert-butyl)-2-methoxy-3-(methylsulfonamido)phenyl)ureido)-naphthalen-1-yl)oxy)pyrimidin-2-yl)amino)-5-methoxyphenoxy)ethoxy)ethoxy)acetic acid;

2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid;

2-(2-(2-((3-((4-((4-(3-(5-(tert-butyl)-2-methoxy-3-(methylsulfonamido)phenyl)ureido)-naphthalen-1-yl)oxy)pyridin-2-yl)amino)-5-methoxyphenyl)sulfonyl)ethoxy)ethoxy)acetic acid;

2-(2-(2-((3-((4-((4-(3-(5-(tert-butyl)-2-methoxy-3-(methylsulfonamido)phenyl)ureido)-naphthalen-1-yl)oxy)pyridin-2-yl)amino)-5-methoxyphenyl)sulfinyl)ethoxy)ethoxy)acetic acid;

2-(2-(2-((3-((4-((4-(3-(5-(tert-butyl)-2-methoxy-3-(methylsulfonyl)phenyl)ureido)naphthalen-1-yl)oxy)pyridin-2-yl)amino)-5-methoxyphenyl)sulfonyl)ethoxy)ethoxy)acetic acid;

2-(2-(2-((3-((4-((4-(3-(5-(tert-butyl)-2-methoxy-3-(methylsulfinyl)phenyl)ureido)naphthalen-1-yl)oxy)pyridin-2-yl)amino)-5-methoxyphenyl)sulfonyl)ethoxy)ethoxy)acetic acid;

2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-(trifluoromethyl)phenoxy)ethoxy)ethoxy) acetic acid;

6-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)pyridazine-3-carboxylic acid;

5-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)-1,2,4-oxadiazole-3-carboxylic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-cyclopropoxyphenoxy)ethoxy)ethoxy) acetic acid;

1-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)cyclopropane-1-carboxylic acid;

4-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)thiophene-2-carboxylic acid;

1-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)-3-methyl-1H-pyrazole-4-carboxylic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-ethylphenoxy)ethoxy)ethoxy)acetic acid;

2-(2-(2-(3-((4-((4-(3-(5-(tert-butyl)-2-(methoxy-d3)-3-(methylsulfonamido)phenyl)ureido)-naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)-N-(methylsulfonyl)acetamide;

2-(2-(2-(3-((4-((4-(3-(5-(tert-butyl)-2-methoxy-3-(methylcarbamoyl)phenyl)ureido)naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)-2-methoxy-3-(methyl-sulfinyl)phenyl)ureido)naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)-2-methoxy-3-(methyl-sulfonyl)phenyl)ureido)naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)-3-(dimethylphosphoryl)-2-methoxyphenyl)ureido)-naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)-2-methoxy-3-(N-methylmethylsulfonamido)phenyl)ureido)-naphthalen-1-yl)oxy)pyridin-2-yl)amino)-5-methoxyphenoxy)ethoxy)ethoxy)acetic acid;

5-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)furan-3-carboxylic acid;

5-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)tetrahydrofuran-3-carboxylic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)propanoic acid;

2-(2-(2-(3-((4-((4-(3-(5-(tert-butyl)-3-(ethylsulfonyl)-2-methoxyphenyl)ureido)naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)-3-(ethylsulfonamido)-2-methoxyphenyl)ureido)naphthalen-1-yl)oxy)pyridin-2-yl)amino)-5-methoxyphenoxy)ethoxy)ethoxy)acetic acid;

2-(2-(2-(3-((4-((4-(3-(5-(tert-butyl)isoxazol-3-yl)ureido)naphthalen-1-yl)oxy)pyridin-2-yl)amino)-5-methoxyphenoxy)ethoxy)ethoxy)acetic acid;

N-(5-(tert-butyl)-2-methoxy-3-(3-(4-((2-((3-methoxy-5-(2-(2-((5-oxo-2,5-dihydroisoxazol-3-yl)methoxy)ethoxy)ethoxy)phenyl)amino)pyridin-4-yl)oxy)naphthalen-1-yl)ureido)phenyl)-methanesulfonamide;

2-((2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethyl)thio)acetic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)propanoic acid, (R)-isomer;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)propanoic acid, (S)-isomer;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)-2-methylpropanoic acid;

1-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethyl)-1H-pyrazole-4-carboxylic acid;

N-(3-(3-(4-((2-((3-(2-(2-((1H-tetrazol-5-yl)methoxy)ethoxy)ethoxy)-5-methoxyphenyl)amino)-pyridin-4-yl)oxy)naphthalen-1-yl)ureido)-5-(tert-butyl)-2-methoxyphenyl)methanesulfonamide;

2-(2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)acetic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-methoxyphenoxy)ethoxy)ethoxy)-N—(N,N-dimethylsulfamoyl)acetamide;

5-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)thiophene-2-carboxylic acid;

5-((2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)methyl)thiophene-3-carboxylic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-(difluoromethoxy)phenoxy)ethoxy)ethoxy)acetic acid;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-ethynylphenoxy)ethoxy)ethoxy)acetic acid;

N-(5-(tert-butyl)-2-methoxy-3-(3-(4-((2-((3-methoxy-5-(2-(2-((5-oxo-4,5-dihydro-1,2,4-oxadiazol-3-yl)methoxy)ethoxy)ethoxy)phenyl)amino)pyridin-4-yl)oxy)naphthalen-1-yl)ureido)phenyl)methanesulfonamide;

2-(2-(2-(3-((4-((4-(3-(5-(tert-butyl)-2-methoxy-3-(methyl-sulfonamido)phenyl)ureido)-naphthalen-1-yl)oxy)pyridin-2-yl)amino)-5-(trifluoromethoxy)phenoxy)ethoxy)ethoxy)acetic acid;

N-(5-(tert-butyl)-2-methoxy-3-(3-(4-((2-((3-methoxy-5-(2-(2-((3-oxo-2,3-dihydroisoxazol-5-yl)methoxy)ethoxy)ethoxy)phenyl)amino)pyridin-4-yl)oxy)naphthalen-1-yl)ureido)phenyl)-methanesulfonamide; and 5-((2-(3-((4-((4-(3-(5-(tert-butyl)-2-methoxy-3-(methylsulfonamido)phenyl)ureido)naphthalen-1-yl)oxy)pyridin-2- yl)amino)-5-methoxyphenoxy)ethoxy)methyl)-1-methyl-1H-pyrrole-2-carboxylic acid,
or a pharmaceutically acceptable salt thereof.

Embodiments of the invention that may be mentioned include those in which the compound of formula I, Ix, Ia or Ib is as hereinbefore defined, either
(a) is, or
(b) is not
2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid, or a pharmaceutically acceptable salt thereof.

Examples of salts of compounds of formula I, Ix, Iy, Ia or Ib include all pharmaceutically acceptable salts, such as, without limitation, acid addition salts of strong mineral acids such as HCl, $H_2SO_4$ and HBr salts (e.g. HCl or HBr salts) and addition salts of strong organic acids such as methanesulfonic acid.

Particular salts of compounds of formula I, Ix, Iy, Ia or Ib that may be mentioned include hydrochloric acid salts, meglumine salts, potassium salts and sodium salts.

References herein to a compound of the invention (a compound of formula I, Ix, Iy, Ia or Ib) are intended to include references to the compound and to all pharmaceutically acceptable salts, solvates, isotopic derivatives and/or tautomers of said compound, unless the context specifically indicates otherwise. In this respect, solvates that may be mentioned include hydrates.

The compounds of the invention (compounds of formula I, Ix, Iy, Ia or Ib) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising a compound of formula I, Ix, Iy, Ia or Ib, as hereinbefore defined, or pharmaceutically acceptable salt thereof, in admixture with a pharmaceutically acceptable adjuvant, diluent or carrier.

(b) A combination product comprising
  (A) a compound of formula I, Ix, Iy, Ia or Ib, as hereinbefore defined, or pharmaceutically acceptable salt thereof, and
  (B) another therapeutic agent,
  wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ix, Iy, Ia or Ib, as hereinbefore defined, or pharmaceutically acceptable salt thereof, and another therapeutic agent, in admixture with a pharmaceutically acceptable adjuvant, diluent or carrier (which formulation is hereinafter referred to as a "combined preparation").

It also encompasses a kit of parts comprising components:
  (i) a pharmaceutical formulation including a compound of formula I, Ix, Iy, Ia or Ib, as hereinbefore defined, or pharmaceutically acceptable salt thereof, in admixture with a pharmaceutically acceptable adjuvant, diluent or carrier; and
  (ii) a pharmaceutical formulation including another therapeutic agent, in admixture with a pharmaceutically-acceptable adjuvant, diluent or carrier,
  which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, said process comprising the step of admixing the compound of formula I, Ix, Iy, Ia or Ib, as hereinbefore defined, or pharmaceutically acceptable salt thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ix, Iy, Ia or Ib, as hereinbefore defined, or pharmaceutically acceptable salt thereof, for use in medicine (or for use as a medicament or as a pharmaceutical).

(e) A compound of formula I, Ix, Iy, Ia or Ib, as hereinbefore defined, or pharmaceutically acceptable salt thereof, or a pharmaceutical formulation or combination product as defined in connection with aspect (a) or (b) of the invention, for use in the treatment or prevention of an inflammatory disease.

(f) The use of
  a compound of formula I, Ix, Iy, Ia or Ib, as hereinbefore defined, or pharmaceutically acceptable salt thereof, or
  a pharmaceutical formulation or combination product as defined in connection with aspect (a) or (b) of the invention,
  for the preparation of a medicament for the treatment or prevention of an inflammatory disease.

(g) A method of treating or preventing an inflammatory disease, said method comprising administering to a subject an effective amount of
  a compound of formula I, Ix, Iy, Ia or Ib, as hereinbefore defined, or pharmaceutically acceptable salt thereof, or
  a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
  a compound of formula I, Ix, Iy, Ia or Ib, as hereinbefore defined, or pharmaceutically acceptable salt thereof, or
  a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

References herein to "preventing an inflammatory disease" include references to preventing (or reducing the likelihood of) the recurrence of an inflammatory disease in a subject who has previously suffered from such a disease (e.g. a subject who has previously received treatment for that disease, for example treatment according to the method described in (g) above).

Thus, still further aspects of the invention that may be mentioned include the following.

(i) A compound of formula I, Ix, Iy, Ia or Ib, as hereinbefore defined, or pharmaceutically acceptable salt thereof, or a pharmaceutical formulation or combination product as defined in connection with aspect (a) or (b) of the invention, for use in reducing the likelihood of the recurrence of an inflammatory disease in a subject who has previously received treatment for that disease (e.g. treatment with a compound of formula I, Ia or Ib, as hereinbefore defined, or pharmaceutically acceptable salt thereof, or a pharmaceutical formulation or combination product as defined in connection with aspect (a) or (b) of the invention).

(j) The use of
- a compound of formula I, Ix, Iy, Ia or Ib, as hereinbefore defined, or pharmaceutically acceptable salt thereof, or
- a pharmaceutical formulation or combination product as defined in connection with aspect (a) or (b) of the invention,
- for the preparation of a medicament for reducing the likelihood of the recurrence of an inflammatory disease in a subject who has previously received treatment for that disease (e.g. treatment with a compound of formula I, Ix, Iy, Ia or Ib, as hereinbefore defined, or pharmaceutically acceptable salt thereof, or a pharmaceutical formulation or combination product as defined in connection with aspect (a) or (b) of the invention).

(k) A method of reducing the likelihood of the recurrence of an inflammatory disease in a subject who has previously received treatment for that disease (e.g. treatment with a compound of formula I, Ix, Iy, Ia or Ib, as hereinbefore defined, or pharmaceutically acceptable salt thereof, or a pharmaceutical formulation or combination product as defined in connection with aspect (a) or (b) of the invention), said method comprising administering to said subject an effective amount of
- a compound of formula I, Ix, Iy, Ia or Ib, as hereinbefore defined, or pharmaceutically acceptable salt thereof, or
- a pharmaceutical formulation or combination product as defined in connection with aspect (a) or (b) of the invention.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration, typical excipients include sugars, calcium stearate, magnesium stearate, pregelatinised starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoroethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of large particle size e.g. an MMAD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac® 70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filled into a multi dose device such as DISKUS.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides, e.g. Suppocire. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars, such as dextrose, fructose, galactose, and/or simply polyols, such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will present in the range of 2 to 5% w/w (e.g. 2 to 4% w/w). Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7, or a target pH of 6.5 to 7.6.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyoxyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers, polycarbophil and Pemulen(R), specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family, vinyl polymers and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate; a further example is ciclesonide);
  beta agonists, particularly beta2 agonists (e.g. terbutaline, salbutamol, salmeterol, formoterol; further examples are vilanterol, olodaterol, reproterol and fenoterol); and
  xanthines (e.g. theophylline).

For example, for the treatment of respiratory disorders (such as COPD or asthma), the other therapeutic agent is one or more agents selected from the list comprising:
  muscarinic antagonists (e.g. tiotropium, umeclidinium, glycopyrronium, aclidinium and daratropium, any of these for example as the bromide salt); and
  phosphodiesterase inhibitors.

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or balsalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g. infliximab, adalimumab, certolizumab pegol or golimumab);
  anti-IL12/IL23 antibodies (e.g. ustekinumab) or small molecule IL12/IL23 inhibitors (e.g. apilimod);
  anti-α4β7 antibodies (e.g. vedolizumab);
  toll-like receptor (TLR) blockers (e.g. BL-7040; Avecia (Cambridge, UK));
  MAdCAM-1 blockers (e.g. PF-00547659);
  antibodies against the cell adhesion molecule α4-integrin (e.g. natalizumab);
  antibodies against the IL2 receptor a subunit (e.g. daclizumab or basiliximab);
  anti-Smad7 antibodies (e.g. mongersen (GED0301; all-P-ambo-2'-deoxy-P-thioguanylyl-(3'→5')-P-thiothymidylyl-(3'→5')-2'-deoxy-5-methyl-P-thiocytidylyl-(3'→5')-2'-deoxy-P-thioguanylyl-(3'→5')-2'-deoxy-P-thiocytidylyl-(3'→5')-2'-deoxy-P-thiocytidylyl-(3'→5')-2'-deoxy-P-thiocytidylyl-(3'→5')-2'-deoxy-P-thiocytidylyl-(3'→5')-P-thiothymidylyl-(3'→5')-P-thiothymidylyl-(3'→5')-2'-deoxy-Pthiocytidylyl-(3'→5')-P-thiothymidylyl-(3'→5')-2'-deoxy-P-thiocytidylyl-(3'→5')-2'-deoxy-P-thiocytidylyl-(3'→5')-2'-deoxy-P-thiocytidylyl-(3'→5')-2'-deoxy-5-methyl-P-thiocytidylyl-(3'→5')-2'-deoxy-P-thioguanylyl-(3'→5')-2'-deoxy-P-thiocytidylyl-(3'→5')-2'-deoxy-P-thioadenylyl-(3'→5')-2'-deoxy-P-thioguanylyl-(3'→5')-2'-deoxycytidine));

sphingosine 1-phosphate receptor 1 (S1P1) modulators (e.g. ozanimod ((S)-5-(3-(1-((2-hydroxyethyl)amino)-2,3-dihydro-1H-inden-4-yl)-1,2,4-oxadiazol-5-yl)-2-isopropoxybenzonitrile), amiselimod (MT1303; 2-amino-2-{2-[4-(heptyloxy)-3-(trifluoromethyl)phenyl]ethyl}propane-1,3-diol) or APD334 (2-[7-[4-cyclopentyl-3-(trifluoromethyl)benzyloxy]-1,2,3,4-tetrahydrocyclopenta[b]indol-3(R)-yl]acetic acid));

JAK inhibitors (e.g. tofacitinib, baricitinib (1-(ethylsulfonyl)-3-[4-(7H-pyrrolo[2,3-d]pyrimidin-4-yl)-1H-pyrazol-1-yl]-3-azetidineacetonitrile), filgotinib (N-[5-[4-[(1,1-dioxo-1,4-thiazinan-4-yl)methyl]phenyl]-[1,2,4]triazolo[1,5-a]pyridin-2-yl]cyclopropanecarboxamide), peficitinib (4-(((1R,2r,3S,5s,7s)-5-hydroxyadamantan-2-yl)amino)-1H-pyrrolo[2,3-b]pyridine-5-carboxamide), upadacitinib ((3S,4R)-3-ethyl-4-(3H-imidazo[1,2-a]pyrrolo[2,3-e]pyrazin-8-yl)-N-(2,2,2-trifluoroethyl)pyrrolidine-1-carboxamide), TD-1473 or R348 (see, for example, US 2014/0206708));

STAT3 inhibitors (e.g. TAK-114; (3E)-1-methyl-3-(2-oxo-1H-indol-3-ylidene)indol-2-one);

receptor-interacting protein-1 (RIP1) kinase inhibitors (e.g. GSK2982772);

Syk inhibitors and prodrugs thereof (e.g. fostamatinib and R-406);

Phosphodiesterase-4 inhibitors (e.g. tetomilast);

HMPL-004;

probiotics;

microbiome modulators (e.g. SGM1019);

Dersalazine;

semapimod/CPSI-2364; and protein kinase C inhibitors (e.g. AEB-071)

(e.g. for the treatment of gastrointestinal disorders (such as Crohn's disease or ulcerative colitis), the other therapeutic agent may be, for example, one or more agents selected from the list comprising:

5-aminosalicylic acid, or a prodrug thereof (such as sulfasalazine, olsalazine or balsalazide);

corticosteroids (e.g. prednisolone, methylprednisolone, or budesonide);

immunosuppressants (e.g. cyclosporin, tacrolimus, methotrexate, azathioprine or 6-mercaptopurine);

anti-TNFα antibodies (e.g. infliximab, adalimumab, certolizumab pegol or golimumab);

anti-IL12/IL23 antibodies (e.g. ustekinumab) or small molecule IL12/IL23 inhibitors (e.g. apilimod);

anti-α4β7 antibodies (e.g. vedolizumab);

MAdCAM-1 blockers (e.g. PF-00547659);

antibodies against the cell adhesion molecule α4-integrin (e.g. natalizumab);

antibodies against the IL2 receptor α subunit (e.g. daclizumab or basiliximab);

JAK3 inhibitors (e.g. tofacitinib or R348);

Syk inhibitors and prodrugs thereof (e.g. fostamatinib and R-406);

Phosphodiesterase-4 inhibitors (e.g. tetomilast);

HMPL-004;

probiotics;

Dersalazine;

semapimod/CPSI-2364; and protein kinase C inhibitors (e.g. AEB-071)).

For the treatment of eye disorders (such as uveitis and keratoconjunctivitis sicca (dry eye)), the other therapeutic agent may be, for example, one or more agents selected from the list comprising:

corticosteroids (e.g. dexamethasone, prednisolone, triamcinolone acetonide, difluprednate or fluocinolone acetonide);

glucocorticoid agonists (e.g. mapracorat);

immunosuppressants (e.g. cyclosporin, voclosporin, azathioprine, methotrexate, mycophenolate mofetil or tacrolimus);

anti-TNFα antibodies (e.g. infliximab, adalimumab, certolizumab pegol, ESBA-105 or golimumab);

anti-IL-17A antibodies (e.g. secukinumab);

mTOR inhibitors (e.g. sirolimus);

VGX-1027;

adenosine A3 receptor agonists (e.g. CF-101);

lifitegrast;

IL1 blockers (e.g. EBI-005; Hou et al. *PNAS* 2013, 110(10), 3913-3918);

RGN-259 (Thymosin β4);

SI-614;

OTX-101;

JNK inhibitors (e.g. XG-104);

MAP kinase signalling inhibitors (e.g. DA-6034; {[2-(3,4-dimethoxyphenyl)-5-methoxy-4-oxochromen-7-yl]oxy}acetic acid);

mucin stimulators (e.g. rebamipide; 2-[(4-chlorobenzoyl)amino]-3-(2-oxo-1H-quinolin-4-yl)propanoic acid);

MIM-D3 (Tavilermide; see, for example, US 2013/0345395);

JAK inhibitors (e.g. tofacitinib, baricitinib (1-(ethylsulfonyl)-3-[4-(7H-pyrrolo[2,3-d]pyrimidin-4-yl)-1H-pyrazol-1-yl]-3-azetidineacetonitrile), filgotinib (N-[5-[4-[(1,1-dioxo-1,4-thiazinan-4-yl)methyl]phenyl]-[1,2,4]triazolo[1,5-a]pyridin-2-yl]cyclopropanecarboxamide), peficitinib (4-(((1R,2r,3S,5s,7s)-5-hydroxyadamantan-2-yl)amino)-1H-pyrrolo[2,3-b]pyridine-5-carboxamide), upadacitinib ((3S,4R)-3-ethyl-4-(3H-imidazo[1,2-a]pyrrolo[2,3-e]pyrazin-8-yl)-N-(2,2,2-trifluoroethyl)pyrrolidine-1-carboxamide), TD-1473 or R348 (see, for example, US 2014/0206708)); and protein kinase C inhibitors (e.g. AEB-071).

(e.g. for the treatment of eye disorders (such as uveitis and keratoconjunctivitis sicca (dry eye)), the other therapeutic agent may be, for example, one or more agents selected from the list comprising:

corticosteroids (e.g. dexamethasone, prednisolone, triamcinolone acetonide, difluprednate or fluocinolone acetonide);

glucocorticoid agonists (e.g. mapracorat);

immunosuppressants (e.g. cyclosporin, voclosporin, azathioprine, methotrexate, mycophenolate mofetil or tacrolimus);

anti-TNFα antibodies (e.g. infliximab, adalimumab, certolizumab pegol, ESBA-105 or golimumab);

anti-IL-17A antibodies (e.g. secukinumab);

mTOR inhibitors (e.g. sirolimus);

VGX-1027;

adenosine A3 receptor agonists (e.g. CF-101);

lifitegrast;

JAK3 inhibitors (e.g. tofacitinib or R348); and protein kinase C inhibitors (e.g. AEB-071)).

In particular embodiments, for the treatment of eye disorders (such as uveitis and keratoconjunctivitis sicca (dry eye)), the other therapeutic agent may be, for example, one or more agents selected from the list comprising:

corticosteroids (e.g. dexamethasone, prednisolone, triamcinolone acetonide, difluprednate or fluocinolone acetonide);

immunosuppressants (e.g. cyclosporin, voclosporin, azathioprine, methotrexate, mycophenolate mofetil or tacrolimus);
anti-TNFα antibodies (e.g. infliximab, adalimumab, certolizumab pegol, ESBA-105 or golimumab);
anti-IL-17A antibodies (e.g. secukinumab);
mTOR inhibitors (e.g. sirolimus);
VGX-1027;
JAK inhibitors (e.g. tofacitinib, baricitinib, filgotinib, peficitinib, upadacitinib or R348) (e.g. JAK3 inhibitors such as tofacitinib or R348); and
protein kinase C inhibitors (e.g. AEB-071).

versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I, which process comprises:

(a) for compounds of formula I in which G represents —[(CH$_2$)$_r$-Het$^1$]$_{0-1}$—C(O)$_2$H, hydrolysis or hydrogenolysis of an ester of formula I(P),

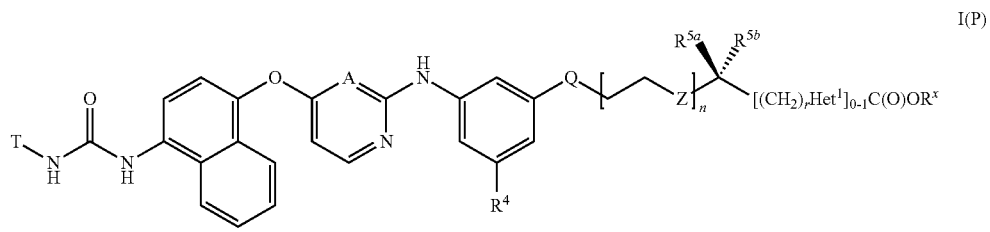

I(P)

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ix, Iy, Ia or Ib (or pharmaceutically acceptable salt thereof) is the sole pharmacologically active ingredient utilised in the treatment.

However, in other embodiments of aspects (e) to (g) above, the compound of formula I, Ix, Iy, Ia or Ib (or pharmaceutically acceptable salt thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:

(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;

(ii) skin diseases or disorders having an inflammatory component, such as atopic dermatitis, allergic dermatitis, contact dermatitis or psoriasis;

(iii) nasal diseases or disorders having an inflammatory component, such as allergic rhinitis, rhinitis or sinusitis;

(iv) eye diseases or disorders having an inflammatory component, such as conjunctivitis, allergic conjunctivitis, glaucoma, diabetic retinopathy, macular oedema (including diabetic macular oedema), central retinal vein occlusion (CRVO), dry and/or wet age related macular degeneration (AMD), post-operative cataract inflammation, or, particularly, keratoconjunctivitis sicca (dry eye, also known as xerophthalmia), uveitis (including posterior, anterior and pan uveitis), corneal graft and limbal cell transplant rejection; and (v) gastrointestinal diseases or disorders having an inflammatory component, such as gluten sensitive enteropathy (coeliac disease), eosinophilic esophagitis, intestinal graft wherein R$^x$ represents C$_{1-6}$ alkyl (e.g. methyl, ethyl or tert-butyl) or benzyl, respectively, and T, R$^4$, R$^{5a}$, R$^{5b}$, A, Q, Z, n, r and Het$^1$ are as hereinbefore defined, for example under conditions known to those skilled in the art, such as by basic hydrolysis with an alkali metal hydroxide at room temperature in the presence of an aqueous solvent system (e.g. a mixture of an aqueous solution, such as a 2 M to 6 M solution, of NaOH with an alcohol such as methanol and a polar aprotic solvent such as THF);

(b) reaction of a compound of formula II,

II with a compound of formula III,

III wherein one of Z$^1$ and Z$^2$ is a structural fragment of formula IVa or IVb,

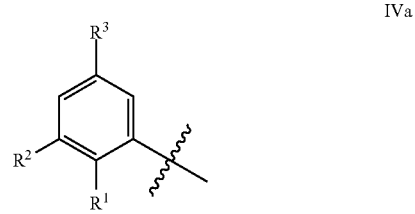

IVa

-continued

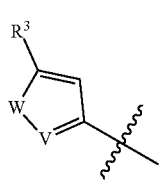

IVb and the other of $Z^1$ and $Z^2$ is a structural fragment of formula V,

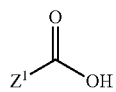

V wherein W, V, $R^1$ to $R^4$, $R^{5a}$, $R^{5b}$, A, Q, Z, G and n are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(c) reaction of a compound of formula IIa,

IIa $$Z^1 \overset{O}{\underset{}{\|}} OH$$

wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula II, which compound is then reacted with a compound of formula III, as defined above, to provide the compound of formula I;

(d) reaction of a compound of formula IIb,

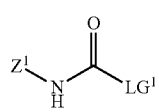

IIb wherein $LG^1$ represents a suitable leaving group (e.g. imidazolyl, chloro, or aryloxy, such as phenoxy) and $Z^1$ is as defined above, with a compound of formula III, as defined above, for example under conditions known to those skilled in the art, such as at ambient temperature (e.g. from ambient to 80° C.), optionally in the presence of an amine base (e.g. triethylamine or a sterically hindered base like N,N-diisopropylethylamine) and a suitable organic solvent (e.g. an aprotic solvent, such as dichloromethane, acetonitrile, tetrahydrofuran or an ester, such as isopropyl acetate);

(e) reaction of a compound of formula VI,

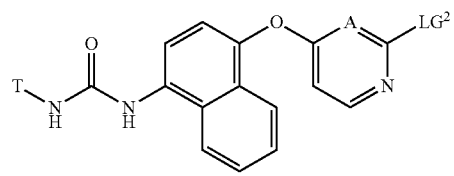

VI wherein $LG^2$ represents a suitable leaving group (e.g. a halo group such as chloro or bromo) and T and A are as hereinbefore defined with a compound of formula VII,

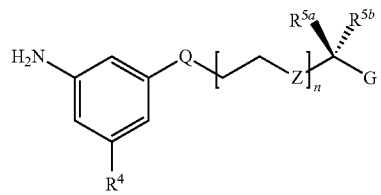

VII wherein $R^4$, $R^{5a}$, $R^{5b}$, Q, Z, G and n are as hereinbefore defined, for example under conditions known to those skilled in the art (e.g. as described in *J. Am. Chem. Soc.* 2011, 133, 15686-15696), such as for compounds of formula I in which A represents N, at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid) or for compounds of formula I in which A represents CH, at elevated temperature (e.g. from 60 to 100° C.) in the presence of a suitable organic solvent (e.g. a polar solvent such as DMF or tert-butanol), a base (e.g. an inorganic base such as potassium carbonate) and a suitable catalyst (e.g. a palladium(II) catalyst such as BrettPhos G3 precatalyst ([(2-dicyclohexylphosphino-3,6-dimethoxy-2',4',6'-triisopropyl-1,1'-biphenyl)-2-(2'-amino-1,1'-biphenyl)]palladium(II) methanesulfonate);

(f) for compounds of formula I in which Q represents $S(O)_{1-2}$, oxidation of a corresponding compound of formula I in which Q represents S, for example under conditions known to those skilled in the art (e.g. at 0 to 25° C. in the presence of a suitable solvent (such as dichloromethane, methanol or a mixture thereof) and a peracid, such as meta-chloroperbenzoic acid);

(g) for compounds of formula I in which Q represents C(O)NH, reaction of a compound of formula VIII,

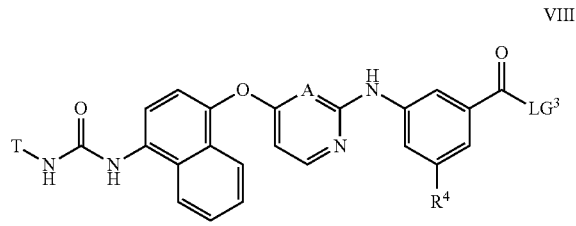

VIII wherein LG$^3$ represents OH, OR$^x$ or a suitable leaving group (such as halo) and T, A, R$^4$ and R$^x$ are as hereinbefore defined, with a compound of formula IX,

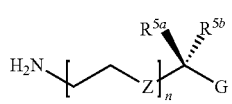

IX wherein R$^{5a}$, R$^{5b}$, Z, G and n are as hereinbefore defined, for example under conditions known to those skilled in the art, such as when LG$^3$ represents OR$^x$, reaction at ambient temperature in the presence of a suitable Lewis acidic catalyst (e.g. a trialkylaluminium reagent such as trimethylaluminium) and an aprotic organic solvent (e.g. THF), when LG$^3$ represents OH, reaction in the presence of a tertiary amine base (e.g., 4-dimethylaminopyridine, a trialkylamine such as triethylamine or diisopropylethylamine or a cyclic amine such as N-methylpyrrolidine or N-methylmorpholine), an amide (peptide) coupling reagent (e.g. T3P, HATU, CDI, BOP, PyBOP, HOAt, HOBt or a carbodiimide such as DCC or diisopropylcarbodiimide) and an aprotic organic solvent (e.g. a chlorinated solvent such as DCM, an ester such as ethyl acetate, an amide of dimethylamine such as DMF, or a mixture of any such solvents) or when LG$^3$ represents a leaving group such as halo, reaction in the presence of a base (e.g. a tertiary amine base as mentioned above) and an aprotic organic solvent (e.g. a chlorinated, ester or amide solvent as mentioned above);

(h) for compounds of formula I in which G represents —[(CH$_2$)$_r$-Het$^1$]$_{0-1}$—C(O)$_2$H, oxidation of an alcohol of formula Xa,

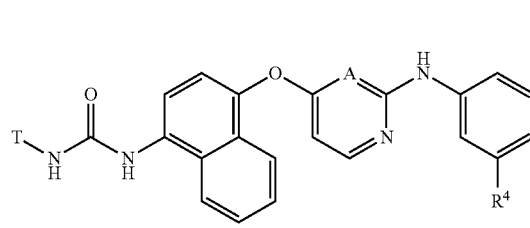

Xa

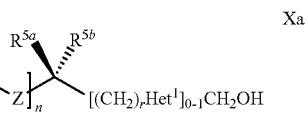

wherein T, R$^4$, R$^{5a}$, R$^{5b}$, A, Q, Z, n, r and Het$^1$ are as hereinbefore defined, for example under conditions known to those skilled in the art (see, for example, http://www.organic-chemistry.org/synthesis/C2O/carboxylicacids/oxidationsalcohols.shtm and Tojo, G.; Fernandez, M. I. *Oxidation of Primary Alcohols to Carboxylic Acids: A Guide to Current Common Practice*, Springer-Verlag, New York, 2007), including reactions using the following oxidants H$_5$IO$_6$ (e.g. in the presence of 1-2 mol % of a catalyst, such as CrO$_3$ or pyridinium chlorochromate, and a solvent such as acetonitrile, or a mixture of acetonitrile and water), a peroxide, such as t-BuOOH (e.g. in the presence of a catalyst such as bismuth(III) oxide), or molecular oxygen or air (e.g. in the presence of: (i) a mixture of a palladium(0) catalyst (e.g. Pd/C), a borohydride (e.g. NaBH$_4$), an inorganic base (e.g. K$_2$CO$_3$ or KOH) and an aqueous alcohol (e.g. ethanol or methanol); (ii) a silver N-heterocyclic carbene catalyst (e.g. a bis(imidazol-2-ylidene) silver catalyst such as a 1,3-bis[(6-bromopyridin-2-yl)methyl]imidazol-2-ylidene silver catalyst) and a hydroxide base such as KOH or a quaternary ammonium hydroxide (e.g. benzyltrimethylammonium hydroxide); (iii) an organocatalyst such as 2-chloroanthraquinone and visible light irradiation; or (iv) one or more catalysts (e.g. VO(acac)$_2$, Cu(II) 2-ethylhexanoate, or a mixture thereof), a strong base (e.g. DABCO) and an ionic liquid, such as a liquid based upon 1-butyl-3-methylimidazolium trifluoromethanesulfonate), alternatively, oxidation of the primary alcohol to the carboxylic acid may be carried out in stepwise fashion, i.e., via the intermediate aldehyde, employing one of the approaches outlined in Tojo, G.; Fernandez, M. I. In *Oxidation of Primary Alcohols to Carboxylic Acids: A Guide to Current Common Practice*, Springer-Verlag, New York, 2007, Chapter 7, pp 105-110; or (i) for compounds of formula I in which G represents —C(O)N(H)OH, —C(O)N(H)OCH$_3$, —C(O)N(H)—S(O)$_2$CH$_3$ or —C(O)N(H)—S(O)$_2$N(CH$_3$)$_2$, coupling of a corresponding compound of formula I in which G represents —CO$_2$H with hydroxylamine, methoxyamine, methanesulfonamide or dimethylsulfamide, respectively, under conditions known to those skilled in the art (e.g. for coupling with methanesulfonamide, reaction in the presence of a tertiary amine base, an amide (peptide) coupling reagent and an aprotic organic solvent, for example as described at (g) above);

(k) for compounds of formula I in which G represents a hydroxy-substituted isoxazole having the structure:

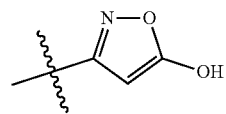 [SMILES: *c1cc(O)on1]

reaction of a compound of formula Xb,

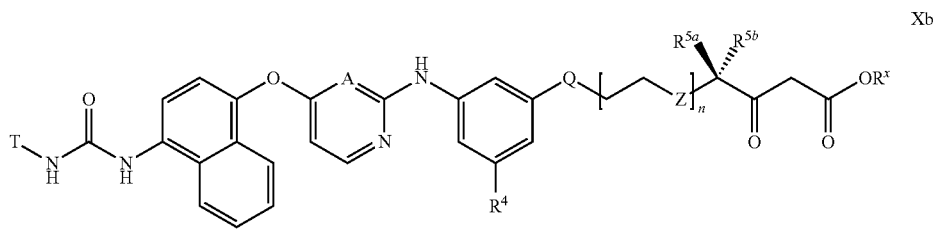

wherein T, A, $R^4$, $R^{5a}$, $R^{5b}$, Q, Z, n and $R^x$ are as hereinbefore defined, with hydroxylamine, for example under conditions known to those skilled in the art (e.g. reaction at elevated temperature, such as at reflux, in the presence of a protic organic solvent, such as ethanol and optionally in the presence of a suitable base, such as sodium bicarbonate);

(l) for compounds of formula I in which G represents tetrazol-5-yl, reaction of a compound of formula Xc,

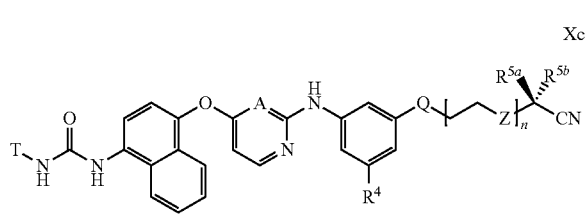

wherein T, A, $R^4$, $R^{5a}$, $R^{5b}$, Q, Z, and n are as hereinbefore defined, with a suitable source of azide (e.g. azidotrimethylsilane), for example under conditions known to those skilled in the art (e.g. reaction at elevated temperature in the presence of an aprotic organic solvent, such as toluene and, optionally, a catalyst, such as dibutyltin oxide);

(m) for compounds of formula I in which G represents 5-oxo-4,5-dihydro-1,2,4-oxadiazol-3-yl, reaction of a compound of formula Xc, as defined above, with hydroxylamine (e.g. under conditions known to those skilled in the art, such as reaction at elevated temperature in the presence of a protic solvent (e.g. EtOH or water, or a mixture of the two)), followed by reaction of the resulting N-hydroxyamidine (amidoxime) compound with a suitable source of the —C(O)— moiety (e.g. a chloroformate, such as isobutyl chloroformate, or phosgene, for example under conditions known to those skilled in the art, such as at sub-ambient temperature in the presence of an aprotic organic solvent (e.g. DMF) and a base (e.g. pyridine));

(n) deprotection of a protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Examples of protected derivatives of compounds of formula I include those where:
an O-atom is protected with a benzyl group, which benzyl group may be removed by hydrogenation, for example in the presence of a palladium catalyst (such as Pd/C);

an O-atom of an acid (e.g. a carboxylic, sulfonic, phosphonic or phosphinic acid) is protected with an alkyl group (such as methyl, ethyl or tert-butyl), which alkyl group may be removed by either basic hydrolysis (e.g. for methyl or ethyl groups, by a hydrolysis reaction using an alkali metal hydroxide such as sodium hydroxide) or acid hydrolysis (e.g. for a tert-butyl group, by a hydrolysis reaction using an acid such as trifluoroacetic acid);

an N-atom of an amine is protected with a carbamate group, such as a benzyl or tert-butyl carbamate, which groups may be removed under similar conditions to those used to remove benzyl or tert-butyl groups from O-atoms.

Protected derivatives of compounds of formula I include compounds of formula I(P).

In the processes described at (b) to (g) above, it may be desirable to protect the $C(O)_2H$ groups in the following compounds:
compounds of formula II, IIa or IIb in which $Z^1$ is a structural fragment of formula V;
compounds of formula III in which $Z^2$ is a structural fragment of formula V; or
compounds of formula VII or IX,
in which compounds G represents —[$(CH_2)_r$-$Het^1$]$_{0-1}$—$C(O)_2H$.

When the $C(O)_2H$ group in these compounds is protected, the protecting group may, for example, be an ester (e.g. wherein $C(O)_2H$ is protected as an ester such as $C(O)OR^x$, wherein $R^x$ is as hereinbefore defined), which ester group may be removed according to procedures known to those skilled in the art (e.g. under conditions such as those described in (a) above).

Compounds of formula II, IIa, IIb, VI and VIII may be prepared according to or by analogy with methods known to those skilled in the art, for example procedures outlined in WO 2014/162126 and WO 2015/092423.

Compounds of formula VII or Xc in which Q represents O or S may be prepared by reaction of a compound of formula X

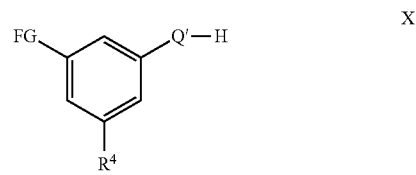

wherein Q' represents O or S, FG represents a real or latent $NH_2$ group (i.e. a group that is readily transformed into an $NH_2$ group, such as nitro or a protected variant NH-PG, where PG is a typical protecting group such as a carbamate ester or carboxamide; see, for example: Greene, T. W.; Wuts, P. G. M. *Protective Groups in Organic Synthesis*; Wiley, 4th revised edition, 2006; ISBN-10: 0471697540) and $R^4$ is as hereinbefore defined, with a compound of formula XI (for the preparation of compounds of formula VII) or of formula XIa (for the preparation of compounds of formula Xc),

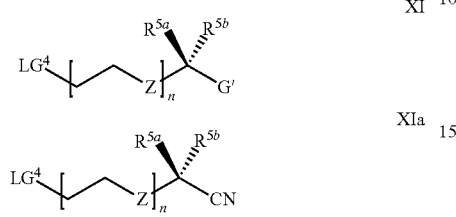

wherein $LG^4$ represents a suitable leaving group (such as methanesulfonate or halo), G' represents —$[(CH_2)_r$-$Het^1]_{0-1}$—$C(O)_2R^y$ or a carboxylic acid isostere (or protected variant thereof), and $R^y$ represents H or $R^x$, and $R^{5a}$, $R^{5b}$, Z, $R^x$ and n are as hereinbefore defined, for example under conditions known to those skilled in the art, followed by:

(i) when FG represents NH-PG, removal of the PG protecting group,
    when FG represents $NO_2$, reduction of $NO_2$ to $NH_2$ or
    when FG represents $C(O)O$—$(C_{1-6}$ alkyl), saponification to provide the corresponding carboxylic acid and then reaction with a suitable azide-forming agent and thermal rearrangement of the resulting acyl azide; and/or (ii) when $R^y$ represents $R^x$, removal of the $R^x$ group, for example by hydrolysis (e.g. as described in respect of process (a) above).

Compounds of formula IX, or protected derivatives thereof, may be prepared according to or by analogy with methods known to those skilled in the art, for example procedures outlined in WO 2011/037610.

Compounds of formula Xb may be prepared by reaction of a corresponding compound of formula I in which G represents —$CO_2H$ with 2,2-dimethyl-1,3-dioxane-4,6-dione (Meldrum's acid) under (peptide) coupling conditions known to those skilled in the art art (e.g. reaction in the presence of a tertiary amine base, an amide (peptide) coupling reagent and an aprotic organic solvent, for example as described at (g) above), followed by thermal degradation (causing loss of one equivalent of acetone and one equivalent of $CO_2$) of the resulting product (an acylated form of Meldrum's acid).

Compounds of formula XI may be prepared by reaction of a compound of formula XII,

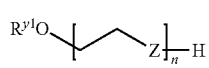

wherein $R^{y1}$ represents H or a protecting group (e.g. benzyl) and n is as hereinbefore defined, with either a compound of formula XIIIa,

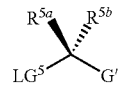

wherein $LG^5$ represents a suitable leaving group (such as methanesulfonate or halo) and $R^{5a}$, $R^{5b}$ and G' are as hereinbefore defined or, for compounds of formula XI in which $R^{5a}$ represents H and G' represents a carboxylic acid isostere (or protected variant thereof) or —$[(CH_2)_r$-$Het^1]_{0-1}$—$C(O)_2R^x$, with a compound of formula XIIIb,

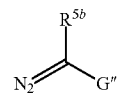

wherein G'' represents a carboxylic acid isostere (or protected variant thereof) or —$[(CH_2)_r$-$Het^1]_{0-1}$—$C(O)_2R^x$, $R^{5b}$ and $R^x$ are as hereinbefore defined, in either case under conditions such as those known to persons skilled in the art, followed by conversion of the $R^{y1}O$— group to a $LG^4$ group, for example, when $R^{y1}$ represents a protecting group, by removal of that protecting group (e.g. under conditions known to those skilled in the art) followed by the use of reagents (e.g. for compounds of formula XII in which $LG^4$ is methanesulfonate, a reagent such as methanesulfonyl chloride) and conditions known to those skilled in the art.

It will be understood by persons skilled in the art that compounds represented by formulae II, IIx and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups $Z^1$ and $Z^2$ which possess chemically-sensitive functional groups, for example, a hydroxyl group or an amino function.

Compounds illustrated above (e.g. intermediates such as compounds of formulae IX, XIa, XII, XIIIa and XIIIb) are either commercially available, or can be obtained using the cited procedures, or can be readily prepared by conventional methods by those skilled in the art. See, for example, Regan, J. et al.; *J. Med. Chem.* 2003, 46, 4676-4686, WO 2000/043384, WO 2007/053346, WO 2007/087448, WO 2007/089512, WO 2009/117080, WO 2013/050756, WO 2014/027209, WO 2014/033446, WO 2014/033447, WO 2014/033449, WO 2014/076484, WO 2014/140582 WO 2014/162121, WO 2014/162126, WO 2015/092423, WO 2016/051187, WO 2016/051188, Lassalas et al., *J. Med. Chem.* (2016), 59, 3183-3203, Ballatore et al., *Chem. Med. Chem.* (2013), 8(3), 385-395 and Boyd et al., *Bioorg. Med. Chem. Lett.* (2015), 25, 1990-1994.

Compounds of formulae Ia, Ix, Iy, Ib and Ic may be prepared by methods analogous to those described above, such as methods in which the above-mentioned intermediates are, where necessary, replaced by compounds having appropriately modified substituent definitions. For example, for the synthesis of compounds of formula Ix or Iy, the following intermediates may be used (wherein $R^1$ to $R^4$, $R^{5a}$, $R^{5b}$, $R^x$, A, Q, n, $LG^2$ and $LG^3$ are as hereinbefore defined).

| Original | Replacement | |
|---|---|---|
| formula I(P) | For synthesis of formula Ix: 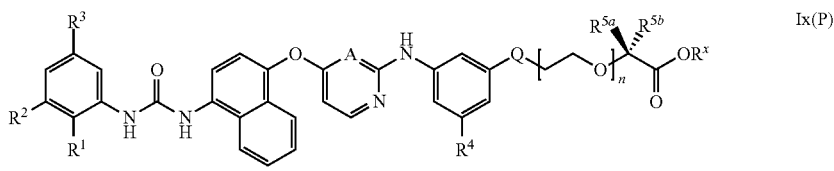 | Ix(P) |
| | For synthesis of formula Ix: 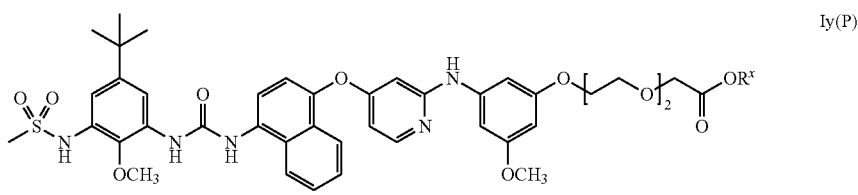 | Iy(P) |
| formula V | For synthesis of formula Ix: 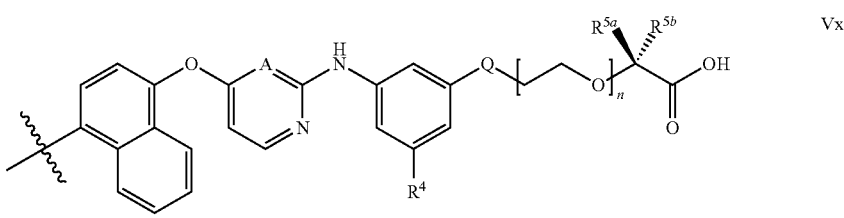 | Vx |
| | For synthesis of formula Iy: 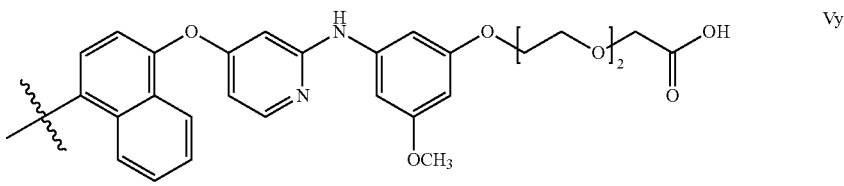 | Vy |
| formula VI | For synthesis of formula Ix: 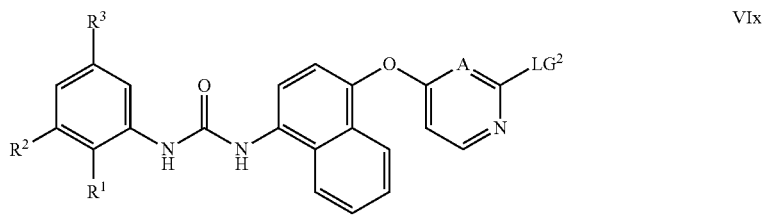 | VIx |
| | For synthesis of formula Iy: 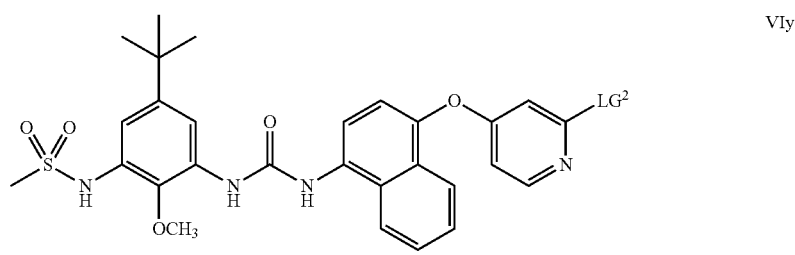 | VIy |

-continued

| Original | Replacement | |
|---|---|---|
| formula VII | For synthesis of formula Ix: 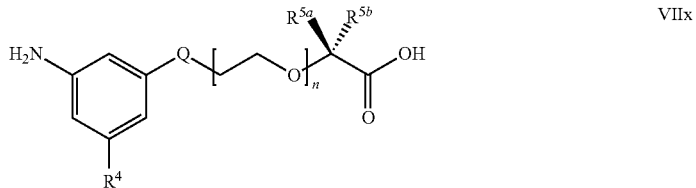 | VIIx |
| | For synthesis of formula Iy: 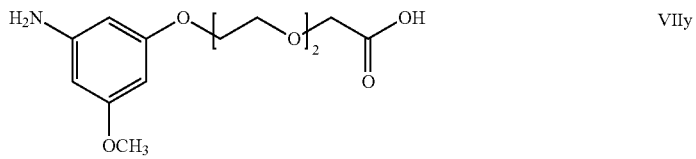 | VIIy |
| formula VIII | For synthesis of formula Ix: 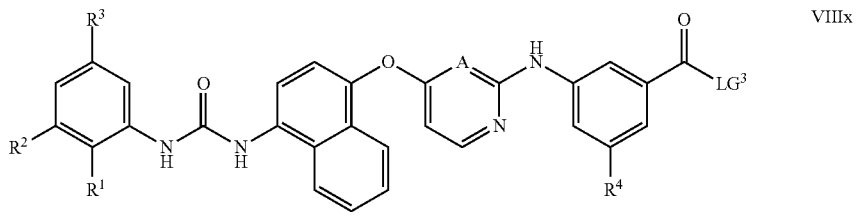<br>For synthesis of formula Iy: not applicable | VIIIx |
| formula IX | For synthesis of formula Ix: <br>For synthesis of formula Iy: not applicable | IXx |
| formula Xa | For synthesis of formula Ix: 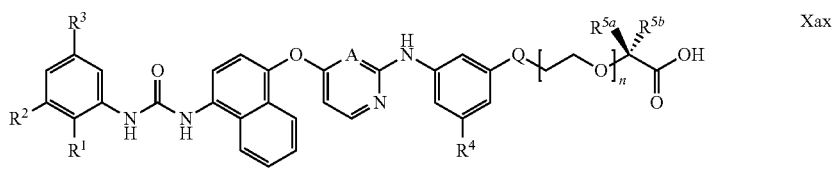<br>For synthesis of formula Iy: 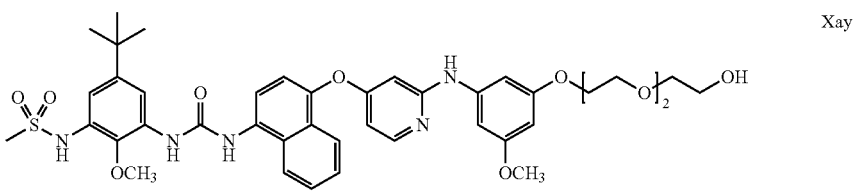 | Xax<br><br>Xay |
| formula XI | For synthesis of formula Ix:  | XIx |

| Original | Replacement |
|---|---|
| formula XIIIa | For synthesis of formula Iy:<br>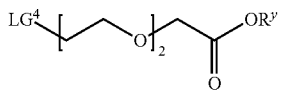<br>XIy<br><br>For synthesis of formula Ix:<br>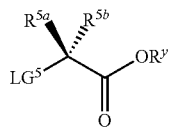<br>XIIIax<br><br>For synthesis of formula Iy:<br>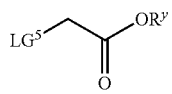<br>XIIIay |
| formula XIIIb | For synthesis of formula Ix:<br>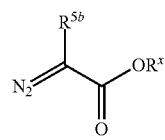<br>XIIIbx<br><br>For synthesis of formula Iy:<br>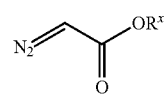<br>XIIIby |

Novel intermediates as described herein form an aspect of the invention. In this respect, further aspects of the invention relate to:

(i) a compound of formula I(P), Ix(P) or Iy(P) as hereinbefore defined, or a salt or protected derivative thereof;
(ii) a compound of formula II, IIa or IIb as hereinbefore defined, wherein $Z^1$ represents a structural fragment of formula V, Vx or Vy, or a salt or protected derivative thereof;
(iii) a compound of formula III as hereinbefore defined, wherein $Z^2$ represents a structural fragment of formula V, Vx or Vy, or a salt or protected derivative thereof; and
(iii) a compound of formula VII, VIIx or VIIy as hereinbefore defined, or a salt or protected derivative thereof.

In these aspects of the invention, embodiments of the compounds of formulae I(P), Ix(P), II, IIa, IIb, III, VII and VIIx that may be mentioned include those in which one or more (e.g. all) of the following apply:
(a) $R^4$ represents methoxy, optionally substituted by one or more (e.g. two or three) halo (e.g. fluoro) substituents or, particularly, $R^4$ represents methoxy;
(b) $R^{5a}$ and $R^{5b}$ both represent H;
(c) Q represents C(O)NH, S, S(O), S(O)$_2$ or, particularly, O;
(d) Z represents O;
(e) n represents 1, 2 or 3 (e.g. 3 or, particularly, 2);
(f) for compounds of formulae I(P), II, IIa, IIb and III, A represents N or, particularly, CH.

Further embodiments of the compounds of formula I(P) or Ix(P) that may be mentioned include those in which one or more (e.g. all) of the following apply:

(a) $R^1$ represents methoxy;
(b) $R^2$ represents —C(O)NH$_2$, —C(O)NHCH$_3$, —S(O)$_{1-2}$CH$_3$, —P(O)(CH$_3$)$_2$, —N(CH$_3$)S(O)$_2$CH$_3$, or —NHS(O)$_2$CH$_3$;
(c) $R^3$ represents trimethylsilyl or tert-butyl;
(d) A represents CH or N;
(e) $R^4$ represents methoxy, optionally substituted by one or more halo substituents;
(f) $R^{5a}$ and $R^{5b}$ both represent H;
(g) Q represents C(O)NH, S, S(O), S(O)$_2$ or O;
(h) Z represents O;
(i) n represents 1, 2 or 3.

In any of such embodiments, as well as in respect of embodiments of compounds of formula Iy(P), $R^x$ may represent $C_{1-6}$ alkyl or benzyl.

Still further embodiments of the compounds of formula I(P) or Ix(P) that may be mentioned include those in which one or more (e.g. all) of the following apply:
(a) $R^1$ represents methoxy;
(b) $R^2$ represents —NHS(O)$_2$CH$_3$;
(c) $R^3$ represents tert-butyl;
(d) A represents CH;
(e) $R^4$ represents methoxy;
(f) $R^{5a}$ and $R^{5b}$ both represent H;
(g) Q represents O;
(h) Z represents O;
(i) n represents 2.

In any of such embodiments, as well as in respect of embodiments of compounds of formula Iy(P), $R^x$ may represent ethyl.

Particular embodiments of the compounds of formulae II, IIa, IIb and III include those in which:
A represents CH;
$R^4$ represents methoxy;
$R^{5a}$ and $R^{5b}$ both represent H;
Q represents O;
Z represents O; and
n represents 2.

Protected derivatives of the compounds of formulae III, VII, VIIx and VIIy include those in which the essential $NH_2$ group is protected. In this respect, such protected derivatives include amides or, particularly, carbamates of those compounds. For example, those protected derivatives include compounds in which the $NH_2$ group is replaced by FG (as defined above, except that it does not represent $NH_2$ (e.g. FG represents nitro)) or, particularly a H-atom of the $NH_2$ group is replaced by:

R'—C(O)—, wherein R' is $C_{1-8}$ alkyl substituted by one or more fluoro groups or R' is H, $C_{1-8}$ alkyl, phenyl or benzyl, which latter two groups are optionally substituted by one or more groups selected from halo, hydroxy, methyl and methoxy; or R"—O—C(O)—, wherein R" is tert-butyl, phenyl, benzyl or fluorenyl, which latter three groups are optionally substituted by one or more groups selected from halo, hydroxy, methyl and methoxy.

For the compounds of formulae II, IIa, IIb, III, VII in which G represents —[(CH$_2$)$_r$-Het$^1$]$_{0-1}$—C(O)$_2$H, and for compounds of formulae VIIx and VIIy, protected derivatives of those compounds additionally (or alternatively) include those in which the carboxyl moiety is protected. In this respect, such protected derivatives also include esters (e.g. wherein C(O)$_2$H is protected as an ester such as C(O)OR$^x$, wherein R$^x$ is as hereinbefore defined) of such compounds.

Particular embodiments of the compounds of formula I(P) or Ix(P) that may be mentioned include:
methyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxybenzamido)ethoxy)ethoxy)acetate;
ethyl 2-(2-(2-(3-((4-((4-(3-(5-(tert-butyl)-2-methoxy-3-(methylsulfonamido)phenyl)ureido)-naphthalen-1-yl)oxy)pyrimidin-2-yl)amino)-5-methoxyphenoxy)ethoxy)ethoxy)acetate; and
ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetate,
or a salt thereof.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compounds of the invention may additionally (or alternatively):

exhibit a long duration of action and/or persistence of action (e.g. in comparison to other previously disclosed p38 MAP kinase inhibitors such as, for example, BIRB796);

exhibit potent inhibition of Syk (e.g. they may have an IC$_{50}$ against Syk of 500 nM or less, such as 350 nM or less);

not strongly inhibit GSK 3α (e.g. they may have an IC$_{50}$ against GSK 3α of 1,000 nM or greater; such as 1,500, 2,000, 3,000, 4,000, 5,000, 6,000, 7,000, 8,000, 9,000 or 10,000 nM or greater);

target a smaller portion of the kinome, i.e., with improved selectivity, as illustrated by lowered KinomeScan Selectivity Scores;

maintain a relatively high local drug concentration between doses (e.g. a high local concentration relative to other previously disclosed p38 MAP kinase inhibitors such as, for example, BIRB796);

exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma, for example as a result of high renal or hepatic extraction);

exhibit little or no β-catenin induction and/or inhibition of mitosis in cells;

display reduced cytotoxicities;

not produce increases in binucleated cells containing micronuclei in the human lymphocyte in vitro micronucleus test;

exhibit little or no time-dependent inhibition of members of the cytochrome P450 superfamily;

show improved chemical stability in the presence of water (e.g. stability to hydrolysis in aqueous mixtures at elevated temperatures) compared to previously disclosed p38 MAP kinase inhibitors such as, for example, BIRB796;

following administration to a patient, give rise to metabolites associated with little or no safety (e.g. toxicity) concerns;

display reduced ocular irritancy or toxicity in both preclinical species and humans following topical administration;

exhibit good aqueous solubility and/or cellular permeability (e.g. exhibit good aqueous solubility and potent inhibition of the release of certain cytokines, such as IL-8 and/or IFNγ, in cells), for example relative to Reference Compound A, (3-(2-(2-(3-((4-((4-(3-(5-(tert-butyl)-2-methoxy-3-(methylsulfonamido)phenyl)-ureido)naphthalen-1-yl)oxy)pyrimidin-2-yl)amino)-5-methoxyphenoxy)ethoxy)ethoxy)-propanoic acid, and/or Reference Compound B, 3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide;

give rise to a faster dissolution rate in intestinal or colonic fluids, for example relative to Reference Compound A and/or Reference Compound B;

be more readily formulated in aqueous solution in the pH range 7-8 with lower quantities of solubilising excipients;

have a high degree of crystallinity; and/or exhibit little or no hygroscopicity in the solid state.

TABLE A peak listing for XRPD profile of product of Example 31, Method 1

| Pos. [°2Th.] | Height [cts] | FWHM [°2Th.] | d-spacing [Å] | Rel. Int. [%] |
|---|---|---|---|---|
| 3.9317 | 997.91 | 0.1023 | 22.47367 | 68.42 |
| 4.4389 | 376.68 | 0.1279 | 19.90685 | 25.83 |
| 5.9292 | 224.18 | 0.1279 | 14.90639 | 15.37 |
| 8.9406 | 240.27 | 0.1535 | 9.89115 | 16.47 |
| 9.4882 | 279.74 | 0.1023 | 9.32147 | 19.18 |
| 11.2243 | 804.76 | 0.1279 | 7.88327 | 55.17 |
| 14.6967 | 1458.55 | 0.2303 | 6.02757 | 100.00 |
| 15.8103 | 156.22 | 0.1535 | 5.60546 | 10.71 |
| 18.0348 | 732.39 | 0.1791 | 4.91876 | 50.21 |
| 18.4303 | 539.12 | 0.1023 | 4.81408 | 36.96 |
| 18.9396 | 749.55 | 0.3582 | 4.68577 | 51.39 |
| 21.0357 | 301.56 | 0.1535 | 4.22334 | 20.68 |
| 22.6909 | 254.38 | 0.1535 | 3.91888 | 17.44 |
| 26.2933 | 130.65 | 0.1279 | 3.38956 | 8.96 |
| 27.5888 | 51.44 | 0.4093 | 3.23328 | 3.53 |
| 27.9150 | 40.67 | 0.1279 | 3.19623 | 2.79 |
| 28.9822 | 37.73 | 0.3070 | 3.08092 | 2.59 |
| 33.3548 | 18.18 | 0.1535 | 2.68635 | 1.25 |

TABLE B peak listing for XRPD profile of product of Example 31, Method 2

| Pos. [°2Th.] | Height [cts] | FWHM [°2Th.] | d-spacing [Å] | Rel. Int. [%] |
|---|---|---|---|---|
| 3.9435 | 937.49 | 0.1023 | 22.40637 | 92.78 |
| 4.4734 | 508.47 | 0.2047 | 19.75372 | 50.32 |
| 5.8834 | 347.72 | 0.2558 | 15.02234 | 34.41 |
| 9.0053 | 212.93 | 0.1791 | 9.82024 | 21.07 |
| 9.5071 | 332.04 | 0.1535 | 9.30301 | 32.86 |
| 11.3151 | 633.79 | 0.2047 | 7.82025 | 62.72 |
| 14.7734 | 1010.46 | 0.2558 | 5.99645 | 100.00 |
| 15.6873 | 215.33 | 0.5117 | 5.64914 | 21.31 |
| 18.0549 | 555.83 | 0.2558 | 4.91331 | 55.01 |
| 19.0099 | 725.20 | 0.3582 | 4.66858 | 71.77 |
| 21.1976 | 433.24 | 0.8187 | 4.19144 | 42.88 |
| 22.7798 | 354.68 | 0.4093 | 3.90378 | 35.10 |
| 26.3822 | 80.59 | 0.3070 | 3.37834 | 7.98 |
| 27.6970 | 45.38 | 0.6140 | 3.22089 | 4.49 |
| 31.6934 | 43.32 | 0.8187 | 2.82328 | 4.29 |

Figure 1:
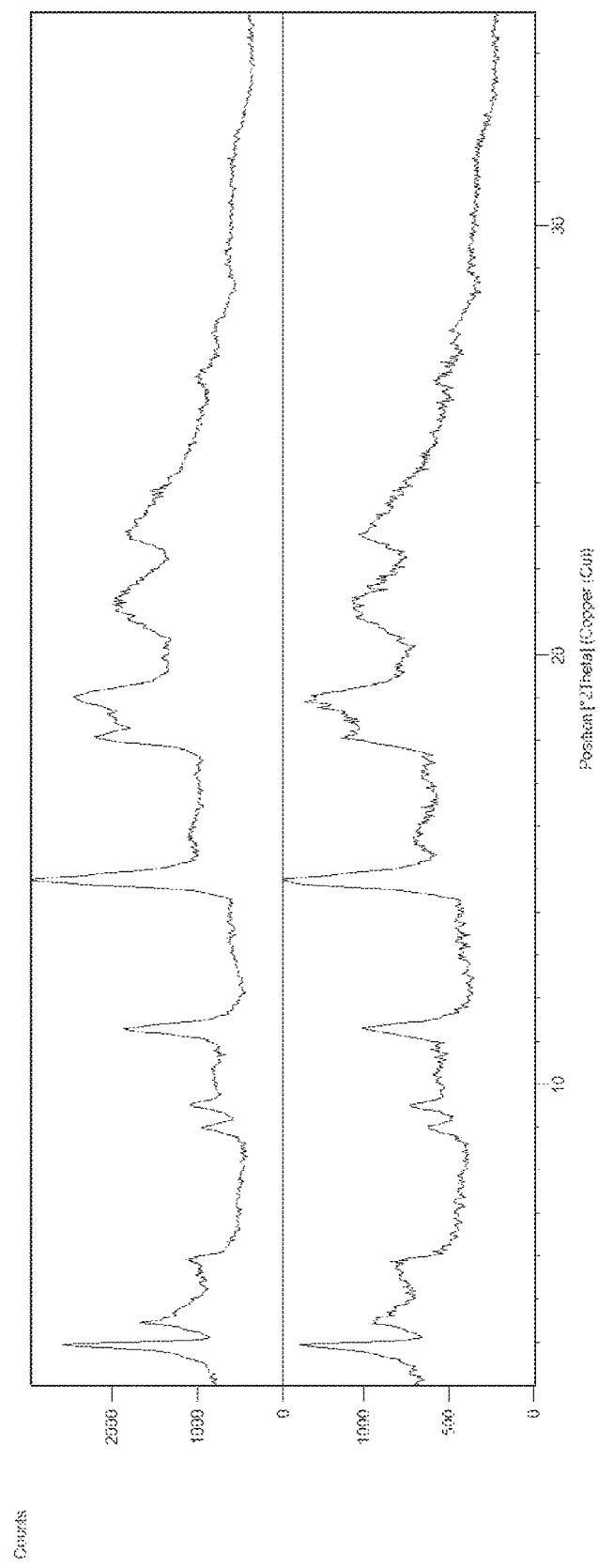
FIG. 1 shows comparative XRPD profiles for two samples of 2-(2-(2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)ethoxy)acetic acid, sodium salt, produced either by Method 1 (upper trace, with peaks as described in Table A below) or Method 2 (lower trace, with peaks as described in Table B below) of Example 31 below.
Figure 2:
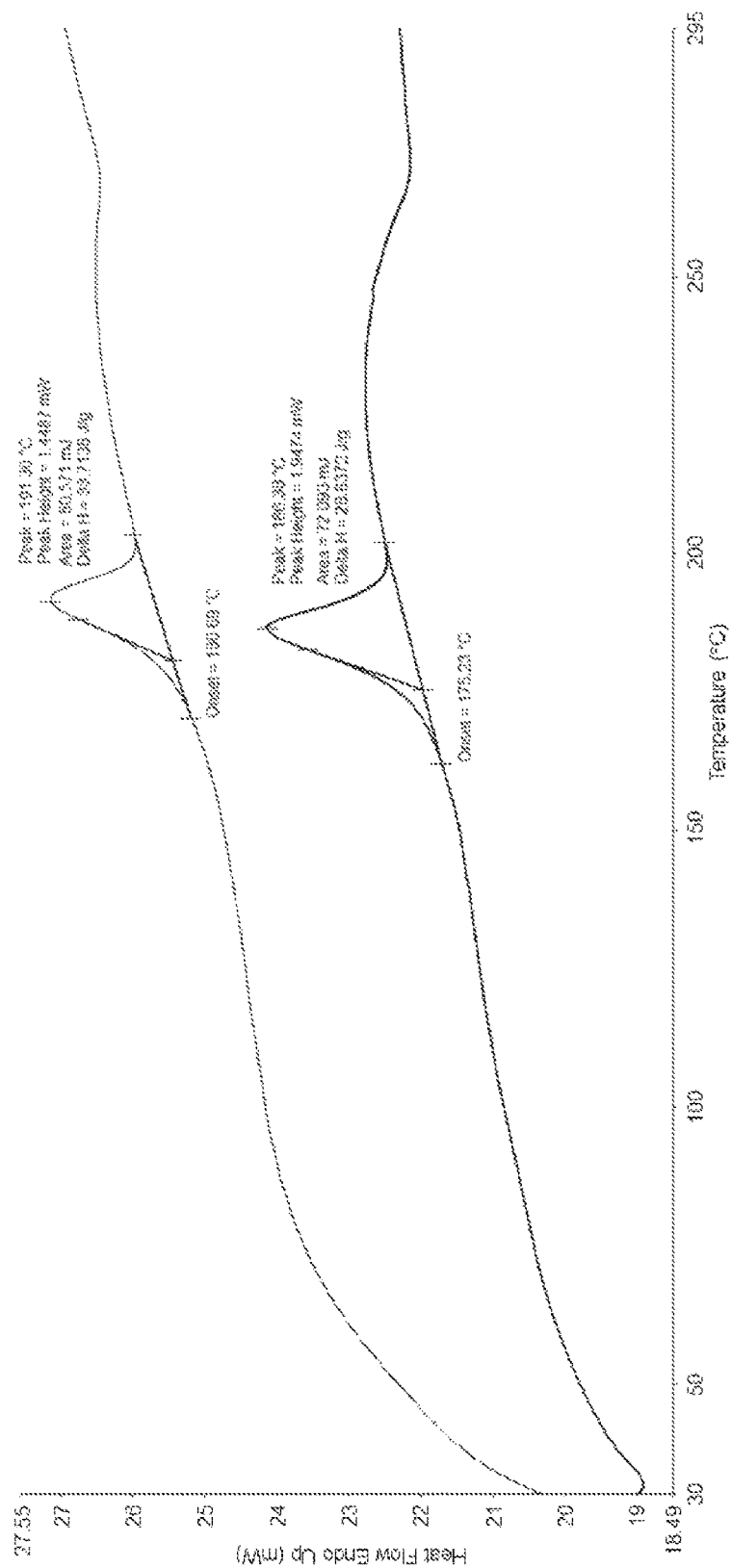

FIG. 2 shows the heat flow traces obtained by DSC analysis of two samples of 2-(2-(2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)ethoxy)acetic acid, sodium salt, produced either by Method 1 (upper line) or Method 2 (lower line) of Example 31 below.

EXPERIMENTAL METHODS

A. General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

B. Analytical Methods

Analytical HPLC was carried out using a Waters Xselect CSH C18, 2.5 μm, 4.6×30 mm column eluting with a gradient of 0.1% Formic Acid in MeCN in 0.1% aqueous Formic Acid or a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid or a Waters Xbridge BEH C18, 2.5 μm, 4.6×30 mm column eluting with a gradient of MeCN in aqueous 10 mM Ammonium Bicarbonate. UV and mass spectra of the eluted peaks were measured using a variable wavelength detector on either an Agilent 1200 or an Agilent Infinity 1260 LCMS with 6120 single quadrupole mass spectrometer with positive and negative ion electrospray.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate or employing a Waters Xbridge BEH C18, 5 μm, 19×50 mm column using a gradient of MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC or by mass and UV at a single wavelength measured by a ZQ single quadrupole mass spectrometer, with positive and negative ion electrospray, and a dual wavelength detector on a Waters FractionLynx LCMS.

$^1$H NMR Spectroscopy: $^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

Preparation of Compounds of the Invention

Example 1

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxybenzamido)ethoxy)ethoxy)acetic acid, hydrochloride salt

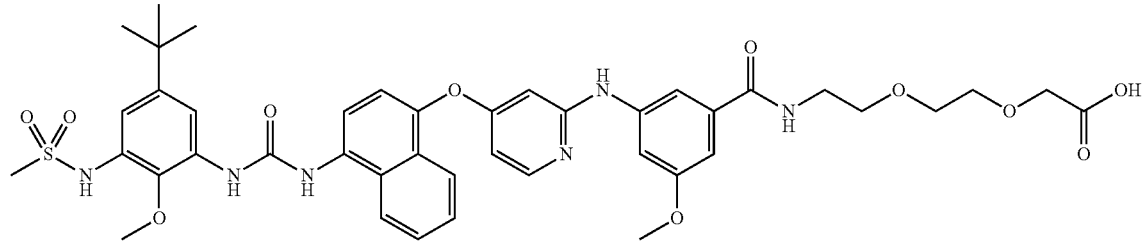 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCOCCOCC(=O)O)c1]

(i) Methyl 3-amino-5-methoxybenzoate

To a stirred suspension of 3-amino-5-methoxybenzoic acid (47 g, 281 mmol) in MeOH (1 L) at 0° C. was added thionyl chloride (123 mL, 1687 mmol) dropwise. The reaction was warmed to rt and stirred for 72 h. The resulting solid was isolated by filtration, washing with diisopropyl ether, affording the product as the HCl salt. The filtrate was evaporated, the residue triturated with MeOH/ether, filtered and washed with ether. The combined solid was suspended in DCM (500 mL) and basified with sat. aq. NaHCO$_3$ solution (300 mL) with vigorous stirring. The organic phase was separated, washed with brine (200 mL), dried (MgSO$_4$), filtered and evaporated under reduced pressure to give a solid. The solid was triturated with ether/isohexane to afford the sub-title compound (46 g) as a solid.

$^1$H NMR (400 MHz, DMSO-d6) δ: 6.83 (dd, 1H), 6.63 (dd, 1H), 6.37 (t, 1H), 5.42 (s, 2H), 3.79 (s, 3H), 3.70 (s, 3H).
LCMS m/z 182 (M+H)$^+$ (ES$^+$)

(ii) Methyl 3-((4-((4-((tert-butoxycarbonyl)amino)naphthalen-1-yl)oxy)pyridin-2-yl)amino)-5-methoxybenzoate A mixture of the product from step (i) above (10.8 g, 59.6 mmol), tert-butyl (4-((2-chloropyridin-4-yl)oxy)naphthalen-1-yl)carbamate (see, for example, WO 2014/162126; 20 g, 53.9 mmol), finely ground potassium carbonate (15.2 g, 110 mmol) and BrettPhos G3 precatalyst (800 mg, 0.883 mmol) in tBuOH (400 mL) was extensively degassed with N$_2$. The reaction was heated under nitrogen at 90° C. (block temperature) for 2 h. The reaction mixture was diluted with DCM (500 mL), filtered through Celite and concentrated in vacuo to afford a brown foam. The foam was triturated with Et$_2$O (500 mL). The resultant solid was filtered, washing with further Et$_2$O (100 mL), and dried in vacuo to affording the sub-title compound (25.6 g) as an off-white/pale-grey solid.

$^1$H NMR (400 MHz, DMSO-d6) δ: 9.37 (s, 1H), 9.19 (s, 1H), 8.13-8.14 (m, 2H), 7.84 (d, 1H), 7.77 (bs, 1H), 7.69 (t, 1H), 7.55-7.65 (m, 3H), 7.36 (d, 1H), 6.96 (bs, 1H), 6.62 (dd, 1H), 6.09 (d, 1H), 3.82 (s, 3H), 3.75 (s, 3H), 1.53 (s, 9H).
LCMS m/z 516 (M+H)$^+$ (ES$^+$)

(iii) Methyl 3-((4-((4-aminonaphthalen-1-yl)oxy)pyridin-2-yl)amino)-5-methoxybenzoate HCl (5 N in iPrOH) (79 mL, 395 mmol) was added to a solution of the product from step (ii) above (20 g, 38.8 mmol) in DCM (250 mL) and the reaction left stirring overnight. Et$_2$O (300 mL) was added and the resulting precipitate was isolated by filtration, washing with further Et$_2$O. The solid was partitioned between DCM (400 mL) and sat. aq. NaHCO$_3$ solution (600 mL). The organic layer was dried via hydrophobic frit and concentrated in vacuo to afford the sub-title compound (15.5 g) as a beige foam.

$^1$H NMR (400 MHz, DMSO-d6) δ: 9.09 (s, 1H), 8.15-8.18 (m, 1H), 8.08 (d, 1H), 7.75 (t, 1H), 7.69 (t, 1H), 7.63-7.65 (m, 1H), 7.43-7.47 (m, 2H), 7.11 (d, 1H), 6.95 (t, 1H), 6.72 (d, 1H), 6.56 (dd, 1H), 6.04 (d, 1H), 5.83 (bs, 2H), 3.82 (s, 3H), 3.75 (s, 3H).
LCMS m/z 416 (M+H)$^+$ (ES$^+$)

(iv) Methyl 3-((4-((4-(3-(5-(tert-butyl)-2-methoxy-3-(methylsulfonamido)phenyl)ureido)-naphthalen-1-yl)oxy)pyridin-2-yl)amino)-5-methoxybenzoate Triethylamine (28 μL, 0.201 mmol) was added to a solution of phenyl (5-(tert-butyl)-2-methoxy-3-(methylsulfonamido)phenyl)carbamate (see, for example, WO 2014/162126; 480 mg, 1.223 mmol) and the product from step (iii) above (412 mg, 0.992 mmol) in iPrOAc (15 mL) at 60° C. (block temperature) and the mixture stirred for 24 h. The solution was cooled to rt and concentrated in vacuo affording a red oil. The crude product was purified by chromatography on the Companion (40 g column, 1-5% MeOH in DCM) to afford the sub-title compound (580 mg) as a pale pink foam.
LCMS m/z 714 (M+H)$^+$ (ES$^+$)

(v) 3-((4-((4-(3-(5-(tert-Butyl)-2-methoxy-3-(methylsulfonamido)phenyl)ureido)naphthalen-1-yl)oxy)pyridin-2-yl)amino)-5-methoxybenzoic acid, hydrochloride salt To a stirred solution of the product from step (iv) above (580 mg, 0.813 mmol) in THF (20 mL) was added NaOH (6M aq.) (2 mL, 12.00 mmol). MeOH (5 mL) was added and the reaction stirred overnight. The reaction was concentrated in vacuo affording a yellow solid. The solid was suspended in 1 M HCl (20 mL) and the resulting gel-like solid filtered, washing with water. The resulting solid was dried for 1 h on the frit then further dried at 40° C. under vacuum affording the sub-title compound (526 mg) as an off-white solid.
LCMS m/z 699.77 (M+H)$^+$ (ES$^+$)

(vi) Methyl 2-(2-(2-aminoethoxy)ethoxy)acetate, trifluoroacetic acid salt

To a stirred solution of methyl 2,2-dimethyl-4-oxo-3,8,11-trioxa-5-azatridecane-13-oate (see, for example, WO 2011/037610; 195 mg, 0.703 mmol) in DCM (2 mL) was added TFA (500 μL, 6.49 mmol) and the mixture stirred at rt for 1 h. The reaction was concentrated in vacuo then re-concentrated from toluene affording the sub-title compound (230 mg) as a colourless oil.

LCMS m/z 178 (M+H)+ (ES+)

(vii) Methyl 2-(2-(2-(3-((4-((4-(3-(5-(tert-butyl)-2-methoxy-3-(methylsulfonamido)phenyl)-ureido) naphthalen-1-yl)oxy)pyridin-2-yl)amino)-5-methoxybenzamido)ethoxy)ethoxy)acetate HATU (120 mg, 0.316 mmol) was added to a stirred solution of the product from step (v) above (150 mg, 0.204 mmol), the product from step (vi) above (100 mg, 0.343 mmol) and Hünig's Base (250 μL, 1.431 mmol) in NMP (2 mL) at rt. The mixture was stirred for 2 h. The reaction was partitioned between water (15 mL) and EtOAc (10 mL). The aqueous phase was extracted with EtOAc (5 mL) and the combined organics washed with water and brine, then dried via hydrophobic frit and concentrated in vacuo. The crude product was purified by chromatography on the Companion (12 g column, 1-5% MeOH in DCM) to afford the sub-title compound (173 mg) as a colourless gum.

LCMS m/z 859 (M+H)+ (ES+)

(viii) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxybenzamido)ethoxy)ethoxy)acetic acid, hydrochloride salt To a stirred solution of the product from step (vii) above (173 mg, 0.201 mmol) in THF (3 mL) was added NaOH (6 M aq.) (0.30 mL, 1.800 mmol). MeOH (1 mL) was added and the resulting solution stirred at rt for 2 h. The reaction was concentrated in vacuo affording a yellow solid. The solid was suspended in 1M HCl (10 mL) and the mixture sonicated. The resulting suspension was filtered and the recovered solid washed with water then dried in vacuo at 40° C. overnight affording the title compound (140 mg) as a colourless solid.

$^1$H NMR (400 MHz, DMSO-d6) δ: 9.61 (bs, 1H), 9.53 (s, 1H), 9.15 (s, 1H), 8.99 (s, 1H), 8.46 (t, 1H), 8.35 (d, 1H), 8.18 (d, 1H), 8.15 (d, 1H), 8.07 (d, 1H), 7.87 (d, 1H), 7.71-7.74 (m, 1H), 7.62-7.66 (m, 1H), 7.43-7.45 (m, 2H), 7.35 (s, 1H), 7.08 (s, 1H), 7.03 (d, 1H), 6.73 (bs, 1H), 6.22 (s, 1H), 4.01 (s, 2H), 3.81 (s, 3H), 3.77 (s, 3H), 3.51-3.60 (m, 6H), 3.40 (q, 2H), 3.10 (s, 3H), 1.27 (s, 9H).

LCMS m/z 845 (M+H)+ (ES+)

Example 2

2-(2-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxyphenoxy) ethoxy)ethoxy)acetic acid (i) Ethyl 2-(2-(2-hydroxyethoxy)ethoxy)acetate A solution of ethyl diazoacetate (1.9 mL, 18.32 mmol) in DCM (20 mL) was added dropwise to a solution of diethylene glycol (5.0 mL, 52.7 mmol) and rhodium(II) acetate dimer (160 mg, 0.362 mmol) in DCM (300 mL) over 1 h. The reaction was stirred at rt overnight. The mixture was evaporated under reduced pressure and the residue purified by chromatography on silica gel (220 g column, 0-100% EtOAc/isohexane) to afford the sub-title compound (2.38 g) as a dark blue oil.

$^1$H NMR (400 MHz, CDCl$_3$) δ: 4.23 (q, 2H), 4.19 (s, 2H), 3.60-4.05 (m, 8H), 1.28 (t, 3H).

(ii) Ethyl 2-(2-(2-((methylsulfonyl)oxy)ethoxy) ethoxy)acetate

Methanesulfonyl chloride (0.6 mL, 7.70 mmol) was added dropwise to a solution of the product from step (i) above (1.20 g, 6.24 mmol) and Et$_3$N (1.7 mL, 12.20 mmol) in DCM (20 mL) at 0-5° C., warmed to rt and stirred for 2 h. The mixture was partitioned between DCM (50 mL) and water (30 mL), the organic layer washed with sat. aq. NaHCO$_3$ (30 mL), dried (MgSO$_4$), filtered and evaporated under reduced pressure. The crude product was purified by chromatography on silica gel (40 g column, 0-70% EtOAc/isohexane) to afford the sub-title compound (1.494 g) as an oil.

$^1$H NMR (400 MHz; CDCl$_3$) δ 4.42-4.39 (m, 2H), 4.24 (q, 2H), 4.15 (s, 2H), 3.82-3.79 (m, 2H), 3.77-3.72 (m, 4H), 3.10 (s, 3H), 1.31 (t, 3H).

(iii) Ethyl 2-(2-(2-(3-methoxy-5-nitrophenoxy) ethoxy)ethoxy)acetate

A mixture of 3-methoxy-5-nitrophenol (1.973 g, 11.67 mmol), the product from step (ii) above (2.92 g, 10.80 mmol) and K$_2$CO$_3$ (4.48 g, 32.4 mmol) in DMF (60 mL) was heated at 60° C. for 20 h. The reaction was cooled to rt then partitioned between ether (200 mL) and water (200 mL). The organic layer was washed with sat. aq. NaHCO$_3$ solution (100 mL) and brine (100 mL) then dried (MgSO$_4$), filtered and evaporated under reduced pressure. The crude product was purified by chromatography on silica gel (80 g column, 0-50% EtOAc/isohexane) to afford the sub-title compound (3.35 g) as a yellow oil.

LCMS m/z 344 (M+H)+ (ES+)

(iv) Ethyl 2-(2-(2-(3-amino-5-methoxyphenoxy) ethoxy)ethoxy)acetate

To a solution of the product from step (iii) above (3.35 g, 9.76 mmol) in EtOH (20 mL) and EtOAc (5 mL) was added Pd/C (5 wt %) (0.5 g, 0.235 mmol). The resulting suspension was stirred under a 5 bar (0.5 MPa) atmosphere of H$_2$ for 8 h. The reaction was purged with N$_2$ then filtered through Celite. The filtrate was concentrated in vacuo affording the sub-title compound (3.0 g) as a pale yellow oil.

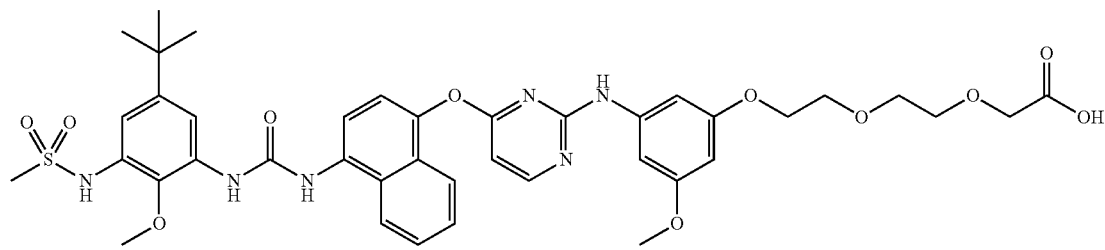 [SMILES: COc1cc(Nc2nccc(Oc3ccc(NC(=O)Nc4cc(C(C)(C)C)cc(NS(C)(=O)=O)c4OC)c4ccccc34)n2)cc(OCCOCCOCC(=O)O)c1]

¹H NMR (400 MHz, DMSO-d6) δ: 5.75 (d, 2H), 5.68 (t, 1H), 5.06 (s, 2H), 4.13 (s, 2H), 4.12 (q, 2H), 3.93-3.96 (m, 2H), 3.68-3.70 (m, 2H), 3.58-3.64 (m, 4H), 3.62 (s, 3H), 1.20 (s, 3H).

LCMS m/z 314 (M+H)⁺ (ES⁺)

(v) Ethyl 2-(2-(2-(3-((4-((4-(3-(5-(tert-butyl)-2-methoxy-3-(methylsulfonamido)phenyl)ureido)-naphthalen-1-yl)oxy)pyrimidin-2-yl)amino)-5-methoxyphenoxy)ethoxy)ethoxy)acetate A mixture of N-(5-(tert-butyl)-3-(3-(4-((2-chloropyrimidin-4-yl)oxy)naphthalen-1-yl)ureido)-2-methoxyphenyl)methanesulfonamide (see, for example, WO 2014/162126; 300 mg, 0.526 mmol), the product from step (iv) above (247 mg, 0.789 mmol) and pTSA hydrate (30 mg, 0.158 mmol) in THF (5 mL) was heated at 65° C. for 40 h. The mixture was cooled, partitioned between EtOAc (100 mL) and sat. aq. NaHCO₃ (50 mL), the organic layer washed with 1 M HCl (50 mL), water (50 mL), dried (MgSO₄), filtered and evaporated under reduced pressure. The crude product was purified by chromatography on silica gel (40 g column, 0-5% MeOH/DCM) to afford the sub-title compound (378 mg) as a foam.

LCMS m/z 847 (M+H)⁺ (ES⁺)

(vi) 2-(2-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxyphenoxy)ethoxy)ethoxy)acetic acid A mixture of the product from step (v) above (376 mg, 0.444 mmol) and 2 M aq. NaOH (700 μL, 1.400 mmol) in THF (5 mL) and MeOH (2 mL) was stirred at rt for 20 h. The solvent was removed in vacuo, the residue dissolved in water (5 mL) and acidified with AcOH. The mixture was evaporated and the residue purified by chromatography on the Companion (RP Flash C18) (40 g column, 15-75% MeCN/10 mM Ammonium Bicarbonate) to afford the title compound (72 mg) as a white solid.

¹H NMR (400 MHz; DMSO-d6) δ 12.57 (s, 1H), 9.43 (s, 1H), 9.37 (s, 1H), 9.15 (s, 1H), 8.94 (s, 1H), 8.42 (d, 1H), 8.28 (d, 1H), 8.19 (d, 1H), 8.11 (d, 1H), 7.85 (d, 1H), 7.70-7.65 (m, 1H), 7.61-7.56 (m, 1H), 7.42 (d, 1H), 7.02 (d, 1H), 6.80 (brs, 2H), 6.54 (d, 1H), 6.04 (s, 1H), 4.00 (s, 2H), 3.89-3.83 (m, 2H), 3.81 (s, 3H), 3.69-3.64 (m, 2H), 3.60-3.54 (m, 4H), 3.51 (s, 3H), 3.10 (s, 3H), 1.27 (s, 9H).

LCMS m/z 819 (M+H)⁺ (ES⁺)

Example 3

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid Method 1

(i) Ethyl 2-(2-(2-(3-((4-((4-((tert-butoxycarbonyl)amino)naphthalen-1-yl)oxy)pyridin-2-yl)amino)-5-methoxyphenoxy)ethoxy)ethoxy)acetate A mixture of tert-butyl (4-((2-chloropyridin-4-yl)oxy)naphthalen-1-yl)carbamate (see, for example, WO 2014/162126; 497 mg, 1.340 mmol), ethyl 2-(2-(2-(3-amino-5-methoxyphenoxy)ethoxy)ethoxy)acetate (see Example 2(iv) above; 420 mg, 1.340 mmol) and K₂CO₃ (556 mg, 4.02 mmol) in DMF (6 mL) was degassed under vacuum, backfilling with N₂ three times. BrettPhos G3 precatalyst (37 mg, 0.041 mmol) was added and the mixture heated to 80° C. for 1 h. The mixture was cooled to rt and partitioned between EtOAc (70 mL) and water (50 mL). The organic layer washed with water (50 mL) and brine (30 mL) then dried (MgSO₄), filtered and concentrated in vacuo. The crude product was purified by chromatography on silica gel (40 g column, 0-100% EtOAc/isohexane) to afford the sub-title compound (870 mg) as a colourless foam.

LCMS m/z 648 (M+H)⁺ (ES⁺)

(ii) Ethyl 2-(2-(2-(3-((4-((4-aminonaphthalen-1-yl)oxy)pyridin-2-yl)amino)-5-methoxyphenoxy)ethoxy)ethoxy)acetate A mixture of the product from step (i) above (690 mg, 1.065 mmol) and TFA (1 mL, 12.98 mmol) in DCM (5 mL) was stirred at rt for 20 h then evaporated. The residue was partitioned between EtOAc (60 mL) and sat. aq. NaHCO₃ solution (40 mL), the organic layer was separated, washed with water (40 mL), dried (MgSO₄), filtered and evaporated under reduced pressure to afford the sub-title compound (572 mg) as a brown gum.

LCMS m/z 548 (M+H)⁺ (ES⁺)

(iii) Ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetate A mixture of phenyl (5-(tert-butyl)-2-methoxy-3-(methylsulfonamido)phenyl)carbamate (see, for example, WO 2014/162126; 490 mg, 1.249 mmol), the product from step (ii) above (570 mg, 1.041 mmol) and Et₃N (50 μL, 0.359 mmol) in THF (10 mL) was heated under reflux for 24 h. The solvent was removed and the residue purified by chromatography on silica gel (40 g column, 0-5% MeOH/DCM) to afford the sub-title compound (736 mg) as a foam.

LCMS m/z 844 (M+H)⁺ (ES⁺)

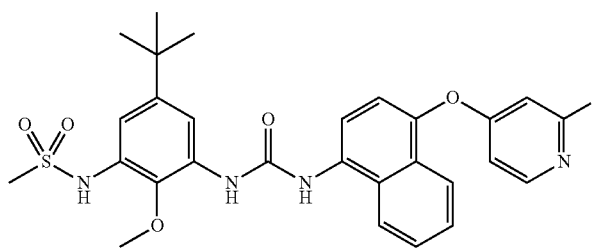
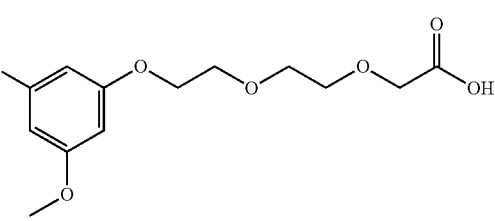

3(iv) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid A mixture of the product from step (iii) above (803 mg, 0.892 mmol) and aq. 2 M NaOH (1.3 mL, 2.60 mmol) in THF (8 mL) and MeOH (3 mL) was stirred at rt for 20 h. The reaction was acidified with AcOH (3 mL) then concentrated in vacuo affording a pale solid. The residue was purified by chromatography on the Companion (RP Flash C18) (40 g column, 15-75% MeCN/10 mM Ammonium Bicarbonate) to afford the title compound (653 mg) as an off-white solid.

$^1$H NMR (400 MHz, DMSO-d6) δ: 9.55 (s, 1H), 9.02 (s, 1H), 8.90 (s, 1H), 8.32 (d, 1H), 8.19 (d, 1H), 8.12 (s, 1H), 8.10 (s, 1H), 7.86 (d, 1H), 7.67-7.71 (m, 1H), 7.58-7.62 (m, 1H), 7.38 (d, 1H), 7.03 (d, 1H), 6.86 (s, 1H), 6.78 (s, 1H), 6.59 (dd, 1H), 6.09 (d, 1H), 6.03 (t, 1H), 3.93-3.96 (m, 2H), 3.93 (s, 2H), 3.81 (s, 3H), 3.69-3.71 (m, 2H), 3.65 (s, 3H), 3.55-3.61 (m, 4H), 3.10 (s, 3H), 1.27 (s, 9H).

LCMS m/z 818 (M+H)$^+$ (ES$^+$)

Method 2

(I) Ethyl 2-[2-(2-benzyloxyethoxy)ethoxy]acetate

To a 5 L flask under nitrogen was added 60% NaH (73.5 g, 1.8375 mol) and THF (2.3 L). The resulting slurry was cooled to 0-5° C. 2-(2-Benzyloxyethoxy)ethanol (300 g, 1.5287 mol) dissolved in THF (700 mL) was then added dropwise over 1 h. Exotherm and gas evolution was observed throughout addition and as the reaction proceeded. The reaction was stirred for 40 mins. Ethyl bromoacetate (207 mL, 1.8375 mol) was then added, dropwise over 1 h, maintaining the temperature <5° C. As the reaction proceeded the mixture turned yellow in colour. The reaction was stirred for 2 h and allowed to warm to rt. LC showed 68% product and 1.6% starting material. To the reaction was added TBME (1 L) and water (1 L). The organics were separated and the aqueous phase re-extracted with TBME (2 L and 1 L). The combined organics were dried, filtered and concentrated in vacuo. The residue (462 g) was purified on silica (3 kg) eluting with 10% EtOAc:heptane (20 L), 20% EtOAc:heptane (10 L), 25% EtOAc:heptane (20 L) and 30% EtOAc:heptane (10 L). The product-containing fractions were concentrated in vacuo to give 322.6 g (74% yield) of the sub-title compound, for which $^1$H NMR analysis indicated a purity of >95%.

$^1$H NMR (400 MHz, CDCl$_3$) δ: 7.25-7.37 (m, 5H), 4.58 (s, 2H), 4.22 (q, 2H), 4.16 (s, 2H), 3.63-3.76 (m, 8H), 1.28 (t, 3H).

(II) Ethyl 2-[2-(2-hydroxyethoxy)ethoxy]acetate

To a 5 L flask under nitrogen was charged 10% Pd/C (32 g), this was followed by the addition of the product of step (I) above (320 g, 1.133 mol) dissolved in EtOH (3.2 L). The reaction was purged with hydrogen for 4 h and then stirred under a hydrogen atmosphere overnight. $^1$H NMR indicated 2.5% starting material remaining, and so the reaction was purged with hydrogen for 2 h. $^1$H NMR then indicated complete reaction. The reaction mixture was filtered through Celite and washed with ethanol (1 L). The filtrate was concentrated in vacuo to give the sub-title compound. The residue was then concentrated in vacuo from toluene (300 mL) and DCM (2×300 mL) to remove any traces of ethanol which may react in the next stage. A total of 217.8 g of the sub-title compound (100% yield) was obtained, accounting for solvent.

Alternatively, the sub-title compound was prepared by the following method: To a 20 L vessel under nitrogen was charged 10% Pd/C (100 g), this was followed by the addition of the product of step (I) above (1003 g), dissolved in DCM (10.3 L). The reaction was stirred under a hydrogen atmosphere overnight, after which NMR analysis indicated complete reaction. The mixture was filtered through celite and washed with DCM (3×1 L). This product thereby obtained was used directly in the next step (mesylation reaction) without further purification (to give an 86% yield over steps (II) and (III)).

$^1$H NMR (400 MHz, CDCl$_3$) δ: 4.23 (q, 2H), 4.13 (s, 2H), 3.68-3.77 (m, 6H), 3.59-3.63 (m, 2H), 2.51-2.57 (br m, 1H), 1.28 (t, 3H).

(III) Ethyl 2-[2-(2-methylsulfonyloxyethoxy)ethoxy]acetate

To a 10 L flask under nitrogen was added the product of step (II) above (219 g, 1.139 mol), DCM (4.4 L) and triethylamine (326 mL, 2.349 mol). The solution turned yellow on addition of the triethylamine. The solution was cooled to 0-5° C. and methanesulfonyl chloride (108.5 mL, 1.4 mol) was added dropwise. The reaction was allowed to warm to 8° C., at which point TLC of the reaction mixture indicated complete reaction. The reaction was concentrated in vacuo. The residue was partitioned between ethyl acetate (4.4 L) and water (2 L). The organics were separated and washed with sat. aqueous NaHCO$_3$ (2 L) and brine (2 L). The aqueous phase was back extracted with ethyl acetate (1 L). The combined organics were dried, filtered and concentrated in vacuo to give the sub-title compound as a red oil (297 g, 97%).

(IV) Ethyl 2-(2-(2-(3-methoxy-5-nitrophenoxy)ethoxy)ethoxy)acetate

To a 5 L flange flask under nitrogen was added 3-methoxy-5-nitrophenol (126.8 g, 0.749 mol), potassium carbonate (288 g, 2.086 mol), DMF (2536 mL) and the product of step (III) above (198.4 g active, 0.7348 mol). The reaction was heated to 60° C. overnight. LC indicated 95.8% product and 1.45% starting material (3-methoxy-5-nitrophenol). The reaction was cooled to rt and the reaction mixture transferred to a 20 L flask. To the mixture was added TBME (10 L) and water (6 L). The organics were separated and washed with sat. aqueous NaHCO$_3$ (6 L) and sat. brine (6 L) before drying, filtering and concentrating in vacuo to yield a total of 243 g of the sub-title compound, accounting for solvent (95% yield). LC indicated a purity of 97.7% (254 nm).

(V) Ethyl 2-(2-(2-(3-amino-5-methoxyphenoxy)ethoxy)ethoxy)acetate

To a 5 L hydrogenation vessel was charged 5% Pd/C (48.6 g), the product of step (IV) above (243 g, 0.708 mol) and ethanol (2.5 L). The vessel was purged with nitrogen three times and then stirred under a hydrogen atmosphere at 5 bar (0.5 MPa) (purged three times with hydrogen) for 6 h. LC indicated complete reaction. The mixture was filtered and washed with ethanol (1200 mL). The organics were then concentrated in vacuo. The residue was then concentrated from heptane (2×500 mL). This gave 212 g (96% yield) of the sub-title compound, for which LC indicated a purity of 98.1% (254 nm). $^1$H NMR indicated a purity of >95%.

(VI) Ethyl 2-(2-(2-(3-((4-((4-(((tert-butoxycarbonyl) amino)naphthalen-1-yl)oxy)pyridin-2-yl)-amino)-5-methoxyphenoxy)ethoxy)ethoxy)acetate To a 5 L flange flask under nitrogen was added the product of step (V) above (190 g, 0.6065 mol), tert-butyl (4-((2-chloropyridin-4-yl)oxy)naphthalen-1-yl)carbamate (see, for example, WO 2014/162126; 246.9 g, 0.6658 mol), DMF (3.4 L) and potassium carbonate (272 g, 1.97 mol). The reaction was vacuum degassed three times and released to nitrogen each time. The resulting slurry was heated to 40° C. and then Brettphos G3 Pd (13.66 g, 0.015 mol) was added. The mixture was then heated to 70° C. and stirred for 30 mins. LC indicated <1% of the product of step (V) above remaining. This was confirmed by NMR. The reaction was cooled to rt and filtered, then the solid was washed with DMF (700 mL). The filtrate was then concentrated in vacuo. The residue was dissolved in ethyl acetate (6 L) and washed with sat. brine (2×4 L). The organics were then dried, filtered and concentrated in vacuo. This gave 393 g (100% yield, accounting for solvent) of the sub-title compound, for which NMR indicated a purity of ~95% and LC indicated a purity of 94.5% (254 nm).

Alternatively, the sub-title compound was prepared by the following method:

To a 50 L vessel under nitrogen was charged the product of step (V) above (967 g) and THF (17425 mL). This was followed by tert-butyl (4-((2-chloropyridin-4-yl)oxy)naphthalen-1-yl)carbamate (see, for example, WO 2014/162126; 1254 g) and potassium carbonate (1387 g). The vessel was vacuum degassed (×3) and released to nitrogen (×3). The reaction was then charged with Pd-173 (39.2 g). The reaction was heated to reflux overnight, after which LC analysis indicated trace starting material. The reaction was cooled to 60° C. and further Pd-173 (6.13 g) was added. The reaction was heated to reflux for 1 h, after which LC analysis indicated complete reaction. The reaction mixture was filtered and the residue washed with THF (9.2 L). The filtrate was concentrated in vacuo and the residue concentrated from ethyl acetate and heptane to remove the residual THF. The material was then purified via chromatography (12 kg silica), eluting with 50% ethyl acetate:heptane (60 L), 70% ethyl acetate:heptane (60 L) and 85% ethyl acetate:heptane (20 L). This gave 1896 g (95% yield, accounting for solvent (EtOAc)) of the sub-title compound, for which NMR indicated a purity of >95%, excluding solvent, and LC indicated a purity of 97.4%.

$^1$H NMR (400 MHz, CDCl$_3$) δ: 8.06 (d, 1H), 7.96 (d, 2H), 7.80-7.88 (br d, 1H), 7.48-7.60 (m, 2H), 7.20 (d, 1H), 6.98 (br s, 1H), 6.61 (s, 1H), 6.38-6.41 (m, 4H), 6.13 (m, 1H), 4.10-4.24 (m, 4H), 3.90-3.94 (m, 2H), 3.77-3.83 (m, 6H), 3.68 (s, 3H), 1.57 (s, 9H), 1.24-1.30 (m, 3H).

(VII) Ethyl 2-(2-(2-(3-((4-((4-aminonaphthalen-1-yl)oxy)pyridin-2-yl)amino)-5-methoxy-phenoxy) ethoxy)ethoxy)acetate To a 5 L flange flask under nitrogen was added the product of step (VI) above (393 g, 0.6067 mol), DCM (1.742 L) and TFA (350 mL, 4.57 mol). The reaction was heated to 30° C. overnight, after which LC analysis indicated 18% starting material remaining. TFA (100 mL) was added to the reaction, which was then heated to reflux for 2 h. LC indicated 1.2% starting material remaining. The reaction was cooled to rt and concentrated in vacuo. The residue was azeotroped with toluene (1 L). The residue was diluted with ethyl acetate (3 L) and treated carefully with sat aqueous NaHCO$_3$ (4 L), at which point off-gassing was observed. The organics were separated and washed with more sat. aqueous NaHCO$_3$ (2 L). The combined aqueous phase was basic as required. The aqueous phase was extracted with ethyl acetate (1 L). The combined organics were dried, filtered and concentrated in vacuo. The residue was subjected to chromatography (4.5 kg silica), eluting with DCM to 5% MeOH:DCM. The product-containing fractions were combined and concentrated in vacuo. A total of 292 g of the sub-title compound (accounting for DCM) was obtained (80% yield), for which $^1$H NMR analysis indicated >95% purity and LC indicated a purity of 98.5% (254 nm).

(VIII) Ethyl 2-(2-(2-(3-methoxy-5-((4-((4-((phenoxycarbonyl)amino)naphthalen-1-yl)oxy)pyridin-2-yl)amino)phenoxy)ethoxy)acetate To a 50 L vessel was charged the product of step (VII) above (1478 g of that product contained ~10% THF) and THF (20.825 L). This was followed by the addition of NaHCO$_3$ (339.7 g). The mixture was cooled to −10° C. and charged with phenyl chloroformate (338.5 mL). The reaction was stirred for 1 h, after which LC indicated 97.5% product and 0.9% starting material. The reaction was then warmed to rt, at which point LC indicated 98% product and 0.32% starting material. The reaction mixture was filtered and washed with THF (2.5 L). The residue was concentrated to 2.6 kg before being dissolved in ethyl acetate:THF (2.9 L:262 mL) and then added by vacuum transfer to a 50 L vessel containing heptane (26.715 L). This led to precipitation of the product. The mixture was stirred for 2 h and filtered. The solids were then dried under vacuum at 40° C. overnight. A total of 1843 g (102% yield, accounting for solvent) of the sub-title compound was obtained, for which NMR indicated a purity of >95%, excluding solvents, and LC indicated a purity of 95.9%.

$^1$H NMR (400 MHz, (CD$_3$)$_2$SO) δ: 10.00-10.40 (br, 2H), 8.28 (d, 1H), 8.01 (d, 1H), 7.83 (d, 1H), 7.77 (d, 1H), 7.60-7.71 (m, 2H), 7.39-7.50 (m, 3H), 7.22-7.28 (m, 3H), 6.78 (dd, 1H), 6.56 (s, 1H), 6.49 (s, 1H), 6.24-6.29 (m, 2H), 4.02-4.09 (4H), 3.96-3.99 (m, 2H), 3.62-3.69 (m, 5H), 3.50-3.58 (m, 4H), 1.14 (t, 3H).

(IX) Ethyl 2-(2-(2-(3-((4-((4-(3-(5-(tert-butyl)-2-methoxy-3-(methylsulfonamido)phenyl)-ureido) naphthalen-1-yl)oxy)pyridin-2-yl)amino)-5-methoxyphenoxy)ethoxy)ethoxy)acetate To a 10 L flask under nitrogen was added the product of step (VII) above (262.8 g, 0.4799 mol), dissolved in iPrOAc (3.15 L). The mixture was heated to 40° C. and phenyl N-(5-(tert-butyl)-2-methoxy-3-((methylsulfonyl)amino) phenyl)carbamate (see, for example, WO 2014/162126; 197.1 g, 0.5022 mol) was added. The mixture was further heated to 50° C. to give a solution which was subsequently treated with triethylamine (13.14 mL, 0.094 mol) and the reaction heated to 68° C. overnight. The reaction was cooled to rt and concentrated in vacuo. A portion of the residue (38 g) was purified via chromatography eluting with 25% EtOAc:DCM to EtOAc. The product containing fractions were concentrated in vacuo, and LC analysis (at 254 nm) indicated a purity of 98.6% for the remainder. This material was combined with the bulk and purified on silica (10 kg) eluting with 25% EtOAc:DCM (80 L), DCM (20 L), 1% MeOH:DCM (20 L), 3% MeOH:DCM (20 L) and 5% MeOH:DCM (50 L). The product containing fractions were combined and concentrated in vacuo. This gave 375 g of material with a LC purity of 95.4% and NMR purity of ~90%. This material further purified via chromatography (10 kg silica). The column was eluted with 1% MeOH:DCM (60 L), 1.5% MeOH:DCM (20 L), 2% MeOH:DCM (20 L), 2.5% MeOH:DCM (20 L), 3% MeOH:DCM (40 L) then 5% MeOH:DCM (40 L). The purest fractions were combined and concentrated in vacuo to give 324 g of the sub-title compound, for which LC analysis (at 254 nm) indicated a purity of 98.9% and NMR indicated a purity of ~95%.

Alternatively, the sub-title compound was prepared by the following method:

The product of step (VIII) above (1902 g) and THF (19.02 L) were charged to a reaction vessel. The reaction was then charged with N-(3-amino-5-(tert-butyl)-2-methoxyphenyl) methanesulfonamide (see, for example, Cirillo, P. F. et al., WO 2002/083628, 24 Oct. 2002; 815 g) and triethylamine (380.4 mL). The reaction was heated to reflux overnight, after which LC analysis indicated complete reaction (86% product and 0.4% starting material). The reaction was cooled to rt and filtered to remove triethylamine hydrochloride. The solids were washed with THF (3.8 L). The filtrate was split into 3 equal portions and concentrated. The portions were then concentrated from 40% ethyl acetate:heptane (3 L) to remove the majority of THF, which would affect column chromatography. Each of the three portions was purified via chromatography (10 kg silica per portion, with the crude material loaded on to the column with 2 L of DCM), eluting with 75% ethyl acetate:heptane (20 L), 80% ethyl acetate:heptane (120 L) and then 85% ethyl acetate:heptane (40 L). This gave material with a 98.0% purity by LC and a purity by NMR analysis of >95%, excluding solvents. The sub-title compound was isolated in 83% yield (687 g).

$^1$H NMR (400 MHz, (CD$_3$)$_2$SO) δ: 9.38 (s, 1H), 9.15 (s, 1H), 8.92 (s, 1H), 8.88 (s, 1H), 8.29 (d, 1H), 8.19 (d, 1H), 8.09-8.13 (m, 2H), 7.86 (d, 1H), 7.70 (t, 1H), 7.60 (t, 1H), 7.38 (d, 1H), 7.02 (d, 1H), 6.90 (s, 1H), 6.79 (s, 1H), 6.57 (dd, 1H), 6.02-6.08 (m, 2H), 4.09-4.13 (m, 4H), 3.96-3.99 (m, 2H), 3.80 (s, 3H), 3.69-3.72 (m, 2H), 3.58-3.65 (m, 7H), 3.10 (s, 3H), 1.27 (s, 9H), 1.18 (t, 3H).

(X) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy) ethoxy)ethoxy)acetic acid To a 10 L flask under nitrogen was added the product of step (IX) above (317 g, 0.374 mol), THF (2.54 L) and methanol (950 mL). This was followed by the addition of 2 M NaOH (633 mL, 1.266 mol), at which point a small exotherm was noted. The reaction was stirred for 1 h. LC analysis indicated complete reaction. To the reaction was added acetic acid (633 mL), which again caused a small exotherm to be noted. The reaction mixture was then concentrated in vacuo to give a viscous oil. Water (3.2 L) was added and the mixture stirred for 20 mins. Initially an oily solid stuck to side of flask, this was scraped from the side of the vessel with a spatula, the solid became a mobile, flocculent solid. The solid was filtered and washed with water (500 mL) and heptane (1.5 L). The solid was then dried overnight under vacuum at 50° C., before being dissolved in 10% methanol:DCM and subjected to chromatography (6 kg silica) eluting with 10% methanol:DCM (60 L), 20% methanol:DCM (60 L) then methanol. The cleanest fractions were combined and concentrated in vacuo to give a viscous oil. The residue was concentrated from THF (2×2 L) to give a foamy solid. The solid (297 g) contained 8.55% THF and 2.29% AcOH. The material was slurried in water (900 mL) overnight twice and filtered to give 268 g of the title compound (262 g, accounting for solvent, 85% yield) with a purity of 98.2% by LC analysis and a purity of >95% by NMR. The material contained 2.11% THF and 0.26% AcOH.

Example 4

The following compounds are prepared by methods analogous to those described above.

(a) 2-(2-(2-((3-((4-((4-(3-(5-(tert-butyl)-2-methoxy-3-(methylsulfonamido)phenyl)ureido)-naphthalen-1-yl)oxy)pyridin-2-yl)amino)-5-methoxyphenyl)sulfonyl)ethoxy)ethoxy)acetic acid

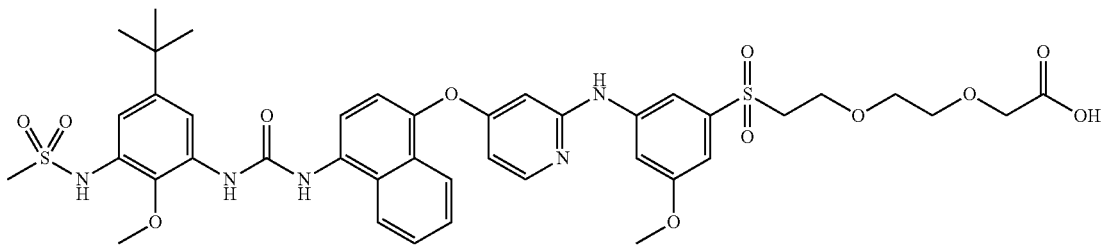 [SMILES: COc1cc(Nc2cc(Oc3ccc(NC(=O)Nc4cc(C(C)(C)C)cc(NS(C)(=O)=O)c4OC)c4ccccc34)ccn2)cc(S(=O)(=O)CCOCCOCC(=O)O)c1]

(b) 2-(2-(2-((3-((4-((4-(3-(5-(tert-butyl)-2-methoxy-3-(methylsulfonamido)phenyl)ureido)-naphthalen-1-yl)oxy)pyridin-2-yl)amino)-5-methoxyphenyl)sulfinyl)ethoxy)ethoxy)acetic acid

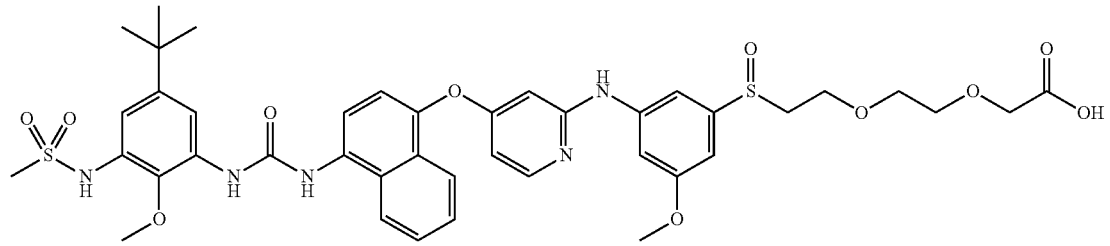 [SMILES: COc1cc(Nc2cc(Oc3ccc(NC(=O)Nc4cc(C(C)(C)C)cc(NS(C)(=O)=O)c4OC)c4ccccc34)ccn2)cc(S(=O)CCOCCOCC(=O)O)c1]

(c) 2-(2-(2-((3-((4-((4-(3-(5-(tert-butyl)-2-methoxy-3-(methylsulfonyl)phenyl)ureido)-naphthalen-1-yl)oxy)pyridin-2-yl)amino)-5-methoxyphenyl)sulfonyl)ethoxy)ethoxy)acetic acid

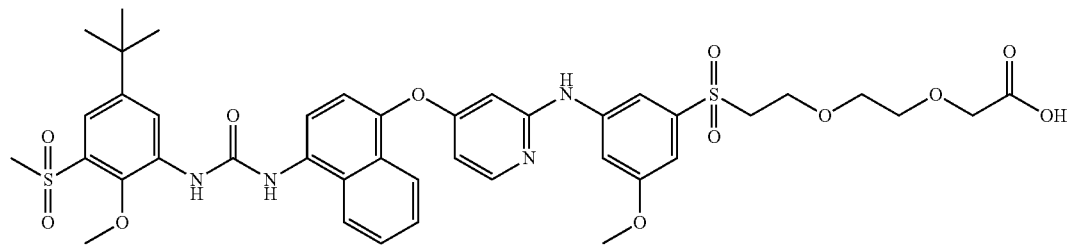 [SMILES: COc1cc(Nc2cc(Oc3ccc(NC(=O)Nc4cc(C(C)(C)C)cc(S(C)(=O)=O)c4OC)c4ccccc34)ccn2)cc(S(=O)(=O)CCOCCOCC(=O)O)c1]

(d) 2-(2-(2-((3-((4-((4-(3-(5-(tert-butyl)-2-methoxy-3-(methylsulfinyl)phenyl)ureido)-naphthalen-1-yl)oxy)pyridin-2-yl)amino)-5-methoxyphenyl)sulfonyl)ethoxy)ethoxy)acetic acid

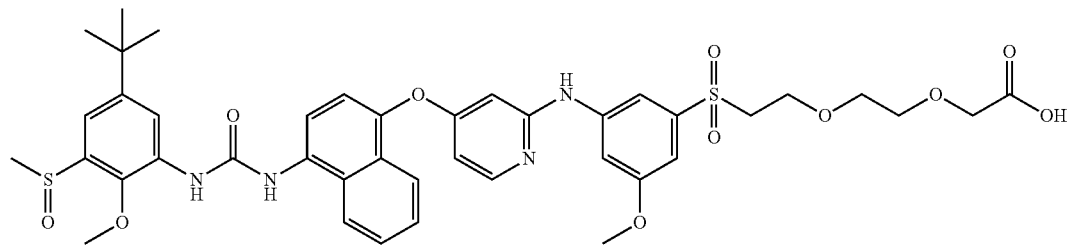 [SMILES: COc1cc(Nc2cc(Oc3ccc(NC(=O)Nc4cc(C(C)(C)C)cc(S(C)=O)c4OC)c4ccccc34)ccn2)cc(S(=O)(=O)CCOCCOCC(=O)O)c1]

(e) 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-(trifluoromethyl)phenoxy)ethoxy)ethoxy)acetic acid

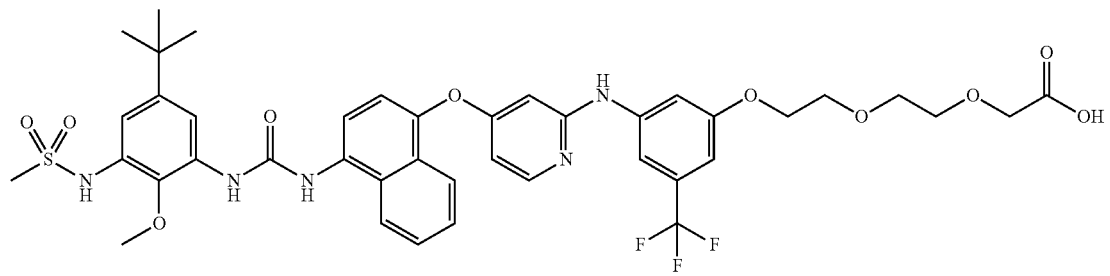 [SMILES: COc1c(NC(=O)Nc2ccc(Oc3ccnc(Nc4cc(OCCOCCOCC(=O)O)cc(C(F)(F)F)c4)c3)c3ccccc23)cc(C(C)(C)C)cc1NS(C)(=O)=O]

(f) 6-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)pyridazine-3-carboxylic acid

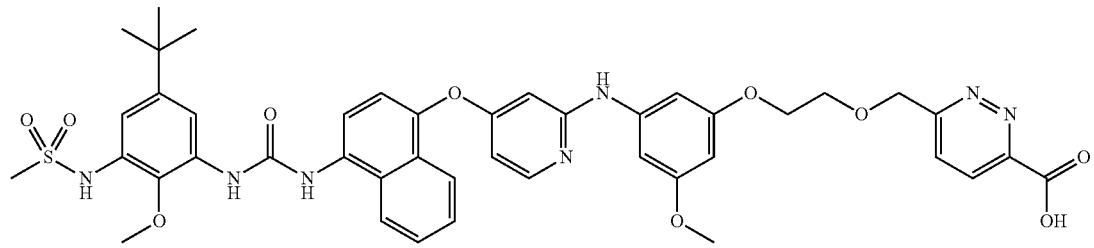 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCc2ccc(C(=O)O)nn2)c1]

(g) 5-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)-1,2,4-oxadiazole-3-carboxylic acid

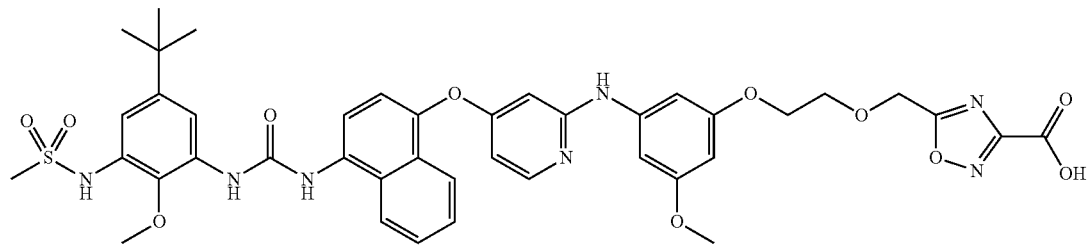 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCc2nc(C(=O)O)no2)c1]

(h) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-cyclopropoxyphenoxy)ethoxy)ethoxy)acetic acid

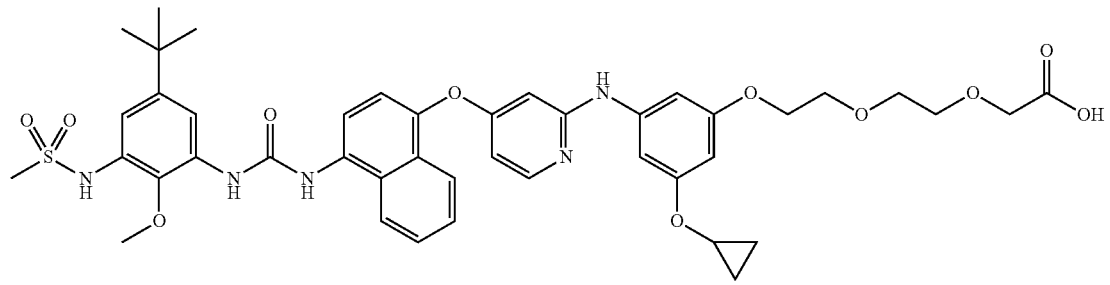 [SMILES: COc1c(NC(=O)Nc2ccc(Oc3ccnc(Nc4cc(OCCOCCOCC(=O)O)cc(OC5CC5)c4)c3)c3ccccc23)cc(C(C)(C)C)cc1NS(C)(=O)=O]

(i) 1-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)cyclopropane-1-carboxylic acid

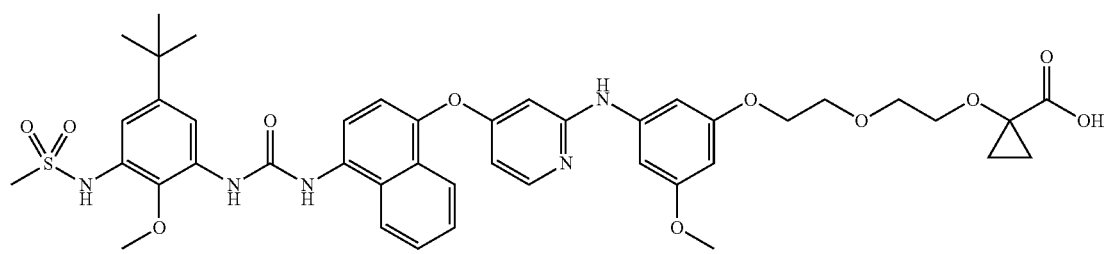 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOC2(C(=O)O)CC2)c1]

(j) 4-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)thiophene-2-carboxylic acid

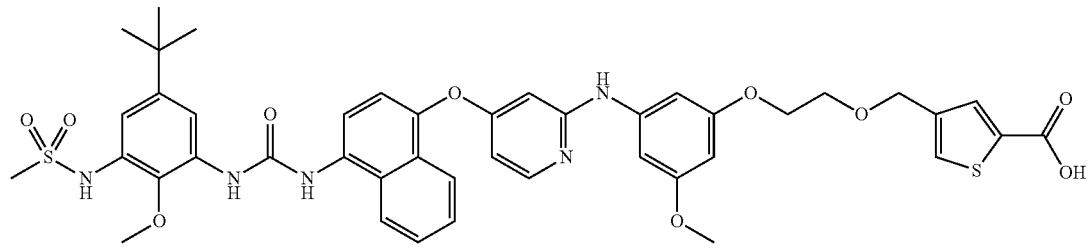 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCc2csc(C(=O)O)c2)c1]

(k) 1-((2-(3-((4-((4-(3-(5-(tert-butyl)-2-methoxy-3-(methylsulfonamido)phenyl)ureido)naphthalen-1-yl)oxy)ethoxy)methyl)thiophene-2-methoxyphenoxy)ethoxy)methyl)-3-methyl-1H-pyrazole-4-carboxylic acid

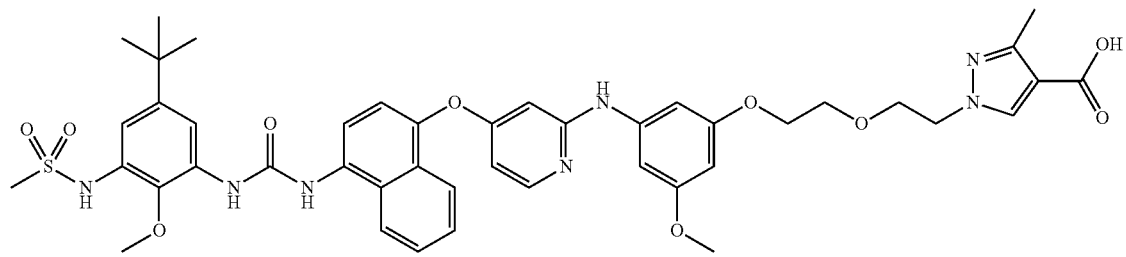 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCn2cc(C(=O)O)c(C)n2)c1]

(l) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-ethylphenoxy)ethoxy)ethoxy)acetic acid

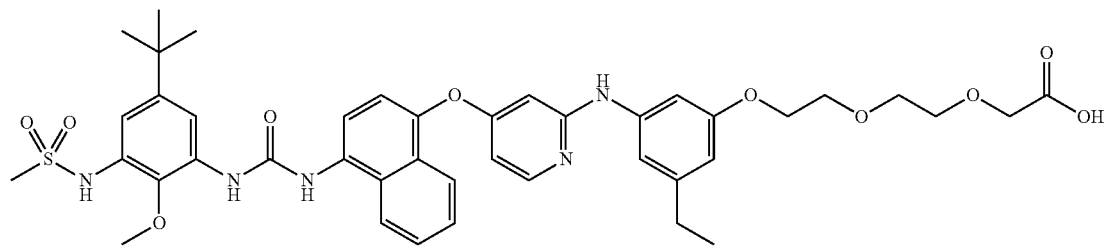 [SMILES: CCc1cc(Nc2cc(Oc3ccc(NC(=O)Nc4cc(C(C)(C)C)cc(NS(C)(=O)=O)c4OC)c4ccccc34)ccn2)cc(OCCOCCOCC(=O)O)c1]

Example 5

2-(2-(2-(3-((4-((4-(3-(5-(tert-Butyl)-2-(methoxy-d3)-3-(methylsulfonamido)phenyl)ureido)-naphthalen-1-yl)oxy)ethoxy)pyridin-2-yl)amino)-5-methoxyphenoxy)ethoxy)ethoxy) acetic acid

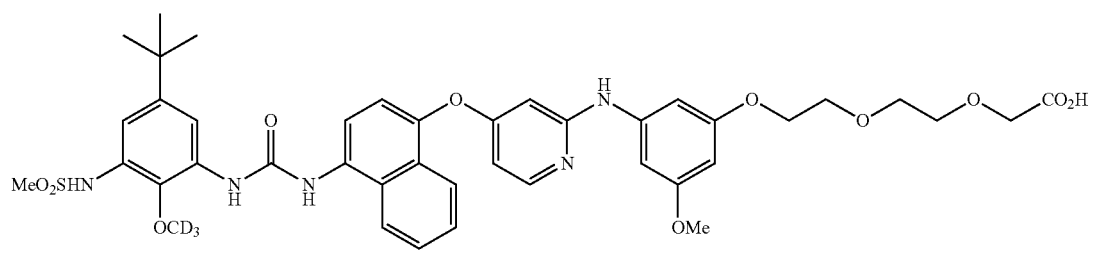

(i) 5-(tert-butyl)-2-(methoxy-d3)-1,3-dinitrobenzene

A mixture of 4-(tert-butyl)-2,6-dinitrophenol (5 g, 20.81 mmol), caesium carbonate (13.56 g, 41.6 mmol) and iodomethane-d3 (1.6 mL, 25.7 mmol) in DMF (50 mL) was stirred at rt for 4 days then partitioned between ether (300 mL) and water (300 mL). The organic layer was separated, washed with water (200 mL), dried (MgSO$_4$), filtered and evaporated under reduced pressure to afford the sub-title compound (4.3 g) as a yellow solid.

$^1$H NMR (400 MHz, CDCl$_3$) δ 8.04 (s, 2H), 1.40 (s, 9H).

(ii) 5-(tert-Butyl)-2-(methoxy-d3)-3-nitroaniline

10% Pd/C (500 mg, Type 39, 50% w/w paste with water) was added to a solution of the product from step (i) above (4.25 g, 16.52 mmol) and cyclohexene (2.5 mL, 24.68 mmol) in EtOH (70 mL). The reaction mixture was heated at 70° C. for 1 h then a further portion of cyclohexene (5 mL) was added. After heating for 1 h, a third portion of cyclohexene (5 mL) was added, heated for 2 h then the reaction mixture cooled and filtered through celite. The filtrate was evaporated under reduced pressure and the residue dissolved in EtOAc/ether (300 mL, 1/1), washed with 0.2M aq HCl (2×150 mL), brine (200 mL), dried (MgSO$_4$), filtered and evaporated under reduced pressure to afford the sub-title compound (3.43 g) as a yellow oil.

$^1$H NMR (400 MHz, CDCl$_3$) δ 7.27 (d, 1H), 7.05 (d, 1H), 1.31 (s, 9H).

m/z 228 (M+H)$^+$ (ES$^+$)

(iii) N-(5-(tert-Butyl)-2-(methoxy-d3)-3-nitrophenyl)methanesulfonamide

To a stirred solution of the product from step (ii) above (3.42 g, 15.05 mmol) in DCM (25 mL) at 0-5° C., was added pyridine (7 mL, 87 mmol) then MsCl (1.9 mL, 24.38 mmol). The mixture was warmed to rt and stirred for 3 days. The mixture was poured into 1 M HCl (200 mL) and extracted with DCM (200 mL). The organic phase was washed with 1 M HCl (100 mL) and brine (100 mL), then dried (MgSO$_4$), filtered and concentrated in vacuo. The crude product was purified by chromatography on silica gel (120 g column, 0-40% EtOAc/isohexane) to afford the sub-title compound (3.9 g) as a solid.

$^1$H NMR (400 MHz, CDCl$_3$) δ 7.88 (s, 1H), 7.66 (s, 1H), 7.06 (s, 1H), 3.09 (s, 3H), 1.36 (s, 9H).

(iv) N-(3-Amino-5-(tert-butyl)-2-(methoxy-d3)phenyl)methanesulfonamide

A mixture of the product from step (iii) above (3.85 g, 12.61 mmol) and 10% Pd—C (500 mg) in EtOH (40 mL) was hydrogenated at 5 bar for 4 h. The mixture was filtered through celite, washing with EtOAc. The filtrate was evaporated under reduced pressure to give a solid that was triturated with ether/isohexane. The solid was filtered and dried to afford the sub-title compound (2.92 g) as a white solid.

$^1$H NMR (400 MHz, DMSO-d6) δ 8.70 (s, 1H), 6.58 (s, 2H), 4.91 (s, 2H), 3.00 (s, 3H), 1.20 (s, 9H).

m/z 276 (M+H)$^+$ (ES$^+$)

(v) Phenyl (5-(tert-butyl)-2-(methoxy-d3)-3-(methylsulfonamido)phenyl)carbamate Phenyl chloroformate (470 μL, 3.75 mmol) was added to a mixture of the product from step (iv) above (1 g, 3.63 mmol) and NaHCO$_3$ (0.610 g, 7.26 mmol) in DCM (20 mL) and THF (10 mL). The mixture was stirred for 20 h then THF (10 mL) was added followed by phenyl chloroformate (150 μL). The mixture was stirred for 5 h then partitioned between DCM (100 mL) and water (50 mL). The organic layer was separated, dried (MgSO$_4$), filtered and evaporated under reduced pressure. The residue was triturated with ether/isohexane, filtered and dried to afford the sub-title compound (1.415 g, 3.54 mmol, 98% yield) as a white solid.

$^1$H NMR (400 MHz, CDCl$_3$) δ 8.01 (bs, 1H), 7.46-7.42 (m, 2H), 7.35 (bs, 1H), 7.32-7.27 (m, 2H), 7.25-7.21 (m, 2H), 6.78 (s, 1H), 3.11 (s, 3H), 1.32 (s, 9H).

m/z 396 (M+H)$^+$ (ES$^+$)

(vi) Ethyl 2-(2-(2-(3-((4-((4-(3-(5-(tert-butyl)-2-(methoxy-d3)-3-(methylsulfonamido)phenyl)-ureido)naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 200 mg, 0.365 mmol) and the product from step (v) above (152 mg, 0.383 mmol) were dissolved in iPrOAc (3 mL, 25.6 mmol) and NEt$_3$ (10.1 μL, 0.073 mmol) added. The mixture was stirred at 75° C. for 16 h and concentrated in vacuo. Crude LCMS showed the sub-title compound to be the major component.

m/z 849.3 (M+H)$^+$ (ES$^+$)

The crude product was purified by chromatography on silica gel (12 g column, 0-5% MeOH/DCM) to afford a white solid (213 mg) that was used directly in step (ii) below.

(vii) 2-(2-(2-(3-((4-((4-(3-(5-(tert-Butyl)-2-(methoxy-d3)-3-(methylsulfonamido)phenyl) ureido)-naphthalen-1-yl)oxy)pyridin-2-yl)amino)-5-methoxyphenoxy)ethoxy)ethoxy) acetic acid A stirred solution of the product from step (vi) above (213 mg, 0.251 mmol) in THF (10 mL) and EtOH (4 mL) was treated with NaOH (2M aq.) solution (0.452 mL, 0.903 mmol) and stirred at rt overnight. the mixture was treated with AcOH (0.5 mL, 8.73 mmol) and concentrated in vacuo. The residue was triturated with water (10 mL) and filtered. The filtrate was treated with formic acid (0.2 mL) and left to precipitate for 48 h then filtered. The combined solids were taken on to purification.

A total of 208 mg crude product was purified by chromatography (RP Flash C18, 26 g column, 15-50% MeCN/10 mM Ammonium Bicarbonate) to afford the title compound (128 mg) as a light pink solid.

$^1$H NMR (400 MHz, DMSO-d6) δ 9.39 (s, 1H), 9.14 (s, 1H), 8.92 (s, 1H), 8.88 (s, 1H) 8.30 (d, 1H), 8.19 (d, 1H), 8.11 (dd, 2H), 7.87 (dd, 1H), 7.70 (ddd, 1H), 7.61 (ddd, 1H), 7.39 (d, 1H), 7.03 (d, 1H), 6.91 (t, 1H), 6.79 (t, 1H), 6.58 (dd, 1H), 6.08 (d, 1H), 6.04 (t, 1H), 4.05-3.95 (m, 4H), 3.71 (dd, 2H), 3.66 (s, 3H), 3.60 (s, 4H), 3.10 (s, 3H), 1.27 (s, 9H).

m/z 821.3 (M+H)$^+$ (ES$^+$)

Example 6

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)-N-(methylsulfonyl)acetamide

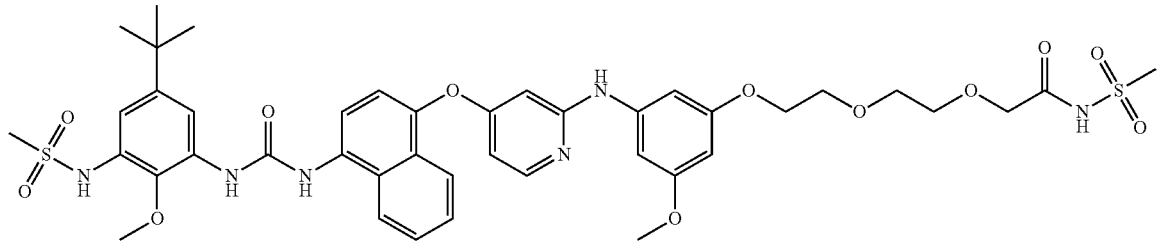

DIPEA (71.1 µL, 0.407 mmol) was added to a solution of 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid (see Example 3 above; 111 mg, 0.136 mmol) and methanesulfonamide (19.36 mg, 0.204 mmol) in dry DMF (2 mL) at rt, followed by HATU (77 mg, 0.204 mmol). The resulting yellow coloured solution was stirred at rt for 3 h. Further portions of methanesulfonamide (19.36 mg, 0.204 mmol), DIPEA (71.1 µL, 0.407 mmol) and HATU (77 mg, 0.204 mmol) were added to the reaction and the resulting solution stirred at rt for 1.5 h. The reaction was then partioned between EtOAc (10 mL) and water (10 mL). The aqueous layer was extracted with EtOAc (2×10 mL). The organic layers were combined, dried (MgSO$_4$) and concentrated in vacuo. The crude product was purified by chromatography (RP Flash C18,12 g column, 15-50% MeCN/10 mM Ammonium Bicarbonate). The product-rich fractions were combined, the pH adjusted to 4 with formic acid and the solvent removed in vacuo The resulting solid was dried at 40° C. under vacuum overnight to afford the title compound (11 mg) as a white solid.

$^1$H NMR (400 MHz, DMSO-d6) δ 9.40 (s, 1H), 8.92 (s, 1H), 8.87 (s, 1H), 8.30 (d, 1H), 8.19 (d, 2H), 8.12 (d, 1H), 8.10 (d, 1H), 7.87 (d, 1H), 7.70 (ddd, 1H), 7.61 (dd, 1H), 7.38 (d, 1H), 7.02 (d, 1H), 6.90-6.75 (m, 2H), 6.57 (dd, 1H), 6.09 (d, 1H), 6.05 (t, 1H), 3.96 (dd, 2H), 3.81 (s, 3H), 3.71-3.66 (m, 7H), 3.56 (s, 3H), 3.10 (s, 3H), 2.74 (s, 3H), 1.27 (s, 9H).

m/z 895.5 (M+H)$^+$ (ES$^+$)

Example 7

2-(2-(2-(3-((4-((4-(3-(5-(tert-Butyl)-2-methoxy-3-(methylcarbamoyl)phenyl)ureido)naphthalen-1-yl)oxy)pyridin-2-yl)amino)-5-methoxyphenoxy)ethoxy)ethoxy)acetic acid (i) Ethyl 2-(2-(2-(3-((4-((4-(3-(5-(tert-Butyl)-2-methoxy-3-(methylcarbamoyl)phenyl)ureido)-naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 125 mg, 0.228 mmol) was dissolved in iPrOAc (3 mL) at 50° C., and phenyl (5-(tert-butyl)-2-methoxy-3-(methylcarbamoyl)phenyl)carbamate (see WO 2014/162126; 85 mg, 0.240 mmol) added to the solution. The resulting mixture was stirred at 50° C. until the mixture became a solution (ca. 5 min) then NEt$_3$ (6.36 µL, 0.046 mmol) added. The resulting solution was heated to 75° C. (block temperature) and left to stir for 16 h. The reaction was cooled to rt and the solvent removed in vacuo. The crude product was purified by chromatography on silica gel (12 g column, 0-5% MeOH/DCM to afford the sub-title compound (161 mg) as a colourless glass.

$^1$H NMR (400 MHz, DMSO-d6) δ 9.47 (s, 1H), 8.88 (d, 2H), 8.44 (d, 1H), 8.29 (d, 1H), 8.17 (q, 1H), 8.14-7.99 (m, 2H), 7.87 (d, 1H), 7.71 (ddd, 1H), 7.61 (ddd, 1H), 7.39 (d, 1H), 7.11 (d, 1H), 6.91 (t, 1H), 6.79 (t, 1H), 6.57 (dd, 1H), 6.09 (d, 1H), 6.04 (t, 1H), 4.16-4.04 (m, 4H), 4.03-3.94 (m, 2H), 3.80 (s, 3H), 3.76-3.68 (m, 2H), 3.65 (s, 3H), 3.64-3.47 (m, 4H), 2.82 (d, 3H), 1.28 (s, 9H), 1.18 (t, 3H).

m/z 810.6 (M+H)$^+$ (ES$^+$)

(ii) 2-(2-(2-(3-((4-((4-(3-(5-(tert-Butyl)-2-methoxy-3-(methylcarbamoyl)phenyl)ureido)-naphthalen-1-yl)oxy)pyridin-2-yl)amino)-5-methoxyphenoxy)ethoxy)ethoxy) acetic acid NaOH (2M aq.) (350 µL, 0.700 mmol) was added to a solution of the compound from step (i) (161 mg, 0.199 mmol) in THF (1.6 mL) and MeOH (0.6 mL) and the resulting yellow solution stirred at rt for 3 h. The reaction was acidified with AcOH (82 µL, 1.427 mmol) and concentrated in vacuo. The crude product was purified by chromatography (RP Flash C18 24 g column, 15-75% MeCN/10 mM Ammonium Bicarbonate). The product-rich fractions were combined and the pH adjusted to pH 6 with formic

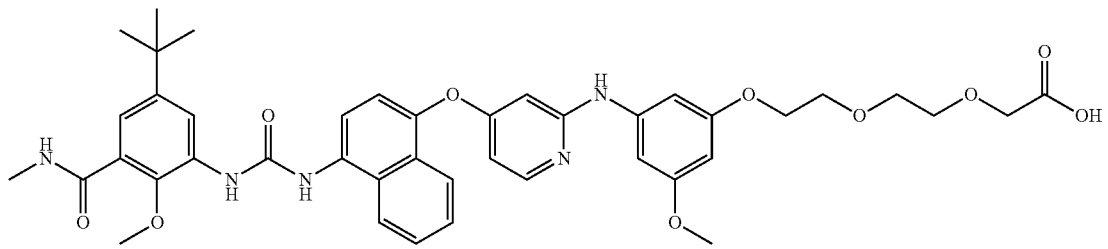 [SMILES: CNC(=O)c1cc(C(C)(C)C)cc(NC(=O)Nc2ccc(Oc3ccnc(Nc4cc(OC)cc(OCCOCCOCC(=O)O)c4)c3)c3ccccc23)c1OC]

acid. The volatile solvent was removed in vacuo. A precipitate formed and was collected by filtration to afford the title compound (70 mg) as a white solid.

¹H NMR (400 MHz, DMSO-d6) δ 12.57 (s, 1H), 9.46 (s, 1H), 8.88 (d, 2H), 8.44 (d, 1H), 8.29 (d, 1H), 8.17 (q, 1H), 8.11 (d, 1H), 8.08 (d, 1H), 7.87 (dd, 1H), 7.71 (ddd, 1H), 7.61 (ddd, 1H), 7.39 (d, 1H), 7.11 (d, 1H), 6.90 (t, 1H), 6.79 (t, 1H), 6.57 (dd, 1H), 6.09 (d, 1H), 6.04 (t, 1H), 4.03 (s, 2H), 3.98 (dd, 2H), 3.80 (s, 3H), 3.75-3.68 (m, 2H), 3.65 (s, 3H), 3.63-3.52 (m, 4H), 2.82 (d, 3H), 1.28 (s, 9H).

m/z 782.0 (M+H)⁺ (ES⁺)

Example 8

2-(2-(2-(3-((4-((4-(3-(5-(tert-Butyl)-2-methoxy-3-(methylsulfinyl)phenyl)ureido)naphthalen-1-yl)oxy)pyridin-2-yl)amino)-5-methoxyphenoxy)ethoxy)ethoxy)acetic acid

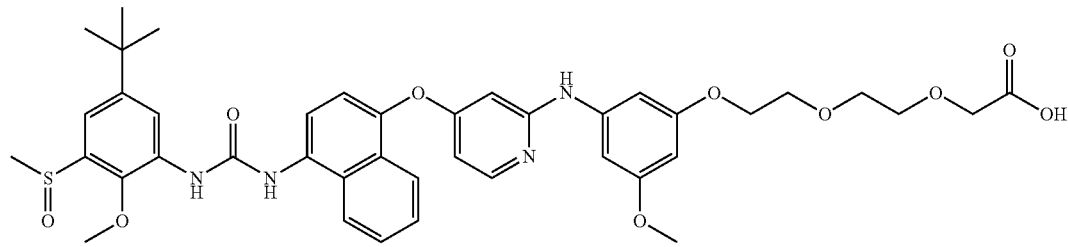 [SMILES: COc1cc(Nc2cc(Oc3ccc(NC(=O)Nc4cc(C(C)(C)C)cc(S(C)=O)c4OC)c4ccccc34)ccn2)cc(OCCOCCOCC(=O)O)c1]

(i) Ethyl 2-(2-(2-(3-((4-((4-(3-(5-(tert-butyl)-2-methoxy-3-(methylsulfinyl)phenyl)ureido)-naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 125 mg, 0.228 mmol) was dissolved in iPrOAc (2 mL) at 50 C, and phenyl (5-(tert-butyl)-2-methoxy-3-(methylsulfinyl)phenyl)carbamate (see WO 2015/092423; 87 mg, 0.240 mmol) added to the solution. The resulting mixture was stirred at 50° C. until the mixture became a solution (ca. 2 min) then NEt₃ (6.36 µL, 0.046 mmol) added. The resulting solution was heated to 75° C. (block temperature) and left to stir for 16 h. The reaction was cooled to rt and the solvent removed in vacuo. The crude product was purified by chromatography on silica gel (12 g column, 0-5% MeOH/DCM) to afford the sub-title compound (172 mg) as a colourless glass.

¹H NMR (400 MHz, DMSO-d6) δ 9.41 (s, 1H), 8.96 (s, 1H), 8.87 (s, 1H), 8.50 (d, 1H), 8.28 (d, 1H), 8.18-8.05 (m, 2H), 7.89-7.83 (m, 1H), 7.71 (ddd, 1H), 7.61 (ddd, 1H), 7.46-7.31 (m, 2H), 6.91 (t, 1H), 6.79 (t, 1H), 6.58 (dd, 1H), 6.09 (d, 1H), 6.04 (t, 1H), 4.18-4.06 (m, 4H), 4.03-3.93 (m, 2H), 3.87 (s, 3H), 3.76-3.67 (m, 2H), 3.66 (s, 3H), 3.63-3.55 (m, 4H), 2.79 (s, 3H), 1.32 (s, 9H), 1.18 (t, 3H).

m/z 815.5 (M+H)+ (ES+)

(ii) 2-(2-(2-(3-((4-((4-(3-(5-(tert-Butyl)-2-methoxy-3-(methylsulfinyl)phenyl)ureido)naphthalen-1-yl)oxy)pyridin-2-yl)amino)-5-methoxyphenoxy)ethoxy)ethoxy) acetic acid NaOH (2M aq.) (350 µL, 0.700 mmol) was added to a solution of the compound from step (i) above (172 mg, 0.211 mmol) in THF (1.6 mL) and MeOH (0.6 mL) and the resulting yellow solution stirred at rt for 3 h. The reaction was acidified with AcOH (82 µL, 1.427 mmol) and the solvent removed in vacuo. The crude product was purified by chromatography (RP Flash C18 12 g column, 15-50% MeCN/10 mM Ammonium Bicarbonate). The product-rich fractions were combined and the pH adjusted to pH 5 with formic acid. The solvent was removed to afford the title compound (130 mg) as a white solid.

¹H NMR (400 MHz, DMSO-d6) δ 9.51 (s, 1H), 9.03 (s, 1H), 8.88 (s, 1H), 8.50 (d, 1H), 8.30 (d, 1H), 8.14-8.03 (m, 2H), 7.87 (dd, 1H), 7.70 (ddd, 1H), 7.65-7.54 (m, 1H), 7.39 (d, 1H), 7.36 (d, 1H), 6.84 (s, 1H), 6.77 (t, 1H), 6.58 (dd, 1H), 6.10 (d, 1H), 6.03 (t, 1H), 3.99 (s, 2H), 3.94 (t, 2H), 3.86 (s, 3H), 3.70 (dd, 2H), 3.65 (s, 3H), 3.62-3.55 (m, 4H), 2.79 (s, 3H), 1.32 (s, 9H).

m/z 787.0 (M+H)⁺ (ES⁺)

Example 9

2-(2-(2-(3-((4-((4-(3-(5-(tert-Butyl)-2-methoxy-3-(methylsulfonyl)phenyl)ureido)-naphthalen-1-yl)oxy)pyridin-2-yl)amino)-5-methoxyphenoxy)ethoxy)ethoxy)acetic acid

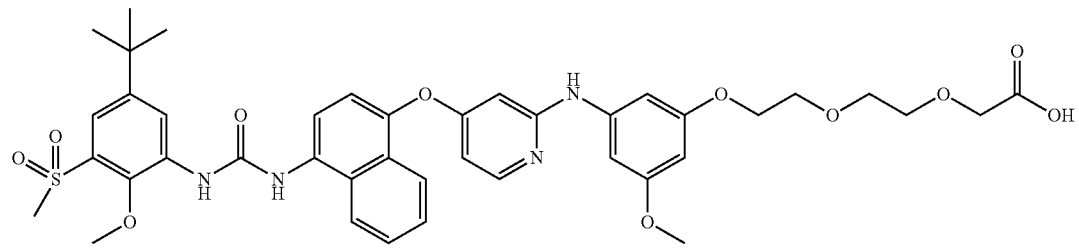 [SMILES: COc1cc(Nc2cc(Oc3ccc(NC(=O)Nc4cc(C(C)(C)C)cc(S(C)(=O)=O)c4OC)c4ccccc34)ccn2)cc(OCCOCCOCC(=O)O)c1]

(i) Ethyl 2-(2-(2-(3-((4-((4-(3-(5-(tert-butyl)-2-methoxy-3-(methylsulfonyl)phenyl)ureido)-naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate

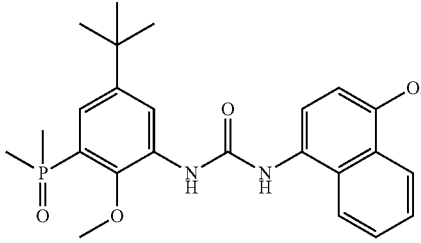

(see Example 3(ii) above; 125 mg, 0.228 mmol) was dissolved in iPrOAc (2 mL) at 50° C., and phenyl (5-(tert-butyl)-2-methoxy-3-(methylsulfonyl)phenyl)carbamate (see WO 2015/092423; 90 mg, 0.240 mmol) added to the solution. The resulting mixture was stirred at 50° C. for ca 5 min, then THF (1 mL) was added. The reactants went into solution then NEt$_3$ (6.36 µL, 0.046 mmol) added. The resulting solution was heated to 75° C. (block temperature) and left to stir for 16 h. The reaction was cooled to rt and the solvent removed in vacuo. The crude product was purified by chromatography on silica gel (12 g column, 0-5% MeOH/DCM) to afford the sub-title compound (151 mg) as a colourless glass.

$^1$H NMR (400 MHz, DMSO-d6) δ 9.46 (s, 1H), 9.08 (s, 1H), 8.87 (s, 1H), 8.68 (d, 1H), 8.29 (d, 1H), 8.12 (s, 1H), 8.10 (d, 1H), 7.88 (dt, 1H), 7.72 (ddd, 1H), 7.62 (ddd, 1H), 7.45 (d, 1H), 7.40 (d, 1H), 6.91 (t, 1H), 6.79 (t, 1H), 6.58 (dd, 1H), 6.09 (d, 1H), 6.04 (t, 1H), 4.19-4.06 (m, 4H), 4.04-3.97 (m, 2H), 3.95 (s, 3H), 3.78-3.69 (m, 2H), 3.66 (s, 3H), 3.64-3.55 (m, 4H), 3.35 (s, 3H), 1.32 (s, 9H), 1.18 (t, 3H).

LCMS m/z 831.5 (M+H)+ (ES+)

(ii) 2-(2-(2-(3-((4-((4-(3-(5-(tert-Butyl)-2-methoxy-3-(methylsulfonyl)phenyl)ureido)naphthalen-1-yl)oxy)pyridin-2-yl)amino)-5-methoxyphenoxy)ethoxy)ethoxy)acetic acid NaOH (2M aq.) (350 µL, 0.700 mmol) was added to a solution of the compound from step (i) (151 mg, 0.182 mmol) in THF (1.6 mL) and MeOH (0.6 mL) and the resulting yellow solution stirred at rt for 3 h. The reaction was acidified with AcOH (82 µL, 1.427 mmol) and the solvent removed in vacuo. The crude product was purified by chromatography (RP Flash C18 12 g column, 15-50% MeCN/10 mM Ammonium Bicarbonate). The product-rich fractions were combined and adjusted to pH 5 with formic acid. The solvent was removed to afford the title compound (114 mg) as a white solid.

$^1$H NMR (400 MHz, DMSO-d6) δ 12.62 (s, 1H), 9.49 (s, 1H), 9.10 (s, 1H), 8.87 (s, 1H), 8.68 (d, 1H), 8.29 (d, 1H), 8.14-8.05 (m, 2H), 7.95-7.80 (m, 1H), 7.72 (ddd, 1H), 7.62 (ddd, J=8.1, 1H), 7.45 (d, 1H), 7.40 (d, 1H), 6.89 (t, 1H), 6.78 (t, 1H), 6.58 (dd, 1H), 6.10 (d, 1H), 6.04 (t, 1H), 4.02 (s, 2H), 4.00-3.92 (m, 5H), 3.76-3.68 (m, 2H), 3.65 (s, 3H), 3.63-3.56 (m, 4H), 3.34 (s, 3H), 1.32 (s, 9H).

m/z 803.0 (M+H)+ (ES+)

Example 10

2-(2-(2-(3-((4-((4-(3-(5-(tert-Butyl)-3-(dimethylphosphoryl)-2-methoxyphenyl)ureido)-naphthalen-1-yl)oxy)pyridin-2-yl)amino)-5-methoxyphenoxy)ethoxy)ethoxy)acetic acid (i) Ethyl 2-(2-(2-(3-((4-((4-(3-(5-(tert-butyl)-3-(dimethylphosphoryl)-2-methoxyphenyl)ureido)-naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 125 mg, 0.228 mmol) was dissolved in iPrOAc (2 mL) at 50° C., and phenyl (5-(tert-butyl)-3-(dimethylphosphoryl)-2-methoxyphenyl)-carbamate (see WO 2015/092423; 90 mg, 0.240 mmol) added to the solution. The resulting mixture was stirred at 50° C. for ca. 5 min and THF (1 mL) added. NEt$_3$ (6.36 µL, 0.046 mmol) was added and the resulting mixture was heated to 75° C. (block temperature) and the resulting solution left to stir for 16 h at 75° C. The reaction was cooled to rt and the solvent removed in vacuo. The crude product was purified by chromatography on silica gel (12 g column, 0-10% MeOH/DCM) to afford the sub-title compound (169 mg) as a pale pink glass.

$^1$H NMR (400 MHz, DMSO-d6) δ 9.22 (s, 1H), 8.87 (s, 1H), 8.45 (s, 1H), 8.28 (d, 1H), 8.11 (d, 1H), 8.08-8.03 (m, 2H), 7.87 (d, 1H), 7.71 (t, 1H), 7.65-7.57 (m, 1H), 7.43-7.34 (m, 2H), 6.90 (t, 1H), 6.79 (t, 1H), 6.57 (dd, 1H), 6.09 (d, 1H), 6.04 (t, 1H), 4.19-4.05 (m, 4H), 4.03-3.94 (m, 2H), 3.71 (s, 2H), 3.65 (s, 3H), 3.64-3.53 (m, 4H), 2.58 (s, 3H), 1.78 (s, 3H), 1.75 (s, 3H), 1.30 (s, 9H), 1.18 (t, 3H).

m/z 829.5 (M+H)+ (ES+)

(ii) 2-(2-(2-(3-((4-((4-(3-(5-(tert-Butyl)-3-(dimethylphosphoryl)-2-methoxyphenyl)ureido)-naphthalen-1-yl)oxy)pyridin-2-yl)amino)-5-methoxyphenoxy)ethoxy)ethoxy)acetic acid NaOH (2M aq.) (350 µL, 0.700 mmol) was added to a solution of the compound from step (i) above (169 mg, 0.204 mmol) in THF (1.6 mL) and MeOH (0.6 mL) and the resulting solution stirred at rt for 3 h. The reaction was acidified with AcOH (82 µL, 1.427 mmol) and the solvent removed in vacuo. The crude product was purified by chromatography (RP Flash C18 12 g column, 15-50% MeCN/10 mM Ammonium Bicarbonate). The product-rich fractions were combined and the pH adjusted to pH 5 with formic acid. The solvent was removed to afford the title compound (131 mg) as a white solid.

¹H NMR (400 MHz, DMSO-d6) δ 9.47 (s, 1H), 9.00 (s, 1H), 8.87 (s, 1H), 8.42 (d, 1H), 8.31 (d, 1H), 8.16-8.06 (m, 2H), 7.87 (dd, 1H), 7.70 (ddd, 1H), 7.61 (ddd, 1H), 7.41-7.31 (m, 2H), 6.85 (t, 1H), 6.77 (t, 1H), 6.58 (dd, 1H), 6.09 (d, 1H), 6.03 (t, 1H), 3.99-3.92 (m, 4H), 3.90 (s, 3H), 3.74-3.67 (m, 2H), 3.65 (s, 3H), 3.62-3.53 (m, 4H), 1.76 (s, 3H), 1.73 (s, 3H), 1.31 (s, 9H).

m/z 801.0 (M+H)⁺ (ES⁺)

Example 11

2-(2-(2-(3-((4-((4-(3-(5-(tert-Butyl)-2-methoxy-3-(N-methylmethylsulfonamido)phenyl)ureido)-naphthalen-1-yl)oxy)pyridin-2-yl)amino)-5-methoxyphenoxy)ethoxy)ethoxy)acetic acid

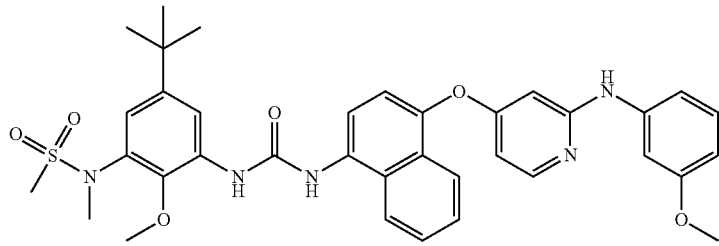
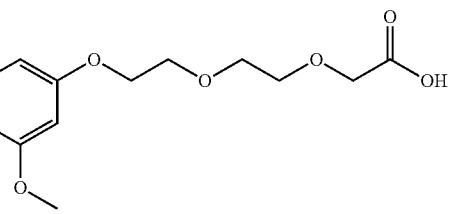

(i) Ethyl 2-(2-(2-(3-((4-((4-(3-(5-(tert-butyl)-2-methoxy-3-(N-methylmethylsulfonamido)phenyl)-ureido)naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 125 mg, 0.228 mmol) was dissolved in iPrOAc (2 mL) at 50° C., and phenyl (5-(tert-butyl)-2-methoxy-3-(N-methylmethylsulfonamido)phenyl) carbamate (see WO 2016/051187; 97 mg, 0.240 mmol) added to the solution. The resulting mixture was stirred at 50° C. for ca 5 min, upon which the reactants dissolved. NEt₃ (6.36 μL, 0.046 mmol) added and the resulting solution was heated to 75° C. (block temperature) and the solution was left to stir for 4 h at 75° C. The solvent was removed and the crude product purified by chromatography on silica gel (12 g column, 0-5% MeOH/DCM) to afford the sub-title compound (83 mg) as a pale pink solid.

¹H NMR (400 MHz, DMSO-d6) δ 9.39 (s, 1H), 8.93 (s, 1H), 8.87 (s, 1H), 8.33 (d, 1H), 8.29 (d, 1H), 8.11 (d, 1H), 8.10 (d, 1H), 7.87 (dd, 1H), 7.70 (ddd, 1H), 7.61 (ddd, 1H), 7.39 (d, 1H), 7.03 (d, 1H), 6.91 (t, 1H), 6.79 (t, 1H), 6.58 (dd, 1H), 6.08 (d, 1H), 6.04 (t, 1H), 4.19-4.03 (m, 4H), 3.98 (dd, 2H), 3.89 (s, 3H), 3.71 (dd, 2H), 3.65 (s, 3H), 3.64-3.56 (m, 4H), 3.25 (s, 3H), 3.15 (s, 3H), 1.29 (s, 9H), 1.18 (t, 3H).

m/z 860.5 (M+H)+ (ES+)

(ii) 2-(2-(2-(3-((4-((4-(3-(5-(tert-Butyl)-2-methoxy-3-(N-methylmethylsulfonamido)phenyl)-ureido) naphthalen-1-yl)oxy)pyridin-2-yl)amino)-5-methoxyphenoxy)ethoxy)ethoxy) acetic acid NaOH (2M aq.) (175 μL, 0.350 mmol) was added to a solution of the compound from step (i) above (83 mg, 0.097 mmol) in THF (1.6 mL) and MeOH (0.6 mL) and the resulting yellow solution stirred at rt for 3 h. The reaction was acidified with AcOH (82 μL, 1.427 mmol) and the solvent removed in vacuo. The crude product was purified by chromatography (RP Flash C18 12 g column, 15-50% MeCN/10 mM Ammonium Bicarbonate). The product-rich fractions were combined and the pH adjusted to pH 5 with formic acid. The solvent was removed to yield the title compound (57 mg) as a pale pink solid.

¹H NMR (400 MHz, DMSO-d6) δ 9.73 (s, 1H), 9.13 (s, 1H), 8.90 (s, 1H), 8.36 (d, 1H), 8.31 (d, 1H), 8.15-8.04 (m, 2H), 7.90-7.82 (m, 1H), 7.67 (ddd, 1H), 7.59 (ddd, 1H), 7.37 (d, 1H), 7.02 (d, 1H), 6.74 (d, 2H), 6.60 (dd, 1H), 6.12 (d, 1H), 6.02 (t, 1H), 3.93-3.82 (m, 5H), 3.78 (s, 2H), 3.72-3.66 (m, 2H), 3.65 (s, 3H), 3.59-3.51 (m, 4H), 3.25 (s, 3H), 3.14 (s, 3H), 1.29 (s, 9H).

m/z 832.0 (M+H)⁺ (ES⁺)

Example 12

5-((2-(3-((4-((4-(3-(5-(tert-Butyl)-2-methoxy-3-(methylsulfonamido)phenyl)ureido)naphthalen-1-yl)oxy)pyridin-2-yl)amino)-5-methoxyphenoxy)ethoxy)methyl)furan-3-carboxylic acid

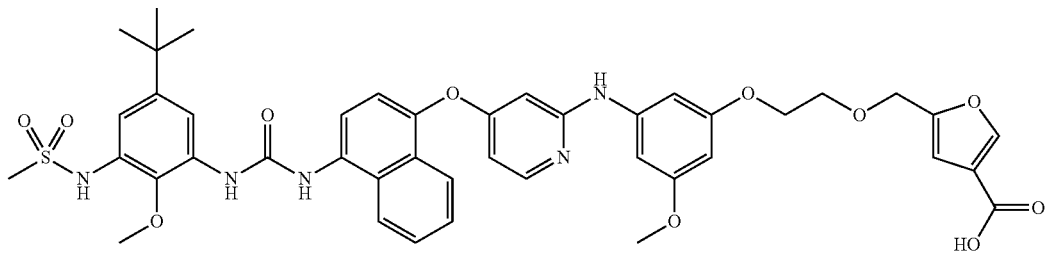 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCc2cc(C(=O)O)co2)c1]

(i) Methyl 5-((2-hydroxyethoxy)methyl)furan-3-carboxylate

To a stirred solution of dry ethane-1,2-diol (0.259 mL, 4.58 mmol) in DMSO (3 mL) at 0° C. was added ᵗBuOK (141 mg, 1.260 mmol) slowly, portion-wise over 10 min.

The resulting solution was further stirred for 30 min at same temperature before adding TBAI (42.3 mg, 0.115 mmol). A homogeneous solution of methyl 5-(chloromethyl)furan-3-carboxylate (200 mg, 1.146 mmol) in DMSO (1 mL) was added dropwise to the above reaction mixture and stirred at rt overnight. 3 mL MeOH was added and the reaction stirred once again overnight. Water (15 mL) was added, the aqueous layer extracted with ethyl acetate (2×15 mL) and dried over anhydrous sodium sulfate. Ethyl acetate was evaporated under reduced pressure. The crude product was purified by chromatography on silica gel (12 g column, 0-5% MeOH/DCM) to afford the sub-title compound (110 mg) as a colourless oil.

$^1$H NMR (400 MHz, DMSO-d6) δ 8.37 (d, 1H), 6.75 (d, 1H), 4.63 (t, 1H), 4.45 (s, 2H), 3.77 (s, 3H), 3.54-3.46 (m, 2H), 3.46-3.40 (m, 2H).

m/z 218.0 (M+NH$_4$)$^+$ (ES$^+$)

(ii) Methyl 5-((2-((methylsulfonyl)oxy)ethoxy)methyl)furan-2-carboxylate

The product from step (i) above (105 mg, 0.525 mmol) was dissolved in 1 mL DCM and NEt$_3$ (88 μL, 0.629 mmol) and MsCl (45.0 μL, 0.577 mmol) were added. The reaction was stirred at rt for 2 h after which time LCMS indicated the reaction had gone to completion. The reaction was diluted with DCM (10 mL), washed with water (10 mL), passed through a phase separator and concentrated in vacuo to yield the sub-title compound (130 mg) as a yellow oil that gradually hardened to a yellow solid.

$^1$H NMR (400 MHz, DMSO-d6) δ 8.39 (d, 1H), 6.79 (d, 1H), 4.56-4.46 (m, 2H), 4.35-4.28 (m, 2H), 3.77 (s, 3H), 3.71-3.63 (m, 2H), 3.17 (s, 3H).

(iii) Methyl 5-((2-(3-methoxy-5-nitrophenoxy)ethoxy)methyl)furan-3-carboxylate

3-Methoxy-5-nitrophenol (75 mg, 0.445 mmol), the product from step (ii) (130 mg, 0.467 mmol) and potassium carbonate (184 mg, 1.335 mmol) were suspended in DMF (0.5 mL) and heated to 85° C. (block temperature) overnight. The reaction was cooled, diluted with water (15 mL) and extracted with TBME (3×15 mL). The combined organic layers were washed with water (20 mL), brine (20 mL), dried (MgSO4), filtered and concentrated in vacuo. The crude product was purified by chromatography on silica gel (24 g column, 0-50% EtOAc/isohexane) to afford the sub-title compound (124 mg) as a yellow oil that gradually became a pale yellow waxy solid.

$^1$H NMR (400 MHz, DMSO-d6) δ 8.38 (d, 1H), 7.34 (d, 2H), 6.98 (t, 1H), 6.78 (d, 1H), 4.53 (d, 2H), 4.28-4.20 (m, 2H), 3.86 (s, 3H), 3.82-3.71 (m, 5H).

m/z 369.0 (M+NH$_4$)$^+$ (ES$^+$)

(iv) Methyl 5-((2-(3-amino-5-methoxyphenoxy)ethoxy)methyl)furan-3-carboxylate

A solution of the product from step (iii) above (120 mg, 0.342 mmol) in EtOH (20 mL) was hydrogenated in the H-Cube (10% Pd/C, 30×4 mm, Full hydrogen, rt, 1 mL/min). A blockage resulted in the solution being exposed to overpressure for ca. 45 mins. The reaction mixture was concentrated in vacuo to yield an oil that was used directly in step (v). LCMS revealed a 2:3 mixture of the sub-title compound (m/z 322.0 (M+H)$^+$ (ES$^+$)) and methyl 5-((2-(3-amino-5-methoxyphenoxy)ethoxy)methyl)tetrahydrofuran-3-carboxylate (m/z 326.0 (M+H)$^+$ (ES$^+$) (107 mg).

(v) Methyl 5-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)tetrahydrofuran-3-carboxylate (Product A) and Methyl 5-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)furan-3-carboxylate (Product B)

A suspension of the product mixture from step (iv) above (95 mg, 0.296 mmol), N-(5-(tert-butyl)-3-(3-(4-((2-chloro-pyridin-4-yl)oxy)naphthalen-1-yl)ureido)-2-methoxyphenyl)methanesulfonamide (see WO 2014/162126; 168 mg, 0.296 mmol), freshly ground potassium carbonate (123 mg, 0.887 mmol), and BrettPhosG3 precatalyst (13.40 mg, 0.015 mmol) in DMF (3 mL) was evacuated and backfilled with nitrogen three times. The reaction was then heated under nitrogen at 85° C. (block temperature) for 16 h. The mixture was cooled, diluted with EtOAc (15 mL), washed with brine and concentrated onto silica gel. Attempted chromatography on silica gel (12 g column, 0-5% (0.7 M Ammonia/MeOH)/DCM) afforded little separation and an impure mixture of products were obtained after trituration with water (3 mL). The product was further purified by chromatography on RP Flash C18 (27 g column, 15-75% MeCN/10 mM Ammonium Bicarbonate) to yield Product A (30 mg) as an off-white solid that was used in Example 13 without further purification.

m/z 858.1 (approximately 75% purity at 254 nm)

Further elution of the RP column yielded Product B (20 mg) as an off-white solid that was taken to the next step without further purification.

m/z 854.1 (approximately 55% purity at 254 nm)

(vi) 5-((2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)methyl)furan-3-carboxylic acid Product B of step (v) above (20 mg, 0.023 mmol) was dissolved in THF (2 mL) and MeOH (0.5 mL). NaOH (2M aq.) (129 μL, 0.258 mmol) was added and the mixture stirred at rt for 1.5 h. The mixture was acidified with AcOH (0.25 mL) and concentrated in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (2.4 mg) as an off-white solid.

$^1$H NMR (400 MHz, DMSO-d6) δ 9.49 (s, 1H), 8.99 (s, 1H), 8.89 (s, 1H), 8.30 (d, 1H), 8.17 (d, 1H), 8.13-8.05 (m, 3H), 7.85 (dd, 1H), 7.69 (ddd, 1H), 7.62-7.56 (m, 1H), 7.38 (d, 1H), 7.01 (d, 1H), 6.86 (t, 1H), 6.78 (t, 1H), 6.63 (s, 1H), 6.58 (dd, 1H), 6.05 (d, 1H), 6.01 (t, 1H), 4.46 (s, 2H), 4.01-3.91 (m, 2H), 3.79 (s, 3H), 3.72-3.66 (m, 2H), 3.64 (s, 3H), 3.09 (s, 3H), 1.26 (s, 9H).

m/z 840.2 (M+H)$^+$ (ES$^+$)

Example 13

5-((2-(3-((4-((4-(3-(5-(tert-Butyl)-2-methoxy-3-(methylsulfonamido)phenyl)ureido)naphthalen-1-yl)oxy)pyridin-2-yl)amino)-5-methoxyphenoxy)ethoxy)methyl)tetrahydrofuran-3-carboxylic acid

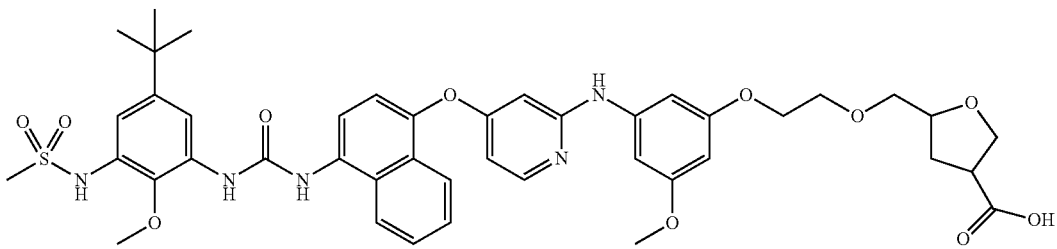 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCC2CC(C(=O)O)CO2)c1]

Product A of Example 12(v) above (30 mg, 0.035 mmol) was dissolved in 0.4 mL THF and 0.1 mL MeOH. NaOH (2M aq.) (192 µL, 0.385 mmol) was added and the mixture stirred at rt for 1.5 h. The reaction was acidified with AcOH (0.25 mL) and concentrated in vacuo. The crude product was purified by preparative HPLC (Waters, Basic (0.1% Ammonium Bicarbonate), Basic, Waters X-Bridge Prep-C18, 5 µm, 19×50 mm column, 35-65% MeCN in Water) to afford the title compound (7 mg) as an off-white solid.

$^1$H NMR (400 MHz, DMSO-d6) δ 9.55 (d, 1H), 8.99 (d, 1H), 8.84 (d, 1H), 8.37 (s, 1H), 8.25 (dd, 1H), 8.09 (t, 1H), 8.06-8.00 (m, 2H), 7.78 (dd, 1H), 7.64-7.58 (m, 1H), 7.53 (ddd, 1H), 7.31 (dd, 1H), 6.95 (d, 1H), 6.78 (dt, 1H), 6.72 (q, 1H), 6.51 (ddd, 1H), 5.97 (dt, 2H), 3.90-3.83 (m, 3H), 3.77-3.69 (m, 4H), 3.66-3.60 (m, 3H), 3.57 (s, 3H), 3.40-3.34 (m, 2H), 3.01 (s, 3H), 2.90-2.82 (m, 1H), 2.07-1.99 (m, 1H), 1.66 (ddd, 1H), 1.19 (s, 9H).

m/z 844.1 (M+H)$^+$

Example 14

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)propanoic acid

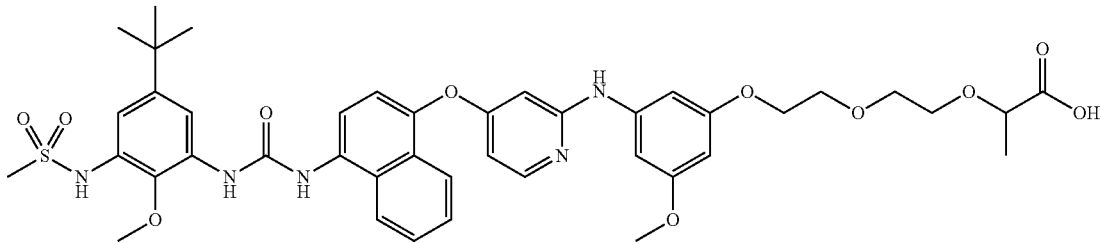 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOC(C)C(=O)O)c1]

(i) Ethyl 2-(2-(2-(benzyloxy)ethoxy)ethoxy)propanoate 2-(2-(Benzyloxy)ethoxy)ethanol (5 g, 25.5 mmol) was dissolved in DCM (50 mL), passed through a phase separator and concentrated in vacuo. It was then redissolved in dry THF (50 mL, 25.5 mmol) under nitrogen and cooled in an ice bath. NaH (60% in mineral oil, 1.070 g, 26.8 mmol) was added portionwise over 10 min and the resulting suspension stirred for 30 min. Ethyl 2-bromopropanoate (3.73 mL, 28.0 mmol) was added dropwise over 15 min. The reaction was stirred overnight, quenched with sat. NH$_4$Cl (5 mL) and the resulting mixture concentrated directly onto silica gel. The crude product was purified by chromatography on silica gel (80 g column, 0-50% EtOAc/isohexane) to afford the sub-title compound (1.51 g) as a colourless oil.

$^1$H NMR (400 MHz, DMSO-d6) δ 7.51-7.09 (m, 5H), 4.50 (s, 2H), 4.11 (qd, 2H), 4.05 (q, 1H), 3.70-3.41 (m, 8H), 1.27 (d, 3H), 1.20 (t, 3H).

(ii) Ethyl 2-(2-(2-hydroxyethoxy)ethoxy)propanoate

The product from step (i) above (1.5 g, 5.06 mmol) was dissolved in EtOH (60 mL, 5.06 mmol) and hydrogenated over Pd—C (0.539 g, 0.506 mmol) at 1 bar H$_2$ for 16 h at rt. The reaction was filtered through celite, the solids washed with EtOH (20 mL) and the mixture concentrated in vacuo to yield the sub-title compound (931 mg) as a colourless oil.

$^1$H NMR (400 MHz, DMSO-d6) δ 4.56 (t, 1H), 4.12 (qd, 2H), 4.04 (q, 1H), 3.67-3.56 (m, 1H), 3.56-3.45 (m, 5H), 3.42 (dd, 2H), 1.27 (d, 3H), 1.21 (t, 3H).

(iii) Ethyl 2-(2-(2-(3-methoxy-5-nitrophenoxy)ethoxy)ethoxy)propanoate

The product from step (ii) above (932 mg, 4.52 mmol) was dissolved in DCM (5 mL) and cooled in an ice bath. NEt$_3$ (756 µL, 5.42 mmol) and MsCl (387 µL, 4.97 mmol) were added sequentially dropwise and the reaction stirred for 1 h in the ice bath. DCM (50 mL) was added and the organic layer washed with brine (2×50 mL), passed through a phase separator and concentrated in vacuo to yield 1.13 g of a yellow oil. 282 mg of this yellow oil, 3-methoxy-5-nitrophenol (160 mg, 0.946 mmol), and potassium carbonate (392 mg, 2.84 mmol) were suspended in DMF (3 mL) and heated to 80° C. overnight. The reaction was cooled and partitioned between TBME (20 mL) and brine (20 mL). The aqueous layer was extracted with TBME (20 mL) and the combined organic layers washed with brine (40 mL), dried (MgSO$_4$), filtered and concentrated in vacuo. The crude product was purified by chromatography on silica gel (12 g column, 0-50% EtOAc/isohexane) to afford the sub-title compound (200 mg) as a yellow oil.

$^1$H NMR (400 MHz, DMSO-d6) δ 7.34 (dt, 2H), 7.00 (t, 1H), 4.29-4.18 (m, 2H), 4.12 (ddq, 2H), 4.05 (q, 1H), 3.86 (s, 3H), 3.81-3.74 (m, 2H), 3.66-3.57 (m, 3H), 3.56-3.46 (m, 1H), 1.26 (d, 3H), 1.19 (t, 3H).

(iv) Ethyl 2-(2-(2-(3-amino-5-methoxyphenoxy)ethoxy)ethoxy)propanoate

To a solution of the product from step (iii) above (200 mg, 0.560 mmol) in EtOH (30 mL) and EtOAc (7 mL) was added Pd/C (5 wt %, type 87 L) (61.3 mg, 0.029 mmol). The resulting suspension was stirred under 3 bar H$_2$ for 1 h. The reaction mixture was filtered through celite and concentrated in vacuo to yield the sub-title compound (130 mg) as a red oil.

$^1$H NMR (400 MHz, DMSO-d6) δ 5.75 (d, 2H), 5.69 (t, 1H), 5.05 (s, 2H), 4.12 (qd, 2H), 4.06 (q, 1H), 4.00-3.91 (m, 2H), 3.73-3.66 (m, 2H), 3.66-3.55 (m, 6H), 3.55-3.49 (m, 1H), 1.28 (d, 3H), 1.20 (t, 3H).

(v) Ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)propanoate A solution of the product from step (iv) above (130 mg, 0.397 mmol), N-(5-(tert-butyl)-3-(3-(4-((2-chloropyridin-4-yl)oxy)naphthalen-1-yl)ureido)-2-methoxyphenyl)methanesulfonamide (see WO 2014/162126; 226 mg, 0.397 mmol), potassium carbonate (165 mg, 1.191 mmol), and BrettPhosG3 precatalyst (18.00 mg, 0.020 mmol) in DMF (3 mL) was degassed with nitrogen for 10 mins. The reaction was heated under nitrogen at 85° C. (block temperature) for 2 h. The reaction was cooled and partitioned between EtOAc (10 mL) and water (10 mL). The aqueous phase was extracted with EtOAc (5 mL). The combined organic phases were washed with brine (5 mL) dried (MgSO$_4$), filtered and concentrated in vacuo affording a dark brown solid. The crude product was purified by chromatography on silica gel (12 g column, 1-6% MeOH in DCM) to afford the sub-title compound (125 mg) as a pale beige foam.

$^1$H NMR (400 MHz, DMSO-d6) δ 9.38 (s, 1H), 9.13 (s, 1H), 8.91 (s, 1H), 8.87 (s, 1H), 8.29 (d, 1H), 8.19 (d, 1H), 8.15-8.07 (m, 2H), 7.87 (dt, 1H), 7.70 (ddd, 1H), 7.61 (ddd, 1H), 7.38 (d, 1H), 7.03 (d, 1H), 6.91 (t, 1H), 6.78 (t, 1H), 6.58 (dd, 1H), 6.08 (d, 1H), 6.04 (t, 1H), 4.11 (qd, 2H), 4.07-4.02 (m, 1H), 3.98 (dd, 2H), 3.81 (s, 3H), 3.75-3.69 (m, 2H), 3.65 (s, 3H), 3.62-3.55 (m, 3H), 3.55-3.47 (m, 1H), 3.10 (s, 3H), 1.31-1.23 (m, 12H), 1.19 (t, 3H).

m/z 860.1 (M+H)$^+$ (ES$^+$)

(vi) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)propanoic acid The product from step (vi) above (120 mg, 0.140 mmol) was dissolved in THF (2 mL) and MeOH (0.5 mL). NaOH (2M aq.) (767 µL, 1.535 mmol) was added and the mixture stirred at rt for 16 h. The reaction was acidified with AcOH (0.25 mL) and concentrated in vacuo. The crude product was purified by chromatography on RP Flash C18 (24 g column, 15-75% MeCN/10 mM Ammonium Bicarbonate). The product containing fractions were combined, acidified with formic acid to ca. pH 4, concentrated in vacuo and the resulting precipitate filtered off washing with water (5 mL) to afford the title compound (64 mg) as an off-white solid.

$^1$H NMR (400 MHz, DMSO-d6) δ 12.48 (s, 1H), 9.36-9.30 (m, 1H), 9.04 (s, 1H), 8.85 (s, 1H), 8.80 (s, 1H), 8.22 (d, 1H), 8.11 (d, 1H), 8.04 (s, 1H), 8.02 (d, 1H), 7.79 (dd, 1H), 7.63 (ddd, 1H), 7.53 (ddd, 1H), 7.31 (d, 1H), 6.95 (d, 1H), 6.82 (t, 1H), 6.71 (t, 1H), 6.50 (dd, 1H), 6.01 (d, 1H), 5.96 (t, 1H), 3.93-3.82 (m, 3H), 3.73 (s, 3H), 3.67-3.61 (m, 2H), 3.59-3.53 (m, 4H), 3.50 (dd, 2H), 3.44-3.37 (m, 1H), 3.02 (s, 3H), 1.19 (s, 9H), 1.18 (d, 3H).

m/z 832.1 (M+H)$^+$ (ES$^+$)

Example 15

2-(2-(2-(3-((4-((4-(3-(5-(tert-Butyl)-3-(ethylsulfonyl)-2-methoxyphenyl)ureido)naphthalen-1-yl)oxy)pyridin-2-yl)amino)-5-methoxyphenoxy)ethoxy)ethoxy)acetic acid

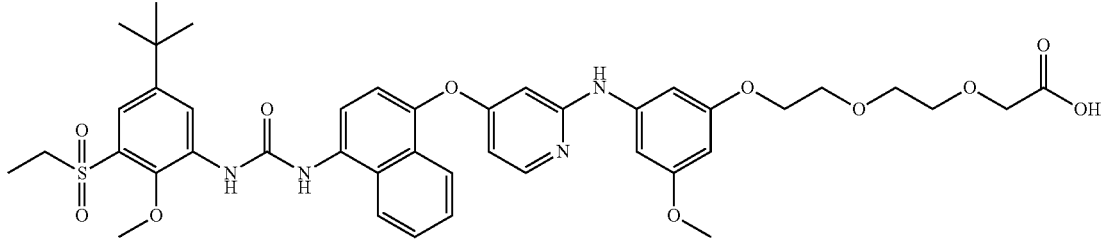 [SMILES: CCS(=O)(=O)c1cc(C(C)(C)C)cc(NC(=O)Nc2ccc(Oc3ccnc(Nc4cc(OC)cc(OCCOCCOCC(=O)O)c4)c3)c3ccccc23)c1OC]

(i) (5-(tert-Butyl)-2-methoxy-3-nitrophenyl)(ethyl)sulfane

Tert-butyl nitrite (3.18 mL, 26.8 mmol) was added dropwise at rt to a stirred, dark brown solution of 1,2-diethyldisulfane (3.29 mL, 26.8 mmol) and 5-(tert-butyl)-2-methoxy-3-nitroaniline (2 g, 8.92 mmol) in MeCN (50 mL). The reaction was then heated to reflux (block temp 80° C.) and the dark brown solution was stirred at reflux for 2 h. The reaction was then cooled to rt and the solvent evaporated. The dark red residue was azeotroped with toluene (3×25 mL). The crude product was purified by chromatography on silica gel (80 g column, 0-20% MTBE:isohexane) to afford the sub-title compound (1.007 g) as an orange oil.

$^1$H NMR (400 MHz, DMSO-d6) δ 7.64 (d, 1H), 7.53 (d, 1H), 3.84 (s, 3H), 3.09 (q, 2H), 1.31 (s, 9H), 1.28 (t, 3H).

(ii) 5-(tert-Butyl)-1-(ethylsulfonyl)-2-methoxy-3-nitrobenzene m-CPBA (1.747 g, 7.80 mmol) was added to a solution of the compound from step (i) above (1 g, 3.71 mmol) in DCM (40 mL) under nitrogen at 0° C. and the resulting orange slurry stirred at 0° C. for 30 min then warmed to rt and stirred at rt for 2.5 h. The reaction was quenched with a solution of sodium thiosulfate (2.348 g, 14.85 mmol) dissolved in water (10 mL) and stirred at rt for 30 min. The layers were diluted with DCM (50 mL) and separated. The organic layer was washed with sat. aq. NaHCO$_3$ (3×20 mL) and dried (MgSO$_4$). The solvent was removed to afford a dark red oil. The crude product was purified by chromatography on silica gel (40 g column, 20-100% DCM: heptane) to afford the sub-title compound (935 mg) as a thick orange oil.

$^1$H NMR (400 MHz, DMSO-d6) δ 8.32 (d, 1H), 8.06 (d, 1H), 3.94 (s, 3H), 3.49 (q, 2H), 1.34 (s, 9H), 1.15 (t, 3H).

m/z 302.2 (M+H)$^+$ (ES$^+$)

(iii) 5-(tert-butyl)-3-(ethylsulfonyl)-2-methoxyaniline

NH$_4$Cl (66.4 mg, 1.241 mmol) was added to a slurry of the compound from step (ii) above (935 mg, 3.10 mmol) and iron (1733 mg, 31.0 mmol) in EtOH (20 mL), water (5 mL) and THF (2 mL). The resulting black slurry was heated to reflux for 1 h. The solution was cooled to rt and filtered through celite, washing with EtOAc (2×20 mL). The solvent was removed in vacuo. The crude product was purified by chromatography on silica gel (40 g column, 0-40% EtOAc: isohexane) to afford the sub-title compound (820 mg) as a thick yellow oil.

m/z 272.3 (M+H)+ (ES+)

(iv) Phenyl (5-(tert-butyl)-3-(ethylsulfonyl)-2-methoxyphenyl)carbamate

Phenyl chloroformate (417 μL, 3.32 mmol) was added to a slurry of the compound from step (iii) (820 mg, 3.02 mmol) and NaHCO$_3$ (762 mg, 9.06 mmol) in DCM (8 mL) and THF (2 mL). The resulting slurry was stirred at rt for 18 h. The reaction was diluted with DCM (10 mL) and washed with water (10 mL) and brine (10 mL). The organic layer was concentrated in vacuo to afford a light orange solid. This was triturated with cyclohexane (10 mL) and the resulting solid collected by filtration, washing with cyclohexane (2×2 mL) to afford the sub-title compound (940 mg) as a beige solid.

m/z 392.3 (M+H)+ (ES+)

(v) Ethyl 2-(2-(2-(3-((4-((4-(3-(5-(tert-Butyl)-3-(ethylsulfonyl)-2-methoxyphenyl)ureido)-naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 100 mg, 0.183 mmol) was dissolved in iPrOAc (2 mL) at 50° C. and the compound from step (iv) above (75 mg, 0.192 mmol) added to the solution. The resulting mixture was stirred at 50° C. for until the carbamate dissolved (ca 5 min) then NEt$_3$ (5.09 μL, 0.037 mmol) was added and the resulting solution stirred at 75° C. for 4 h. The solvent was removed. The crude product was purified by chromatography on silica gel (12 g column, 0-5% MeOH/DCM). The product was repurified by chromatography (RP Flash C18 12 g column, 15-75% MeCN/10 mM Ammonium Bicarbonate) to afford the sub-title compound (86 mg) as a light pink solid.

$^1$H NMR (400 MHz, DMSO-d6) δ 9.49 (s, 1H), 9.07 (s, 1H), 8.88 (s, 1H), 8.70 (d, 1H), 8.29 (d, 1H), 8.14-8.04 (m, 2H), 7.88 (d, 1H), 7.71 (t, 1H), 7.62 (t, 1H), 7.42 (d, 1H), 7.40 (d, 1H), 6.90 (t, 1H), 6.78 (t, 1H), 6.58 (dd, 1H), 6.09 (d, 1H), 6.04 (t, 1H), 4.19-4.06 (m, 4H), 3.98 (t, 2H), 3.94 (s, 3H), 3.75-3.68 (m, 2H), 3.65 (s, 3H), 3.64-3.55 (m, 4H), 3.44 (q, 2H), 1.31 (s, 9H), 1.22-1.12 (m, 6H).

m/z 845.5 (M+H)+ (ES+)

(vi) 2-(2-(2-(3-((4-((4-(3-(5-(tert-Butyl)-3-(ethylsulfonyl)-2-methoxyphenyl)ureido)naphthalen-1-yl)oxy)pyridin-2-yl)amino)-5-methoxyphenoxy)ethoxy)ethoxy)acetic acid NaOH (2M aq.) (175 μL, 0.350 mmol) was added to a solution of the compound from step (v) above (86 mg, 0.102 mmol) in THF (1.6 mL) and MeOH (0.6 mL) and the resulting solution stirred at rt overnight. The reaction was quenched with AcOH (24.14 μL, 0.422 mmol) and the solvent removed in vacuo. The crude product was purified by chromatography (RP Flash C18 12 g column, 15-75% MeCN/10 mM Ammonium Bicarbonate). The product-rich fractions were neutralised with formic acid and concentrated to afford the title compound (67 mg) as a light beige solid.

$^1$H NMR (400 MHz, DMSO-d6) δ 9.68 (s, 1H), 9.21 (s, 1H), 8.88 (s, 1H), 8.69 (d, 1H), 8.32 (d, 1H), 8.14-8.07 (m, 2H), 7.87 (d, 1H), 7.76-7.66 (m, 1H), 7.66-7.56 (m, 1H), 7.42 (d, 1H), 7.39 (d, 1H), 6.79 (s, 1H), 6.75 (t, 1H), 6.59 (dd, 1H), 6.11 (d, 1H), 6.03 (t, 1H), 3.99-3.86 (m, 7H), 3.69 (dd, 2H), 3.65 (s, 3H), 3.58 (q, 4H), 3.44 (q, 2H), 1.31 (s, 9H), 1.15 (q, 3H).

m/z 817.5 (M+H)$^+$ (ES$^+$)

Example 16

2-(2-(2-(3-((4-((4-(3-(5-(tert-Butyl)-3-(ethylsulfonamido)-2-methoxyphenyl)ureido)naphthalen-1-yl)oxy)pyridin-2-yl)amino)-5-methoxyphenoxy)ethoxy)ethoxy)acetic acid

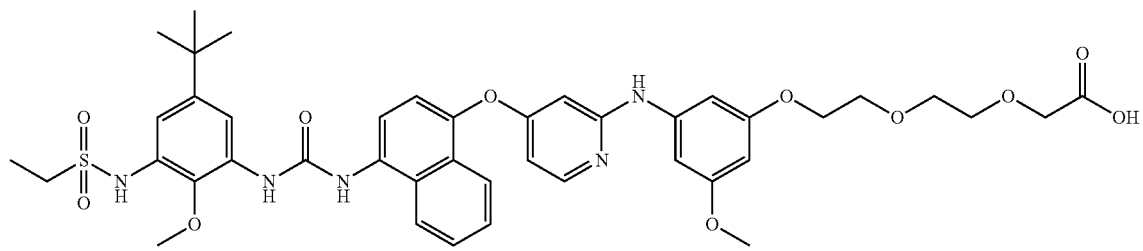 [SMILES: CCS(=O)(=O)Nc1cc(C(C)(C)C)cc(NC(=O)Nc2ccc(Oc3ccnc(Nc4cc(OC)cc(OCCOCCOCC(=O)O)c4)c3)c3ccccc23)c1OC]

(i) N-(5-(tert-butyl)-2-methoxy-3-nitrophenyl)ethanesulfonamide

Ethanesulfonyl chloride (475 µL, 5.02 mmol) was added at 0° C. to a solution of 5-(tert-butyl)-2-methoxy-3-nitroaniline (750 mg, 3.34 mmol) and pyridine (1082 µL, 13.38 mmol) in DCM (10 mL). The resulting solution was stirred at 0° C. for 5 min, then at rt for 16 h. The reaction was washed with 2 M HCl (10 mL) and brine (10 mL) and concentrated in vacuo. The crude product was purified by chromatography on silica gel (12 g column, 0-20% EtOAc/isohexane) to afford the sub-title compound, 915 mg of a yellow oil that solidified on standing. The solid was triturated with ether: isohexane (1:1 ratio, 10 mL) to afford the sub-title compound (686 mg) as a pale yellow solid.

$^1$H NMR (400 MHz, DMSO-d6) δ 9.57 (s, 1H), 7.68 (s, 2H), 3.82 (s, 3H), 3.22 (q, 2H), 1.40-1.18 (m, 12H).

m/z 315 (M−H)− (ES−)

(ii) N-(3-amino-5-(tert-butyl)-2-methoxyphenyl)ethanesulfonamide

10% Pd/C, 50% Paste in water, Type 39 (46.2 mg, 0.434 mmol) was added to a solution of the compound from step (i) above (686 mg, 2.168 mmol) in EtOH (5 mL) and EtOAc (2 mL) and the resulting slurry stirred under $H_2$ at 5 bar pressure overnight. The reaction was filtered through celite, washing with EtOAc (50 mL). The solvent was removed in vacuo to afford the sub-title compound (600 mg) as a light pink solid.

$^1$H NMR (400 MHz, DMSO-d6) δ 8.67 (s, 1H), 6.61-6.52 (m, 2H), 4.88 (s, 2H), 3.63 (s, 3H), 3.09 (q, 2H), 1.25 (t, 3H), 1.20 (s, 9H).

m/z 287.3 (M+H)+ (ES+)

(iii) Phenyl (5-(tert-butyl)-3-(ethylsulfonamido)-2-methoxyphenyl)carbamate

Phenyl chloroformate (289 µL, 2.305 mmol) was added to a slurry of the compound from step (ii) above (600 mg, 2.095 mmol) and $NaHCO_3$ (528 mg, 6.29 mmol) in DCM (8 mL) and THF (2 mL). The resulting slurry was stirred at rt for 2 h. The reaction was diluted with DCM (10 mL) and washed with water (10 mL) and brine (10 mL). The organic layer was concentrated in vacuo to afford an orange oil that solidified upon standing. This was triturated with cyclohexane (10 mL) and the resulting solid collected by filtration, washing with cyclohexane (2×2 mL) to afford the sub-title compound (788 mg, 1.842 mmol, 88% yield) as a light beige solid.

$^1$H NMR (400 MHz, DMSO-d6) δ 9.49 (s, 1H), 9.12 (s, 1H), 7.54 (s, 1H), 7.47-7.36 (m, 2H), 7.30-7.19 (m, 3H), 7.17 (d, 1H), 3.77 (s, 3H), 3.15 (q, 2H), 1.28 (t, 3H), 1.24 (s, 9H).

m/z 429.4 (M+Na)+ (ES+)

(iv) Ethyl 2-(2-(2-(3-((4-((4-(3-(5-(tert-butyl)-3-(ethylsulfonamido)-2-methoxyphenyl)ureido)-naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 100 mg, 0.183 mmol) was dissolved in iPrOAc (2 mL) at 50° C. and the compound from step (iii) (97 mg, 0.240 mmol) added to the solution. The resulting mixture was stirred at 50° C. until the carbamate dissolved (ca 5 min). $NEt_3$ (5.09 µL, 0.037 mmol) was added and the resulting solution stirred at 75° C. for 4 h. The solvent was removed in vacuo. Chromatography on silica gel (12 g column, 0-5% MeOH/DCM) did not afford sufficient purity. The crude product was repurified by chromatography (RP Flash C18 12 g column, 15-75% MeCN/10 mM Ammonium Bicarbonate) to afford the sub-title compound (70 mg) as a light pink solid.

$^1$H NMR (400 MHz, DMSO-d6) δ 9.37 (s, 1H), 9.12 (s, 1H), 8.90 (s, 1H), 8.87 (s, 1H), 8.29 (d, 1H), 8.16 (d, 1H), 8.12 (d, 1H), 8.10 (s, 1H), 7.91-7.83 (m, 1H), 7.74-7.65 (m, 1H), 7.61 (ddd, 1H), 7.38 (d, 1H), 7.02 (d, 1H), 6.90 (t, 1H), 6.78 (t, 1H), 6.58 (dd, 1H), 6.08 (d, 1H), 6.04 (t, 1H), 4.14-4.06 (m, 4H), 4.02-3.94 (m, 2H), 3.81 (s, 3H), 3.71 (dd, 2H), 3.65 (s, 3H), 3.64-3.56 (m, 4H), 3.21-3.12 (m, 2H), 1.31 (t, 3H), 1.26 (s, 9H), 1.18 (t, 3H).

m/z 860.5 (M+H)+ (ES+).

(v) 2-(2-(2-(3-((4-((4-(3-(5-(tert-Butyl)-3-(ethylsulfonamido)-2-methoxyphenyl)ureido)-naphthalen-1-yl)oxy)pyridin-2-yl)amino)-5-methoxyphenoxy)ethoxy)ethoxy)acetic acid NaOH (2M aq.) (40.7 µL, 0.081 mmol) was added to a solution of the compound from step (iv) above (70 mg, 0.081 mmol) in THF (1.6 mL) and MeOH (0.6 mL) and the resulting solution stirred at rt overnight. The reaction was quenched with AcOH (24.1 µL, 0.422 mmol) and the solvent removed in vacuo. The crude product was purified by chromatography (RP Flash C18 12 g column, 15-75% MeCN/10 mM Ammonium Bicarbonate). The product-rich fractions were neutralised with formic acid and concentrated to afford the title compound (68 mg) as a light beige solid.

$^1$H NMR (400 MHz, DMSO-d6) δ 9.47 (s, 1H), 8.96 (s, 1H), 8.88 (s, 1H), 8.31 (d, 1H), 8.17 (d, 1H), 8.12 (s, 1H), 8.10 (d, 1H), 7.86 (dd, 1H), 7.69 (ddd, 1H), 7.60 (ddd, 1H), 7.38 (d, 1H), 7.02 (d, 1H), 6.86 (t, 1H), 6.78 (t, 1H), 6.58 (dd, 1H), 6.09 (d, 1H), 6.03 (t, 1H), 4.01-3.90 (m, 4H), 3.81 (s, 3H), 3.73-3.68 (m, 2H), 3.65 (s, 3H), 3.63-3.55 (m, 4H), 3.20-3.13 (m, 2H), 1.31 (t, 3H), 1.26 (s, 9H).

m/z 832.5 (M+H)+ (ES+)

Example 17

2-(2-(2-(3-((4-((4-(3-(5-(tert-Butyl)isoxazol-3-yl)ureido)naphthalen-1-yl)oxy)pyridin-2-yl)amino)-5-methoxyphenoxy)ethoxy)ethoxy)acetic acid

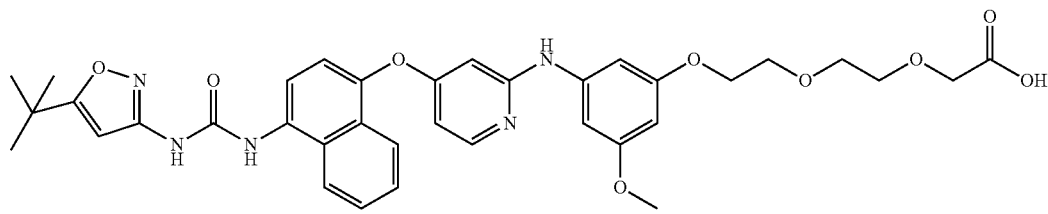 [SMILES: COc1cc(Nc2cc(Oc3ccc(NC(=O)Nc4cc(C(C)(C)C)on4)c4ccccc34)ccn2)cc(OCCOCCOCC(=O)O)c1]

(i) Phenyl (5-(tert-butyl)isoxazol-3-yl)carbamate

A slurry of phenyl chloroformate (0.492 mL, 3.92 mmol), 5-(tert-butyl)isoxazol-3-amine (0.5 g, 3.57 mmol) and NaHCO$_3$ (0.899 g, 10.70 mmol) in DCM (8 mL) and THF (2 mL) was stirred at rt for 4 h. The reaction was diluted with DCM (10 mL), washed with water (10 mL), brine (10 mL) and the solvent evaporated to give a colourless oil that was stirred in cyclohexane (10 mL) for 10 min. A white solid formed that was collected by filtration to afford the sub-title compound (674 mg) as a white solid.

$^1$H NMR (400 MHz, DMSO-d6) δ 11.16 (s, 1H), 7.47-7.41 (m, 2H), 7.28 (ddt, 1H), 7.25-7.19 (m, 2H), 6.44 (s, 1H), 1.30 (s, 9H).

m/z 261.3 (M+H)$^+$ (ES$^+$)

(ii) Ethyl 2-(2-(2-(3-((4-((4-(3-(5-(tert-Butyl)isoxazol-3-yl)ureido)naphthalen-1-yl)oxy)pyridin-2-yl)amino)-5-methoxyphenoxy)ethoxy)ethoxy)acetate Ethyl 2-(2-(2-(3-((4-((4-aminonaphthalen-1-yl)oxy)pyridin-2-yl)amino)-5-methoxyphenoxy)ethoxy)ethoxy)acetate (see Example 3(ii) above; 100 mg, 0.183 mmol) was dissolved in iPrOAc (2 mL) at 50° C. and the product from (i) (62.4 mg, 0.240 mmol) added to the solution and stirred at 50° C. until the carbamate dissolved (ca 5 min). NEt$_3$ (5.1 µL, 0.037 mmol) was added and the resulting solution stirred at 75° C. for 4 h. The solvent was removed in vacuo. Chromatography on silica gel (12 g column, 0-5% MeOH/DCM) did not afford sufficient purity and the crude product was further purified by chromatography (RP Flash C18 12 g column, 15-75% MeCN/10 mM Ammonium Bicarbonate) to afford the sub-title compound (86 mg) as a white solid.

$^1$H NMR (400 MHz, DMSO-d6) δ 9.93 (s, 1H), 9.12 (s, 1H), 8.87 (s, 1H), 8.18 (d, 1H), 8.11 (d, 1H), 8.06 (d, 1H), 7.87 (d1H), 7.71 (ddd, 1H), 7.62 (ddd, 1H), 7.39 (d, 1H), 6.90 (t, 1H), 6.78 (t, 1H), 6.57 (dd, 1H), 6.52 (s, 1H), 6.08 (d, 1H), 6.04 (t, 1H), 4.16-4.05 (m, 4H), 4.02-3.95 (m, 2H), 3.71 (dd, 2H), 3.65 (s, 3H), 3.64-3.57 (m, 4H), 1.32 (s, 9H), 1.19 (t, 3H).

m/z 714.2 (M+H)+ (ES+)

(iii) 2-(2-(2-(3-((4-((4-(3-(5-(tert-Butyl)isoxazol-3-yl)ureido)naphthalen-1-yl)oxy)pyridin-2-yl)amino)-5-methoxyphenoxy)ethoxy)ethoxy)acetic acid NaOH (2M aq.) (175 µL, 0.350 mmol) was added to a solution of the compound from step (i) above (86 mg, 0.120 mmol) in THF (1.6 mL) and MeOH (0.6 mL) and the resulting solution stirred at rt overnight. The reaction was quenched with AcOH (24.1 µL, 0.422 mmol) and the solvent removed in vacuo. The crude product was purified by chromatography (RP Flash C18 12 g column, 15-75% MeCN/10 mM Ammonium Bicarbonate). The product-rich fractions were neutralised with formic acid and concentrated to afford the title compound (59 mg) as a white solid.

$^1$H NMR (400 MHz, DMSO-d6) δ 10.23 (s, 1H), 9.45 (s, 1H), 8.87 (s, 1H), 8.21 (t, 1H), 8.11 (d, 1H), 8.03 (d, 1H), 7.87 (dd, 1H), 7.69 (ddd, 1H), 7.65-7.55 (m, 1H), 7.37 (d, 1H), 6.77 (s, 1H), 6.73 (t, 1H), 6.60 (dd, 1H), 6.52 (s, 1H), 6.09 (d, 1H), 6.03 (t, 1H), 3.96 (s, 2H), 3.89 (d, 2H), 3.69 (dd, 2H), 3.65 (s, 3H), 3.62-3.54 (m, 4H), 1.32 (s, 9H) m/z 686.5 (M+H)$^+$ (ES$^+$).

Example 18

N-(5-(tert-Butyl)-2-methoxy-3-(3-(4-((2-((3-methoxy-5-(2-(2-((5-oxo-2,5-dihydroisoxazol-3-yl)methoxy)ethoxy)ethoxy)phenyl)amino)pyridin-4-yl)oxy)naphthalen-1-yl)ureido)phenyl)methanesulfonamide

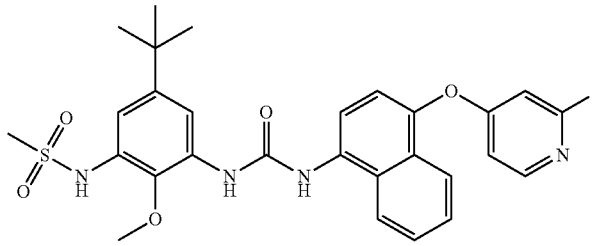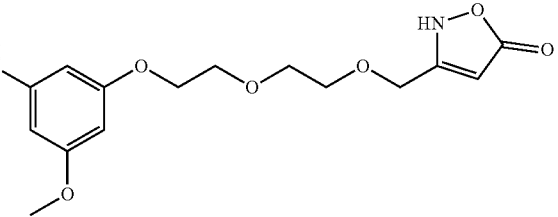

(i) 1-[5-tert-butyl-3-(methanesulfonamido)-2-methoxy-phenyl]-3-[4-[[2-[3-[2-[2-[2-(2,2-dimethyl-4,6-dioxo-1,3-dioxan-5-yl)-2-oxo-ethoxy]ethoxy]ethoxy]-5-methoxy-anilino]-4-pyridyl]oxy]-1-naphthyl]urea To a solution of 2-(2-(2-(3-((4-((4-(3-(5-(tert-butyl)-2-methoxy-3-(methylsulfonamido)phenyl)-ureido)naphthalen-1-yl)oxy)pyridin-2-yl)amino)-5-methoxyphenoxy)ethoxy)ethoxy)acetic acid (see Example 3 above; 500 mg, 0.611 mmol) in DCM (3 mL) and THF (3 mL) was added DMAP (74.7 mg, 0.611 mmol). The resulting suspension was cooled to 0° C. and DCC (139 mg, 0.672 mmol) added. The resulting suspension was stirred at 0° C. for 10 min, then 2,2-dimethyl-1,3-dioxane-4,6-dione (26.4 mg, 0.183 mmol) added. The resulting suspension was stirred at 0° C. for 10 min then at rt overnight. Further portions of DCC (37.8 mg, 0.183 mmol) and 2,2-dimethyl-1,3-dioxane-4,6-dione (26.4 mg, 0.183 mmol) were added to the yellow suspension and stirring continued for 4 h. The solvent was removed to afford an orange solid that was suspended in cold DCM (3 mL) and filtered (sinter funnel, Grade 1 Whatman paper), washing with cold DCM (3×2 mL). The filtrate chilled and refiltered through a plug of cotton wool and solvent was removed affording a light yellow solid. The crude product was purified by chromatography on silica gel (12 g column, 0-100% EtOAc/isohexane, then 4% MeOH:DCM) to afford the sub-title compound (771 mg) as a white solid.

m/z 944.6 (M+H)$^+$ (ES$^+$)

(ii) Ethyl 4-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)-3-oxobutanoate The product from step (i) above (403 mg, 0.324 mmol) was slurried in EtOH (50 mL) and heated to reflux for 24 h. The solvent was removed in vacuo to afford a gum that was product was purified by chromatography on silica gel (40 g column, 0-10% MeOH/DCM,) to afford the sub-title compound (200 mg, 0.205 mmol, 63.2% yield) as a colourless gum.

m/z 886.5 (M+H)$^+$ (ES$^+$)

(iii) N-(5-(tert-Butyl)-2-methoxy-3-(3-(4-((2-((3-methoxy-5-(2-(2-((5-oxo-2,5-dihydroisoxazol-3-yl)methoxy)ethoxy)ethoxy)phenyl)amino)pyridin-4-yl)oxy)naphthalen-1-yl)ureido)phenyl)-methanesulfonamide A suspension of the product from (ii) (100 mg, 0.113 mmol), hydroxylamine hydrochloride (31.3 mg, 0.450 mmol) and sat. aq. sodium bicarbonate (512 μL, 0.563 mmol) in EtOH (2.5 mL) was heated to reflux for 1 h, after which time a homogeneous solution was obtained. The reaction was cooled to rt and concentrated in vacuo. The crude product was purified by chromatography (RP Flash C18 12 g column, 15-75% MeCN/10 mM Ammonium Bicarbonate). The product-rich fractions were combined and the pH adjusted to 7 with formic acid, the organic solvent was evaporated under a flow of N$_2$, protecting the sample from light. The aqueous solvent was then removed on a rotary evaporator, at 30° C., to afford the title compound (20 mg) as a light pink solid.

$^1$H NMR (400 MHz, DMSO-d6) δ 9.58 (s, 1H), 9.02 (s, 1H), 8.94 (s, 1H), 8.32 (d, 1H), 8.18 (d, 1H), 8.12 (s, 1H), 8.10 (d, 1H), 7.86 (dd, 1H), 7.69 (ddd, 1H), 7.60 (ddd, 1H), 7.38 (d, 1H), 7.02 (d, 1H), 6.88 (t, 1H), 6.78 (t, 1H), 6.58 (dd, 1H), 6.07 (d, 1H), 6.03 (t, 1H), 4.06 (s, 2H), 3.95 (dd, 2H), 3.91 (s, 1H), 3.80 (s, 3H), 3.68 (dd, 2H), 3.65 (s, 3H), 3.59-3.52 (m, 2H), 3.52-3.44 (m, 2H), 3.09 (s, 3H), 1.27 (s, 9H).

m/z 857.5 (M+H)$^+$ (ES$^+$)

Example 19

2-((2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethyl)thio)acetic acid

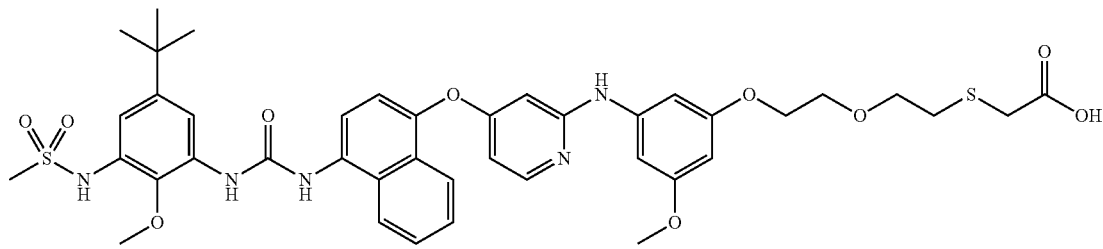 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCSCC(=O)O)c1]

(i) Methyl 2,2,3,3-tetramethyl-4,7-dioxa-10-thia-3-siladodecan-12-oate 2,2'-Oxydiethanol (7.05 mL, 80.5 mmol), NEt$_3$ (8.36 mL, 60 mmol) and DMAP (0.020 g, 0.164 mmol) were dissolved in DCM (100 mL) and cooled in an ice bath. A solution of TBSCl (7.28 g, 48.3 mmol) in DCM (20 mL) was added dropwise over 15 mins and the mixture allowed to warm to room temperature overnight. The organic layer was washed with saturated NaHCO$_3$ (100 mL), saturated NH$_4$Cl (100 mL), and then saturated NaCl (100 mL), passed through a phase separator and concentrated in vacuo to yield a colourless oil (8.95 g). To a solution of this oil (2.0 g) and NEt$_3$ (1.82 mL, 13.07 mmol) in DCM (20 mL) at 0-5° C. was added MsCl (0.611 mL, 7.84 mmol) dropwise. The resulting mixture warmed to rt and stirred for 2 h, diluted with DCM (30 mL) and the organic layer washed with water (50 mL), brine (50 mL), passed through a phase separator and concentrated in vacuo to yield 2.45 g of a light yellow oil. NaH (60% in mineral oil, 0.731 g, 18.27 mmol) was suspended in DMF (10 mL, 129 mmol), cooled in an ice bath and methyl 2-mercaptoacetate (1.515 mL, 16.60 mmol) added dropwise under nitrogen. After 30 min at rt the mixture was cooled in an ice bath and the light yellow oil from above (2.36 g) was added as a solution in DMF (5 mL) and stirred for 2 h. Sat. NH$_4$Cl(aq) (50 mL) was added and the aqueous layer extracted with EtOAc (2×50 mL). The combined organic layers were washed with brine, dried (Na2SO4), filtered and concentrated in vacuo onto silica gel. The crude product was purified by chromatography on silica gel (80 g column, 0-20% EtOAc/isohexane) to afford the sub-title compound (1.22 g) as a colourless oil.

$^1$H NMR (400 MHz, DMSO-d6) δ 3.71-3.65 (m, 2H), 3.63 (s, 3H), 3.59 (t, 2H), 3.47-3.42 (m, 2H), 3.42-3.37 (m, 2H), 2.74 (t, 2H), 0.86 (s, 9H), 0.04 (s, 6H)

(ii) Methyl 2-((2-(2-hydroxyethoxy)ethyl)thio)acetate

The product from step (i) above (546 mg, 1.770 mmol) was dissolved in AcOH: water (3 mL; 2:1 ratio) and stirred at rt for 1 h. The solvent was then removed in vacuo to yield the sub-title compound (347 mg) as a colourless oil.

$^1$H NMR (400 MHz, DMSO-d6) δ 4.57 (t, 1H), 3.60 (s, 3H), 3.53 (t, 2H), 3.48-3.40 (m, 2H), 3.40-3.33 (m, 4H), 2.70 (t, 2H).

(iii) Methyl 2-((2-(2-((methylsulfonyl)oxy)ethoxy)ethyl)thio)acetate

The product from step (ii) above (344 mg, 1.771 mmol) was dissolved in DCM (5 mL) and cooled in an ice bath. NEt$_3$ (370 μL, 2.66 mmol) followed by MsCl (166 μL, 2.125 mmol) were added dropwise and the mixture left to warm to rt overnight. The mixture was diluted with DCM (10 mL) and the organic layer washed with 0.1 M HCl (10 mL). The mixture was passed through a phase separator and concentrated in vacuo to yield the sub-title compound (396 mg) as light yellow oil.

$^1$H NMR (400 MHz, DMSO-d6) δ 4.32-4.20 (m, 2H), 3.64-3.61 (m, 2H), 3.60 (s, 3H), 3.58 (t, 2H), 3.37 (s, 2H), 3.15 (s, 3H), 2.73 (t, 2H).

(iv) Methyl 2-((2-(2-(3-methoxy-5-nitrophenoxy)ethoxy)ethyl)thio)acetate

3-Methoxy-5-nitrophenol (118 mg, 0.699 mmol), the product from step (iii) above (200 mg, 0.734 mmol) and potassium carbonate (290 mg, 2.098 mmol) were suspended/dissolved in DMF (3 mL) and heated to 80° C. overnight. The reaction was cooled and partitioned between TBME (20 mL) and brine (20 mL). The aqueous layer was extracted with TBME (20 mL) and the combined organic layers washed with brine (40 mL), dried (MgSO$_4$), filtered and concentrated in vacuo. The crude product was purified by chromatography on silica gel (12 g column, 0-50% EtOAc/isohexane) to afford the sub-title compound (170 mg) as a yellow oil.

$^1$H NMR (400 MHz, DMSO-d6) δ 7.35 (dt, 2H), 7.00 (t, 1H), 4.29-4.15 (m, 2H), 3.86 (s, 3H), 3.79-3.73 (m, 2H), 3.66 (t, 2H), 3.63 (s, 3H), 3.42 (s, 2H), 2.77 (t, 2H).

m/z 346.0 (M+H)$^+$ (ES$^+$)

(v) Methyl 2-((2-(2-(3-amino-5-methoxyphenoxy)ethoxy)ethyl)thio)acetate

The product from step (iv) above (170 mg, 0.492 mmol) was dissolved in EtOH (4 mL, 68.5 mmol) and H$_2$O (0.5 mL). Iron (165 mg, 2.95 mmol) and NH$_4$Cl (211 mg, 3.94 mmol) were added and the flask evacuated and backfilled with nitrogen three times. The reaction mixture was heated to 80° C. with vigorous stirring for 2 h. LCMS revealed complete conversion to the sub-title compound. The mixture was cooled, filtered through celite and the solids washed with EtOH (10 mL). The solution was concentrated in vacuo to yield the sub-title as a light yellow oil (120 mg).

m/z 316.0 (M+H)$^+$ (ES$^+$)

(vi) Methyl 2-((2-(2-(3-((4-((4-(3-(5-(tert-Butyl)-2-methoxy-3-(methylsulfonamido)phenyl)-ureido)naphthalen-1-yl)oxy)pyridin-2-yl)amino)-5-methoxyphenoxy)ethoxy)ethyl)thio)acetate A suspension of the product from step (v) above (120 mg, 0.380 mmol), N-(5-(tert-butyl)-3-(3-(4-((2-chloropyridin-4-yl)oxy)naphthalen-1-yl)ureido)-2-methoxyphenyl)methanesulfonamide (see WO 2014/162126; 217 mg, 0.380 mmol), Pd-175 (7.43 mg, 9.51 µmol) and freshly ground potassium carbonate (158 mg, 1.141 mmol) in DMF (3 mL) was degassed by 3 cycles of evacuation and backfilling with nitrogen. The reaction was heated to 70° C. (block temperature) for 2 h then concentrated in vacuo. The crude product was purified by chromatography on RP Flash C18 (26 g column, 25-100% MeCN/10 mM Ammonium Bicarbonate) to afford the sub-title compound (152 mg) as a colourless, glassy solid.

$^1$H NMR (400 MHz, DMSO-d6) δ 9.40 (s, 1H), 9.16 (s, 1H), 8.93 (s, 1H), 8.89 (s, 1H), 8.34-8.26 (m, 1H), 8.19 (d, 1H), 8.12 (d, 1H), 8.10 (d, 1H), 7.86 (dd, 1H), 7.71 (ddd, 1H), 7.61 (ddd, 1H), 7.39 (d, 1H), 7.02 (d, 1H), 6.90 (t, 1H), 6.79 (t, 1H), 6.58 (dd, 1H), 6.07 (d, 1H), 6.03 (t, 1H), 4.02-3.94 (m, 2H), 3.81 (s, 3H), 3.74-3.68 (m, 2H), 3.65 (s, 3H), 3.62 (s, 3H), 3.41 (s, 2H), 3.10 (s, 3H), 2.77 (t, 2H), 1.27 (s, 9H).

m/z 848.0 (M+H)$^+$ (ES$^+$)

(vii) 2-((2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethyl)thio)acetic acid The product from step (vi) (150 mg, 0.177 mmol) was dissolved in THF (4 mL). NaOH (2M aq.) (973 µL, 1.946 mmol) was added and the mixture stirred at rt overnight. The reaction was acidified with AcOH (0.25 mL) and concentrated in vacuo. The crude product was purified by chromatography on RP Flash C18 (24 g column, 15-75% MeCN/10 mM Ammonium Bicarbonate). The product containing fractions were combined, acidified with formic acid to ca. pH 4, concentrated in vacuo and the resulting precipitate filtered off, washed with water (5 mL) and dried in vacuo at 50° C. for 24 h to afford the title compound (78 mg) as a white solid.

$^1$H NMR (400 MHz, DMSO-d6) δ 12.54 (s, 1H), 9.40 (s, 1H), 9.17 (s, 1H), 8.93 (s, 1H), 8.89 (s, 1H), 8.29 (d, 1H), 8.19 (d, 1H), 8.12 (d, 1H), 8.10 (d, 1H), 7.86 (dd, 1H), 7.71 (ddd, 1H), 7.61 (ddd, 1H), 7.39 (d, 1H), 7.02 (d, 1H), 6.90 (t, 1H), 6.79 (t, 1H), 6.58 (dd, 1H), 6.07 (d, 1H), 6.03 (t, 1H), 4.03-3.93 (m, 2H), 3.80 (s, 3H), 3.74-3.67 (m, 2H), 3.67-3.58 (m, 5H), 3.29 (s, 2H), 3.10 (s, 3H), 2.76 (t, 2H), 1.27 (s, 9H).

m/z 833.9 (M+H)$^+$ (ES$^+$)

Example 20

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)propanoic acid (Enantiomers 1 and 2)

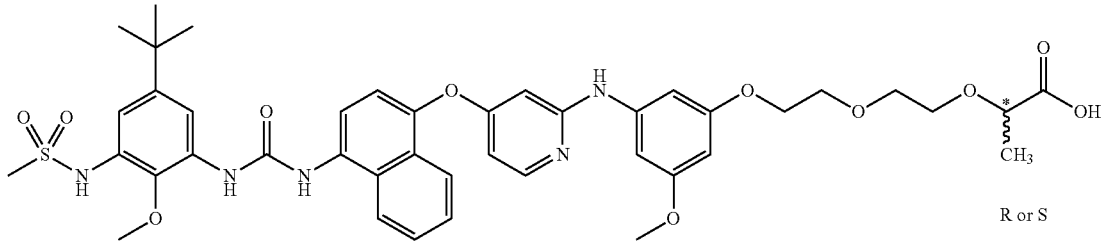 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOC(C)C(=O)O)c1 ; "R or S"]

The title compound of Example 14 (40 mg, 0.048 mmol) was submitted to preparative chiral HPLC purification (Gilson, Daicel Chirapak IC column, 30% EtOH in 4:1 hexane:DCM (0.2% diethyl amine) to obtain two enantiontiomers: Enantiomer 1 (9.2 mg) and Enantiomer 2 (5.2 mg). The absolute stereochemistry of the two enantiomers is not known.

(a) Enantiomer 1

$^1$H NMR (400 MHz, DMSO-d6) δ 9.59 (s, 1H), 9.04 (s, 1H), 8.89 (s, 1H), 8.33 (d, 1H), 8.15 (d, 1H), 8.13-8.07 (m, 2H), 7.86 (dd, 1H), 7.68 (ddd, 1H), 7.59 (ddd, 1H), 7.36 (d, 1H), 7.02 (d, 1H), 6.80-6.71 (m, 2H), 6.58 (dd, 1H), 6.10 (d, 1H), 6.02 (t, 1H), 3.93-3.85 (m, 2H), 3.80 (s, 4H), 3.68 (dd, 2H), 3.64 (s, 3H), 3.55 (t, 2H), 3.46-3.42 (m, 1H), 3.08 (s, 3H), 1.26 (s, 9H), 1.21 (d, 3H).

m/z 832.1 (M+H)$^+$

Chiral HPLC (Daicel Chiralpak IC, 5 um, 4.6×250 mm, 45 min method, 1.0 mL/min, 30% EtOH in DCM/Hexane (1:4) (0.2% DEA) RT=8.9 min, 84% ee @ 254 nm.

(b) Enantiomer 2

$^1$H NMR (400 MHz, DMSO-d6) δ 9.55 (s, 1H), 9.02 (s, 1H), 8.89 (s, 1H), 8.33 (d, 1H), 8.16 (d, 1H), 8.12 (d, 1H), 8.10 (d, 1H), 7.88-7.84 (m, 1H), 7.69 (ddd, 1H), 7.60 (ddd, 1H), 7.37 (d, 1H), 7.02 (d, 1H), 6.81 (t, 1H), 6.76 (t, 1H), 6.59 (dd, 1H), 6.10 (d, 1H), 6.03 (t, 1H), 3.92 (t, 2H), 3.84 (d, 4H), 3.74-3.67 (m, 2H), 3.65 (s, 3H), 3.56 (t, 2H), 3.45-3.42 (m, 1H), 3.09 (s, 3H), 1.27 (s, 9H), 1.23 (d, 3H).

m/z 832.1 (M+H)$^+$ (ES$^+$)

Chiral HPLC (Daicel Chiralpak IC, 5 um, 4.6×250 mm, 45 min method, 1.0 mL/min, 30% EtOH in DCM/Hexane (1:4) (0.2% DEA) RT=11.2 min, 98% ee @ 254 nm.

Example 21

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)-2-methylpropanoic acid

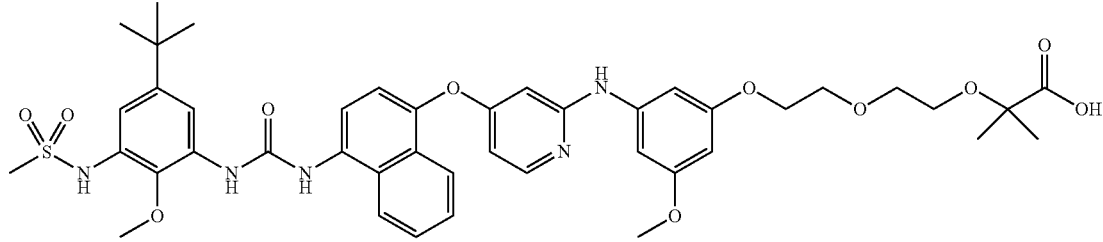 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOC(C)(C)C(=O)O)c1]

(i) Ethyl 2-(2-(2-(benzyloxy)ethoxy)ethoxy)-2-methylpropanoate

Ethyl 2-(2-(2-(benzyloxy)ethoxy)ethoxy)propanoate (1.1 g, 3.71 mmol) was dissolved in THF (35 mL) and cooled to −78° C. LiHMDS (1 M in THF, 4.08 mL, 4.08 mmol) was added and the reaction stirred for 1 h. MeI (2M in TBME) (2.04 mL, 4.08 mmol) was added and the mixture warmed to rt and stirred overnight. The reaction was quenched with NH$_4$Cl (2 mL) and concentrated directly onto silica. The crude product was purified by chromatography on silica gel (80 g column, 0-40% EtOAc/isohexane) to afford the sub-title compound (328 mg) as a colourless oil.

$^1$H NMR (400 MHz, CDCl$_3$) δ 7.31-7.17 (m, 5H), 4.50 (s, 2H), 4.11 (q, 2H), 3.65-3.53 (m, 6H), 3.53-3.48 (m, 2H), 1.36 (s, 6H), 1.21 (t, 3H).

(ii) Ethyl 2-methyl-2-(2-(2-((methylsulfonyl)oxy)ethoxy)ethoxy)propanoate

The product from step (i) above (390 mg, 1.25 mmol) was dissolved in EtOH (30 mL, 1.257 mmol) and 5 wt % Pd—C (type 87 L, 134 mg, 0.063 mmol) added. The mixture was stirred at rt under 4 bar of H$_2$ for 16 h. HPLC confirmed consumption of the starting material. The reaction mixture was filtered through celite, washing the solids with EtOH (50 mL) and concentrated in vacuo to yield a colourless oil.

The oil was dissolved in dry DCM (10 mL) and cooled in a water ice bath. NEt$_3$ (192 μL, 1.378 mmol) and MsCl (98 μL, 1.263 mmol) were added and the mixture allowed to warm to rt with stirring overnight. The reaction was diluted with DCM (30 mL), washed with 0.1 M HCl (20 mL) and the aqueous layer further extracted with DCM (10 mL). The combined organic layers were passed through a phase separator and concentrated in vacuo to afford the sub-title compound (313 mg) as a colourless oil.

$^1$H NMR (400 MHz, DMSO-d6) δ 4.34-4.27 (m, 2H), 4.10 (q, 2H), 3.71-3.63 (m, 2H), 3.59-3.50 (m, 2H), 3.48-3.40 (m, 2H), 3.18 (s, 3H), 1.32 (s, 6H), 1.19 (t, 3H).

(iii) Ethyl 2-(2-(2-(3-methoxy-5-nitrophenoxy)ethoxy)ethoxy)-2-methylpropanoate

3-Methoxy-5-nitrophenol (188 mg, 1.112 mmol), the product from step (ii) above (316 mg, 1.059 mmol) and freshly-ground potassium carbonate (439 mg, 3.18 mmol) were suspended in DMF (3 mL) and heated to 80° C. overnight. The reaction was cooled and partitioned between TBME (20 mL) and brine (20 mL). The aqueous layer was extracted with TBME (20 mL) and the combined organic layers washed with brine (40 mL), dried (MgSO4), filtered and concentrated in vacuo. The crude product was purified by chromatography on silica gel (80 g column, 0-40% EtOAc/isohexane) to afford the sub-title compound (346 mg) as a yellow oil.

$^1$H NMR (400 MHz, DMSO-d6) δ 7.35 (dt, 2H), 7.00 (t, 1H), 4.26-4.19 (m, 2H), 4.11 (q, 2H), 3.86 (s, 3H), 3.80-3.75 (m, 2H), 3.58 (dd, 2H), 3.47 (dd, 2H), 1.33 (s, 6H), 1.19 (t, 3H).

(iv) Ethyl 2-(2-(2-(3-amino-5-methoxyphenoxy)ethoxy)ethoxy)-2-methylpropanoate

The product from step (iii) above (335 mg, 0.902 mmol) was dissolved in EtOH (5 mL) and Pd/C (5 wt % type 87 L, 28.8 mg, 0.014 mmol) added. The reaction was stirred under 1 bar H$_2$ for 2 h. The reaction was filtered through celite, washing with EtOH (50 mL) and concentrated in vacuo. The crude product was purified by chromatography on silica gel (12 g column, 0-5% (0.7 M Ammonia/MeOH)/DCM) to afford the sub-title compound (226 mg) as a red oil.

$^1$H NMR (400 MHz, DMSO-d6) δ 5.78-5.72 (m, 2H), 5.68 (t, 1H), 5.07 (s, 2H), 4.11 (q, 2H), 3.99-3.87 (m, 2H), 3.75-3.65 (m, 2H), 3.62 (s, 3H), 3.58-3.53 (m, 2H), 3.48-3.43 (m, 2H), 1.33 (s, 6H), 1.19 (d, 3H).

m/z 342.1 (M+H)$^+$ (ES$^+$)

(v) Ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)-2-methylpropanoate A suspension of the product from step (iv) above (210 mg, 0.615 mmol), N-(5-(tert-butyl)-3-(3-(4-((2-chloropyridin-4-yl)oxy)naphthalen-1-yl)ureido)-2-methoxyphenyl)methanesulfonamide (see WO 2014/162126; 350 mg, 0.615 mmol) and freshly ground potassium carbonate (255 mg, 1.845 mmol) in DMF (3 mL) was degassed by 3 cycles of evacuation and backfilling with nitrogen. The mixture was heated to 40° C. for 5 min and BrettPhosG3 precatalyst

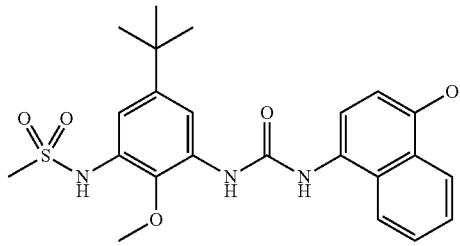

(13.94 mg, 0.015 mmol) was added as a solution in DMF (1 mL). The flask was evacuated and backfilled with nitrogen and then heated to 75° C. (block temperature) for 4 h. The reaction was cooled to rt and a further portion of freshly ground potassium carbonate (255 mg, 1.845 mmol) and Pd-173 (14 mg) was added. The reaction was degassed by evacuation and backfilling with nitrogen 3 times and heated to 75° C. (block temperature) for 12 h, diluted with DCM (50 mL), washed with brine (50 mL), passed through a phase separator and concentrated in vacuo. The crude product was purified by chromatography on RP Flash C18 (40 g column, 25-100% MeCN/10 mM Ammonium Bicarbonate) to afford the sub-title compound (77 mg) as a brown solid.

$^1$H NMR (400 MHz, DMSO-d6) δ 9.39 (s, 1H), 8.90 (d, 2H), 8.31-8.28 (m, 1H), 8.19 (d, 1H), 8.14-8.07 (m, 2H), 7.87 (dd, 1H), 7.71 (ddd, 1H), 7.61 (ddd, 1H), 7.39 (d, 1H), 7.02 (d, 1H), 6.91 (t, 1H), 6.78 (t, 1H), 6.58 (dd, 1H), 6.07 (d, 1H), 6.03 (t, 1H), 4.10 (q, 2H), 4.01-3.95 (m, 2H), 3.81 (s, 3H), 3.74-3.69 (m, 2H), 3.65 (s, 3H), 3.55 (dd, 2H), 3.46 (dd, 2H), 3.10 (s, 3H), 1.32 (s, 6H), 1.27 (s, 9H), 1.19 (t, 3H). m/z 848.0 (M+H)$^+$ (ES$^+$)

(vi) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)-2-methylpropanoic acid The product from step (v) (77 mg, 0.088 mmol) was dissolved in THF (2 mL) and MeOH (0.5 mL). NaOH (2M aq.) (485 μL, 0.969 mmol) was added and the mixture stirred at rt overnight. The reaction was acidified with AcOH (0.25 mL) and concentrated in vacuo. The crude product was purified by chromatography on RP Flash C18 (24 g column, 15-75% MeCN/10 mM Ammonium Bicarbonate). The product containing fractions were combined, acidified with formic acid to ca. pH 4 and concentrated in vacuo. The solid was then redissolved in the minimum amount of EtOH (ca. 1 mL) and water (0.5 mL) added dropwise to crash out the white solid. The vial was then centrifuged at 2000 rpm for 2 min and the supernatant decanted to yield the title compound (40 mg) as a white solid.

$^1$H NMR (400 MHz, DMSO-d6) δ 12.50 (s, 1H), 9.38 (s, 1H), 9.11 (s, 1H), 8.91 (s, 1H), 8.87 (s, 1H), 8.29 (d, 1H), 8.18 (d, 1H), 8.14-8.07 (m, 2H), 7.87 (dd, 1H), 7.70 (ddd, 1H), 7.61 (ddd, 1H), 7.38 (d, 1H), 7.02 (d, 1H), 6.90 (t, 1H), 6.78 (t, 1H), 6.57 (dd, 1H), 6.08 (d, 1H), 6.03 (t, 1H), 3.97 (dd, 2H), 3.81 (s, 3H), 3.71 (dd, 2H), 3.65 (s, 3H), 3.56 (dd, 2H), 3.48 (dd, 2H), 3.10 (s, 3H), 1.31 (s, 6H), 1.27 (s, 9H). m/z 846.1 (M+H)$^+$ (ES$^+$)

Example 22

1-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethyl)-H-pyrazole-4-carboxylic acid

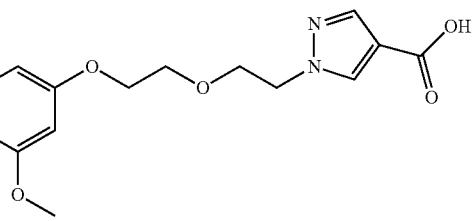

(i) Methyl 1-(2-(2-(benzyloxy)ethoxy)ethyl)-1H-pyrazole-4-carboxylate

Potassium carbonate (822 mg, 5.95 mmol) was added to a solution of 2-(2-(benzyloxy)ethoxy)ethyl methanesulfonate (598 mg, 2.181 mmol) and methyl 1H-pyrazole-4-carboxylate (250 mg, 1.982 mmol) in DMF (15 mL) and heated to 60° C. for 2 days. The reaction was cooled to rt, diluted with EtOAc (50 mL) and washed sequentially with water (30 mL), sat. aq. NaHCO$_3$ (30 mL) and 20% v/v brine (30 mL). The organic layer was dried (MgSO$_4$) and concentrated in vacuo. The crude product was purified by chromatography on silica gel (12 g column, 0-100% EtOAc/isohexane) to afford the sub-title compound (472 mg) as a colourless oil.

$^1$H NMR (400 MHz, DMSO-d6) δ 8.33 (d, 1H), 7.87 (d, 1H), 7.38-7.30 (m, 2H), 7.30-7.24 (m, 3H), 4.44 (s, 2H), 4.32 (t, 2H), 3.80 (t, 2H), 3.72 (s, 3H), 3.58-3.53 (m, 2H), 3.53-3.48 (m, 2H).

m/z 305.1 (M+H)$^+$ (ES$^+$)

(ii) Methyl 1-(2-(2-hydroxyethoxy)ethyl)-1H-pyrazole-4-carboxylate

Pd/C 10% in 50% paste in water (Type 39) (33.0 mg, 0.310 mmol) was added to a solution of the product from step (i) above (472 mg, 1.551 mmol) in EtOH (4 mL) and the resulting slurry stirred under H$_2$ at 1 bar pressure overnight. The reaction was filtered through celite, washing with EtOAc (2×20 mL) and the solvent removed to afford the sub-title compound (326 mg) as a colourless oil.

$^1$H NMR (400 MHz, DMSO-d6) δ 8.33 (d, 1H), 7.87 (d, 1H), 4.59 (t, 1H), 4.31 (t, 2H), 3.78 (t, 2H), 3.74 (s, 3H), 3.48-3.42 (m, 2H), 3.42-3.37 (m, 2H).

(iii) Methyl 1-(2-(2-((methylsulfonyl)oxy)ethoxy)ethyl)-1H-pyrazole-4-carboxylate MsCl (142 μL, 1.826 mmol) was added to a solution of the product from step (ii) above (326 mg, 1.522 mmol) in DCM (10 mL) and TEA (424 μL, 3.04 mmol) at 0° C., and the resulting solution stirred at rt overnight. A second aliquot of NEt₃ (424 µL, 3.04 mmol) and MsCl (142 µL, 1.826 mmol) was added at rt, and the reaction stirred at rt for further 3 h. The reaction was diluted with DCM (50 mL) and washed with 20% v/v brine (50 mL). The solvent was removed to afford an orange oil. The crude product was purified by chromatography on silica gel (12 g column, 0-10% MeOH/DCM) to afford the sub-title compound (431 mg) as an orange oil.

¹H NMR (400 MHz, DMSO-d6) δ 8.33 (d, 1H), 7.88 (d, 1H), 4.33 (t, 2H), 4.27 (m, 2H), 3.83 (t, 2H), 3.74 (s, 3H), 3.65 (dt, 2H), 3.12 (s, 3H).

m/z 293.3 (M+H)⁺ (ES⁺)

(iv) Methyl 1-(2-(2-(3-methoxy-5-nitrophenoxy)ethoxy)ethyl)-1H-pyrazole-4-carboxylate Potassium carbonate (611 mg, 4.42 mmol) was added to a solution of 3-methoxy-5-nitrophenol (274 mg, 1.622 mmol) and the product from step (iii) above (431 mg, 1.474 mmol) in DMF (15 mL) and heated to 60° C. for 2 days. The reaction was cooled to rt, diluted with EtOAc (50 mL) and washed sequentially with water (30 mL), sat. aq. NaHCO₃ (30 mL) and 20% v/v brine (30 mL). The organic layer was dried (MgSO₄) and concentrated in vacuo. The crude product was purified by chromatography on silica gel (12 g column, 0-100% EtOAc/isohexane) to afford the sub-title compound (387 mg) as a colourless oil.

¹H NMR (400 MHz, DMSO-d6) δ 8.30 (d, 1H), 7.83 (d, 1H), 7.31 (dt, 2H), 6.94 (t, 1H), 4.33 (t, 2H), 4.22-4.11 (m, 2H), 3.90-3.82 (m, 5H), 3.78-3.72 (m, 2H), 3.71 (s, 3H).

m/z 366.4 (M+H)⁺ (ES⁺)

(v) Methyl 1-(2-(2-(3-amino-5-methoxyphenoxy)ethoxy)ethyl)-1H-pyrazole-4-carboxylate A slurry of the product from step (iv) above (378 mg, 1.035 mmol), NH₄Cl (22.14 mg, 0.414 mmol) and iron (578 mg, 10.35 mmol) in EtOH (20 mL), water (2 mL) and THF (3 mL) was heated to reflux for 1 h. The reaction was cooled to rt and filtered through celite, washing with EtOAc (2×20 mL). The solvent was removed in vacuo. The crude product was purified by chromatography on silica gel (12 g column, 0-10% MeOH/DCM) to afford the sub-title compound (300 mg) as a yellow oil.

¹H NMR (400 MHz, DMSO-d6) δ 8.34 (d, 1H), 7.88 (d, 1H), 5.75 (t, 1H), 5.73 (t, 1H), 5.66 (t, 1H), 5.06 (s, 2H), 4.33 (t, 2H), 3.94-3.87 (m, 2H), 3.84 (t, 2H), 3.73 (s, 3H), 3.70-3.64 (m, 2H), 3.62 (s, 3H).

m/z 336.3 (M+H)⁺ (ES⁺)

(vi) Methyl 1-(2-(2-(3-((4-((4-(3-(5-(tert-butyl)-2-methoxy-3-(methylsulfonamido)phenyl)-ureido)naphthalen-1-yl)oxy)pyridin-2-yl)amino)-5-methoxyphenoxy)ethoxy)ethyl)-1H-pyrazole-4-carboxylate A suspension of N-(5-(tert-butyl)-3-(3-(4-((2-chloropyridin-4-yl)oxy)naphthalen-1-yl)ureido)-2-methoxyphenyl)methanesulfonamide (see WO 2014/162126; 239 mg, 0.420 mmol), the product from step (v) above (141 mg, 0.420 mmol), freshly ground potassium carbonate (174 mg, 1.261 mmol) in DMF (2 mL) in a vial was evacuated and backfilled with nitrogen 3 times. The mixture was heated to 40° C. and Pd 175 (9.52 mg, 10.51 µmol) added. The reaction mixture was heated at 75° C. for 2 h. The reaction was then cooled and filtered. The filtrate was partitioned between EtOAc (50 mL) and 20% v/v brine (50 mL). The organic layer was dried (MgSO₄), filtered and concentrated. The crude product was purified by chromatography on silica gel (12 g column, 0-10% MeOH/DCM) to afford the sub-title compound (240 mg) as a light brown solid.

m/z 868.1 (M+H)⁺ (ES⁺)

(vii) Methyl 1-(2-(2-(3-((4-((4-(3-(5-(tert-butyl)-2-methoxy-3-(methylsulfonamido)phenyl)-ureido)naphthalen-1-yl)oxy)pyridin-2-yl)amino)-5-methoxyphenoxy)ethoxy)ethyl)-1H-pyrazole-4-carboxylate NaOH (2M aq.) (415 µL, 0.830 mmol) was added to a solution of the product from step (vi) above (240 mg, 0.277 mmol) in THF (1.6 mL) and MeOH (0.6 mL) and the resulting solution stirred at rt overnight. Further NaOH (2M aq.) (415 µL, 0.830 mmol) was added and the reaction stirred at rt for 2 h. The reaction was quenched with AcOH (24.14 µL, 0.422 mmol) and the solvent removed in vacuo. The crude product was purified by chromatography (RP Flash C18 12 g column, 15-75% MeCN/10 mM Ammonium Bicarbonate) to afford the title compound (130 mg, 0.149 mmol, 54.0% yield) as a white solid.

¹H NMR (400 MHz, DMSO-d₆) δ 9.40 (s, 1H), 8.92 (s, 1H), 8.86 (s, 1H), 8.29 (d, 1H), 8.23 (s, 1H), 8.18 (d, 1H), 8.11 (d, 1H), 8.09 (d, 1H), 7.87 (dd, 1H), 7.79 (d, 1H), 7.70 (ddd, 1H), 7.61 (ddd, 1H), 7.38 (d, 1H), 7.02 (d, 1H), 6.87 (t, 1H), 6.80 (t, 1H), 6.57 (dd, 1H), 6.08 (d, 1H), 6.02 (t, 1H), 4.32 (t, 2H), 4.00-3.89 (m, 2H), 3.84 (t, 2H), 3.81 (s, 3H), 3.73-3.67 (m, 2H), 3.65 (s, 3H), 3.10 (s, 3H), 1.27 (s, 9H).

m/z 854.5 (M+H)⁺ (ES⁺)

Example 23

N-(3-(3-(4-((2-((3-(2-(2-((1H-Tetrazol-5-yl)methoxy)ethoxy)ethoxy)-5-methoxyphenyl)amino)-pyridin-4-yl)oxy)naphthalen-1-yl)ureido)-5-(tert-butyl)-2-methoxyphenyl)methanesulfonamide

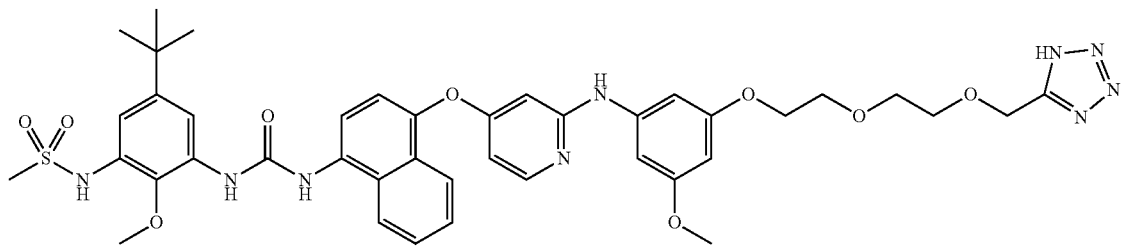 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOCc2nnn[nH]2)c1]

(i) 2,2,3,3-Tetramethyl-4,7,10-trioxa-3-siladodecane-12-nitrile

A solution of 2-(2-((tert-butyldimethylsilyl)oxy)ethoxy)ethanol (2 g, 6.35 mmol) in THF (10 mL) was added dropwise to a slurry of NaH (60% in oil, 0.356 g, 8.89 mmol) in dry THF (40 mL) at 0° C. under nitrogen. The resulting slurry was stirred at 0° C. for 20 min, and a solution of bromoacetonitrile (0.44 mL, 6.35 mmol) in dry THF (10 mL) added to the reaction mixture. The resulting dark coloured solution was allowed to warm to rt and stirred at rt overnight. The reaction was quenched with MeOH (0.5 mL) and diluted with 20% v/v brine (20 mL) and EtOAc (50 mL). The layers were separated and the aqueous layer extracted with EtOAc (3×20 mL). The combined organic extractions were dried (MgSO$_4$) and concentrated in vacuo. The crude product was purified by chromatography on silica gel (24 g column, 0-100% EtOAc/isohexane) to afford the sub-title compound (840 mg) as a thick brown oil.

$^1$H NMR (400 MHz, DMSO-d6) δ 4.44 (s, 2H), 3.65 (dd, 2H), 3.62-3.56 (m, 2H), 3.56-3.49 (m, 2H), 3.41 (dd, 2H), 0.82 (s, 9H), 0.00 (s, 6H).

m/z 282 (M+Na)$^+$ (ES$^+$)

(ii) 2-(2-(2-Hydroxyethoxy)ethoxy)acetonitrile

The compound from step (i) above (728 mg, 2.81 mmol) was stirred in AcOH (5 mL) and water (2.5 mL) for 1 h. The solvent was removed and the residue azeotroped with toluene (3×5 mL) to afford the sub-title compound (409 mg) as a thick colourless oil.

$^1$H NMR (400 MHz, DMSO-d6) δ 4.53 (bs, 1H), 4.44 (s, 2H), 3.65-3.57 (m, 2H), 3.57-3.49 (m, 2H), 3.49-3.41 (m, 2H), 3.41-3.35 (m, 2H).

(iii) 2-(2-(Cyanomethoxy)ethoxy)ethyl methanesulfonate

MsCl (322 μL, 4.14 mmol) was added to a solution of the compound from step (ii) above (429 mg, 2.96 mmol) and NEt$_3$ (824 μL, 5.91 mmol) in DCM (15 mL) at 0° C., then the resulting solution stirred at rt overnight. The reaction was diluted with DCM (50 mL) and washed with 20% v/v brine (100 mL). The organic layer was passed through a hydrophobic frit and concentrated. The crude product was purified by chromatography on silica gel (12 g column, 0-100% EtOAc/isohexane) to afford the sub-title compound (640 mg) as a colourless oil.

$^1$H NMR (400 MHz, DMSO-d6) δ 4.50 (s, 2H), 4.39-4.25 (m, 2H), 3.72-3.64 (m, 4H), 3.64-3.59 (m, 2H), 3.19 (s, 3H).

(iv) 2-(2-(2-(3-Methoxy-5-nitrophenoxy)ethoxy)ethoxy)acetonitrile

Freshly ground potassium carbonate (1189 mg, 8.60 mmol) was added to a solution of 3-methoxy-5-nitrophenol (533 mg, 3.15 mmol) and the compound from step (iii) above (640 mg, 2.87 mmol) in DMF (15 mL) and heated to 60° C. overnight. The reaction was cooled to rt, diluted with EtOAc (100 mL) and washed with 20% v/v brine (100 mL). The organic layer was dried (MgSO$_4$) and concentrated in vacuo. The crude product was purified by chromatography on silica gel (40 g column, 0-100% EtOAc/isohexane) to afford the sub-title compound (743 mg) as a yellow oil.

$^1$H NMR (400 MHz, DMSO-d6) δ 7.35 (t, 1H), 7.33 (t, 1H), 7.00 (t, 1H), 4.49 (s, 2H), 4.26-4.18 (m, 2H), 3.86 (s, 3H), 3.81-3.72 (m, 2H), 3.71-3.59 (m, 4H).

m/z 319.2 (M+Na)$^+$ (ES$^+$)

(v) 2-(2-(2-(3-Amino-5-methoxyphenoxy)ethoxy)ethoxy)acetonitrile

Iron (754 mg, 13.5 mmol) followed by ammonium chloride (28.9 mg, 0.54 mmol) was added to a solution of the compound from step (iv) above (400 mg, 1.35 mmol) in EtOH (13 mL), THF (5 mL) and water (2 mL) and the resulting slurry heated to reflux for 2 h. The reaction was cooled and filtered through celite, washing with EtOAc (2×20 mL). The solvent was removed in vacuo. The crude product was purified by chromatography on silica gel (24 g column, 0-100% EtOAc/isohexane) to afford the sub-title compound (263 mg, 0.938 mmol, 69.5% yield) as a thick light yellow oil.

$^1$H NMR (400 MHz, DMSO-d6) δ 5.75 (d, 2H), 5.69 (t, 1H), 5.05 (s, 2H), 4.49 (s, 2H), 4.00-3.91 (m, 2H), 3.71-3.63 (m, 6H), 3.63 (s, 3H).

m/z 267.3 (M+H)$^+$ (ES$^+$)

(vi) N-(5-(tert-Butyl)-3-(3-(4-((2-((3-(2-(2-(cyanomethoxy)ethoxy)ethoxy)-5-methoxyphenyl)amino)pyridin-4-yl)oxy)naphthalen-1-yl)ureido)-2-methoxyphenyl)methanesulfonamide A suspension of N-(5-(tert-butyl)-3-(3-(4-((2-chloropyridin-4-yl)oxy)naphthalen-1-yl)ureido)-2-methoxyphenyl) methanesulfonamide (see WO 2014/162126; 310 mg, 0.54 mmol), the compound from step (v) above (145 mg, 0.54 mmol) and freshly ground potassium carbonate (226 mg, 1.63 mmol) in DMF (3 mL) was evacuated, back filling with nitrogen 3 times. The mixture was heated under nitrogen to 40° C. and Pd-175 (10.6 mg, 0.014 mmol) added. The reaction mixture was heated at 75° C. for 2 h, cooled and filtered. The filtrate was partitioned between EtOAc (50 mL) and 20% v/v brine (50 mL). The organic layer was dried (MgSO$_4$), filtered and concentrated. The crude product was purified by chromatography on silica gel (12 g column, 0-10% MeOH/DCM) to afford a thick brown oil. The material was dissolved in DCM (5 mL) and washed with 20% v/v brine (10 mL). The solvent was removed to afford the sub-title compound (362 mg) as a beige solid.

$^1$H NMR (400 MHz, DMSO-d6) δ 9.38 (s, 1H), 9.13 (s, 1H), 8.91 (s, 1H), 8.87 (s, 1H), 8.29 (d, 1H), 8.18 (d, 1H), 8.12 (d, 1H), 8.10 (d, 1H), 7.87 (dd, 1H), 7.70 (ddd, 1H), 7.61 (ddd, 1H), 7.38 (d, 1H), 7.02 (d, 1H), 6.91 (t, 1H), 6.79 (t, 1H), 6.58 (dd, 1H), 6.08 (d, 1H), 6.04 (t, 1H), 4.48 (s, 2H), 4.04-3.92 (m, 2H), 3.81 (s, 3H), 3.72 (dt, 2H), 3.69-3.58 (m, 7H), 3.10 (s, 3H), 1.27 (s, 9H).

m/z 799.4 (M+H)$^+$ (ES$^+$)

(vii) N-(3-(3-(4-((2-((3-(2-(2-((1H-Tetrazol-5-yl)methoxy)ethoxy)ethoxy)-5-methoxyphenyl)amino)pyridin-4-yl)oxy)naphthalen-1-yl)ureido)-5-(tert-butyl)-2-methoxyphenyl)methanesulfonamide TMSN$_3$ (49.8 μL, 0.37 mmol) was added to a slurry of the compound from step (vi) above (100 mg, 0.12 mmol) and dibutyltin oxide (31 mg, 0.12 mmol) in toluene (2 mL) and the resulting slurry heated to 100° C. for 1 h. The reaction was cooled to rt and quenched with MeOH (2 mL). The solvent was removed and the crude product purified by chromatography (RP Flash C18, 12 g column, 15-75% MeCN/10 mM Ammonium Bicarbonate). The product-rich fractions were combined and the pH adjusted to 7 with formic acid. The solvent was removed to afford an off-white solid. This was dissolved in EtOH (1 mL) and precipitated with water (4 mL). The resulting precipitate was collected by filtration to afford the title compound (31 mg) as an off-white solid.

¹H NMR (400 MHz, DMSO-d6) δ 9.38 (s, 1H), 9.13 (s, 1H), 8.91 (s, 1H), 8.87 (s, 1H), 8.29 (d, 1H), 8.19 (d, 1H), 8.11 (d, 1H), 8.10 (d, 1H), 7.87 (dd, 1H), 7.70 (ddd, 1H), 7.61 (ddd, 1H), 7.38 (d, 1H), 7.02 (d, 1H), 6.90 (t, 1H), 6.78 (t, 1H), 6.57 (dd, 1H), 6.08 (d, 1H), 6.03 (t, 1H), 4.84 (s, 2H), 4.03-3.93 (m, 2H), 3.81 (s, 3H), 3.74-3.68 (m, 2H), 3.68-3.58 (m, 7H), 3.10 (s, 3H), 1.27 (s, 9H).
m/z 842.1 (M+H)⁺ (ES⁺)

Example 24

2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)acetic acid

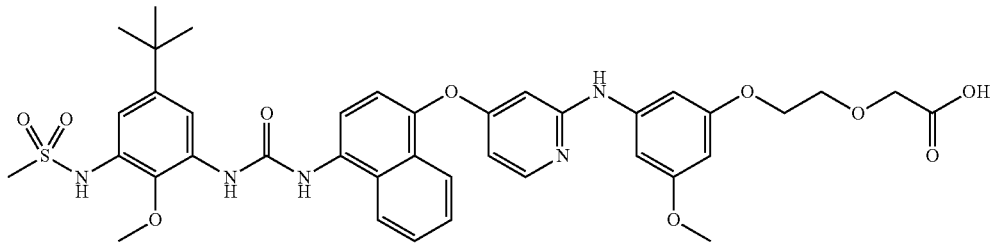 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCC(=O)O)c1]

(i) Ethyl 2-(2-(3-methoxy-5-nitrophenoxy)ethoxy)acetate

Potassium carbonate (1.226 g, 8.87 mmol) was added to a slurry of 3-methoxy-5-nitrophenol (0.5 g, 2.96 mmol), ethyl 2-(2-chloroethoxy)acetate (0.440 mL, 2.96 mmol) and sodium iodide (0.222 g, 1.478 mmol) in DMF (20 mL) and stirred at 70° C. for 2 h. The heating was increased to 90° C. and the reaction left to stir for 24 h. The reaction was cooled to rt and partitioned between EtOAc (100 mL) and 20% v/v brine (100 mL), the organic layer washed with 20% v/v brine (50 mL), dried (MgSO₄) and concentrated in vacuo. The crude product was purified by chromatography on silica gel (24 g column, 0-50% EtOAc/isohexane). The material obtained was dissolved in EtOAc (50 mL) and washed with NaOH (2 M aq, 2×50 mL). The organic layer was dried (MgSO₄) and concentrated in vacuo to afford the sub-title compound (300 mg) as a light yellow oil.
¹H NMR (400 MHz, DMSO-d6) δ 7.40-7.30 (m, 2H), 7.00 (t, 1H), 4.30-4.21 (m, 2H), 4.20 (s, 2H), 4.12 (q, 2H), 3.90-3.79 (m, 5H), 1.20 (t, 3H).
m/z 322.2 (M+Na)⁺ (ES⁺)

(ii) Ethyl 2-(2-(3-amino-5-methoxyphenoxy)ethoxy)acetate

Iron (560 mg, 10.0 mmol) followed by ammonium chloride (21.4 mg, 0.40 mmol) was added to a solution of the compound from step (i) above (300 mg, 1.00 mmol) in EtOH (13 mL), THF (5 mL) and water (2 mL) and the resulting slurry heated to reflux for 1 h and stirred at rt overnight. The reaction was filtered through celite, washing with EtOAc (2×10 mL) and the filtrate concentrated in vacuo. The crude product was purified by chromatography on silica gel (24 g column, 0-100% EtOAc/isohexane) to afford the sub-title compound (233 mg) as a thick brown oil.
¹H NMR (400 MHz, DMSO-d6) δ 5.75 (p, 2H), 5.68 (t, 1H), 5.05 (br s, 2H), 4.17 (s, 2H), 4.12 (q, 2H), 4.00-3.94 (m, 2H), 3.83-3.71 (m, 2H), 3.63 (s, 3H), 1.21 (t, 3H).
m/z 270.3 (M+H)⁺ (ES⁺)

(iii) Ethyl 2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)acetate A suspension of N-(5-(tert-butyl)-3-(3-(4-((2-chloropyridin-4-yl)oxy)naphthalen-1-yl)ureido)-2-methoxyphenyl)methanesulfonamide (see WO 2014/162126; 211 mg, 0.37 mmol), the compound from step (ii) above (100 mg, 0.37 mmol) and freshly ground potassium carbonate (154 mg, 1.11 mmol) in DMF (3 mL) was evacuated back filling with nitrogen 3 times. The mixture was heated under nitrogen to 40° C. and Pd-175 (7.2 mg, 9.28 μmol) added. The reaction mixture was heated at 75° C. for 2 h. The reaction was then cooled and filtered. The filtrate was partitioned between EtOAc (50 mL) and 20% v/v brine (50 mL). The organic layer was dried (MgSO₄), filtered and concentrated. The crude product was purified by chromatography on silica gel (12 g column, 0-10% MeOH/DCM) to afford the coupling product as a thick brown oil. The material was dissolved in DCM (5 mL) and washed with 20% v/v brine (10 mL). The solvent was removed to afford the sub-title compound (233 mg) as a beige solid.
¹H NMR (400 MHz, DMSO-d6) δ 9.38 (s, 1H), 9.13 (s, 1H), 8.91 (s, 1H), 8.87 (s, 1H), 8.29 (d, 1H), 8.19 (d, 1H), 8.11 (dd, 2H), 7.87 (dt, 1H), 7.70 (ddd, 1H), 7.61 (ddd, 1H), 7.38 (d, 1H), 7.03 (d, 1H), 6.91 (t, 1H), 6.79 (t, 1H), 6.58 (dd, 1H), 6.08 (d, 1H), 6.03 (t, 1H), 4.18 (s, 2H), 4.11 (q, 2H), 4.06-3.96 (m, 2H), 3.85-3.74 (m, 5H), 3.66 (s, 3H), 3.10 (s, 3H), 1.27 (s, 9H), 1.19 (t, 3H).
m/z 802.1 (M+H)⁺ (ES⁺)

(iv) 2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)acetic acid NaOH (2M aq, 462 μL, 0.92 mmol) was added to a solution of the compound from step (iv) above (247 mg) in THF (1.6 mL) and MeOH (0.6 mL) and the resulting solution stirred at rt overnight. The reaction was quenched with AcOH (106 μL, 1.848 mmol) and the solvent removed in vacuo. The crude product was purified by chromatography (RP Flash C18, 12 g column, 15-75% MeCN/10 mM Ammonium Bicarbonate) and product rich fractions combined and the pH adjusted to ca. 7 with formic acid. The solvent was then removed to afford a white solid. This was slurried in hot EtOH (2 mL), then triturated with water (2 mL). The resulting solid was collected by filtration, washing with water (2×1 mL) to afford the title compound (145 mg) as a white solid.
¹H NMR (400 MHz, DMSO-d6) δ 12.63 (s, 1H), 9.42 (s, 1H), 9.13 (s, 1H), 8.92 (s, 1H), 8.88 (s, 1H), 8.30 (d, 1H), 8.19 (d, 1H), 8.12 (d, 1H), 8.10 (d, 1H), 7.87 (dd, 1H), 7.70 (ddd, 1H), 7.61 (ddd, 1H), 7.38 (d, 1H), 7.02 (d, 1H), 6.89 (s, 1H), 6.78 (t, 1H), 6.58 (dd, 1H), 6.08 (d, 1H), 6.04 (t, 1H), 4.07 (s, 2H), 4.03-3.91 (m, 2H), 3.81 (s, 3H), 3.80-3.72 (m, 2H), 3.66 (s, 3H), 3.10 (s, 3H), 1.27 (s, 9H).
m/z 774.4 (M+H)+ (ES+)

Example 25

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)-N—(N,N-dimethylsulfamoyl)acetamide

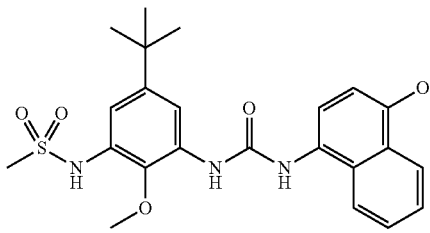

CDI (26.2 mg, 0.16 mmol) was added to a solution of 2-(2-(2-(3-((4-((4-(3-(5-(tert-butyl)-2-methoxy-3-(methylsulfonamido)phenyl)ureido)naphthalen-1-yl)oxy)pyridin-2-yl)amino)-5-methoxyphenoxy)ethoxy)ethoxy)acetic acid (see Example 3 above; 120 mg, 0.14 mmol) in dry DMF (2 mL) at rt and the resulting solution stirred at 50° C. for 1 h. Dimethylsulfamide (36.4 mg, 0.293 mmol) and DBU (44.2 μL, 0.293 mmol) were added to the solution and the reaction stirred at rt overnight. A further portion of dimethylsulfamide (36.4 mg, 0.293 mmol) and DBU (44.2 μL, 0.293 mmol) was added and the reaction stirred at rt for a further 2 h. The reaction was quenched with water (0.1 mL) and the crude reaction solution purified by chromatography (RP Flash C18, 12 g column, 15-50% MeCN/10 mM Ammonium Bicarbonate). The product rich fractions were combined and the volatile solvent removed in vacuo. The pH was then adjusted to 7 with formic acid and the resulting solid collected by filtration, washing with water (2×1 mL), to afford the title compound (48 mg) as a white solid.
$^1$H NMR (400 MHz, DMSO-d6) δ 11.26 (s, 1H), 9.38 (s, 1H), 9.13 (s, 1H), 8.91 (s, 1H), 8.87 (s, 1H), 8.29 (d, 1H), 8.19 (d, 1H), 8.12 (d, 1H), 8.10 (s, 1H), 7.87 (dd, 1H), 7.70 (ddd, 1H), 7.61 (ddd, 1H), 7.38 (d, 1H), 7.03 (d, 1H), 6.91 (t, 1H), 6.79 (t, 1H), 6.58 (dd, 1H), 6.08 (d, 1H), 6.04 (t, 1H), 4.06 (s, 2H), 4.02-3.94 (m, 2H), 3.81 (s, 3H), 3.75-3.69 (m, 2H), 3.66 (s, 3H), 3.61 (s, 4H), 3.10 (s, 3H), 2.80 (s, 6H), 1.27 (s, 9H).
m/z 924.5 (M+H)+ (ES+)

Example 26

5-((2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)methyl)thiophene-2-carboxylic acid

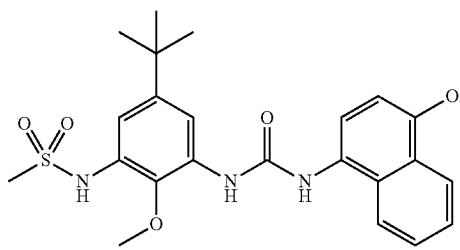

(i) Methyl 5-(hydroxymethyl)thiophene-2-carboxylate

Methyl 5-formylthiophene-2-carboxylate (311 mg, 1.82 mmol) was dissolved in MeOH (4 mL), cooled in an ice bath and NaBH$_4$ (68 mg, 1.82 mmol) added portion wise over ten minutes. The reaction was stirred for 2 h after which time sat. aq. ammonium chloride (10 mL) was added. The aqueous phase was extracted with DCM (2×15 mL), passed through a phase separator and concentrated in vacuo to yield the sub-title compound (303 mg) as a colourless oil.
$^1$H NMR (400 MHz, CDCl$_3$) δ 7.61 (d, 1H), 6.92 (dt, 1H), 4.86-4.69 (m, 2H), 3.81 (s, 3H).

(ii) Methyl 5-(chloromethyl)thiophene-2-carboxylate

The product from step (i) (287 mg, 1.66 mmol) was dissolved in dry CHCl$_3$ (3 mL) and cooled to 0° C. DMF (0.05 mL, 3.60 mmol) and thionyl chloride (3 eq, 0.36 mL) were added and the mixture stirred for 2 h. The reaction was quenched at 0° C. with MeOH (0.5 mL), diluted with DCM (15 mL), washed with brine (15 mL), passed through a phase separator and concentrated in vacuo. The sub-title compound (303 mg) was isolated as colourless oil.
$^1$H NMR (400 MHz, CDCl$_3$) δ 7.58 (d, 1H), 7.00 (dt, 1H), 4.69 (d, 2H), 3.82 (s, 3H).

(iii) Methyl 5-((2-hydroxyethoxy)methyl)thiophene-2-carboxylate

To a stirred solution of dry ethane-1,2-diol (0.35 mL, 6.29 mmol) in DMSO (1.5 mL) at 0° C. was added potassium tert-butoxide (194 mg, 1.73 mmol) portion wise over 10 min. The resulting solution was stirred for 30 min at same temperature before adding TBAI (58.1 mg, 0.15 mmol). A homogeneous solution of the product from step (ii) above (300 mg, 1.57 mmol) in DMSO (0.5 mL) was added dropwise to the above reaction mixture and stirred at rt overnight. MeOH (3 mL) was added and the reaction stirred overnight. Cold water (25 mL) was added and the aqueous layer extracted with ethyl acetate (2×25 mL) and the combined organic layers concentrated in vacuo. The crude product was purified by chromatography on silica gel (12 g column, 0-5% MeOH/DCM) to afford the sub-title compound (115 mg) as a yellow oil.

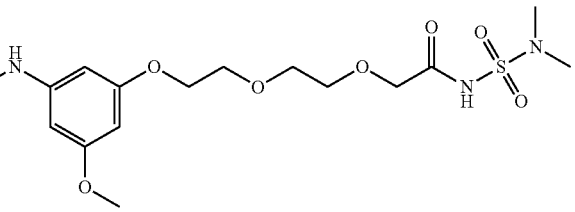

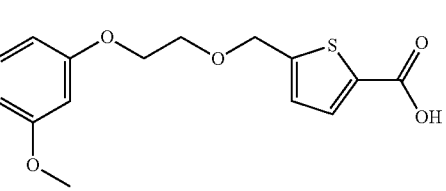

¹H NMR (400 MHz, DMSO-d6) δ 7.70 (d, 1H), 7.14 (dt, 1H), 4.78-4.63 (m, 3H), 3.81 (s, 3H), 3.58-3.44 (m, 4H).

(iv) Methyl 5-((2-((methylsulfonyl)oxy)ethoxy) methyl)thiophene-2-carboxylate

The product from step (iii) above (115 mg, 0.53 mmol) was dissolved in DCM (5 mL) and cooled in an ice bath. NEt₃ (111 μL, 0.79 mmol) followed by MsCl (49.7 μL, 0.63 mmol) were added dropwise and the mixture left to warm to rt overnight. The mixture was diluted with DCM (10 mL) and the organic layer washed with 0.1 M HCl (10 mL). The mixture was passed through a phase separator and concentrated in vacuo to yield the sub-title compound (125 mg) as light yellow oil.
¹H NMR (400 MHz, DMSO-d₆) δ 7.71 (d, 1H), 7.19-7.14 (m, 1H), 4.77 (d, 2H), 4.41-4.30 (m, 2H), 3.82 (s, 3H), 3.77-3.69 (m, 2H), 3.19 (s, 3H).

(v) Methyl 5-((2-(3-Methoxy-5-nitrophenoxy) ethoxy)methyl)thiophene-2-carboxylate 3-Methoxy-5-nitrophenol (65.0 mg, 0.384 mmol), the product from step (iv) above (125 mg, 0.40 mmol) and potassium carbonate (159 mg, 1.15 mmol) were suspended/dissolved in DMF (3 mL) and heated to 80° C. overnight. The reaction was cooled and partitioned between TBME (20 mL) and brine (20 mL). The aqueous layer was extracted with TBME (20 mL) and the combined organic layers washed with brine (40 mL), dried (MgSO₄), filtered and concentrated in vacuo. The crude product was purified by chromatography on silica gel (12 g column, 0-50% EtOAc/isohexane) to afford the sub-title compound (105 mg) as a yellow solid.
¹H NMR (400 MHz, DMSO-d6) δ 7.70 (d, 1H), 7.35 (dt, 2H), 7.15 (dt, 1H), 6.99 (t, 1H), 4.79 (d, 2H), 4.36-4.19 (m, 2H), 3.89-3.78 (m, 9H).

(vi) Methyl 5-((2-(3-amino-5-methoxyphenoxy) ethoxy)methyl)thiophene-2-carboxylate The product from step (v) above (105 mg, 0.286 mmol) was dissolved in EtOH (4 mL, 68.5 mmol). Pd—C (type 87 L) (30.4 mg, 0.014 mmol) was added and the reaction stirred under an atmosphere of hydrogen (1 bar) for 1 h. The mixture was filtered through celite and the solids washed with ethanol (10 mL). The solution was concentrated directly onto silica. The crude product was purified by chromatography on silica gel (12 g column, 0-5% (0.7 M Ammonia/MeOH)/DCM) but did not yield a product of sufficient purity. The product was repurified by chromatography on silica gel (12 g column, 0-5% (0.7 M Ammonia/MeOH)/DCM) to afford the sub-title compound (57 mg) as a dark red oil.
m/z 338.1 (M+H)⁺ (ES⁺)

(vii) Methyl 5-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)thiophene-2-carboxylate N-(5-(tert-butyl)-3-(3-(4-((2-chloropyridin-4-yl)oxy) naphthalen-1-yl)ureido)-2-methoxyphenyl)-methanesulfonamide (see WO 2014/162126; 96 mg, 0.169 mmol), the product from step (vi) above (57 mg, 0.169 mmol), Pd-175 (6.60 mg, 8.45 μmol) and freshly ground potassium carbonate (70.0 mg, 0.507 mmol) in DMF (2 mL) were degassed by evacuation and backfilling with nitrogen three times. The resulting mixture was heated to 70° C. for 2 h after which time a further portion of Pd-175 (13.2 mg, 8.45 μmol) was added dropwise as a solution in DMF (2 mL) over 2 h. The reaction was cooled and concentrated in vacuo. The crude product was purified by chromatography (RP Flash C18) (12 g column, 25-100% MeCN/10 mM Ammonium Bicarbonate) to afford the sub-title compound (23 mg) as a dark red solid.
¹H NMR (400 MHz, DMSO-d6) δ 9.38 (s, 1H), 9.13 (s, 1H), 8.90 (s, 1H), 8.87 (s, 1H), 8.32-8.27 (m, 1H), 8.20-8.14 (m, 1H), 8.13-8.06 (m, 2H), 7.90-7.84 (m, 1H), 7.74-7.66 (m, 2H), 7.61 (ddd, 1H), 7.38 (d, 1H), 7.17-7.11 (m, 1H), 7.03 (d, 1H), 6.90 (t, 1H), 6.80 (t, 1H), 6.58 (dd, 1H), 6.08 (d, 1H), 6.04 (t, 1H), 4.77 (d, 2H), 4.03 (dd, 2H), 3.84-3.74 (m, 7H), 3.65 (s, 3H), 3.08 (s, 3H), 1.27 (s, 9H).

(viii) 5-((2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy) ethoxy)methyl)thiophene-2-carboxylic acid The product from step (vii) above (22 mg, 0.025 mmol) was dissolved in THF (0.75 mL) and MeOH (0.25 mL). NaOH (2M aq.) (139 μL, 0.27 mmol) was added and the mixture stirred at rt overnight. The reaction was acidified with AcOH (0.25 mL) and concentrated in vacuo. The crude product was purified by chromatography on RP Flash C18 (12 g column, 15-75% MeCN/10 mM Ammonium Bicarbonate). The product-containing fractions were combined, acidified with formic acid to ca. pH 4 and concentrated in vacuo to yield the title compound (7.8 mg) as a white solid.
¹H NMR (400 MHz, DMSO-d6) δ 9.44 (s, 1H), 8.94 (s, 1H), 8.88 (s, 1H), 8.30 (d, 1H), 8.18 (d, 1H), 8.14-8.07 (m, 2H), 7.89-7.84 (m, 1H), 7.69 (ddd, 1H), 7.60 (ddd, 1H), 7.46 (d, 1H), 7.38 (d, 1H), 7.04 (d, 1H), 7.03 (d, 1H), 6.89 (t, 1H), 6.81 (t, 1H), 6.57 (dd, 1H), 6.08 (d, 1H), 6.04 (t, 1H), 4.71 (s, 2H), 4.02 (dd, 2H), 3.81 (s, 3H), 3.79-3.73 (m, 2H), 3.65 (s, 3H), 3.10 (s, 3H), 1.27 (s, 9H).
m/z 856.2 (M+H)⁺ (ES⁺)

Example 27

5-((2-(3-((4-(4-(3-(5-(tert-Butyl)-2-methoxy-3-(methylsulfonamido)phenyl)ureido)-naphthalen-1-yl)oxy)pyridin-2-yl)amino)-5-methoxyphenoxy) ethoxy)methyl)thiophene-3-carboxylic acid

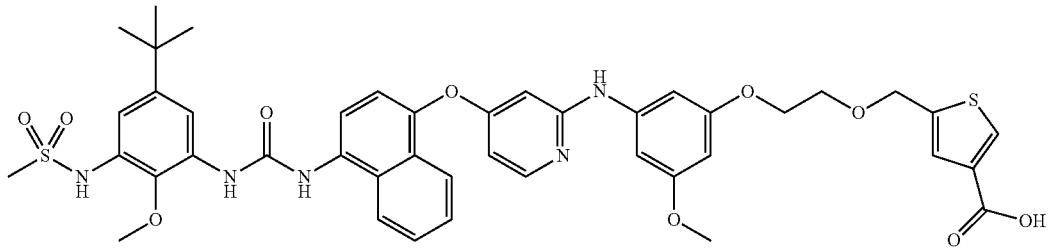 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCc2cc(C(=O)O)cs2)c1]

(i) Methyl 5-(hydroxymethyl)thiophene-3-carboxylate

Methyl 5-formylthiophene-2-carboxylate (311 mg, 1.82 mmol) was dissolved in MeOH (4 mL), cooled to 0° C. and NaBH$_4$ (114 mg, 2.11 mmol) was added portionwise over ten minutes. The reaction was stirred for 2 h and sat. aq. ammonium chloride (10 mL) added. The aqueous phase was extracted with DCM (2×15 mL), passed through a phase separator and concentrated in vacuo to yield the sub-title compound (209 mg) as a colourless oil.

$^1$H NMR (400 MHz, CDCl$_3$) δ 8.04 (d, 1H), 7.40 (dt, 1H), 4.82 (dd, 2H), 3.85 (s, 3H), 1.97 (t, 1H).

(ii) Methyl 5-(chloromethyl)thiophene-3-carboxylate

The product from step (i) above (209 mg, 1.21 mmol) was dissolved in dry CHCl$_3$ (3 mL) and cooled to 0° C. DMF (0.05 mL, 3.60 mmol) and thionyl chloride (0.26 mL, 3.6 mmol) were added and the mixture stirred for 2 h. The reaction was quenched at 0° C. with MeOH (0.5 mL). The reaction was diluted with DCM (15 mL), washed with brine (15 mL), passed through a phase separator and concentrated in vacuo to yield the sub-title compound (190 mg) as a colourless oil.

$^1$H NMR (400 MHz, CDCl$_3$) δ 8.07 (d, J=1.4 Hz, 1H), 7.48 (dt, J=1.4, 0.8 Hz, 1H), 4.76 (d, J=0.7 Hz, 2H), 3.86 (s, 3H).

(iii) Methyl 5-((2-hydroxyethoxy)methyl)thiophene-3-carboxylate

To a stirred solution of dry ethane-1,2-diol (0.22 mL, 3.99 mmol) in DMSO (1.5 mL) at 0° C. was added potassium tert-butoxide (123 mg, 1.09 mmol) portion wise over 10 min. The resulting solution was further stirred for 30 min at the same temperature before adding TBAI (36.8 mg, 0.10 mmol). A homogeneous solution of the product from step (ii) above (190 mg, 0.99 mmol) in DMSO (0.5 mL) was added dropwise and stirred at rt overnight. MeOH (3 mL) was added and the reaction stirred overnight. Cold water (15 mL) was added, the aqueous layer extracted with ethyl acetate (2×25 mL) and the combined organic layers concentrated in vacuo. The crude product was purified by chromatography on silica gel (12 g column, 0-5% MeOH/DCM) to afford the sub-title compound (106 mg) as a yellow oil.

$^1$H NMR (400 MHz, DMSO-d6) δ 8.31 (d, 1H), 7.40 (dt, 1H), 4.72-4.62 (m, 3H), 3.79 (s, 3H), 3.55-3.49 (m, 2H), 3.49-3.42 (m, 2H).

(iv) Methyl 5-((2-((methylsulfonyl)oxy)ethoxy)methyl)thiophene-3-carboxylate The product from step (iii) above (105 mg, 0.486 mmol) was dissolved in DCM (5 mL) and cooled to 0° C. NEt$_3$ (102 µL, 0.728 mmol) followed by MsCl (45.4 µL, 0.583 mmol) were added dropwise and the mixture left to warm to rt overnight. The mixture was diluted with DCM (10 mL) and the organic layer washed with 0.1 M HCl (10 mL). The aqueous layer was further extracted with DCM (5 mL), the combined organic layers passed through a phase separator and concentrated in vacuo to yield the sub-title compound (115 mg) as a light yellow oil.

$^1$H NMR (400 MHz, DMSO-d6) δ 8.33 (d, 1H), 7.45-7.41 (m, 1H), 4.72 (d, 2H), 4.47-4.26 (m, 2H), 3.79 (s, 3H), 3.75-3.61 (m, 2H), 3.22-3.09 (m, 3H).

(v) Methyl 5-((2-(3-methoxy-5-nitrophenoxy)ethoxy)methyl)thiophene-3-carboxylate 3-Methoxy-5-nitrophenol (59.0 mg, 0.349 mmol), the product from step (iv) above (110 mg, 0.366 mmol) and potassium carbonate (145 mg, 1.046 mmol) were suspended/dissolved in DMF (3 mL) and heated to 80° C. overnight. The reaction was cooled and partitioned between TBME (20 mL) and brine (20 mL). The aqueous layer was extracted with TBME (20 mL) and the combined organic layers washed with brine (40 mL), dried (MgSO$_4$), filtered and concentrated in vacuo. The crude product was purified by chromatography on silica gel (12 g column, 0-50% EtOAc/isohexane) to afford the sub-title compound (92 mg) as a yellow solid.

$^1$H NMR (400 MHz, DMSO-d$_6$) δ 8.30 (d, 1H), 7.45-7.40 (m, 1H), 7.34 (dt, 2H), 6.99 (t, 1H), 4.75 (d, 2H), 4.31-4.20 (m, 2H), 3.86 (s, 3H), 3.83-3.80 (m, 2H), 3.79 (s, 3H).

(vi) Methyl 5-((2-(3-amino-5-methoxyphenoxy)ethoxy)methyl)thiophene-3-carboxylate The product from step (v) above (92 mg, 0.25 mmol) was dissolved in EtOH (4 mL, 68.5 mmol) with water (0.5 mL). Iron (84 mg, 1.50 mmol) and ammonium chloride (107 mg, 2.00 mmol) were added and the reaction mixture heated to 70° C. with vigorous stirring for 2 h. The mixture was cooled, filtered through celite and the solids washed with ethanol (10 mL). The solvent was removed in vacuo. The crude product was purified by chromatography on silica gel (12 g column, 0-5% (0.7 M Ammonia/MeOH)/DCM) to afford the sub-title compound (42 mg) as an orange oil.

$^1$H NMR (400 MHz, DMSO-d6) δ 8.31 (d, 1H), 7.47-7.40 (m, 1H), 5.79-5.73 (m, 2H), 5.69 (t, 1H), 5.05 (s, 2H), 4.73 (d, 2H), 4.06-3.90 (m, 2H), 3.79 (s, 3H), 3.76-3.71 (m, 2H), 3.62 (s, 3H).

(vii) Methyl 5-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)thiophene-3-carboxylate A suspension of the product from step (vi) above (37 mg, 0.11 mmol), N-(5-(tert-butyl)-3-(3-(4-((2-chloropyridin-4-yl)oxy)naphthalen-1-yl)ureido)-2-methoxyphenyl)methanesulfonamide (see WO 2014/162126; 62.4 mg, 0.110 mmol), Pd-175 (4.28 mg, 5.48 µmol) and freshly ground potassium carbonate (45.5 mg, 0.32 mmol) in DMF (3 mL) was degassed by 3 cycles of evacuation and backfilling with nitrogen. The reaction was heated to 70° C. for 2 h. A further portion of Pd-175 (8.48 mg, 10.9 µmol) was added dropwise in DMF (2 mL) over 2 h. The reaction was concentrated in vacuo. The crude product was purified by chromatography on RP Flash C18 (12 g column, 25-100% MeCN/10 mM Ammonium Bicarbonate) to afford the sub-title compound (36 mg) as a beige solid.

$^1$H NMR (400 MHz, DMSO-d6) δ 9.38 (s, 1H), 9.13 (s, 1H), 8.90 (s, 1H), 8.87 (s, 1H), 8.36-8.25 (m, 2H), 8.18 (d, 1H), 8.11 (d, 1H), 8.10 (s, 1H), 7.89-7.84 (m, 1H), 7.70 (ddd, 1H), 7.61 (ddd, 1H), 7.44-7.40 (m, 1H), 7.38 (d, 1H), 7.03 (d, 1H), 6.90 (t, 1H), 6.79 (t, 1H), 6.57 (dd, 1H), 6.08 (d, 1H), 6.04 (t, 1H), 4.73 (d, 2H), 4.06-3.99 (m, 2H), 3.81 (s, 3H), 3.78 (s, 3H), 3.77-3.72 (m, 2H), 3.65 (s, 3H), 3.10 (s, 3H), 1.27 (s, 9H).

(viii) 5-((2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)methyl)thiophene-3-carboxylic acid The product from step (vii) above (33 mg, 0.038 mmol) was dissolved in THF (2 mL) and MeOH (0.5 mL). NaOH (2M aq., 209 µL, 0.417 mmol) was added and the mixture stirred at rt overnight. The reaction was acidified with AcOH (0.25 mL) and concentrated in vacuo. The crude product was purified by chromatography on RP Flash C18 (24 g column, 15-75% MeCN/10 mM Ammonium Bicarbonate). The product-containing fractions were combined, acidified with formic acid to ca. pH 4, concentrated in vacuo. The resulting solid was redissolved in the minimum amount of ethanol (ca. 0.3 mL) and water (0.2 mL) added dropwise to crash out the white solid. The vial was centrifuged at 2000 rpm for 5 minutes and the supernatant decanted. The resulting solid was dried in vacuo at 55° C. for 48 h to yield the title compound as a white solid.

$^1$H NMR (400 MHz, DMSO-d6) δ 12.68 (bs, 1H), 9.38 (s, 1H), 9.12 (bs, 1H), 8.91 (s, 1H), 8.87 (s, 1H), 8.29 (d, 1H), 8.20 (d, 1H), 8.19 (d, 1H), 8.14-8.07 (m, 2H), 7.87 (dd, 1H), 7.70 (ddd, 1H), 7.61 (ddd, 1H), 7.42-7.33 (m, 2H), 7.03 (d, 1H), 6.90 (t, 1H), 6.80 (t, 1H), 6.57 (dd, 1H), 6.08 (d, 1H), 6.04 (t, 1H), 4.72 (d, 2H), 4.06-3.98 (m, 2H), 3.81 (s, 3H), 3.78-3.71 (m, 2H), 3.65 (s, 3H), 3.10 (s, 3H), 1.27 (s, 9H).

m/z 856.2 (M+H)$^+$ (ES$^+$)

Example 28

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-(difluoromethoxy)phenoxy)ethoxy)ethoxy)acetic acid

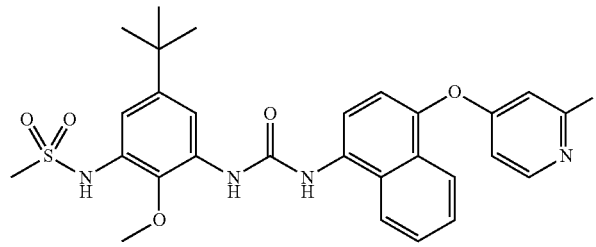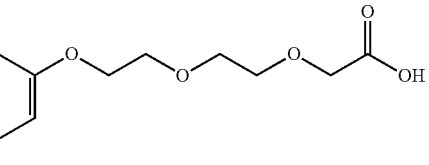

(i) 1-Bromo-3-(difluoromethoxy)-5-nitrobenzene

A mixture of 3-bromo-5-nitrophenol (460 mg, 2.11 mmol), sodium 2-chloro-2,2-difluoroacetate (804 mg, 5.28 mmol) and Cs$_2$CO$_3$ (1375 mg, 4.22 mmol) in DMF (8 mL) was heated at 100° C. for 1 h. The mixture was partitioned between TBME (50 mL) and water (50 mL), the aqueous layer extracted with TBME (30 mL) and the combined organic layers washed with brine (50 mL). The organic layer was concentrated in vacuo to yield the sub-title compound (400 mg) as a colourless oil.

$^1$H NMR (400 MHz, CDCl$_3$) δ 8.25 (t, 1H), 7.96 (t, 1H), 7.69-7.62 (m, 1H), 6.60 (t, 1H).

(ii) 3-(Difluoromethoxy)-5-nitrophenol

A mixture of KOH (197 mg, 2.98 mmol) and the product from step (i) above (200 mg, 0.746 mmol) in water (1.5 mL) and dioxane (1.5 mL) was degassed for 5 minutes prior to the addition of di-tert-butyl(2',4',6'-triisopropyl-[1,1'-biphenyl]-2-yl)phosphine (17.4 mg, 0.041 mmol) and Pd$_2$(dba)$_3$ (17.0 mg, 0.019 mmol). The resulting mixture was degassed for a further 2 minutes and then heated under a nitrogen atmosphere at 100° C. for 3 h. The reaction was cooled and partitioned between 1 M HCl (20 mL) and EtOAc (20 mL). The organic layer was washed with water (20 mL), brine (20 mL), dried (MgSO$_4$) and concentrated in vacuo to yield the sub-title compound (176 mg) as a dark brown oil.

$^1$H NMR (400 MHz, CDCl$_3$) δ 7.56 (d, 2H), 6.96 (t, 1H), 6.57 (t, 1H).

(iii) Ethyl 2-(2-(2-(3-(difluoromethoxy)-5-nitrophenoxy)ethoxy)ethoxy)acetate The product from step (ii) above (174 mg, 0.71 mmol), ethyl 2-(2-(2-((methylsulfonyl)oxy)ethoxy)ethoxy)acetate (see Example 2(ii) above; 202 mg, 0.74 mmol) and potassium carbonate (295 mg, 2.13 mmol) were suspended/dissolved in DMF (4 mL) and heated to 60° C. for 16 h. The reaction was cooled and partitioned between TBME (20 mL) and brine (20 mL). The aqueous layer was extracted with TBME (20 mL) and the combined organic layers washed with brine (40 mL) and concentrated onto silica gel. The crude product was purified by chromatography on silica gel (12 g column, 0-50% EtOAc/isohexane) to afford the sub-title compound (147 mg) as a yellow oil.

$^1$H NMR (400 MHz, DMSO-d6) δ 7.68-7.61 (m, 1H), 7.61 (t, 1H), 7.45 (t, 1H), 7.29 (t, 1H), 4.33-4.24 (m, 2H), 4.17-4.06 (m, 4H), 3.83-3.73 (m, 2H), 3.62 (s, 4H), 1.19 (t, 3H).

m/z 397.1 (M+NH$_4$)$^+$ (ES$^+$)

(iv) Ethyl 2-(2-(2-(3-amino-5-(difluoromethoxy)phenoxy)ethoxy)ethoxy)acetate A solution of the product from step (iii) above (147 mg, 0.36 mmol) and Pd/C (Type 87 L, 5 wt %) (39.2 mg, 0.02 mmol) in EtOH (20 mL) were stirred under 2 bar H$_2$ for 2 h. The reaction was filtered through celite, washing with EtOH (10 mL) and the mixture concentrated in vacuo. The crude product was purified by chromatography on silica gel (12 g column, 0-5% (0.7 M Ammonia/MeOH)/DCM) to afford the sub-title compound (89 mg) as a yellow oil.

$^1$H NMR (400 MHz, DMSO-d6) δ 7.09 (t, 1H), 5.99 (t, 1H), 5.94 (t, 1H), 5.88 (t, 1H), 5.37 (s, 2H), 4.16-4.08 (m, 4H), 4.00-3.95 (m, 2H), 3.74-3.67 (m, 2H), 3.66-3.57 (m, 4H), 1.20 (t, 3H).

m/z 350.1 (M+H)$^+$ (ES$^+$)

(v) Ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-(difluoromethoxy)phenoxy)ethoxy)ethoxy)acetate N-(5-(tert-Butyl)-3-(3-(4-((2-chloropyridin-4-yl)oxy)naphthalen-1-yl)ureido)-2-methoxyphenyl)-methanesulfonamide (see WO 2014/162126; 128 mg, 0.22 mmol), the product from step (iv) above, Pd-175 (8.7 mg, 0.01 mmol) and freshly ground potassium carbonate (93 mg, 0.67 mmol) were dissolved in DMF (1 mL) and degassed by evacuation and backfilling with nitrogen three times. The resulting mixture was heated to 70° C. for 2 h. The reaction mixture was cooled and loaded directly onto a reverse phase column. The crude product was purified by chromatography (RP Flash C18, 12 g column, 25-100% MeCN/10 mM Ammonium Bicarbonate) to afford the sub-title compound (116 mg) as a yellow solid.

$^1$H NMR (400 MHz, DMSO-d6) δ 9.39 (s, 1H), 9.13 (s, 1H), 9.08 (s, 1H), 8.90 (s, 1H), 8.30 (d, 1H), 8.17 (d, 1H), 8.16-8.09 (m, 2H), 7.90-7.84 (m, 1H), 7.71 (ddd, 1H), 7.61 (ddd, 1H), 7.39 (d, 1H), 7.17 (t, 1H), 7.14 (t, 1H), 7.08 (t, 1H), 7.03 (d, 1H), 6.63 (dd, 1H), 6.26 (t, 1H), 6.08 (d, 1H), 4.14-4.06 (m, 4H), 4.06-3.99 (m, 2H), 3.81 (s, 3H), 3.76-3.70 (m, 2H), 3.64-3.57 (m, 4H), 3.09 (s, 3H), 1.27 (s, 9H), 1.18 (t, 3H).

m/z 882.3 (M+H)$^+$ (ES$^+$)

(vi) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-(difluoromethoxy)phenoxy)ethoxy)ethoxy)acetic acid The product from step (v) above (116 mg, 0.13 mmol) was dissolved in THF (3 mL) and MeOH (1 mL). NaOH (2M aq., 723 μL, 1.447 mmol) was added and the mixture stirred at rt overnight. The reaction was acidified with AcOH (0.25 mL) and concentrated in vacuo. The crude product was purified by chromatography on RP Flash C18 (24 g column, 15-75% MeCN/10 mM Ammonium Bicarbonate). The product containing fractions were combined, acidified with formic acid to ca. pH 4, concentrated in vacuo and the resulting precipitate filtered off washing with water (5 mL). The solid was then redissolved in the minimum amount of ethanol (ca. 1 mL) and water (0.5 mL) added dropwise to crash out a white solid. The vial was then centrifuged at 2000 rpm for 5 minutes and the supernatant decanted. The resulting solid was dried in vacuo at 55° C. for 48 h to yield the title compound (58 mg) as a white solid.

$^1$H NMR (400 MHz, DMSO-d6) δ 9.42 (s, 1H), 9.09 (s, 1H), 8.93 (s, 1H), 8.30 (d, 1H), 8.18 (d, 1H), 8.14 (d, 1H), 8.11 (d, 1H), 7.86 (dd, 1H), 7.70 (ddd, 1H), 7.61 (ddd, 1H), 7.39 (d, 1H), 7.15 (t, 1H), 7.14 (t, 1H), 7.08 (t, 1H), 7.03 (d, 1H), 6.63 (dd, 1H), 6.27 (t, 1H), 6.09 (d, 1H), 4.08-3.94 (m, 4H), 3.81 (s, 3H), 3.76-3.69 (m, 2H), 3.60 (s, 4H), 3.10 (s, 3H), 1.27 (s, 9H).

m/z 854.2 (M+H)$^+$ (ES$^+$)

Example 29

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-ethynylphenoxy)ethoxy)ethoxy)acetic acid

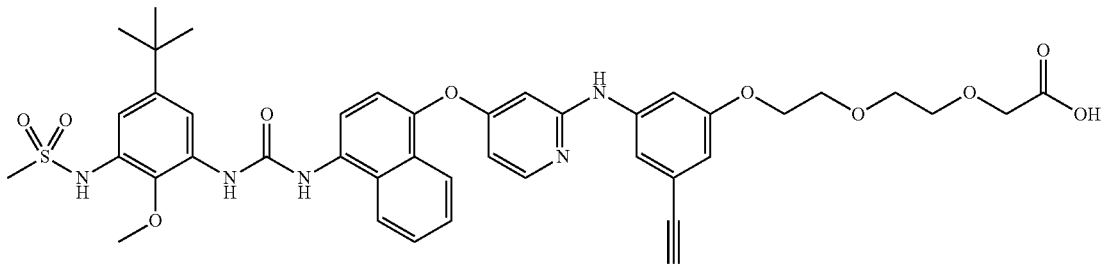 [SMILES: C#Cc1cc(Nc2cc(Oc3ccc(NC(=O)Nc4cc(C(C)(C)C)cc(NS(C)(=O)=O)c4OC)c4ccccc34)ccn2)cc(OCCOCCOCC(=O)O)c1]

(i) tert-Butyl 2-(2-(2-(benzyloxy)ethoxy)ethoxy)acetate

Sodium hydride (4.08 g, 102 mmol) was added portionwise to an ice bath-cooled solution of 2-(2-(benzyloxy)ethoxy)ethanol (9.14 mL, 51.0 mmol) in THF (200 mL) over 15 minutes. The reaction was stirred for 1 h after which time tert-butyl 2-bromoacetate (8.97 mL, 61.1 mmol) in THF (50 mL) was added dropwise over 1 h. The reaction was stirred at ice bath temperature for 3 h and quenched with ammonium chloride (50 mL). TBME (250 mL) was added and the organic layer washed with brine (2×200 mL). The organic layer was concentrated onto silica and the crude product was purified by chromatography on silica gel (220 g column, 0-50% EtOAc/isohexane) to afford the sub-title compound (1.95 g) as a colourless oil.

$^1$H NMR (400 MHz, DMSO-d6) δ 7.43-7.20 (m, 5H), 4.50 (s, 2H), 3.99 (s, 2H), 3.66-3.47 (m, 8H), 1.42 (s, 9H).

(ii) tert-Butyl 2-(2-(2-hydroxyethoxy)ethoxy)acetate

The product from step (i) above (1.83 g, 5.90 mmol) was dissolved in methanol (30 mL) and Pd—C (type 87 L, 5 wt. %, 0.627 g, 0.29 mmol) added. The mixture was stirred at room temperature under 4 bar of hydrogen for 16 h. The reaction mixture was filtered through celite, washing the solids with EtOH (50 mL) and concentrated in vacuo to yield the sub-title compound (1.23 g) as a colourless oil.

$^1$H NMR (400 MHz, DMSO-d6) δ 4.57 (t, 1H), 3.99 (s, 2H), 3.60-3.51 (m, 4H), 3.51-3.40 (m, 4H), 1.43 (s, 9H).

(iii) tert-Butyl 2-(2-(2-((methylsulfonyl)oxy)ethoxy)ethoxy)acetate

The product from step (ii) above (1.23 g, 5.58 mmol) was dissolved in DCM (30 mL) and cooled in an ice bath. EtN$_3$ (1.16 mL, 8.38 mmol) followed by MsCl (0.52 mL, 6.70 mmol) were added dropwise and the mixture left to warm to room temperature overnight. The mixture was diluted with DCM (10 mL) and the organic layer washed with 0.1 M HCl (10 mL). The mixture was passed through a phase separator and concentrated in vacuo to yield the sub-title compound (1.83 g) as light yellow oil.

$^1$H NMR (400 MHz, DMSO-d6) δ 4.35-4.28 (m, 2H), 4.00 (s, 2H), 3.73-3.65 (m, 2H), 3.64-3.54 (m, 4H), 3.18 (s, 3H), 1.43 (s, 9H).

(iv) tert-Butyl 2-(2-(2-(3-bromo-5-nitrophenoxy)ethoxy)ethoxy)acetate 3-bromo-5-nitrophenol (0.626 g, 2.87 mmol), the product from step (iii) above (1 g, 3.02 mmol) and potassium carbonate (1.191 g, 8.62 mmol) were suspended/dissolved in 3 mL DMF and heated to 80° C. overnight. The reaction was cooled and partitioned between TBME (20 mL) and brine (20 mL). The aqueous layer was extracted with TBME (20 mL) and the combined organic layers washed with brine (40 mL), dried (MgSO$_4$), filtered and concentrated in vacuo. The crude product was purified by chromatography on silica gel (40 g column, 0-50% EtOAc/isohexane) to afford the sub-title compound (965 mg) as a yellow oil.

$^1$H NMR (400 MHz, DMSO-d6) δ 8.04-7.89 (m, 1H), 7.79-7.72 (m, 1H), 7.70 (dd, 1H), 4.32-4.22 (m, 2H), 3.99 (s, 2H), 3.82-3.72 (m, 2H), 3.66-3.54 (m, 4H), 1.42 (s, 9H).

m/z 439.1 (M+NH$_4$)$^+$ (ES$^+$)

(v) tert-Butyl 2-(2-(2-(3-nitro-5-((triisopropylsilyl)ethynyl)phenoxy)ethoxy)ethoxy)acetate Pd(PPh)$_4$ (86 mg, 0.075 mmol) was added to a degassed suspension of the product from step (iv) above (314 mg, 0.747 mmol), CuI (7.11 mg, 0.037 mmol), and ethynyltriisopropylsilane (0.268 mL, 1.195 mmol) in triethylamine (1 mL) and DMF (3 mL). The mixture was heated at 85° C. (block temp.) for 1 h then cooled and concentrated directly onto silica gel. The crude product was purified by chromatography on silica gel (24 g column, 0-50% EtOAc/isohexane) to afford the sub-title compound (255 mg) as a light yellow oil.

$^1$H NMR (400 MHz, DMSO-d6) δ 7.82-7.71 (m, 2H), 7.47-7.45 (m, 1H), 4.34-4.23 (m, 2H), 3.98 (s, 2H), 3.81-3.73 (m, 2H), 3.66-3.54 (m, 4H), 1.41 (s, 9H), 1.19-1.03 (m, 21H).

(vi) tert-Butyl 2-(2-(2-(3-amino-5-((triisopropylsilyl)ethynyl)phenoxy)ethoxy)ethoxy)acetate The product from step (v) above (255 mg, 0.489 mmol) was dissolved in EtOH (6 mL) and H$_2$O (0.75 mL). Iron (164 mg, 2.93 mmol) and ammonium chloride (209 mg, 3.91 mmol) were added and the flask evacuated and backfilled with nitrogen three times. The reaction mixture was heated to 80° C. with vigorous stirring for 2 h. The mixture was cooled, filtered through celite and the solids washed with ethanol (10 mL). The resulting crude product was dissolved in DCM (20 mL), washed with water (20 mL), passed through a phase separator and concentrated in vacuo to yield the sub-title compound (203 mg) as an orange oil.

$^1$H NMR (400 MHz, DMSO-d6) δ 6.30 (dd, 1H), 6.17 (t, 1H), 6.14 (dd, 1H), 5.24 (s, 2H), 4.03-3.96 (m, 4H), 3.72-3.67 (m, 2H), 3.60 (s, 4H), 1.42 (s, 9H), 1.09 (s, 21H).

m/z 492.3 (M+H)$^+$ (ES$^+$)

(vii) tert-Butyl 2-(2-(2-(3-((4-((4-(3-(5-(tert-butyl)-2-Methoxy-3-(methylsulfonamido)phenyl)-ureido)naphthalen-1-yl)oxy)pyridin-2-yl)amino)-5-((triisopropylsilyl)ethynyl)phenoxy)ethoxy)-ethoxy)acetate N-(5-(tert-butyl)-3-(3-(4-((2-chloropyridin-4-yl)oxy)naphthalen-1-yl)ureido)-2-methoxyphenyl)-methanesulfonamide (see WO 2014/162126; 231 mg, 0.407 mmol), the product from step (vi) above (200 mg, 0.407 mmol), Pd-175 (15.8 mg, 0.02 mmol) and freshly ground potassium carbonate (169 mg, 1.220 mmol) were dissolved/suspended in DMF (3 mL) and degassed by evacuation and backfilling with nitrogen three times. The resulting mixture was heated to 70° C. for 2 h. The reaction mixture was cooled and partitioned between TBME (30 mL) and water (30 mL). The organic layer was washed with water (20 mL) and concentrated in vacuo to yield the sub-title compound (152 mg) as a brown solid.

$^1$H NMR (400 MHz, DMSO-d6) δ 9.38 (s, 1H), 9.13 (s, 1H), 9.00 (s, 1H), 8.91 (s, 1H), 8.30 (d, 1H), 8.18 (d, 1H), 8.15-8.07 (m, 2H), 7.89-7.83 (m, 1H), 7.73-7.68 (m, 1H), 7.63-7.58 (m, 1H), 7.56 (t, 1H), 7.39 (d, 1H), 7.17 (t, 1H), 7.03 (d, 1H), 6.61 (dd, 1H), 6.48 (dd, 1H), 6.07 (d, 1H), 4.10-4.01 (m, 2H), 3.99 (s, 2H), 3.81 (s, 3H), 3.76-3.68 (m, 2H), 3.60 (s, 4H), 3.09 (s, 3H), 1.40 (s, 9H), 1.27 (s, 9H), 1.16-1.02 (m, 21H).

m/z 1024.3 (M+H)$^+$ (ES$^+$)

(viii) 2-(2-(2-(3-((4-((4-(3-(5-(tert-butyl)-2-Methoxy-3-(methylsulfonamido)phenyl)ureido)-naphthalen-1-yl)oxy)pyridin-2-yl)amino)-5-ethynylphenoxy)ethoxy)ethoxy)acetic acid The product from step (vii) above (152 mg, 0.14 mmol) was dissolved in THF (4 mL) and TBAF (1M in THF) (156 µL, 0.15 mmol) added. The reaction was stirred for 60 h at room temperature then partitioned between DCM (40 mL) and water (40 mL). The organic layer was washed with brine (50 mL), passed through a phase separator and concentrated in vacuo. The crude material (100 mg) was dissolved in DCM (1 mL) and TFA (178 µL, 2.30 mmol) added. The reaction was stirred for 16 h and a further portion of TFA (178 µL, 2.30 mmol) added. The volatiles were removed in vacuo and the crude product purified by chromatography (RP Flash C18, 12 g column, 15-75% MeCN/10 mM Ammonium Bicarbonate). The product was further purified by preparative HPLC (Basic, Waters X-Bridge Prep-C18, 5 µm, 19×50 mm column, 35-65% MeCN in Water) to yield the title compound (6 mg) as a light yellow solid.

$^1$H NMR (400 MHz, DMSO-d$_6$) δ 9.61 (s, 1H), 9.08 (s, 1H), 9.04 (s, 1H), 8.33 (d, 1H), 8.17 (d, J=2.3 Hz, 1H), 8.15 (d, 1H), 8.10 (d, 1H), 7.86 (dd, 1H), 7.69 (ddd, 1H), 7.60 (ddd, 1H), 7.38 (d, 1H), 7.32 (t, 1H), 7.26 (s, 1H), 7.02 (d, 1H), 6.63 (dd, 1H), 6.51 (dd, 1H), 6.11 (d, 1H), 4.06 (s, 1H), 3.96 (d, 2H), 3.84-3.78 (m, 4H), 3.70 (dd, 2H), 3.57 (s, 4H), 3.09 (s, 3H), 1.27 (s, 9H).

m/z 812.2 (M+H)$^+$ (ES$^+$)

Example 30

N-(5-(tert-Butyl)-2-methoxy-3-(3-(4-((2-((3-methoxy-5-(2-(2-((5-oxo-4,5-dihydro-1,2,4-oxadiazol-3-yl)methoxy)ethoxy)ethoxy)phenyl)amino)pyridin-4-yl)oxy)naphthalen-1-yl)ureido)phenyl)methanesulfonamide

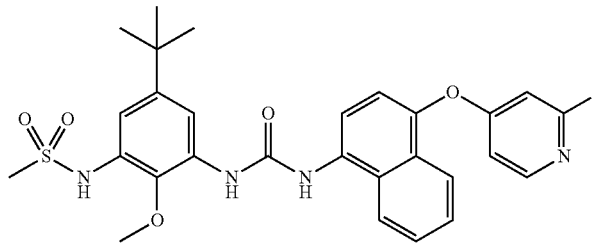

A suspension of N-(5-(tert-butyl)-3-(3-(4-((2-((3-(2-(2-(cyanomethoxy)ethoxy)ethoxy)-5-methoxyphenyl)amino)pyridin-4-yl)oxy)naphthalen-1-yl)ureido)-2-methoxyphenyl)methanesulfonamide (see Example 23(vi) above; 79 mg, 0.01 mmol) in EtOH (2 mL) and hydroxylamine (50% in water) (6.0 μL, 0.198 mmol) was heated to 75° C. and left to stir overnight. The solvent was removed and the residue azeotroped with toluene (2×1 mL) to afford a clear oil; m/z 832.1 (M+H)+ (ES+). The crude product was dissolved in DMF (2.5 mL) and cooled to 0° C. Pyridine (8.8 μl, 0.109 mmol) was added, followed by isobutyl chloroformate (0.013 mL, 0.099 mmol) and the resulting solution stirred at 0° C. for 30 min, then at rt for 20 min. The reaction was quenched with water (10 mL) and extracted with EtOAc (3×5 mL). The combined organic extractions were washed with brine (5 mL), passed through a hydrophobic frit and concentrated in vacuo to give a brown oil; m/z 932.5 (M+H)+ (ES+). The crude material was dissolved in a mixture of EtOH (2.5 mL) and sat. aq. NaHCO$_3$ (0.5 mL) and stirred at 65° C. overnight. The reaction was filtered and diluted with DMF (1 mL). The EtOH was removed under a flow of air, then the crude reaction mixture was purified by chromatography on the Companion (RP Flash C18) (12 g column, 15-75% MeCN/10 mM Ammonium Bicarbonate). The product-rich fractions were combined and the pH adjusted to ca. 7 with formic acid. The solvent was removed in vacuo to afford a dark brown gum. This was repurified by preparative HPLC (Waters, Basic (0.1% Ammonium Bicarbonate), Basic, Waters X-Bridge Prep-C18, 5 μm, 19×50 mm column, 30-60% MeCN in Water) and the product-rich fractions freeze-dried to afford the title compound as a colourless gum (5 mg).

$^1$H NMR (400 MHz, DMSO-d6) δ 9.39 (s, 1H), 9.13 (s, 1H), 8.91 (s, 1H), 8.88 (s, 1H), 8.29 (d, 1H), 8.19 (d, 1H), 8.11 (d, 1H), 8.10 (d, 1H), 7.87 (dd, 1H), 7.70 (ddd, 1H), 7.61 (ddd, 1H), 7.38 (d, 1H), 7.03 (d, 1H), 6.89 (t, 1H), 6.80 (t, 1H), 6.58 (d, 1H), 6.53 (s, 1H), 6.08 (d, 1H), 6.04 (t, 1H), 4.34 (s, 2H), 4.03-3.91 (m, 2H), 3.81 (s, 3H), 3.74-3.68 (m, 2H), 3.65 (s, 3H), 3.63-3.54 (m, 4H), 3.10 (s, 3H), 1.27 (s, 9H).

m/z 857.7 (M+H)+ (ES+)

Example 31

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid, sodium salt

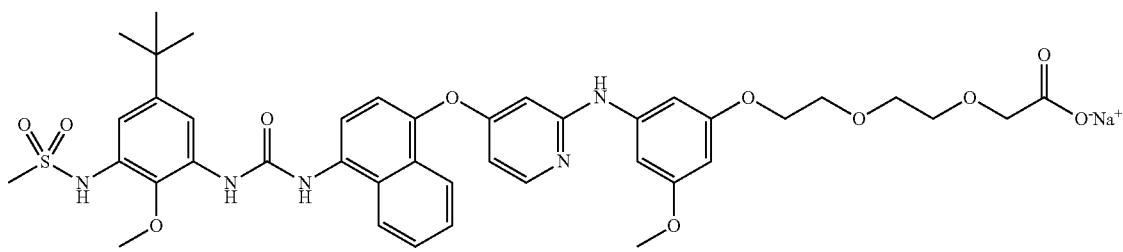

Method 1

To a 5 L flask under nitrogen was added IPA/water (90:10; 2.56 L, 12 volumes), the solvent was heated to 55° C. at which temperature 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid (see Example 3 above; 213.9 g, 0.261 mol) was charged gradually over 15 minutes. A formal solution was obtained after an additional 7 minutes agitation. To the solution (pink) was added sodium hydrogen carbonate (1.05 equiv.; 0.274 mol, 274 mL), maintaining the temperature at 53° C. The solution was cooled to 50° C. over 20 minutes and seeded with the sodium salt of 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetic acid (1.0 g); the seed maintained and cooling was continued at 10° C./hour to 25° C. after which point 8 volumes of IPA (1.71 L) was charged over 2 hours. The batch was agitated for 18 hours at this temperature and then cooled to 0° C. and aged for 1.5 hours ahead of isolation via filtration. The cake and vessel rinse were performed using the batch liquors, the cake pulled dry and the solids dried in vacuo at 50° C. for 18 hours. A yield of 81% was obtained (177.9 g) for the title compound as a faint red solid; purity by HPLC was reported at 99.24 area % and proton NMR indicated a batch that conformed to structure with 0.58% wt IPA and 0.55% wt water (solvents determined by HRGC and KF respectively). The batch was dried at 50° C. under vacuum to take the IPA level down to 2,238 ppm (0.22%). The sodium content was 2.5% by ion chromatography.

$^1$H NMR (400 MHz, DMSO-d6) δ: 9.95 (s, 1H), 9.24 (s, 1H), 8.93 (s, 1H), 8.38 (d, 1H), 8.08-8.12 (m, 3H), 7.83 (d, 1H), 7.55-7.67 (m, 2H), 7.35 (d, 1H), 7.01 (d, 1H), 6.65-6.72 (m, 2H), 6.60 (dd, 1H), 6.11 (d, 1H), 6.00 (t, 1H), 3.77-3.84 (m, 5H), 3.63-3.68 (m, 7H), 3.53 (s, 4H), 3.05 (s, 3H), 1.25 (s, 9H).

Method 2

Ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetate (see Example 3(iii) above; 413 g gross (containing 3.14% ethyl acetate, equivalent to 400 g active, 472.8 mmol, 1 eq.) was mixed with acetone/water (800 mL and 800 mL, 2 vol and 2 vol) and NaOH (37.8 g, 945.7 mmol, 2 eq.) and stirred overnight at 22° C. The reaction was acidified to pH 7.07 (pH range of 6.9 to 7.3 is acceptable) using AcOH (26.6 mL, 465 mmol, 0.9836 eq.), after which IPA (4000 mL, 10 vol) was added (though 12 volumes of IPA have been shown to give similar yields and purity). The resulting mixture was cooled to 10° C. over 1 h and stirred for 1 h (for larger scale preparations, the mixture can instead be stirred overnight at 7° C.) before being filtered to provide a crude product (329 g) 83% yield (for which: purity as determined by LC was 98.9%, with <0.1% starting material; XRD and DSC analysis indicated the form as produced by Method 1 above; and NMR analysis indicated 1.3% NaOAc and 0.4% IPA). The crude product (329 g, 392 mmol, 1 eq.) was slurried in 8 vol of 15% water:IPA (395 mL water:2237 mL IPA) at 22° C. for 2 h. The resulting mixture was then heated to 45° C. for 2 h, before being cooled to 30° C. and then filtered. This gave the title compound (315 g) at 94% recovery from the crude product, for which the NaOAc content was 0.39% and IPA was 0.36%. The overall yield for the reaction was 79%.

Example 32

2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-(trifluoromethoxy)phenoxy)ethoxy)ethoxy)acetic acid (i) 3-Hydroxy-5-(trifluoromethoxy)benzoic acid A solution of 3-bromo-5-(trifluoromethoxy)benzoic acid (3200 mg, 11.23 mmol) and NaOH (2520 mg, 44.9 mmol) in water (30 mL) and dioxane (30 mL) was degassed for 5 minutes prior to the addition of Pd$_2$(dba)$_3$ (206 mg, 0.225 mmol) and di-tert-butyl(2',4',6'-triisopropyl-[1,1'-biphenyl]-2-yl)phosphine (215 mg, 0.505 mmol). The resulting mixture was degassed for a further 2 minutes and then heated under a nitrogen atmosphere at 100° C. for 2.5 h. The mixture was diluted with water (150 mL) and washed with diethyl ether (3×75 mL). The aqueous layer was then acidified with HCl (1 M, 33 mL) to ~pH 3 and extracted with ethyl acetate (3×75 mL). The combined organic layers were washed with saturated brine (50 mL), dried over MgSO$_4$, filtered, and concentrated under reduced pressure to afford a yellow oil. The oil was redissolved in diethyl ether (10 mL) and diluted with isohexane (30 mL). The resulting precipitate was collected by filtration and washed with isohexane (10 mL) to yield the sub-title compound (1.71 g) as a tan solid.

$^1$H NMR (400 MHz, DMSO-d6) δ 13.34 (bs, 1H), 10.57 (bs, 1H), 7.36 (dd, 1H), 7.28-7.20 (m, 1H), 6.99-6.90 (m, 1H).

(ii) Benzyl 3-(2-(2-(2-(tert-butoxy)-2-oxoethoxy)ethoxy)ethoxy)-5-(trifluoromethoxy)benzoate The product from step (i) above (210 mg, 0.945 mmol) and potassium carbonate (392 mg, 2.84 mmol) was dissolved/suspended in DMF (1.25 mL) and benzyl bromide (0.112 mL, 0.945 mmol) added. The mixture was stirred at room temperature for 4 h. Potassium carbonate (392 mg, 2.84 mmol), DMF (4 mL) and tert-butyl 2-(2-(2-((methylsulfonyl)oxy)ethoxy)ethoxy)acetate (see Example 29(iii) above; 310 mg, 1.040 mmol) were added and the reaction heated to 70° C. for 16 h. The reaction was cooled and partitioned between TBME (50 mL) and water (50 mL). The aqueous layer was extracted with DCM (50 mL), the combined organic layers washed with brine (50 mL) and concentrated in vacuo. The crude product was purified by chromatography on silica gel (12 g column, 0-50% EtOAc/iso-hexane) to afford the sub-title compound (278 mg) as a colourless oil.

$^1$H NMR (400 MHz, DMSO-d6) δ 7.52 (dd, 1H), 7.50-7.45 (m, 2H), 7.45-7.34 (m, 4H), 7.34-7.29 (m, 1H), 5.38 (s, 2H), 4.28-4.17 (m, 2H), 3.98 (s, 2H), 3.82-3.72 (m, 2H), 3.65-3.55 (m, 4H), 1.40 (s, 9H).

m/z 532.2 (M+NH$_4$)$^+$ (ES$^+$)

(iii) 3-(2-(2-(2-(tert-Butoxy)-2-oxoethoxy)ethoxy)ethoxy)-5-(trifluoromethoxy)benzoic acid The product from step (ii) above (278 mg, 0.540 mmol) and Pd—C (57.5 mg, 0.027 mmol) were dissolved/sus-

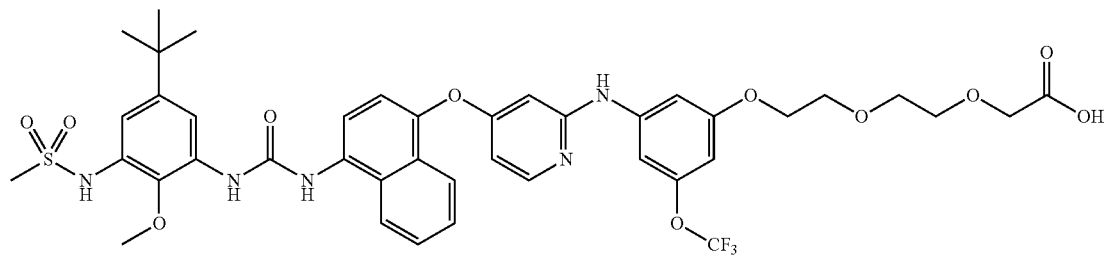 [SMILES: COc1c(NC(=O)Nc2ccc(Oc3ccnc(Nc4cc(OCCOCCOCC(=O)O)cc(OC(F)(F)F)c4)c3)c3ccccc23)cc(C(C)(C)C)cc1NS(C)(=O)=O]

pended in EtOH (10 mL) and stirred under an atmosphere of H$_2$ (2 bar) for 16 h. The reaction was filtered and concentrated in vacuo to yield the sub-title compound (214 mg) as a glassy solid.

$^1$H NMR (400 MHz, DMSO-d6) δ 13.51 (s, 1H), 7.48 (dd, 1H), 7.42-7.34 (m, 1H), 7.26-7.20 (m, 1H), 4.26-4.18 (m, 2H), 3.99 (s, 2H), 3.82-3.71 (m, 2H), 3.66-3.54 (m, 4H), 1.41 (s, 9H).

(iv) tert-Butyl 2-(2-(2-(3-(((benzyloxy)carbonyl) amino)-5-(trifluoromethoxy)phenoxy)ethoxy)-ethoxy)acetate NEt$_3$ (0.071 ml, 0.513 mmol) was added to a stirred solution of benzyl alcohol (0.355 mL, 3.42 mmol), the product from step (iii) above (145 mg, 0.342 mmol) and diphenyl phosphorylazide (0.081 mL, 0.376 mmol) in toluene (2 mL, 0.342 mmol). The reaction was heated to 80° C. for 2 h and concentrated in vacuo. The crude product was purified by chromatography on silica gel (4 g column, 0-50% EtOAc/isohexane) to afford the sub-title compound (53 mg) as a colourless oil.
m/z 547.2 (M+NH$_4$)$^+$ (ES$^+$)

(v) tert-Butyl 2-(2-(2-(3-amino-5-(trifluoromethoxy) phenoxy)ethoxy)ethoxy)acetate The product from step (iv) above (50 mg, 0.094 mmol) and Pd—C (20.1 mg, 9.44 μmol) was dissolved/suspended in EtOH (10 mL) and stirred under an atmosphere of H$_2$ (2 bar) for 16 h. The reaction was cooled, filtered through celite, washing with EtOH (10 mL) and concentrated in vacuo to yield the sub-title compound (38 mg) as a red oil.
m/z 396.1 (M+H)$^+$ (ES$^+$)

(vi) tert-Butyl 2-(2-(2-(3-((4-((4-(3-(5-(tert-butyl)-2-methoxy-3-(methylsulfonamido)phenyl)-ureido) naphthalen-1-yl)oxy)pyridin-2-yl)amino)-5-(trifluoromethoxy)phenoxy)ethoxy)ethoxy)-acetate N-(5-(tert-butyl)-3-(3-(4-((2-chloropyridin-4-yl)oxy) naphthalen-1-yl)ureido)-2-methoxyphenyl)-methanesulfonamide (see WO 2014/162126; 54.7 mg, 0.096 mmol), the product from step (v) above (38 mg, 0.096 mmol), Pd-175 (7.51 mg, 9.61 μmol) and freshly ground potassium carbonate (39.8 mg, 0.288 mmol) were degassed by evacuation and backfilling with nitrogen three times. The resulting mixture was heated to 70° C. for 2 h. The reaction mixture was cooled and injected directly onto a RP column. The crude product was purified by chromatography (RP Flash C18, 12 g column, 25-100% MeCN/10 mM Ammonium Bicarbonate) to afford the sub-title compound (52 mg) as a light yellow solid.

$^1$H NMR (400 MHz, DMSO-d6) δ 9.39 (s, 1H), 9.19 (s, 1H), 9.14 (s, 1H), 8.91 (s, 1H), 8.30 (d, 1H), 8.18 (d, 1H), 8.16 (d, 1H), 8.12 (d, 1H), 7.86 (dd, 1H), 7.71 (ddd, 1H), 7.61 (ddd, 1H), 7.40 (d, 1H), 7.31 (s, 1H), 7.28 (t, 1H), 7.03 (d, 1H), 6.66 (dd, 1H), 6.40 (t, 1H), 6.07 (d, 1H), 4.07-4.02 (m, 2H), 3.98 (s, 2H), 3.81 (s, 3H), 3.76-3.71 (m, 2H), 3.59 (s, 4H), 3.10 (s, 3H), 1.40 (s, 9H), 1.27 (s, 9H).

(vii) 2-(2-(2-(3-((4-((4-(3-(5-(tert-Butyl)-2-methoxy-3-(methylsulfonamido)phenyl)ureido)-naphthalen-1-yl)oxy)pyridin-2-yl)amino)-5-(trifluoromethoxy) phenoxy)ethoxy)ethoxy)acetic acid The product from step (vi) above (50 mg, 0.054 mmol) was dissolved in THF (1 mL) and NaOH (2 M aq, 269 μL, 0.539 mmol) added. The mixture was stirred overnight and then acidified to pH 4 with AcOH (0.25 mL) and concentrated in vacuo. The crude product was purified by chromatography (RP Flash C18, 4 g column, 35-65% MeCN/10 mM Ammonium Bicarbonate), the product containing fractions were acidified to pH 4 with formic acid (0.6 mL) and concentrated in vacuo to afford the title compound (20 mg) as a light beige solid.

$^1$H NMR (400 MHz, DMSO-d$_6$) δ 9.59 (s, 1H), 9.23 (s, 1H), 9.02 (s, 1H), 8.33 (d, 1H), 8.17 (d, 1H), 8.16 (d, 1H), 8.11 (d, 1H), 7.86 (dd, 1H), 7.69 (ddd, J=8.4, 1H), 7.60 (ddd, 1H), 7.39 (d, 1H), 7.33 (s, 1H), 7.24 (t, 1H), 7.03 (d, 1H), 6.65 (dd, 1H), 6.42-6.39 (m, 1H), 6.10 (d, 1H), 4.03 (dd, 2H), 3.84 (s, 2H), 3.81 (s, 3H), 3.75-3.68 (m, 2H), 3.58 (s, 4H), 3.09 (s, 3H), 1.27 (s, 9H).
m/z 872.2 (M+H)$^+$ (ES$^+$)

Example 33

N-(5-(tert-Butyl)-2-methoxy-3-(3-(4-((2-((3-methoxy-5-(2-(2-((3-oxo-2,3-dihydroisoxazol-5-yl) methoxy)ethoxy)ethoxy)phenyl)amino)pyridin-4-yl) oxy)naphthalen-1-yl)ureido)phenyl) methanesulfonamide

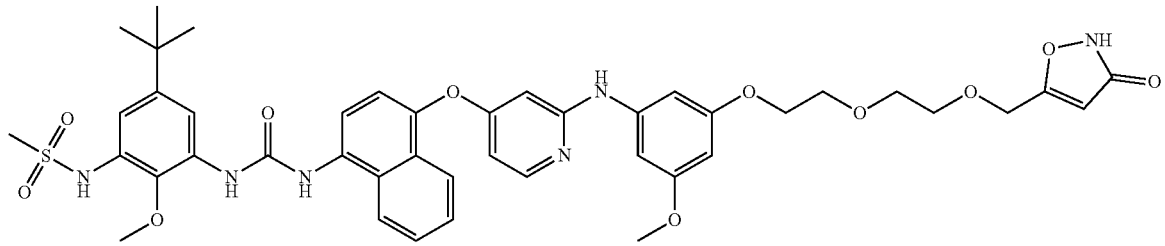 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOCc2cc(=O)[nH]o2)c1]

A slurry of ethyl 4-(2-(2-(3-((4-((4-(3-(5-(tert-butyl)-2-methoxy-3-(methylsulfonamido)phenyl)-ureido)naphthalen-1-yl)oxy)pyridin-2-yl)amino)-5-methoxyphenoxy) ethoxy)ethoxy)-3-oxobutanoate (see Example 18(ii) above; 359 mg, 0.404 mmol) in MeOH (3.5 mL) and water (0.5 mL) was cooled to 0° C. and NaOH (2 M aq) (404 μL, 0.809 mmol) was added. The resulting solution was stirred at 0° C. for 10 min. A solution of hydroxylamine hydrochloride (84 mg, 1.213 mmol) in MeOH (200 μL) was prepared and cooled to 0° C. NaOH (2 M aq) (606 μL, 1.213 mmol) was added to the hydroxylamine solution, and stirred at 0° C. for 10 min. The hydroxylamine solution was then added to the solution of enolate and stirred at 0° C. for 2 h. The solution was then added dropwise to conc HCl (100 μL, 3.29 mmol) at 75° C., and stirred at 75° C. for 1 h. The heating was removed and the pH was adjusted to ca 7 with NaOH (2 M aq.) and diluted with water (20 mL). The aqueous layer was extracted with EtOAc (3×10 mL) and the combined organic extracts washed with 20% v/v brine (10 mL). The organic layer was passed through a hydrophobic frit and concentrated in vacuo. The crude product was purified by preparative HPLC (Waters, Basic (0.1% Ammonium Bicarbonate), Basic, Waters X-Bridge Prep-C18, 5 μm, 19×50 mm column, 35-65% MeCN in Water) and the product rich fractions freeze dried to afford the title compound (38 mg) as a light yellow solid.

$^1$H NMR (400 MHz, DMSO-d6) δ 9.47 (s, 1H), 8.94 (s, 1H), 8.70 (s, 1H), 8.34 (d, 1H), 8.13-8.05 (m, 2H), 7.84 (d, 1H), 7.67 (ddd, 1H), 7.63-7.54 (m, 2H), 7.36 (d, 1H), 7.03 (d, 1H), 6.91-6.84 (m, 2H), 6.56 (dd, 1H), 6.09 (d, 1H), 6.04 (t, 1H), 4.05 (s, 1H), 4.00-3.94 (m, 2H), 3.84 (s, 1H), 3.78 (s, 3H), 3.73-3.67 (m, 2H), 3.66 (s, 3H), 3.59-3.54 (m, 2H), 3.52-3.47 (m, 2H), 2.61 (s, 3H), 1.22 (s, 9H).

m/z 857.2 (M+H)$^+$ (ES$^+$)

Example 34

5-((2-(3-((4-((4-(3-(5-(tert-Butyl)-2-methoxy-3-(methylsulfonamido)phenyl)ureido)naphthalen-1-yl)oxy)pyridin-2-yl)amino)-5-methoxyphenoxy)ethoxy)methyl)-1-methyl-1H-pyrrole-2-carboxylic acid

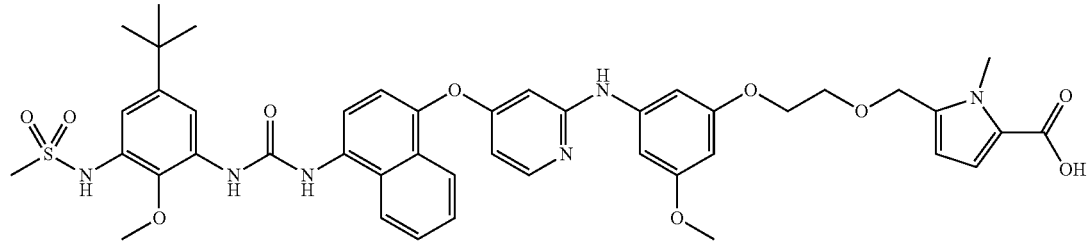 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCc2ccc(C(=O)O)n2C)c1]

(i) Methyl 5-(hydroxymethyl)-1-methyl-1H-pyrrole-2-carboxylate

Sodium borohydride (0.249 g, 6.58 mmol) was added to a solution of methyl 5-formyl-1-methyl-1H-pyrrole-2-carboxylate (1.1 g, 6.58 mmol) in a mixture of MeOH (50 mL) and THF (15 mL) at 0° C. and the resulting solution stirred at 0° C. for 2 h. The reaction was slowly quenched with sat. aq. ammonium chloride (50 mL) and a white solid crashed out. The solution was filtered, and the filtrate extracted with DCM (2×50 mL). The solvent was removed in vacuo. The crude material was dissolved in DCM (2 mL) and passed through a plug of silica, washing with 5% MeOH in DCM (200 mL). The solvent was removed in vacuo to afford the sub-title compound as a brown oil (1.12 g).

m/z 170.6 (M+H)$^+$ (ES$^+$)

(ii) Methyl 5-((2-(benzyloxy)ethoxy)methyl)-1-methyl-1H-pyrrole-2-carboxylate

NaH (60% in oil, 213 mg, 5.32 mmol) was added in two portions over 5 min to a solution of the compound from step (i) above (600 mg, 3.55 mmol), ((2-bromoethoxy)methyl)benzene (0.6 mL, 3.79 mmol) and sodium iodide (532 mg, 3.55 mmol) in dry DMF (50 mL) under nitrogen at 0° C., and the resulting solution stirred at rt overnight. The reaction was quenched with MeOH (3 mL) then diluted with 20% v/v brine (100 mL). The aqueous layer was extracted with EtOAc (3×100 mL), and the combined organic extractions washed with 20% v/v brine (50 mL). The organic layer was dried (MgSO$_4$) and concentrated in vacuo. The crude product was purified by chromatography on silica gel (40 g column, 0-100% EtOAc/isohexane) to afford the sub-title compound (213 mg) as a thin colourless oil.

$^1$H NMR (400 MHz, DMSO-d6) δ 7.39-7.24 (m, 5H), 6.80 (d, 1H), 6.15 (d, 1H), 4.51 (s, 2H), 4.48 (s, 2H), 3.83 (s, 3H), 3.74 (s, 3H), 3.65-3.49 (m, 4H).

m/z 304.1 (M+H)$^+$ (ES$^+$)

(iii) Methyl 5-((2-hydroxyethoxy)methyl)-1-methyl-1H-pyrrole-2-carboxylate

Pd/C 10% in 50% paste in water (Type 39) (14.94 mg, 0.140 mmol) was added to a solution of the compound from step (ii) above (213 mg, 0.702 mmol) in EtOH (4 mL) and the resulting slurry stirred under hydrogen at 1 bar pressure for 4 h. The reaction was filtered through celite, washing with EtOAc (20 mL) and the solvent removed to afford the sub-title compound (137 mg) as a thin colourless oil.

$^1$H NMR (400 MHz, DMSO-d6) δ 6.80 (d, 1H), 6.16 (d, 1H), 4.63 (t, 1H), 4.49 (s, 2H), 3.84 (s, 3H), 3.74 (s, 3H), 3.54-3.47 (m, 2H), 3.47-3.41 (m, 2H).

m/z 236.1 (M+Na)$^+$ (ES$^+$)

(iv) Methyl 5-((2-(3-methoxy-5-nitrophenoxy)ethoxy)methyl)-1-methyl-1H-pyrrole-2-carboxylate DIAD (339 μL, 1.745 mmol) was added to a solution of the compound from step (iii) above (310 mg, 1.454 mmol), 3-methoxy-5-nitrophenol (295 mg, 1.745 mmol) and triphenylphosphine (458 mg, 1.745 mmol) in dry THF (15 mL) at 0° C., and the resulting red solution stirred at rt overnight. The yellow solution was diluted with EtOAc (30 mL) and washed with water (20 mL). The organic layer was dried (MgSO$_4$) and concentrated in vacuo. The crude product was purified by chromatography on the Companion (40 g column, 0-100% EtOAc/isohexane) to afford the desired Mitsunobu product as a yellow solid. The product was dissolved in EtOAc (50 mL) and washed sequentially with NaOH (2 M aq., 2×50 mL), water (50 mL) and 20% v/v brine (50 mL). The organic layer was dried (MgSO$_4$) and concentrated in vacuo to afford the sub-title compound (638 mg) as a light yellow solid.

$^1$H NMR (400 MHz, DMSO-d6) δ 7.33 (m, 2H), 6.96 (t, 1H), 6.79 (d, 1H), 6.18 (d, 1H), 4.57 (s, 2H), 4.30-4.17 (m, 2H), 3.85 (s, 3H), 3.83 (s, 3H), 3.79-3.74 (m, 2H), 3.73 (s, 3H).

m/z 387.1 (M+Na)$^+$ (ES$^+$)

(v) Methyl 5-((2-(3-amino-5-methoxyphenoxy)ethoxy)methyl)-1-methyl-1H-pyrrole-2-carboxylate Iron powder (978 mg, 17.51 mmol) followed by ammonium chloride (37.5 mg, 0.700 mmol) was added to a solution of the compound from step (iv) above (638 mg, 0.841 mmol) in EtOH (13 mL), THF (5 mL) and water (2 mL) and the resulting slurry heated to reflux for 2 h. The reaction was cooled and filtered through celite, washing with EtOAc (2×20 mL). The solvent was removed in vacuo. The crude product was purified by chromatography on silica gel (24 g column, 0-100% EtOAc/isohexane) to afford the sub-title compound (238 mg) as a thick colourless oil.

$^1$H NMR (400 MHz, DMSO-d6) δ 6.80 (d, 1H), 6.18 (d, 1H), 5.75 (m, 2H), 5.67 (t, 1H), 5.05 (s, 2H), 4.55 (s, 2H), 3.99-3.93 (m, 2H), 3.85 (s, 3H), 3.74 (s, 3H), 3.71-3.65 (m, 2H), 3.62 (s, 3H).

m/z 335.0 (M+H)$^+$ (ES$^+$)

(vi) Methyl 5-((2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)methyl)-1-methyl-1H-pyrrole-2-carboxylate A suspension of N-(5-(tert-butyl)-3-(3-(4-((2-chloropyridin-4-yl)oxy)naphthalen-1-yl)ureido)-2-methoxyphenyl)methanesulfonamide (see WO 2014/162126; 405 mg, 0.712 mmol), the compound from step (v) above (238 mg, 0.712 mmol), freshly ground potassium carbonate (295 mg, 2.135 mmol) in DMF (3 mL) was evacuated back filling with nitrogen 3 times. The mixture was heated under nitrogen to 40° C. and Pd-175 (13.90 mg, 0.018 mmol) added. The reaction mixture was heated at 75° C. for 2 h. The reaction was then cooled and filtered. The filtrate was partitioned between EtOAc (50 mL) and 20% v/v brine (50 mL). The organic layer was passed through a hydrophobic frit then concentrated. The crude product was purified by chromatography (RP Flash C18) (24 g column, 15-80% MeCN/10 mM Ammonium Bicarbonate) to afford the sub-title compound (350 mg) as a white solid.

$^1$H NMR (400 MHz, DMSO-d6) δ 9.38 (s, 1H), 9.13 (s, 1H), 8.91 (s, 1H), 8.87 (s, 1H), 8.29 (d, 1H), 8.18 (d, 1H), 8.11 (d, 1H), 8.10 (d, 1H), 7.87 (dt, 1H), 7.70 (ddd, 1H), 7.61 (ddd, 1H), 7.38 (d, 1H), 7.03 (d, 1H), 6.89 (t, 1H), 6.86-6.77 (m, 2H), 6.58 (dd, 1H), 6.17 (d, 1H), 6.08 (d, 1H), 6.02 (t, 1H), 4.55 (s, 2H), 4.07-3.95 (m, 2H), 3.84 (s, 3H), 3.81 (s, 3H), 3.73 (s, 3H), 3.72-3.69 (m, 2H), 3.65 (s, 3H), 3.10 (s, 3H), 1.27 (s, 9H).

m/z 867.3 (M+H)$^+$ (ES$^+$)

(vii) 5-((2-(3-((4-((4-(3-(5-(tert-Butyl)-2-methoxy-3-(methylsulfonamido)phenyl)ureido)-naphthalen-1-yl)oxy)pyridin-2-yl)amino)-5-methoxyphenoxy)ethoxy)methyl)-1-methyl-1H-pyrrole-2-carboxylic acid NaOH (2M aq) (606 μl, 1.211 mmol) was added to a solution of the compound from step (vi) above (350 mg, 0.404 mmol) in THF (3 mL) and MeOH (1.2 mL) and the resulting solution stirred at rt for 8 h. A further portion of NaOH (2M aq) (606 μL, 1.211 mmol) was added and the resulting solution stirred at rt overnight. The solution was quenched with AcOH (139 μL, 2.422 mmol) and the solvent removed in vacuo. The crude product was purified by chromatography (RP Flash C18) (12 g column, 15-75% MeCN/10 mM Ammonium Bicarbonate). The product rich fractions were combined and the pH adjusted to 7 with formic acid. The volatile solvent was removed in vacuo during which a solid crashed out. This was collected by filtration, washing with water (2×2 mL) and the solid dried in vacuo at 40° C. overnight to afford the title compound (165 mg) as a white solid.

$^1$H NMR (400 MHz, DMSO-d6) δ 12.19 (s, 1H), 9.38 (s, 1H), 9.13 (s, 1H), 8.91 (s, 1H), 8.87 (s, 1H), 8.29 (d, 1H), 8.19 (d, 1H), 8.12 (d, 1H), 8.10 (d, 1H), 7.87 (dd, 1H), 7.70 (ddd, 1H), 7.61 (ddd, 1H), 7.38 (d, 1H), 7.03 (d, 1H), 6.90 (t, 1H), 6.79 (t, 1H), 6.74 (d, 1H), 6.57 (dd, 1H), 6.13 (d, 1H), 6.08 (d, 1H), 6.03 (t, 1H), 4.53 (s, 2H), 4.06-3.93 (m, 2H), 3.84 (s, 3H), 3.81 (s, 3H), 3.75-3.68 (m, 2H), 3.65 (s, 3H), 3.10 (s, 3H), 1.27 (s, 9H).

m/z 853.0 (M+H)$^+$ (ES$^+$)

Biological Testing: Experimental Methods

Enzyme Binding Assays (Kinomescan)

Kinase enzyme binding activities of compounds disclosed herein may be determined using a proprietary assay which measures active site-directed competition binding to an immobilized ligand (Fabian, M. A. et al., Nature Biotechnol., 2005, 23:329-336). These assays may be conducted by DiscoverX (formerly Ambit; San Diego, Calif.). The percentage inhibition produced by incubation with a test compound may be calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen) are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38α inactive target MAPKAP-K2 (Invitrogen, 600 ng/mL) and FRET peptide (8 μM; a phosphorylation target for MAPKAP-K2) is then added, then the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 μL of 200 ng/mL protein instead of 2.5 μL of 80 ng/mL protein) for mixing with the test compound (tested at either 1 μg/mL, 0.1 μg/mL, 0.01 μg/mL or 0.001 μg/mL).

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL of either 4 μg/mL, 0.4 g/mL, 0.04 μg/mL, or 0.004 μg/mL) for 2 hr at RT. The FRET peptides (8 μM, 2.5 μL), and appropriate ATP solution (2.5 μL, 400 μM) are then added to the enzymes/compound mixtures and the whole is incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 1 µg/mL, 0.1 µg/mL, 0.01 µg/mL, or 0.001 µg/mL, 2.5 µL each) for 2 hr at RT. The FRET peptides (8 µM, 2.5 µL), and appropriate ATP solutions (2.5 µL, 800 µM for c-Src, and 60 µM ATP for Syk) are then added to the enzymes/compound mixtures and the mixture incubated for 1 hr. Development reagent (protease, 5 µL) is added for 1 hr prior to detection in a fluorescence microplate reader (Varioskan® Flash, Thermo-Fisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 µL) is mixed with the test compound (2.5 µL at either 4 µg/mL, 0.4 µg/mL, 0.04 µg/mL, or 0.004 µg/mL) for 2 hr at RT. The FRET peptide (8 µM, 2.5 µL), which is a phosphorylation target for GSK3α, and ATP (40 µM, 2.5 µL) are then added to the enzyme/compound mixture and the resulting mixture incubated for 1 hr. Development reagent (protease, 5 µL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein. In addition, the concentrations of test compound employed are either 10 µg/mL, 1 µg/mL, 0.1 µg/mL, or 0.01 µg/mL Cellular Assays The compounds of the invention were studied using one or more of the following assays.

(a) Inhibition of p38 MAPKα and Lck in Jurkat Cells

Jurkat T cells were cultured in starve medium (RPMI 1640+5% FBS) for 24 h prior to the experiment. Cells were harvested and resuspended at $10 \times 10^6$ cells/mL in starve medium and then plated into round-bottomed 96 well plates at $1 \times 10^6$ cells/well. Serial dilutions of test compound were added (1% final DMSO concentration) for 2 h prior to stimulation. Following pre-incubation with compound, cells were stimulated with $H_2O_2$ (0.05% final) for 5 min. The reaction was stopped by centrifugation at 2000 rpm (3 min, 4° C.), then the supernatant was removed and 100 µL of cold fix/perm solution (BD Fix/Perm kit #554714) added. Plates were incubated for 20 min at 4° C. before centrifugation and washing with supplied 1× wash medium (BD Fix/Perm kit #554714). Cells were stained for either phospho-p38α (T180/182), supplied by Cell Signalling Technology (9211 s), or phospho-Lck (Y394), supplied by R&D (MAB7500). Antibodies were diluted to 5 µg/mL (R&D) or 1:200 (Cell Signalling Technology) in wash medium, before being incubated 1 h at 4° C. in the dark. Following 3 repeat washes with ice cold wash buffer, secondary antibody (anti-rabbit-FITC #F1362 or anti-mouse-FITC #F2883, both from Sigma) was added at a dilution of 1:1000 and incubated for 1 h at 4° C. in the dark. Cells were washed 3× times in cold wash buffer then, following a final wash in cold PBS, were resuspended in 150 µL cold PBS. Cells were analysed by flow cytometry using BD Accuri C6.

(aa) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 µg/mL of LPS (from E. Coli: 0111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 µg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (Escherichia Coli 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, Thermo-Fisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 µg/mL eBioscience and 3 µg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hr) and pre-treated with compounds at the desired concentration for 2 hours before addition of 5 ng/mL of IL-1β (Abcan) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages, they are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 μg/mL; Invitrogen, Paisley, UK) to arrest cells in metaphase. To observe mitotic cells, PBMCs are permeabilised and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., Mutation Research, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting HeLa cells with HRV until 80% of the cells are cytopathic.

BEAS2B cells are infected with HRV at an MOI of 5 and incubated for 2 hr at 33° C. with gentle shaking to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM-1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution with 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced Cytopathic Effect (CPE) in MRC5 Cells

MRC5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at a MOI of 0.001 in the LHC8 Media: RPMI-1640 (50:50) containing 15 mM magnesium chloride and incubated for 1 hr at 37° C. for adsorption. The cells are washed with PBS (3×200 μL), then fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 μL) for 20 min, washed with WB (3×200 μL) (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No.ab43812, Abcam) in 5% BSA in PBS-tween. After washing, cells are incubated with an HRP-conjugated secondary antibody solution (50 µL) in 5% BSA in PBS-Tween (lot 00053170, Cat.No. P0447, Dako) and then TMB substrate added (50 µL; substrate reagent pack, lot 269472, Cat. No. DY999, R&D Systems, Inc.). This reaction is stopped by the addition of 2N $H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colons of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-β-catenin antibody solution (50 µL) in 1% BSA/PBS (BD, Oxford, UK).

After washing with washing buffer (3×200 µL; PBS containing 0.05% Tween-20), cells are incubated with a HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, ThermoFisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising the Reference compound N-(4-(4-(3-(3-tert-butyl-1-p-tolyl-1H-pyrazol-5-yl)ureido)naphthalen-1-yloxy) pyridin-2-yl)-2-methoxyacetamide (1 µg/mL), which is defined as unity.

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2 \times 10^5$ cells per well in 100 µL RPMI/10% FBS on 96 well flat bottomed plate (Corning Costar). 25 µL of test compound are diluted to the appropriate concentration (8× final concentration) in normal medium and added to duplicate wells on the plate to achieve a dose response range of 0.03 ng/mL-250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$ and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments of size 3-4 mm. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 μm cell strainer, washed twice, resuspended in RPMI-1640 medium (Sigma-Aldrich) containing 10% fetal calf serum, 100 U/mL penicillin and 100 μg/mL streptomycin, and used for cell culture.

Freshly isolated LPMCs ($2\times10^5$ cells/well) are stimulated with 1 μg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows: The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 μg/mL streptomycin, 50 μg/mL gentamycin, and 1 μg/mL amphotericin (Sigma-Aldrich). Established colonies of myofibroblasts are seeded into 25-$cm^2$ culture flasks and cultured in DMEM supplemented with 20% FBS and antibiotics to at least passage 4 to provide a sufficient quantity for use in stimulation experiments.

Subconfluent monolayers of myofibroblasts, seeded in 12-well plates at $3\times10^5$ cells per well, are starved in serum-free medium for 24 h at 37° C., 5% $CO_2$, before being cultured for 24 h in the presence of either DMSO control or appropriate concentrations of compound. After 24 h, the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are isolated from human peripheral blood as follows: Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 μg/mL) and 1 mM $CaCl_2$) to achieve $5\times10^6$ cells/mL.

$5\times10^4$ cells are added to each well of a V-bottom 96 well plate and are incubated (30 mins, 37° C.) with the appropriate concentration of test compound (0.3-1000 ng/mL) or vehicle (DMSO, 0.5% final conc). Degranulation is stimulated by addition of fMLP (final concentration 1 μM). After a further incubation (30 mins, 37° C.), the cells are removed by centrifugation (5 mins, 1500 rpm) and the supernatants transferred to a flat bottom 96 well plate. An equal volume of tetramethylbenzidine (TMB) is added and, after 10 mins, the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $1\times10^5$ Jurkat cells (immortalised human T lymphocytes) are added to the appropriate number of wells of a 96 well plate in 100 μL of media (RPMI supplemented with 10% foetal bovine serum). 1 μL of DMSO control (final concentration 1.0% v/v) or test compound (final concentration 20, 5 or 1 μg/mL) is added to the wells and incubated at 37° C., 5% $CO_2$. After 24 hours, the plate is centrifuged at 1200 rpm for 3 minutes and the supernatant discarded. Cells are then resuspended in 150 μL (final concentration 7.5 μg/mL) of propidium iodide (PI) in PBS and incubated at 37° C., 5% $CO_2$ for 15 minutes. After 15 minutes, cells are analysed by flow cytometry (BD accuri) using the FL3 window. The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr, the animals are anesthetized, their tracheas cannulated and BALF extracted by infusing and then withdrawing from their lungs 1.0 mL of PBS via the tracheal catheter. Total and differential white cell counts in the BALF samples are measured using a Neubauer haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are represented as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 μL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study, DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study, animals are weighed every day and stool observations are made and recorded as a score, based on stool consistency. At the time of sacrifice on Day +6, the large intestine is removed and the length and weight are recorded. Sections of the colon are taken for either MPO analysis, to determine neutrophil infiltration, or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 µL) is administered intra-colonically via a plastic catheter with BID dosing of the vehicle, reference or test compound continuing for 2 or 4 days. During the study, animals are weighed every day and stool observations are made and recorded as a score, based on stool consistency. At the time of sacrifice on Day 2 (or Day 4), the large intestine is removed and the length and weight recorded. Sections of the colon are taken for histopathology scoring to determine disease severity.

(v) Adoptive Transfer in Mice

On Study day 0, female Balb/C mice are terminated and spleens obtained for CD45RB$^{high}$ cell isolation (Using SCID IBD cell Separation protocol). Approximately 4×10$^5$ cells/mL CD45RB$^{high}$ cells are then injected intraperitoneally (100 µL/mouse) into female SCID animals. On study day 14, mice are weighed and randomized into treatment groups based on body weight. On Day 14, compounds are administered BID, via oral gavage, in 5% polyoxyethylene 40 stearate in 20 mM pH 7.8 aqueous phosphate buffer in a dose volume of 5 mL/kg. Treatment continues until study day 49, at which point the animals are necropsied 4 hours after the morning administration. The colon length and weight are recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

(vi) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker, and receive a single intravitreal administration into the right vitreous humor (5 µL dose volume) of 100 ng/animal of LPS (*Escherichia coli* 0111:B4 prepared in PBS, Sigma Aldrich, UK) using a 32-gauge needle. Untreated rats are injected with PBS. Test compound or vehicle (4% polyoxyl 40 stearate, 4% mannitol in PBS (pH 7.4)) are administered by the topical route onto the right eye (10 µL) of animals 1 hour prior to LPS, at the time of LPS administration, and 1, 2 and 4 hours post LPS administration. Before administration, the solution to be administered is sonicated to ensure a clear solution. 6 hours after LPS dosing, animals are euthanized by overdose with pentobarbitone (via cardiac puncture). Immediately after euthanasia, 10 µL of aqueous humor is collected from the right eye of the rats by puncture of the anterior chamber using a 32 gauge needle under a surgical microscope. The aqueous humor is diluted in 20 µL of PBS and total cell counts are measured immediately using a Countess automated cell counter (Invitrogen). Following collection of the aqueous humour, the right eye of each animal is enucleated and dissected into front (anterior) and back (posterior) sections around the lens. Each section is weighed and homogenised in 500 µL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

TABLE 1

Results from in vitro p38 MAPKα (Method 2), c-Src and Syk inhibition assays

| Test Compound Example No. | IC50 Values for Enzyme Inhibition (nM) | | |
| --- | --- | --- | --- |
| | p38 MAPKα | c-Src | Syk |
| 1 | — | — | — |
| 2 | 23 | 14 | 8 |
| 3 | 23 | 18 | 12 |

TABLE 2

Inhibition of cytokine release in stimulated cells (assays (b) and (c) above).

| Test Compound Example No. | IC50 Values in PBMCs (nM) | | |
| --- | --- | --- | --- |
| | IL-8 | IFNγ | TNFα |
| 1 | 115.1 | — | — |
| 2 | 24.6 | 39.4 | — |
| 3 | 17.3 | 31.8 | 10.8 |
| 5 | 19.5 | — | — |
| 6 | 18.1 | — | — |
| 7 | 20.8 | — | — |
| 8 | 8.0 | — | — |
| 9 | 11.7 | — | — |
| 10 | 26.5 | — | — |
| 11 | 11.7 | — | — |
| 12 | 5.6 | — | — |
| 13 | 2.8 | — | — |
| 14 | 7.3 | — | — |
| 15 | 16.4 | — | — |
| 16 | 16.3 | — | — |
| 17 | 17.2 | — | — |
| 18 | 29.3 | — | — |
| 19 | 2.9 | — | — |
| 20(a) | 10.4 | — | — |
| 20(b) | 19.1 | — | — |
| 21 | 14.4 | — | — |
| 22 | 18.1 | — | — |
| 23 | 29.2 | — | — |
| 24 | 61.9 | — | — |
| 25 | 26.3 | — | — |
| 26 | 15.3 | — | — |
| 27 | 7.3 | — | — |
| 28 | 20.6 | — | — |

As illustrated in Table 3 below, compounds of the examples of the present invention are substantially less cytotoxic than the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide; WO 2010/112936), displaying enhanced viabilities in cell cytotoxicity assay (r) above (Table 3). In addition, the compounds of the examples of the present invention are substantially less cytotoxic at 20 µg/mL than the Reference Compound A (3-(2-(2-(3-((4-((4-(3-(5-(tert-butyl)-2-methoxy-3-(methylsulfonamido)phenyl)ureido)naphthalen-1-yl)oxy)-pyrimidin-2-yl)amino)-5-methoxyphenoxy)ethoxy)ethoxy)propanoic acid; WO 2014162126).

TABLE 3

Effect of compounds of the examples on Jurkat cell
viability (assay (r) above; NT = not tested).

| Test compound | % Viability at 1 µg/mL | % Viability at 5 µg/mL | % Viability at 20 µg/mL |
|---|---|---|---|
| Reference compound | 29 | 26 | 24 |
| Reference compound A | 96 | 93 | 48 |
| 1 | NT | NT | NT |
| 2 | 99 | 99 | 97 |
| 3 | 99 | 99 | 96 |

As illustrated in Table 4 below, the compound of Example 3 was also screened in the in vivo (adoptive transfer) assay (v) above alongside Reference Compound A, (3-(2-(2-(3-((4-((4-(3-(5-(tert-butyl)-2-methoxy-3-(methylsulfonamido)phenyl)ureido)naphthalen-1-yl)oxy)pyrimidin-2-yl)amino)-5-methoxyphenoxy)ethoxy)ethoxy)propanoic acid, and Reference Compound B, 3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide {Fyfe, M. C. T., WO 2014/140582}. Analysis of the relative ratios of colon weight to length in naïve, control and treated animals at the end of the study revealed that the compound of Example 3 provided superior activity compared to the two Reference Compounds in this T cell driven in vivo model of colonic inflammation using a simple aqueous-based vehicle.

TABLE 4

Summary of results from adoptive transfer mouse model.

| Treatment group | Dose | Colon weight:length | % Inhibition |
|---|---|---|---|
| Naïve | N/A | 0.021 ± 0.001 | 100 |
| Vehicle control | N/A | 0.043 ± 0.007 | 0 |
| Reference Compound A | 3 mg/kg[†] | 0.047 ± 0.007 | −14 |
| Reference Compound B | 3 mg/kg | 0.041 ± 0.005 | 11 |
| Example 3 | 3 mg/kg | 0.032 ± 0.004 | 49 |

[†]Dose was lowered to 0.6 mg/kg on day 27 because of poor tolerability (body weight loss).

Summary of Additional Studies

Determination of Solubilities in Fasted-State Simulated Colonic Fluid (FaSSCoF)

The solubilities of compounds of the invention in FaSSCoF at pH 6.5 are determined using a modification of a previously-reported procedure (Vertzoni, M., et al. *Pharm. Res.* 2010, 27, 2187-2196). In place of the bile salt extract employed in the original procedure (which extract is no longer available), the modified procedure uses a mixture of sodium taurocholate (0.15 g), glycocholic acid (0.15 g), ursodeoxycholic acid (0.05 g), cholic acid (0.05 g), and glycodeoxycholic acid (0.05 g). These five bile acids are ground together with a mortar and pestle to produce a fine white powder that is incorporated into the FaSSCoF, as outlined below.

Fasscof Medium:

Tris(hydroxymethyl)aminomethane (Tris; 0.275 g) and maleic acid (0.44 g) are dissolved in water (35 mL) to give a solution whose pH is adjusted to 6.5 by treatment with 0.5M NaOH (ca. 12 mL). The solution is then made up to 50 mL with water. A portion of this Tris/maleate buffer solution (ca. 25 mL) is added to a 0.5 L round-bottomed flask, before being treated with 0.00565 g of the bile acid mixture described above. Solutions of phosphatidylcholine (0.0111 g) in DCM (0.15 mL) and palmitic acid (0.0013 g) in DCM (0.15 mL) are added, then the organic solvent is evaporated off under reduced pressure at 40° C. until a clear solution, with no perceptible DCM odour, is achieved. The volume of the evaporated solution is adjusted to 50 mL by addition of the remainder of Tris/maleate buffer, then BSA (0.115 g) is added, before being dissolved by gentle agitation.

Solubility Determination:

Test compounds are suspended in the pH 6.5 FaSSCoF medium to give a maximum final concentration of 2-10 mg/mL. The suspensions are equilibrated at 25° C. for 24 h, before being filtered through a glass fibre C filter. The filtrates are then diluted as appropriate for injection and quantification by HPLC with reference to a standard. Different volumes of the standard, diluted and undiluted sample solutions are injected and the solubilities are calculated using the peak areas determined by integration of the peak found at the same retention time as the principal peak in the standard injection.

FaSSCoF solubilities are shown in Table 5 below, which reveals that compounds of the Examples (or salts thereof) exhibited solubilities in the FaSSCoF medium at pH 6.5 in excess of 0.03 mg/mL, while some displayed solubilities greater than 1 mg/mL. The pH 6.5 FaSSCoF solubilities measured for compounds of the Examples were superior to those of both Reference Compound A, (3-(2-(2-(3-((4-((4-(3-(5-(tert-butyl)-2-methoxy-3-(methylsulfonamido)phenyl)ureido)naphthalen-1-yl)oxy)pyrimidin-2-yl)amino)-5-methoxyphenoxy)ethoxy)ethoxy)propanoic acid, and Reference Compound B, 3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-(2-(2-methoxyethoxy)ethoxy)ethyl)benzamide {Fyfe, M. C. T., WO 2014/140582}.

TABLE 5

Solubilities measured for certain compounds of the Examples of the present invention, or salts thereof, in FaSSCoF at pH 6.5.

| Test Compound | pH 6.5 FaSSCoF Solubility (mg/mL) | | | |
|---|---|---|---|---|
| Example No. | Run 1 | Run 2 | Run 3 | Run 4 |
| Reference Compound A | 0.007 | 0.007 | — | — |
| Reference Compound A (sodium salt) | 0.18 | 0.12 | 0.03 | 0.03 |
| Reference Compound B | <0.001 | <0.001 | — | — |
| 2 | 0.09 | 0.06 | — | — |
| 2 (sodium salt) | 0.58 | — | — | — |
| 3 | 0.28 | 0.20 | — | — |
| 31 | 1.90 | 2.10 | — | — |
| 8 | 2.8 | 3.2 | — | — |
| 9 | 0.46 | 0.54 | — | — |
| 14 | 1.2 | 1.1 | — | — |
| 17 | 1.7 | 1.5 | — | — |
| 19 | 0.03 | 0.03 | — | — |
| 20(a) | 0.62 | 0.64 | — | — |

Further studies also revealed that, in phosphate-buffered saline at either pH 6.5 with 0.5% by weight of simulated intestinal fluid or pH 7.2, the compound of Example 31 (i.e. the sodium of the compound of Example 3) was both more soluble than, and had a faster dissolution rate than, both of Reference Compounds A (hydrochloride salt) and B.

Microcentrifuge Dissolution Tests

In vitro non-sink dissolution performance of the Compound of Example 3 was evaluated alongside Reference Compounds A and B employing microcentrifuge dissolution tests in which samples were either 1) transferred from intestinal buffer (IB) to colonic buffer (CB) or 2) dosed directly into intestinal media containing simulated bile-salt micelles (IB-SIF). Dissolution performance of the compounds at various timepoints was determined by centrifugation and analysis of the supernatant concentrations by off-line reverse-phase HPLC analysis.

1) Transfer from Intestinal Buffer (IB) to Colonic Buffer (CB) Experiment

Test compounds (0.45 mg±0.05 mg) were weighed into a microcentrifuge tube, then 0.900 mL of IB receptor solution—phosphate buffered saline (PBS) warmed to 37° C. at pH 6.5—was added. A timer was started and the sample tubes were vortexed at the maximum setting for 1 minute. When the timer read 3, 13 and 23 min—corresponding to the 25, 15 and 5 min timepoints, respectively—the sample tubes were centrifuged for 1 min at 15,800 Relative Centrifugal Force (RCF). At each timepoint, a portion of the supernatant (50 µL) was added to diluent {250 µL of 75/25 THF/Water (v/v)} and the compound concentrations were measured by off-line HPLC analysis (Table 6a). After a further 5 min, 0.900 mL of CB receptor solution—pH 10.7 PBS solution—was added, such that the pH was adjusted to 7.2, and the timer was reset to 0 min. When the timer read 2, 8, 18, 38, 88 and 1,198 min—corresponding to the 4, 10, 20, 40, 90 and 1,200 min timepoints, respectively—the sample tubes were centrifuged for 1 min at 15,800 RCF. At each timepoint, a portion of the supernatant (50 µL) was added to diluent {250 µL of 75/25 THF/Water (v/v)} and the compound concentrations were measured by off-line HPLC analysis (Table 6a). The HPLC samples for the 90 and 1,200 min timepoints were additionally centrifuged for 8 min at 80,000 rpm at 37° C. in an ultracentrifuge (UCF), then the supernatant (50 µL) was added to diluent {250 µL of 75/25 THF/Water (v/v)} and the compound concentrations were measured by off-line HPLC analysis (Table 6b) to determine the concentration of free drug+drug in micelles.

TABLE 6a

Concentrations (µg/mL) measured during dissolution test 1).

| Test Cpd | IB Timepoint (min) | | | | CB Timepoint (min) | | | | | |
|---|---|---|---|---|---|---|---|---|---|---|
| Example No. | −30 | −25 | −15 | −5 | 4 | 10 | 20 | 40 | 90 | 1,200 |
| Reference Compound A | 0.0 | 2.9 | 4.6 | 5.3 | 11.4 | 11.5 | 10.7 | 10.7 | 8.4 | 7.9 |
| Reference Compound B | 0.0 | 1.9 | 1.0 | 2.2 | 5.0 | 1.9 | 0.9 | 0.6 | 0.0 | 4.9 |
| 3 | 0.0 | 5.3 | 7.5 | 8.5 | 9.3 | 9.1 | 14.3 | 48.3 | 60.7 | 85.4 |

TABLE 6b

Additional concentrations (µg/mL) measured during dissolution test 1).

| | UCF Timepoint (min) | |
|---|---|---|
| Test Compound Example No. | 90 | 1,200 |
| Reference Compound A | 5.1 | 3.9 |
| Reference Compound B | 0.0 | 1.6 |
| 3 | 34.1 | 74.9 |

2) Experiment with Direct Dosing into Intestinal Media Containing Simulated Bile-Salt Micelles (IB-SIF)

Test compounds (0.45 mg±0.05 mg) were weighed into a microcentrifuge tube then 1.800 mL of IB-SIF receptor solution—prepared previously by dissolution of 0.250 g SIF powder (Biorelevant.com) in 50 mL of pH 6.5 PBS warmed to 37° C.—was added. A timer was started and the sample tubes were vortexed at the maximum setting for 1 minute. When the timer read 2, 8, 18, 38, 88 and 1,198 min—corresponding to the 4, 10, 20, 40, 90 and 1,200 min timepoints, respectively—the sample tubes were centrifuged for 1 min at 15,800 RCF. Then, at each timepoint, the supernatant (50 µL) was added to diluent {250 µL of 75/25 THF/Water (v/v)} and the compound concentrations were measured by off-line HPLC analysis (Table 7a). To determine the concentration of free drug+drug in micelles, the HPLC samples for the 90 and 1,200 min timepoints were additionally centrifuged for 8 min at 80,000 rpm at 37° C. in an ultracentrifuge (UCF), then the supernatant (50 µL) was added to diluent {250 µL of 75/25 THF/Water (v/v)} and the compound concentrations were measured by off-line HPLC analysis (Table 7b).

TABLE 7a

Concentrations (µg/mL) measured during dissolution test 2).

| Test Compound | IB Timepoint (min) | | | | | | |
|---|---|---|---|---|---|---|---|
| Example No. | 0 | 4 | 10 | 20 | 40 | 90 | 1,200 |
| Reference Compound A | 0.0 | 39.8 | 63.4 | 83.5 | 96.5 | 99.9 | 101.0 |
| Reference Compound B | 0.0 | 1.1 | 0.9 | 1.3 | 1.0 | 0.7 | 3.0 |
| 3 | 0.0 | 255.7 | 255.9 | 251.7 | 249.2 | 253.5 | 239.0 |

TABLE 7b

Additional concentrations (µg/mL) measured during dissolution test 2).

| | UCF Timepoint (min) | |
|---|---|---|
| Test Compound Example No. | 90 | 1,200 |
| Reference Compound A | 87.0 | 88.8 |
| Reference Compound B | 0.7 | 2.9 |
| 3 | 229.4 | 169.9 |

Abbreviations

AcOH glacial acetic acid
aq aqueous
5-ASA 5-aminosalicylic acid
ATP adenosine-5′-triphosphate BALF bronchoalveolar lavage fluid
BID bis in die (twice-daily)
BINAP 2,2'-bis(diphenylphosphino)-1,1'-binaphthyl
BOP (benzotriazol-1-yloxy)tris(dimethylamino)phosphonium hexafluorophosphate
br broad
BrdU 5-bromo-2'-deoxyuridine
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCC dicyclohexylcarbodiimide
DCM dichloromethane
DIAD diisopropyl azodicarboxylate
DIPEA diisopropylethylamine
DMAP 4-dimethylaminopyridine
DMEM Dulbecco's modified eagle medium
DMF N,N-dimethylformamide
DMSO dimethyl sulfoxide
DPPA diphenylphosphoryl azide
d-U937 cells PMA differentiated U-937 cells
EDTA ethylenediaminetetraacetic acid
ELISA enzyme-linked immunosorbent assay
(ES⁻) electrospray ionization, negative mode
(ES⁺) electrospray ionization, positive mode
Et ethyl
Et$_3$N triethylamine
EtOAc ethyl acetate
EtOH ethanol
FACS fluorescence-activated cell sorting
FBS foetal bovine serum
FCS foetal calf serum
fMLP formyl-methionyl-leucyl-phenylalanine
FRET fluorescence resonance energy transfer
GSK3α glycogen synthase kinase 3α
HBEC primary human bronchial epithelial cells
HBSS Hank's balanced salt solution
HPLC high performance liquid chromatography
HPMC hydroxypropylmethylcellulose
h or hr hour(s)
HATU 2-(1H-7-azabenzotriazol-1-yl)-1,1,3,3-tetramethyl uronium hexafluorophosphate
HOAt 1-hydroxy-7-azabenzotriazole
HOBt hydroxybenzotriazole
HRP horseradish peroxidise
HRV human rhinovirus
ICAM-1 inter-cellular adhesion molecule 1
IFNγ interferon-γ
IL interleukin
iPrOAc isopropyl acetate
JNK c-Jun N-terminal kinase
LC liquid chromatography
Lck lymphocyte-specific protein tyrosine kinase
LiHMDS lithium bis(trimethylsilyl)amide
LPS lipopolysaccharide
m multiplet
(M+H)⁺ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile MeOH methanol
MHz megahertz
min or mins minute(s)
MMAD mass median aerodynamic diameter
MOI multiplicity of infection
MPO myeloperoxidase
MTT 3-(4,5-dimethylthiazol-2-yl)-2,5-diphenyltetrazolium bromide
MS mass spectrometry
m/z mass-to-charge ratio
NMP N-methyl pyrrolidinone
NMR nuclear magnetic resonance (spectroscopy)
OD optical density
PBMC peripheral blood mononuclear cell
PBS phosphate buffered saline
Ph phenyl
PHA phytohaemagglutinin
PMA phorbol myristate acetate
pTSA 4-methylbenzenesulfonic acid (para-toluenesulfonic acid)
PyBOP (benzotriazol-1-yloxy)tripyrrolidinophosphonium hexafluorophosphate
q quartet
rt or RT room temperature
RP HPLC reverse phase high performance liquid chromatography
rpm revolutions per minute
RPMI Roswell Park Memorial Institute
RSV respiratory syncytial virus
s singlet
sat or satd saturated
SCID severe combined immunodeficiency
SCX solid supported cation exchange (resin)
SDS sodium dodecyl sulfate
S$_N$Ar nucleophilic aromatic substitution
Syk Spleen tyrosine kinase
t triplet
T3P 1-propanephosphonic acid cyclic anhydride
TBAI tetrabutylammonium iodide
TBAF tetrabutylammonium fluoride
TBDMS tert-butyldimethylsilyl
TBME tert-butyl methyl ether
TBSCl tert-butyldimethylsilyl chloride
tBuXPhos 2-di-tert-butylphosphino-2',4',6'-triisopropylbiphenyl
TCID$_{50}$ 50% tissue culture infectious dose
TEA triethylamine
THF tetrahydrofuran
TFA trifluoroacetic acid
TGFβ transforming growth factor beta
TIPS triisopropylsilyl
TMB 3,3',5,5'-tetramethylbenzidine
TMS-Cl trimethylsilyl chloride
TNFα tumor necrosis factor alpha Prefixes n-, s-, i-, t- and tert- have their usual meanings: normal, secondary, iso, and tertiary.

What is claimed is:

1. A compound of formula I(P):

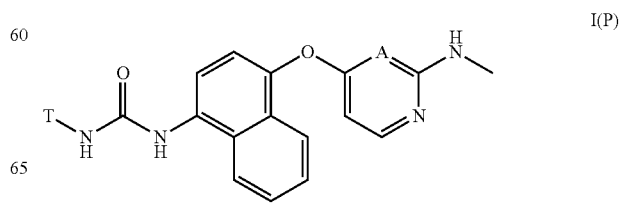

I(P)

-continued

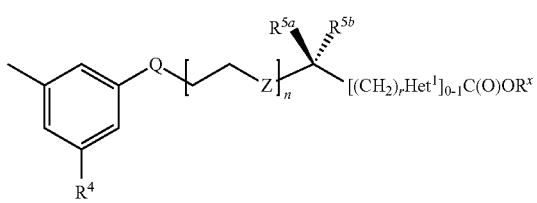

or a salt thereof,
wherein:
wherein $R^x$ represents $C_{1-6}$ alkyl or benzyl;
T represents

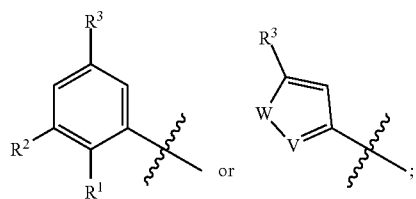

W represents O, S or $NCH_3$;
V represents N or $CR^1$;
$R^1$ represents $C_{1-3}$ alkoxy, $C_{1-3}$ alkyl, $C_{2-3}$ alkenyl, $C_{2-3}$ alkynyl, which latter four groups are optionally substituted by one or more substituents selected from halo, hydroxy and $C_{1-2}$ alkoxy, or $R^1$ represents H;
$R^2$ represents $-NR^{A1}S(O)_2R^{B1}$, $-S(O)_{1-2}R^{B2}$, $-P(O)R^{B3}R^{B4}$, $-C(O)NR^{A2}R^{A3}$ or $-CH_2NR^{A4}C(O)R^{A5}$;
$R^{A1}$ to $R^{A5}$ independently represent H or $C_{1-3}$ alkyl optionally substituted by one or more substituents selected from halo, hydroxy, $NR^C R^D$ and $C_{1-2}$ alkoxy, or $R^{A2}$ and $R^{A3}$ together represent $C_{3-6}$ n-alkylene or $C_{4-5}$ n-alkylene interrupted between C2 and C3 by $-O-$, $-S(O)_q-$ or $-N(R^E)-$;
$R^{B1}$ to $R^{B4}$ independently represent $C_{1-3}$ alkyl or $C_{3-6}$ cycloalkyl, which latter two groups are optionally substituted by one or more halo substituents;
$R^C$ and $R^D$ independently represent H or $C_{1-3}$ alkyl, which latter substituent is optionally substituted by hydroxyl or $C_{1-2}$ alkoxy, or $R^C$ and $R^D$ together combine to form $C_{4-6}$ alkylene optionally interrupted between C2 and C3 by $-O-$, $-S(O)_q-$ or $-N(R^E)-$;
$R^E$ represents H or methyl;
q represents 0, 1 or 2;
$R^3$ represents $C_{2-7}$ alkyl, $C_{2-7}$ alkenyl, $C_{2-7}$ alkynyl or $C_{3-7}$ cycloalkyl, which latter four groups are optionally substituted by hydroxyl, $C_{1-2}$ alkoxy or halo, or $R^3$ represents morpholinyl or trimethylsilyl;
A represents CH or N;
$R^4$ represents $C_{1-3}$ alkoxy, $C_{3-5}$ cycloalkoxy, or $C_{1-3}$ alkyl, which latter three groups are optionally substituted by one or more halo substituents, or $R^4$ represents ethynyl, cyano, $S(O)_2CH_3$, halo or H;
Q represents O, $S(O)_p$, $SO_2N(R^6)$ or $C(O)N(R^6)$;
n represents 1, 2 or 3;
p represents 0, 1 or 2;
$R^{5a}$ and $R^{5b}$ independently represent H, methyl or halo, or $R^{5a}$ and $R^{5b}$ together represent $C_{2-6}$ n-alkylene;
when n represents 1, Z represents O, S or $NR^7$ or,
when n represents 2 or 3, Z represents either
   an O-atom on each occurrence, or
   either an S-atom or $NR^7$ on one occurrence and an O-atom on each other occurrence;
$R^6$ and $R^7$ independently represent H or methyl;
r represents 0 or, when $Het^1$ is attached to $(CH_2)_r$ via a ring heteroatom, r may alternatively represent 1; and
$Het^1$ represents
   a 5- or 6-membered heterocyclic group that is fully aromatic, which group contains one or more heteroatoms selected from N, O and S or
   a 4- to 7-membered heterocyclic group that is fully saturated or partially unsaturated, and is monocyclic or is fused or bridged bicyclic, which group contains one or more heteroatoms selected from N, O and S,
wherein $Het^1$ is optionally substituted by one or more substituents selected from $C_{1-3}$ alkyl, $C_{1-3}$ alkoxy, halo, hydroxyl and oxo.

2. A compound of formula I(P) as claimed in claim 1, wherein:
$R^1$ represents methoxy;
$R^2$ represents $-NHS(O)_2CH_3$;
$R^3$ represents tert-butyl;
A represents CH;
$R^4$ represents methoxy;
$R^{5a}$ and $R^{5b}$ both represent H;
Q represents O;
Z represents O;
n represents 2; and/or
$R^x$ represents ethyl.

3. A compound as claimed in claim 1 which compound is:

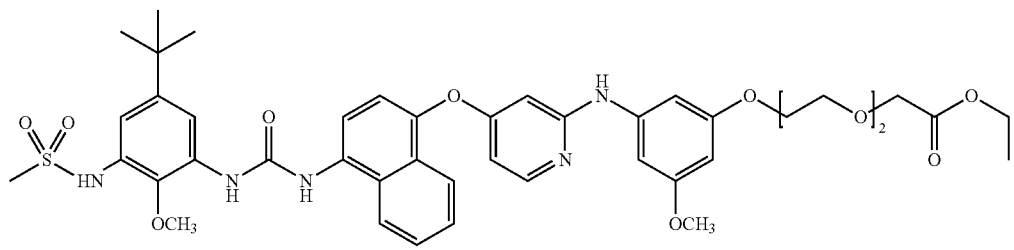

(ethyl 2-(2-(2-(3-((4-((4-(3-(5-(tert-butyl)-2-methoxy-3-(methylsulfonamido)phenyl)ureido)-naphthalen-1-yl)oxy)pyridin-2-yl)amino)-5-methoxyphenoxy)ethoxy)ethoxy)acetate), or a salt thereof.

4. A compound:
(a) of formula II or IIb:

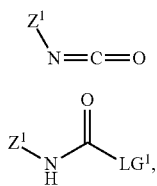

or a salt or protected derivative thereof,
wherein
LG¹ represents a leaving group; and
Z¹ is a structural fragment of formula V:

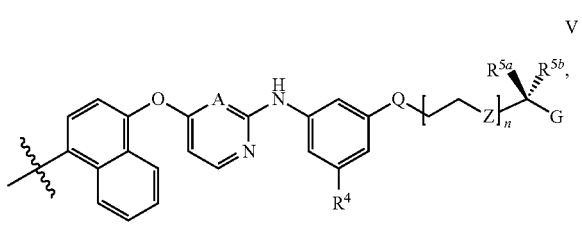

wherein G represents —[(CH$_2$)$_r$-Het$^1$]$_{0-1}$—C(O)$_2$H or a carboxylic acid isostere and R$^4$, R$^{5a}$, R$^{5b}$, A, Q, Z, n and Het$^1$ are as defined in claim 1 and;
wherein the protected derivative of the compound of formula II or IIb is a compound in which, when G represents —[(CH$_2$)$_r$-Het$^1$]$_{0-1}$—C(O)$_2$H, the C(O)$_2$H moiety is protected as an ester of formula C(O)OR$^x$, wherein R$^x$ represents C$_{1-6}$ alkyl or benzyl; or
(b) of formula III,

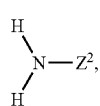

or a salt or protected derivative thereof, wherein Z² is a structural fragment of formula V, as defined above,
wherein the protected derivative of the compound of formula III is a compound (i) in which the NH$_2$ group of formula III is replaced by nitro, or in which a H-atom of the NH$_2$ group of formula III is replaced by R'—C(O)—, wherein R' is C$_{1-8}$ alkyl optionally substituted by one or more fluoro groups or R' is H, phenyl or benzyl, which latter two groups are optionally substituted by one or more groups selected from halo, hydroxy, methyl and methoxy; or R"—O—C(O)—, wherein R" is tert-butyl, phenyl, benzyl or fluorenyl, which latter three groups are optionally substituted by one or more groups selected from halo, hydroxy, methyl and methoxy; and/or (ii) in which, when G represents —[(CH$_2$)$_r$-Het$^1$]$_{0-1}$—C(O)$_2$H, the C(O)$_2$H moiety of formula III is protected as an ester of formula C(O)OR$^x$, wherein R$^x$ represents C$_{1-6}$ alkyl or benzyl.

5. A compound of formula II, IIb or III as claimed in claim 4, or a salt or protected derivative thereof, wherein:
A represents CH;
R$^4$ represents methoxy;
R$^{5a}$ and R$^{5b}$ both represent H;
Q represents O;
Z represents O; and/or
n represents 2.

6. A compound of formula III, or a salt thereof, as claimed in claim 4, which compound is

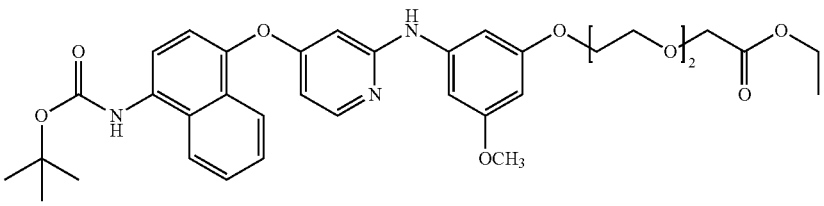

(ethyl 2-(2-(2-(3-((4-((4-((tert-butoxycarbonyl)amino)naphthalen-1-yl)oxy)pyridin-2-yl)amino)-5-methoxyphenoxy)ethoxy)ethoxy)acetate) or

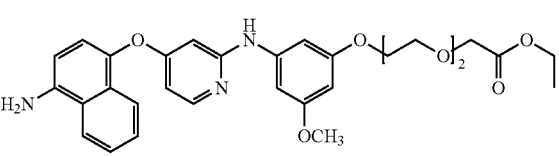

(ethyl 2-(2-(2-(3-((4-((4-aminonaphthalen-1-yl)oxy)pyridin-2-yl)amino)-5-methoxyphenoxy)ethoxy)ethoxy)acetate).

7. A compound of formula IIb, or a salt or protected derivative thereof, as claimed in claim 4, wherein LG¹ represents imidazolyl, chloro, or aryloxy.

8. A compound of formula IIb, or a salt or protected derivative thereof, as claimed in claim 4, wherein:
LG¹ represents phenoxy; and
G represents C(O)$_2$H, wherein the protected derivative of the compound of formula IIb is a compound in which the $C(O)_2H$ moiety is protected as an ester of formula $C(O)OR^x$, wherein $R^x$ represents $C_{1-6}$ alkyl or benzyl.

9. A compound of formula IIb, or a salt or protected derivative thereof, as claimed in claim 8, wherein A represents CH;
$R^4$ represents methoxy;
$R^{5a}$ and $R^{5b}$ both represent H;
Q represents O;
Z represents O; and/or
n represents 2.

\* \* \* \* \*